(12) United States Patent
Thorn

(10) Patent No.: US 10,584,147 B2
(45) Date of Patent: Mar. 10, 2020

(54) PROCOAGULANT FUSION COMPOUND

(71) Applicant: Bioverativ Therapeutics Inc., Waltham, MA (US)

(72) Inventor: Karina Thorn, Farum (DK)

(73) Assignee: Biovertiv Therapeutics Inc., Waltham, MA (US)

( * ) Notice: Subject to any disclaimer, the term of this patent is extended or adjusted under 35 U.S.C. 154(b) by 589 days.

(21) Appl. No.: 15/035,145

(22) PCT Filed: Nov. 7, 2014

(86) PCT No.: PCT/US2014/064541
§ 371 (c)(1),
(2) Date: May 6, 2016

(87) PCT Pub. No.: WO2015/070014
PCT Pub. Date: May 14, 2015

(65) Prior Publication Data
US 2016/0289273 A1    Oct. 6, 2016

Related U.S. Application Data

(60) Provisional application No. 61/901,973, filed on Nov. 8, 2013, provisional application No. 61/981,446, filed on Apr. 18, 2014.

(51) Int. Cl.
*C07K 14/745* (2006.01)
*C07K 14/00* (2006.01)
*A61K 38/00* (2006.01)

(52) U.S. Cl.
CPC .............. *C07K 14/00* (2013.01); *A61K 38/00* (2013.01); *C07K 2319/00* (2013.01); *C07K 2319/30* (2013.01)

(58) Field of Classification Search
None
See application file for complete search history.

(56) References Cited

U.S. PATENT DOCUMENTS

| | | | |
|---|---|---|---|
| 4,179,337 A | 12/1979 | Davis et al. |
| 4,444,878 A | 4/1984 | Paulus |
| 4,694,778 A | 9/1987 | Learn et al. |
| 4,745,055 A | 5/1988 | Schenk et al. |
| 4,757,006 A | 7/1988 | Toole, Jr. et al. |
| 4,868,112 A | 9/1989 | Toole, Jr. |
| 4,965,199 A | 10/1990 | Capon et al. |
| 4,994,371 A | 2/1991 | Davie et al. |
| 5,004,803 A | 4/1991 | Kaufman et al. |
| 5,112,950 A | 5/1992 | Meulien et al. |
| 5,122,614 A | 6/1992 | Zalipsky |
| 5,171,844 A | 12/1992 | Van et al. |
| 5,364,771 A | 11/1994 | Lollar et al. |
| 5,539,063 A | 7/1996 | Hakimi et al. |
| 5,543,502 A | 8/1996 | Nordfang et al. |
| 5,585,089 A | 12/1996 | Queen et al. |
| 5,589,369 A | 12/1996 | Seidman et al. |
| 5,591,669 A | 1/1997 | Krimpenfort et al. |
| 5,595,886 A | 1/1997 | Chapman et al. |
| 5,610,278 A | 3/1997 | Nordfang et al. |
| 5,643,575 A | 7/1997 | Martinez et al. |
| 5,648,260 A | 7/1997 | Winter et al. |
| 5,658,570 A | 8/1997 | Newman et al. |
| 5,693,761 A | 12/1997 | Queen et al. |
| 5,693,762 A | 12/1997 | Queen et al. |
| 5,693,780 A | 12/1997 | Newman et al. |
| 5,712,122 A | 1/1998 | Boime et al. |
| 5,739,277 A | 4/1998 | Presta et al. |
| 5,756,096 A | 5/1998 | Newman et al. |
| 5,789,203 A | 8/1998 | Chapman et al. |
| 5,811,524 A | 9/1998 | Brams et al. |
| 5,834,250 A | 11/1998 | Wells et al. |
| 5,846,951 A | 12/1998 | Gregoriadis |

(Continued)

FOREIGN PATENT DOCUMENTS

| | | |
|---|---|---|
| EP | 0068763 A2 | 1/1983 |
| EP | 0097994 A2 | 1/1984 |

(Continued)

OTHER PUBLICATIONS

Benard, S.A., et al., "Identification of Peptide Antagonists to Glycoprotein Ibα that Selectively Inhibit von Willebrand Factor Dependent Platelet Aggregation," Biochemistry 47(16): 4674-4682, American Chemical Society, United States (2008).
Better, M., et al., "*Escherichia Coli* Secretion of an Active Chimeric Antibody Fragment," Science 240(4855):1041-1043, Association for the Advancement of Science, United States (1988).
Bi, L., et al., "Targeted Disruption of the Mouse Factor VIII Gene Produces a Model of Haemophilia A," Nature Genetics 10(1):119-121, Nature Publishing Co., United States (1995).
Bird, R.E., et al., "Single-Chain Antigen-Binding Proteins," Science 242(4877):423-426, Association for the Advancement of Science, United States (1988).
Bovenschen, N., et al., "LDL Receptor Cooperates with LDL Receptor-Related Protein in Regulating Plasma Levels of Coagulation Factor VIII in Vivo," Blood 106(3):906-912, The American Society of Hematology, United States (2005).

(Continued)

*Primary Examiner* — Michael Szperka
(74) *Attorney, Agent, or Firm* — Lathrop GPM LLP; James H. Velema, Esq.

(57) ABSTRACT

The present invention provides a fusion compound comprising a procoagulant compound and an immunoglobulin constant region or a portion thereof and methods of making and using the fusion compound. The fusion compounds of the present disclosure are useful for the treatment of coagulation disorders, such as hemophilia. In some aspects, the invention includes a method of reducing or preventing aggregates which comprise a procoagulant compound comprising fusing the procoagulant compound to an immunoglobulin constant region or a portion thereof wherein the procoagulant compound comprises an amino acid sequence. In another embodiment, the fusion compound forms less aggregates compared to a compound consisting of the procoagulant compound.

16 Claims, 7 Drawing Sheets
Specification includes a Sequence Listing.

(56) References Cited

U.S. PATENT DOCUMENTS

| | | |
|---|---|---|
| 5,859,204 A | 1/1999 | Lollar |
| 5,869,046 A | 2/1999 | Presta et al. |
| 5,892,019 A | 4/1999 | Schlom et al. |
| 5,919,452 A | 7/1999 | Le et al. |
| 5,939,598 A | 8/1999 | Kucherlapati et al. |
| 5,972,885 A | 10/1999 | Spira et al. |
| 6,005,079 A | 12/1999 | Casterman et al. |
| 6,030,613 A | 2/2000 | Blumberg et al. |
| 6,048,720 A | 4/2000 | Dalborg et al. |
| 6,060,447 A | 5/2000 | Chapman et al. |
| 6,075,181 A | 6/2000 | Kucherlapati et al. |
| 6,086,875 A | 7/2000 | Blumberg et al. |
| 6,096,871 A | 8/2000 | Presta et al. |
| 6,121,022 A | 9/2000 | Presta et al. |
| 6,194,551 B1 | 2/2001 | Idusogie et al. |
| 6,228,620 B1 | 5/2001 | Chapman et al. |
| 6,242,195 B1 | 6/2001 | Idusogie et al. |
| 6,251,632 B1 | 6/2001 | Lillicrap et al. |
| 6,277,375 B1 | 8/2001 | Ward |
| 6,316,226 B1 | 11/2001 | Van et al. |
| 6,346,513 B1 | 2/2002 | Van et al. |
| 6,376,463 B1 | 4/2002 | Lollar |
| 6,458,563 B1 | 10/2002 | Lollar |
| 6,485,726 B1 | 11/2002 | Blumberg et al. |
| 6,528,624 B1 | 3/2003 | Idusogie et al. |
| 6,538,124 B1 | 3/2003 | Idusogie et al. |
| 6,696,245 B2 | 2/2004 | Winter et al. |
| 6,737,056 B1 | 5/2004 | Presta |
| 6,765,087 B1 | 7/2004 | Casterman et al. |
| 6,821,505 B2 | 11/2004 | Ward |
| 6,998,253 B1 | 2/2006 | Presta et al. |
| 7,033,590 B1 | 4/2006 | Scheiflinger et al. |
| 7,041,635 B2 | 5/2006 | Kim et al. |
| 7,083,784 B2 | 8/2006 | Dall'Acqua et al. |
| 7,317,091 B2 | 1/2008 | Lazar et al. |
| 7,381,408 B2 | 6/2008 | Mezo et al. |
| 7,404,956 B2 | 7/2008 | Peters et al. |
| 7,589,178 B2 | 9/2009 | Le et al. |
| 7,951,918 B2 | 5/2011 | Glaser et al. |
| 8,283,319 B2 | 10/2012 | Schulte et al. |
| 8,388,965 B2 | 3/2013 | Rao et al. |
| 8,673,860 B2 | 3/2014 | Schellenberger et al. |
| 8,933,197 B2 | 1/2015 | Bogin et al. |
| 2003/0069395 A1 | 4/2003 | Sato et al. |
| 2003/0235536 A1 | 12/2003 | Blumberg |
| 2004/0132028 A1 | 7/2004 | Stumpp et al. |
| 2005/0100990 A1 | 5/2005 | Saenko et al. |
| 2006/0115876 A1 | 6/2006 | Pan et al. |
| 2006/0228331 A1 | 10/2006 | Peschke et al. |
| 2007/0191597 A1 | 8/2007 | Jain et al. |
| 2007/0218067 A1 | 9/2007 | Buttner et al. |
| 2007/0231329 A1 | 10/2007 | Lazar et al. |
| 2007/0237765 A1 | 10/2007 | Lazar et al. |
| 2007/0237766 A1 | 10/2007 | Lazar et al. |
| 2007/0237767 A1 | 10/2007 | Lazar et al. |
| 2007/0243188 A1 | 10/2007 | Lazar et al. |
| 2007/0248603 A1 | 10/2007 | Lazar et al. |
| 2007/0286859 A1 | 12/2007 | Lazar et al. |
| 2008/0004206 A1 | 1/2008 | Rosen et al. |
| 2008/0057056 A1 | 3/2008 | Lazar et al. |
| 2008/0153751 A1 | 6/2008 | Rosen et al. |
| 2008/0161243 A1 | 7/2008 | Rosen et al. |
| 2008/0194481 A1 | 8/2008 | Rosen et al. |
| 2008/0261877 A1 | 10/2008 | Ballance et al. |
| 2008/0318276 A1 | 12/2008 | Persson et al. |
| 2009/0041744 A1 | 2/2009 | Ostergaard et al. |
| 2009/0087411 A1 | 4/2009 | Fares et al. |
| 2009/0291890 A1 | 11/2009 | Madison et al. |
| 2010/0022445 A1 | 1/2010 | Scheiflinger et al. |
| 2010/0189682 A1 | 7/2010 | Schellenberger et al. |
| 2010/0239554 A1 | 9/2010 | Schellenberger et al. |
| 2010/0260706 A1 | 10/2010 | Bogin et al. |
| 2010/0292130 A1 | 11/2010 | Skerra et al. |
| 2010/0323956 A1 | 12/2010 | Schellenberger et al. |
| 2011/0046060 A1 | 2/2011 | Schellenberger et al. |
| 2011/0046061 A1 | 2/2011 | Schellenberger et al. |
| 2011/0077199 A1 | 3/2011 | Schellenberger et al. |
| 2011/0172146 A1 | 7/2011 | Schellenberger et al. |
| 2014/0303084 A1 | 10/2014 | Thorn et al. |

FOREIGN PATENT DOCUMENTS

| | | |
|---|---|---|
| EP | 0120694 A2 | 10/1984 |
| EP | 0125023 A1 | 11/1984 |
| EP | 0255694 A1 | 2/1988 |
| EP | 0256654 A2 | 2/1988 |
| EP | 0266663 A1 | 5/1988 |
| EP | 0295597 A2 | 12/1988 |
| WO | WO-8704187 A1 | 7/1987 |
| WO | WO-8800831 A1 | 2/1988 |
| WO | WO-8803558 A1 | 5/1988 |
| WO | WO-8803559 A1 | 5/1988 |
| WO | WO-8803565 A1 | 5/1988 |
| WO | WO-8807089 A1 | 9/1988 |
| WO | WO-8808035 A1 | 10/1988 |
| WO | WO-9109122 A1 | 6/1991 |
| WO | WO-9320093 A1 | 10/1993 |
| WO | WO-9411503 A2 | 5/1994 |
| WO | WO-9614339 A1 | 5/1996 |
| WO | WO-9805787 A1 | 2/1998 |
| WO | WO-9823289 A1 | 6/1998 |
| WO | WO-9951642 A1 | 10/1999 |
| WO | WO-9958572 A1 | 11/1999 |
| WO | WO-0009560 A2 | 2/2000 |
| WO | WO-0032767 A1 | 6/2000 |
| WO | WO-0042072 A2 | 7/2000 |
| WO | WO-0187922 A2 | 11/2001 |
| WO | WO-0202781 A1 | 1/2002 |
| WO | WO-0244215 A2 | 6/2002 |
| WO | WO-02060919 A2 | 8/2002 |
| WO | WO-0240544 A3 | 10/2002 |
| WO | WO-03020764 A2 | 3/2003 |
| WO | WO-03074569 A2 | 9/2003 |
| WO | WO-03077834 A2 | 9/2003 |
| WO | WO-2004016750 A2 | 2/2004 |
| WO | WO-2004029207 A2 | 4/2004 |
| WO | WO-2004035752 A2 | 4/2004 |
| WO | WO-2004063351 A2 | 7/2004 |
| WO | WO-2004074455 A2 | 9/2004 |
| WO | WO-2004099249 A2 | 11/2004 |
| WO | WO-2005040217 A2 | 5/2005 |
| WO | WO-2005070963 A1 | 8/2005 |
| WO | WO-2005077981 A2 | 8/2005 |
| WO | WO-2005092925 A2 | 10/2005 |
| WO | WO-2005123780 A2 | 12/2005 |
| WO | WO-2006019447 A1 | 2/2006 |
| WO | WO-2006047350 A2 | 5/2006 |
| WO | WO-2006085967 A2 | 8/2006 |
| WO | WO-2007021494 A2 | 2/2007 |
| WO | WO-2007103515 A2 | 9/2007 |
| WO | WO-2007149406 A2 | 12/2007 |
| WO | WO-2008033413 A2 | 3/2008 |
| WO | WO-2008118507 A2 | 10/2008 |
| WO | WO-2008155134 A1 | 12/2008 |
| WO | WO-2009023270 A2 | 2/2009 |
| WO | WO-2009051717 A2 | 4/2009 |
| WO | WO-2009058322 A1 | 5/2009 |
| WO | WO-2009130198 A2 | 10/2009 |
| WO | WO-2009137254 A2 | 11/2009 |
| WO | WO-2009140015 A2 | 11/2009 |
| WO | WO-2010091122 A1 | 8/2010 |
| WO | WO-2010144502 A2 | 12/2010 |
| WO | WO-2010144508 A1 | 12/2010 |
| WO | WO-2011028228 A1 | 3/2011 |
| WO | WO-2011028229 A1 | 3/2011 |
| WO | WO-2011028344 A2 | 3/2011 |
| WO | WO-2011069164 A2 | 6/2011 |
| WO | WO-2012006623 A1 | 1/2012 |
| WO | WO-2012006633 A1 | 1/2012 |

(56) References Cited

FOREIGN PATENT DOCUMENTS

WO   WO-2012006635 A1   1/2012
WO   WO-2012170969 A2 * 12/2012 ........... C07K 14/745

OTHER PUBLICATIONS

Bovenschen, N., "LDL Receptor Polymorphisms Revisited," Blood 116(25):5439-5440, The American Society of Hematology, United States (2010).
Brutlag, D.L., et al., "Improved Sensitivity of Biological Sequence Database Searches," Computer Applications in the Biosciences 6(3):237-245, Oxford University Press, England (1990).
Caliceti, P., et al., "Biopharmaceutical Properties of Uricase Conjugated to Neutral and Amphiphilic Polymers," Bioconjugate Chemistry 10(4):638-646, American Chemical Society, United States (1999).
Cameron, C., et al., "The Canine Factor VIII cDNA and 5' Flanking Sequence," Thrombosis and Haemostasis 79(2):317-322, Schattauer, Germany (1998).
Capon, D.J., et al., "Designing CD4 Immunoadhesins for AIDS Therapy," Nature 337(6207):525-531, Nature Publishing Group, England (1989).
Cho, J.W. and Troy, F.A. II, "Polysialic Acid Engineering: Synthesis of Polysialylated Neoglycosphingolipids by Using the Polysialyltransferase from Neuroinvasive *Escherichia Coli* K1," Proceedings of the National Academy of Sciences USA 91(24):11427-11431, National Academy of Sciences, United States (1994).
Cutler, J.A., et al., "The Identification and Classification of 41 novel Mutations in the Factor VIII Gene (F8C)," Human Mutation 19(3):274-278, Wiley-Liss, Inc.,United States (2002).
Davies, J. and Riechmann, L., "Single Antibody Domains as Small Recognition Units: Design and in Vitro Antigen Selection of Camelized, Human VH Domains with Improved Protein Stability," Protein Engineering 9(6):531-537, Oxford University Press, England (1996).
Dawson, P.E. and Kent, S.B., "Synthesis of Native Proteins by Chemical Ligation," Annual Review of Biochemistry 69:923-960, Annual Review, United States (2000).
Döbeli, H., et al., "Role of the Carboxy-Terminal Sequence on the Biological Activity of Human Immune Interferon (IFN-γ)," Journal of Biotechnology 7:199-216, Elsevier Science Publishers B.V., Netherlands (1988).
Decanniere, K., et al., "A Single-Domain Antibody Fragment in Complex with RNase A: Non-Canonical Loop Structures and Nanomolar Affinity using Two CDR Loops," Structure 7(4):361-370, Elsevier Science Ltd., United States (1999).
Delgado, C., et al., "The Uses and Properties of PEG-Linked Proteins," Critical Reviews in Therapeutic Drug Carrier Systems 9(3-4):249-304, CRC Press, Inc., United States (1992).
Dennis, M.S., et al., "Albumin Binding as a General Strategy for Improving the Pharmacokinetics of Proteins," The Journal of Biological Chemistry 277(38):35035-35043, American Society for Biochemistry and Molecular Biology, United States (2002).
Desmyter, A., et al., "Crystal Structure of a Camel Single-Domain VH Antibody Fragment in Complex with Lysozyme," Nature Structural Biology 3(9):803-811, Nature Publishing Group, England (1996).
Dumoulin, M., et al., "Single-Domain Antibody Fragments with High Conformational Stability," Protein Science 11(3):500-515, Cold Spring Harbor Laboratory Press, United States (2002).
Eaton, D.L., et al., "Construction and Characterization of an Active Factor VIII Variant Lacking the Central One-Third of the Molecule," Biochemistry 25(26):8343-8347, American Chemical Society, United States (1986).
Falkner, F.G. and Zachau, H.G., "Expression of Mouse Immunoglobulin Genes in Monkey Cells," Nature 298(5871):286-288, Nature Publishing Group, England (1982).
Frank, R., "Spot-Synthesis: an Easy Technique for the Positionally Addressable, Parallel Chemical Synthesis on a Membrane Support," Tetrahedron 48(42):9217-9232, Pergamon Press Ltd., England (1992).

Gayle, R.B., III., et al., "Identification of Regions in Interleukin-1α Important for Activity," The Journal of Biological Chemistry 268(29):22105-22111, The American Society for Biochemistry and Molecular Biology, Inc., United States (1993).
GenBank, "Coagulation Factor VII Isoform a Preproprotein [*Homo sapiens*]," Accession No. NP_000122.1 accessed at https://www.ncbi.nlm.nih.gov/protein/NP_000122, accessed on Jan. 15, 2015, 4 pages.
GenBank, "coagulation factor VIII isoform a preproprotein [*Homo sapiens*]," Accession No. NP_000123.1 accessed at https://www.ncbi.nlm.nih.gov/protein/NP_000123.
GenBank, "*Homo Sapiens* Transferrin (TF), mRNA," Accession No. NM001063.3 published on May 25, 2014, accessed at http://www.ncbi.nlm.nih.gov/nuccore/NM_001063, accessed on Sep. 24, 2014, 5 pages.
GenBank, "*Homo Sapiens* Transferrin (TF), mRNA," Accession No. XM002793 published on May 13, 2002, accessed at https://www.ncbi.nlm.nih.gov/nuccore/XM_002793.7?report=genbank, accessed on Sep. 24, 2014, 2 pages.
GenBank, "*Homo Sapiens* Transferrin (TF), mRNA," Accession No. XM039847 published on Jul. 16, 2001, accessed at http://www.ncbi.nlm.nih.gov/nuccore/XM_039847.1?report=genbank, accessed on Sep. 24, 2014, 2 pages.
GenBank, "*Homo Sapiens* Transferrin (TF), mRNA," Accession No. XM039845 published Jul. 16, 2001, accessed at https://www.ncbi.nlm.nih.gov/nuccore/XM_039845.1?report=genbank, accessed on Sep. 24, 2014, 2 pages.
GenBank, "Human Transferrin mRNA, Complete cds," Accession No. M12530.1, published on Jan. 14, 1995, accessed at http://www.ncbi.nlm.nih.gov/nuccore/M1253014, accessed on Jan. 15, 2015, 2 pages.
GenBank, "Transferrin [human, liver, mRNA, 2347 nt]," Accession No. S95936.1, published on May 7, 1993, accessed at http://www.ncbi.nlm.nih.gov/nuccore/S95936, accessed on Sep. 24, 2014, 2 pages.
Genbank, "transferrin precursor [*Homo sapiens*]" Accession AAA61140.1, accessed at http://www.ncbi.nlm.nih.gov/protein/AAA61140, accessed on Mar. 29, 2016, 3 pages.
Gitschier, J., et al., "Characterization of the Human Factor VIII Gene," Nature 312(5992):326-330, Nature Publishing Group, England (1984).
Guichard, G., et al., "Antigenic Mimicry of Natural L-Peptides with Retro-Inverso-Peptidomimetics," Proceedings of the National Academy of Sciences 91(21):9765-9769, National Academy of Sciences, United States (1994).
Hamers-Casterman, C., et al., "Naturally Occurring Antibodies Devoid of Light Chains," Nature 363(6428):446-448, Nature Publishing Group, England (1993).
Healey, J.F., et al., "The cDNA and Derived Amino Acid Sequence of Porcine Factor VIII," Blood 88(11):4209-4214, The American Society of Hematology, United States (1996).
Ho, S.N., et al., "Site-Directed Mutagenesis by Overlap Extension Using the Polymerase Chain Reaction," Gene 77(1):51-59, Elsevier Science Publishers B.V., Netherlands (1989).
Hoeben, R.C., et al., "Expression of Functional Factor VIII in Primary Human Skin Fibroblasts after Retrovirus-mediated Gene Transfer," The Journal of Biological Chemistry 265(13):7318-7323, The American Society for Biochemistry and Molecular Biology, United States (1990).
Holt, L.J., et al., "Anti-Serum Albumin Domain Antibodies for Extending the Half-Lives of Short Lived Drugs," Protein Engineering, Design and Selection 21(5):283-288, Oxford University Press, England (2008).
Huston, J.S., et al., "Protein Engineering of Antibody Binding Sites: Recovery of Specific Activity in an Anti-Digoxin Single-Chain Fv Analogue Produced in *Escherichia coli*," Proceedings of the National Academy of Sciences USA 85(16):5879-5883, National Academy of Sciences, United States (1988).
International Search Report and Written Opinion for International Application No. PCT/US2014/064541, ISA/US, Alexandria, Virginia, United States, dated Mar. 25, 2015, 10 pages.
Jendreyko, N., et al., "Protein Synthesis, Post-Translation Modification, and Degradation: Intradiabodies, Bispecific, Tetravalent

(56) References Cited

OTHER PUBLICATIONS

Antibodies for the Simultaneous Functional Knockout of Two Cell Surface Receptors," The Journal of Biological Chemistry 278(48):47812-47819, The American Society for Biochemistry and Molecular Biology, Inc., United States (2003).

Jones, E.W., et al., "Proteinase Mutants of *Saccharomyces cerevisiae*," Genetics 85:23-33, Genetics Society of America, United States (1977).

Kasper, C.K., et al., "A More Uniform Measurement of Factor VIII Inhibitors," Thrombosis ET Diathesis Haemorhagica 34(1):612, F.K. Schattauer Verlag, New York (1975) (Abstract).

Kingsman, A.J., et al., "Replication in *Saccharomyces cerevisiae* of Plasmid pBR313 Carrying DNA from the Yeast Trpl Region," Gene 7(2):141-152, Elsevier/North-Holland Biomedical Press, Netherlands (1979).

Kohler, G., "Immunoglobulin chain loss in hybridoma lines," Proceedings of the National Academy of Sciences USA 77(4):2197-2199, National Academy of Sciences, United States, (1980).

Konig, T. and Skerra, A., "Use of an Albumin-Binding Domain for the Selective Immobilisation of Recombinant Capture Antibody Fragments on ELISA Plates," Journal of Immunological Methods 218(1-2):73-83, Elsevier Science B.V., Netherlands (1998).

Kortt, A.A., et al., "Solution Properties of *Escherichia Coli*-Expressed VH Domain of Anti-Neuraminidase Antibody NC41," Journal of Protein Chemistry 14(3):167-178, Plenum Publishing Corporation, United States (1995).

Kraulis, P.J., et al., "The Serum Albumin-Binding Domain of *Streptococcal* Protein G is a Three-Helical Bundle: a Heteronuclear NMR study," FEBS Letters 378(2):190-194, Elsevier Science B.V,Netherlands (1996).

Lai, E., et al., "Conserved Organization of the Human and Murine T-cell Receptor Beta-Gene Families," Nature 331(6156):543-546, Nature Publishing Group, England (1988).

Langner, K-D., et al., "Synthesis of Biologically Active Deletion Mutants of Human Factor VIII:C," Behring Institute Mitteilungen 82:16-25, Behringwerke AG, Germany (1988).

Lauritzen, B., et al., "rFVIIa and a New Enhanced rFVIIa-Analogue, NN1731, Reduce Bleeding in Clopidogrel-Treated and in Thrombocytopenic Rats," Journal of Thrombosis and Haemostasis 7(4):651-657, International Society on Thrombosis and Haemostasis, England (2009).

Lenting, P.J., et al., "Biochemistry of FVIII and Inhibitors: The Disappearing Act of Factor VIII," Haemophilia 16(102):6-15, Blackwell Publishing Ltd, England (2010).

Linhult, M., et al., "Mutational Analysis of the Interaction Between Albumin-Binding Domain from *Streptococcal* Protein G and Human Serum Albumin," Protein Science 11(2):206-213, Cold Spring Harbor Laboratory Press, United States (2002).

Martinelli, N., et al., "Polymorphisms at LDLR Locus may be Associated with Coronary Artery Disease through Modulation of Coagulation Factor VIII Activity and Independently from Lipid Profile," Blood 116(25):5688-5697, The American Society of Hematology, United States (2010).

Mei, B., et al., "Expression of Human Coagulation Factor VIII in a Human Hybrid Cell Line, HKB11," Molecular Biotechnology 34(2):165-178, Humana Press Inc., United States (2006).

Mei, B., et al., "Rational Design of a Fully active, Long-Acting PEGylated Factor VIII for Hemophilia A Treatment," Blood 116(2):270-279, The American Society of Hematology, United States (2010).

Meulien, P., et al., "A New Recombinant Procoagulant Protein Derived from the cDNA Encoding Human Factor VIII," Protein Engineering 2(4):301-306, IRL Press Ltd., England (1988).

Milenic, D.E., et al., "Construction, Binding Properties, Metabolism, and Tumor Targeting of a Single-Chain Fv Derived from the Pancarcinoma Monoclonal Antibody CC49," Cancer Research 51:6363-6371, American Association of Cancer Research, United States (1991).

Morpurgo, M., et al., "Covalent Modification of Mushroom Tyrosinase with Different Amphiphic Polymers for Pharmaceutical and Biocatalysis Applications," Applied Biochemistry and Biotechnology 56(1):59-72, Humana Press, Inc., United States (1996).

Morrison, S.L., "Sequentially Derived Mutants of the Constant Region of the Heavy Chain of Murine Immunoglobulins," The Journal of Immunology 123(2):793-800, The Williams & Wilkins Co., United States (1979).

Morrison, S.L., et al., "Chimeric Human Antibody Molecules: Mouse Antigen-Binding Domains with Human Constant Region Domains," Proceedings of the National Academy of Sciences USA 81(21):6851-6855, National Academy of Sciences, United States (1984).

Morrison, S.L., "Transfectomas Provide Novel Chimeric Antibodies," Science 229(4719):1202-1207, Association for the Advancement of Science, United States (1985).

Morrison, S.L., "Transfer and Expression of Immunoglobulin Genes," Annual Review of Immunology 2:239-256, Annual Reviews, Inc., United States (1984).

Muller, D. and Kontermann, R.E., "Recombinant Bispecific Antibodies for Cellular Cancer Immunotherapy," Current Opinion in Molecular Therapeutics 9(4):319-326, The Thomson Corporation, United States (2007).

Mullinax, R.L., et al., "Identification of Human Antibody Fragment Clones Specific for Tetanus Toxoid in a Bacteriophage λ Immunoexpression Library," Proceedings of the National Academy of Sciences USA 87(20):8095-8099, National Academy of Sciences, United States (1990).

Mézière, C., et al., "In Vivo T Helper Cell Response to Retro-Inverso Peptidomimetics," The Journal of Immunology 159(7):3230-3237, American Association of Immunologists, United States (1997).

Neumann, E., et al., "Gene Transfer into Mouse Lyoma Cells By Electroporation in High Electric Fields," The EMBO Journal 1(7):841-845, IRL Press Limited, England (1982).

Newman, R., et al., "'Primatization' of Recombinant Antibodies for Immunotherapy of Human Diseases: a Macaque/Human Chimeric Antibody Against Human CD4," Biotechnology 10(11):1455-1460, Nature Publishing Group, England (1992).

Pantoliano, M.W., et al., "Conformational Stability, Folding, and Ligand-Binding Affinity of Single-Chain Fv Immunoglobulin Fragments Expressed in *Escherichia Coli*," Biochemistry 30(42):10117-10125, American Chemical Society, United States (1991).

Raso, V. and Griffin, T., "Hybrid Antibodies with Dual Specificity for the Delivery of Ricin to Immunoglobulin-Bearing Target Cells," Cancer Research 41(6):2073-2078, American Association of Cancer Research, United States (1981).

Ron, D., et al., "Expression of Biologically Active Recombinant Keratinocyte Growth Factor: Structure/Function Analysis of Amino-Terminal Truncation Mutants," The Journal of Biological Chemistry 268(4):2984-2988, American Society for Biochemistry and Molecular Biology, United States (1993).

Roovers, R.C., et al., "Efficient Inhibition of EGFR Signaling and of Tumour Growth by Antagonistic Anti-EGFR Nanobodies," Cancer Immunology, Immunotherapy 56(3):303-317, Springer Verlag, Germany (2007).

Roth, J. et al., "From Microbes to Man" in Polysialic Acid, Roth J., Rutishauser U., Troy F.A., eds., pp. 335-348, BirkhauserVerlag, Basel, Switzerland (1993).

Sarver, N., et al., "Stable Expression of Recombinant Factor VIII Molecules Using a Bovine Papillomavirus Vector," DNA 6(6):553-564, Mary Ann Liebert, Inc., United States (1987).

Schellenberger, V., et al., "A Recombinant Polypeptide Extends the in Vivo Half-Life of Peptides and Proteins in a Tunable Manner," Nature Biotechnology 27(12):1186-1190, Nature America, Inc., United States (2009).

Skerra, A. and Plückthun, A., "Assembly of a Functional Immunoglobulin Fv Fragment in *Escherichia Coli*," Science 240(4855):1038-1041, Association for the Advancement of Science, United States (1988).

Sommermeyer, V.K., et al., "Klinisch Verwendete Hydroxyethylstarke: Physikalisch-Chemische Charakterisierung," Krankenhauspharmazie 8(8):271-278, Deutscher Apotheker Verlag, Birkenwaldstr, Germany (1987).

(56) References Cited

OTHER PUBLICATIONS

Stinchcomb, D.T., et al., "Isolation and Characterisation of a Yeast Chromosomal Replicator," Nature 282(5734):39-43, Nature Publishing Group, England (1979).

Strickland, D.K. and Medved, L., "Low-Density Lipoprotein Receptor-Related Protein (LRP)-Mediated Clearance of Activated Blood Coagulation Co-Factors and Proteases: Clearance Mechanism or Regulation?," Journal of Thrombosis and Haemostasis 4(7):1484-1486, International Society on Thrombosis and Haemostasis, England (2006).

Takkinen, K., et al., "An Active Single-Chain Antibody Containing a Cellulase linker Domain is Secreted by *Escherichia Col*," Protein Engineering Design and Selection 4(7):837-841, Oxford University Press, England (1991).

Toole, J.J., et al., "A Large Region (≈95 kDa) of Human Factor VIII is Dispensable for in vitro Procoagulant Activity," Proceedings of the National Academy of Sciences USA 83(16):5939-5942, National Academy of Sciences, United States (1986).

Toole, J.J., et al., "Molecular Cloning of a cDNA Encoding Human Antihaemophilic Factor," Nature 312(5992):342-347, Nature Publishing Group, England (1984).

Tranholm, M., et al., "Improved Hemostasis with Superactive Analogs of Factor VIIa in a Mouse Model of Hemophilia A," Blood 102(10):3615-3620, American Society of Hematology, United States (2003).

Tranholm, M., et al., "Recombinant Factor VIIa Reduces Bleeding in Severely Thrombocytopenic Rabbits," Thrombosis Research 109(4):217-223, Elsevier Science B.V., Netherlands (2003).

Trussel, S., et al., "New Strategy for the Extension of the Serum Half-Life of Antibody Fragments," Bioconjugate Chemistry 20(12):2286-2292, American Chemical Society, United States (2009).

Tschumper, G. and Carbon, J., "Sequence of a Yeast DNA Fragment Containing a Chromosomal Replicator and the TRP1 Gene," Gene 10(2):157-166, Elsevier/North-Holland, Netherlands (1980).

Vehar, G.A., et al., "Structure of Human Factor VIII," Nature 312(5992):337-342, Nature Publishing Group, England (1984).

Vorobjev, P.E., et al., "Oligonucleotide Conjugated to Linear and Branched High Molecular Weight Polyethylene Glycol as Substrates for RNase H," Nucleosides & Nucleotides 18(11-12):2745-2750, Marcel Dekker, Inc., United States (1999).

Ward, E.S., et al., "Binding Activities of a Repertoire of Single Immunoglobulin Variable Domains Secreted from *Escherichia Coli*," Nature 331:544-546, Nature Publishing Group, England (1989).

Weidler, B., et al., "Pharmakokinetische Merkmale als Kriterien fur den klinischen Einsatz von Hydroxyethylstarke," Arzneimittel-Forschung 41(5):494-498, Editio Cantor, Germany (1991).

Wigler, M., et al., "Biochemical Transfer of Single-Copy Eucaryotic Genes Using Total Cellular DNA as Donor," Cell 14(3):725-731, Cell Press, United States (1978).

Wood, W.I., et al., "Expression of Active Human Factor VIII from Recombinant DNA Clones," Nature 312(5992):330-337, Nature Publishing Group, England (1984).

Non-final Office Action dated Nov. 13, 2015 in U.S. Appl. No. 14/125,040, 371(c) date of May 13, 2014.

* cited by examiner

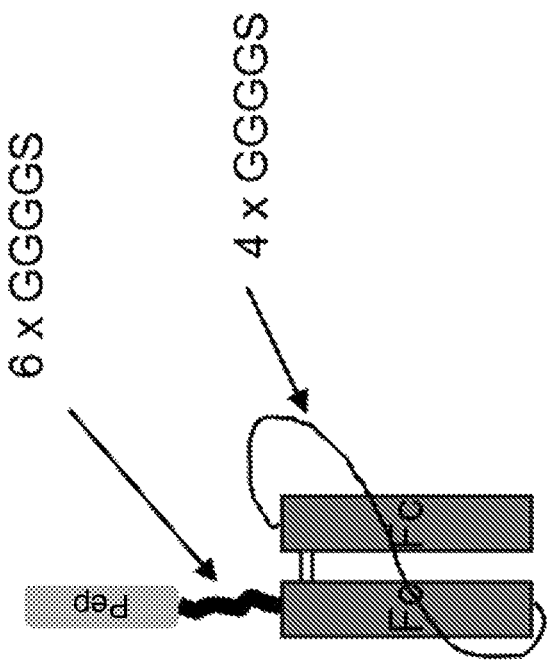
Figure 1A: Schematic illustration of Fc-048

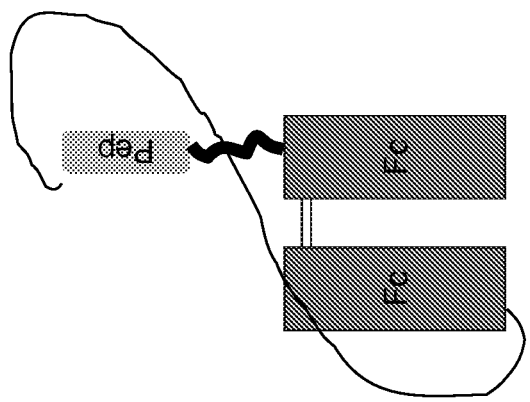
Figure 1B: Schematic illustration of Fc-050

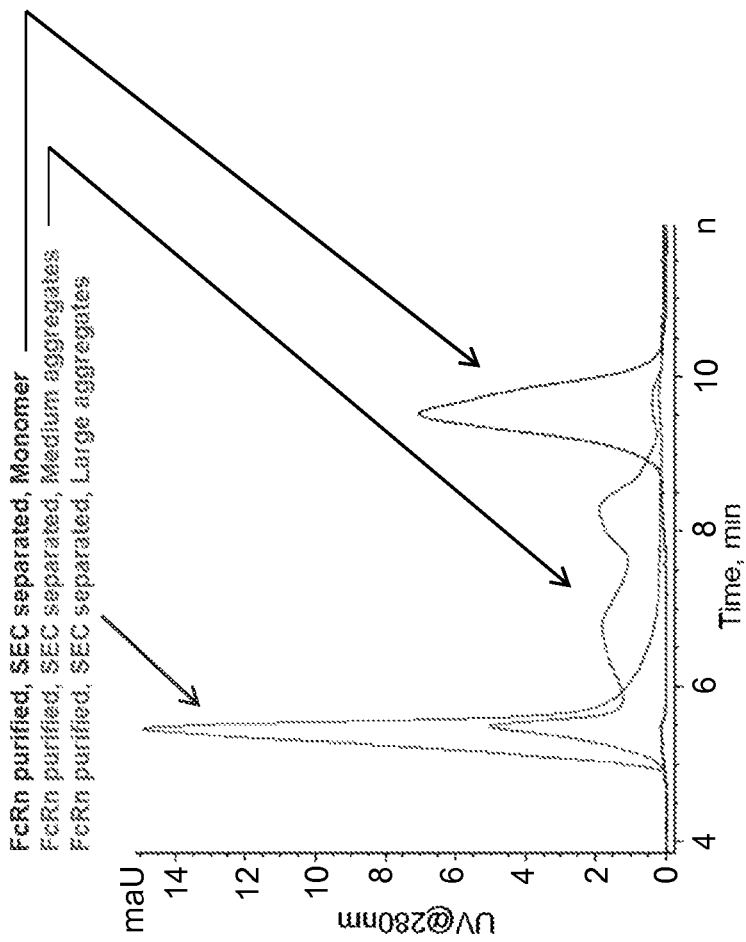
Figure 2: Analytical SEC spectra of isolated monomeric, medium and large aggregate Fc-048 (5 µg injection of each)

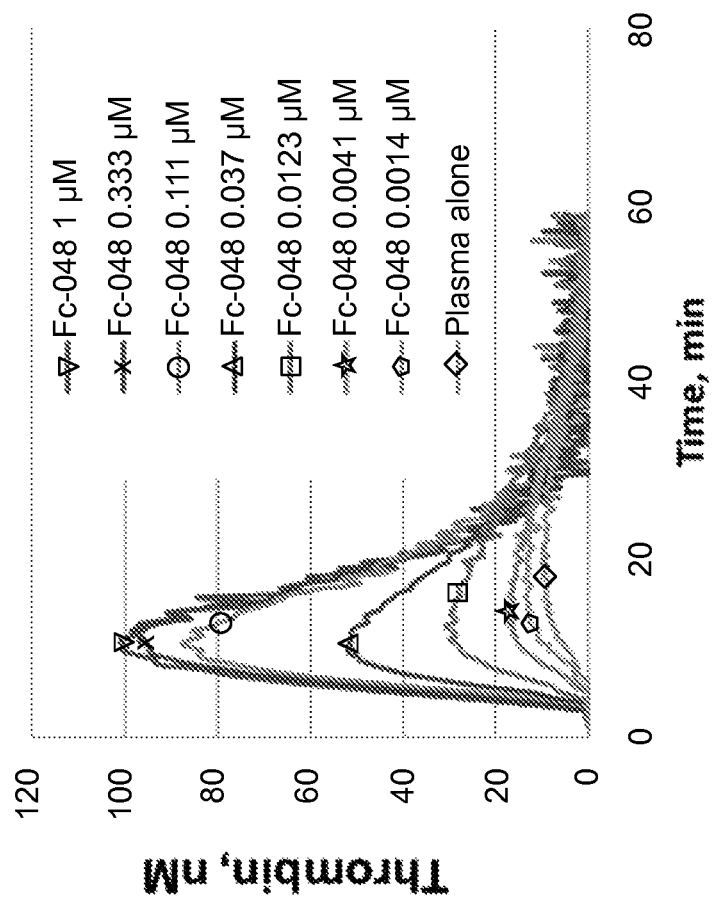
Figure 3A: TGA profile of Fc-048 containing a mixture of monomer and aggregates

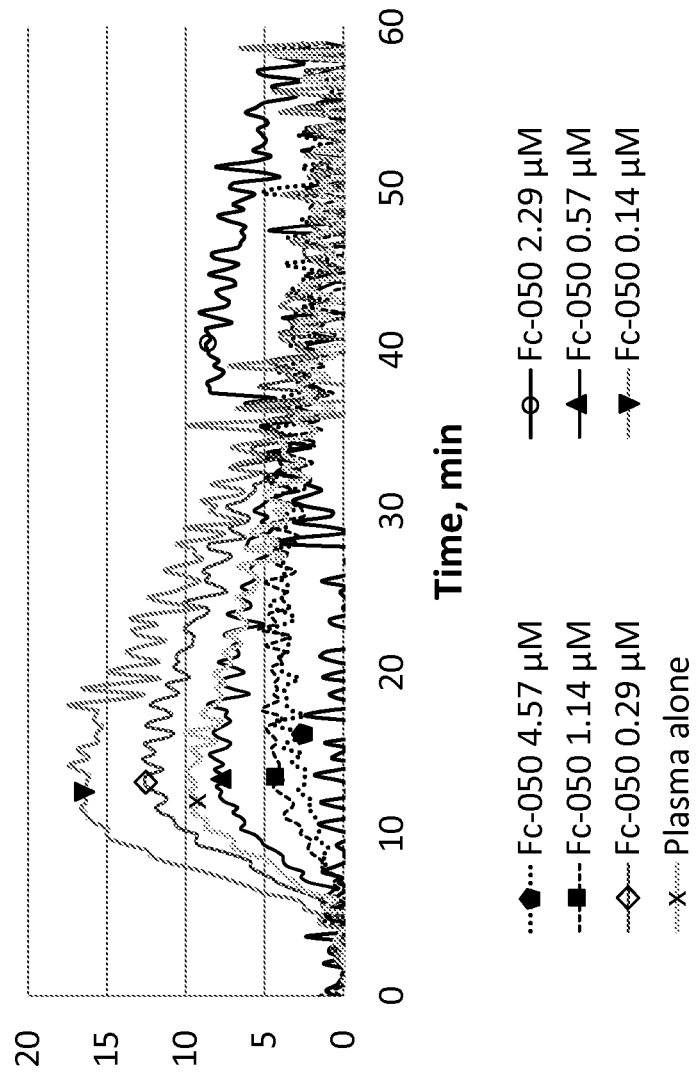
Figure 3B: TGA profile of Fc-050 containing a mixture of monomer and aggregates

Figure 4: TGA profile of isolated monomeric and aggregate Fc-048
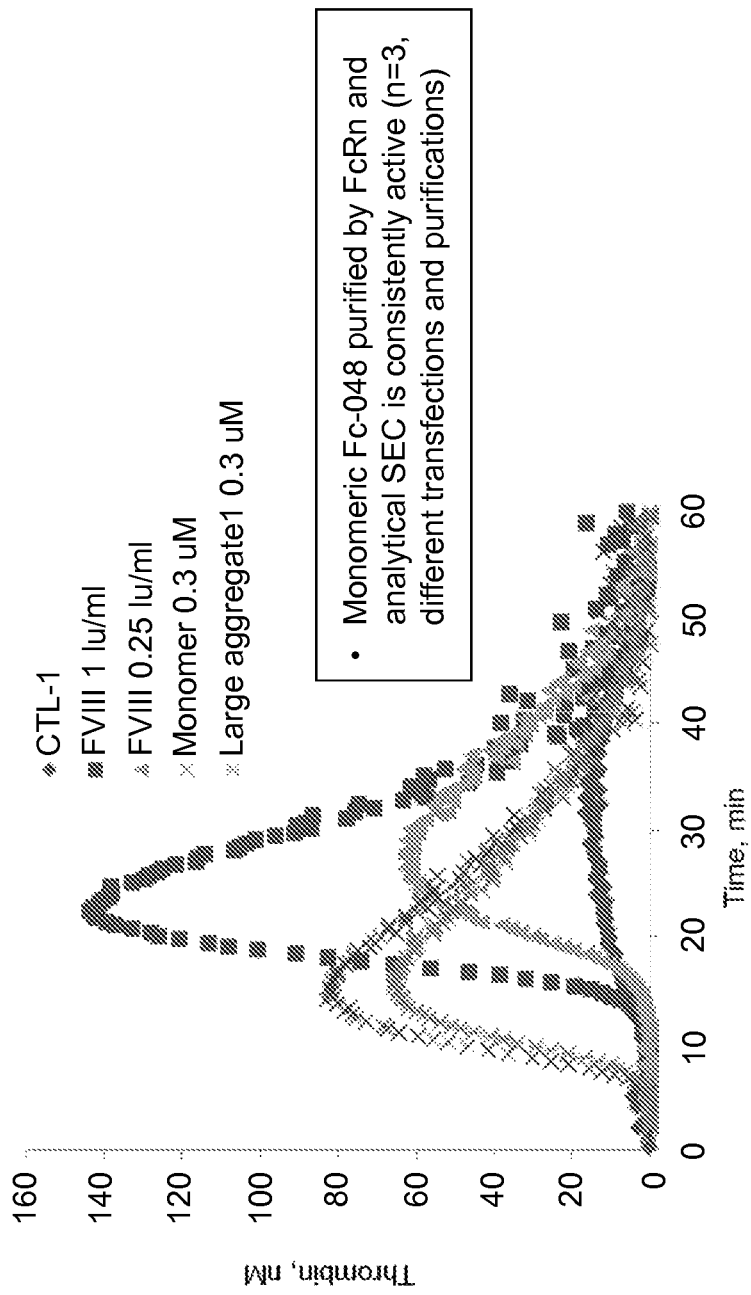

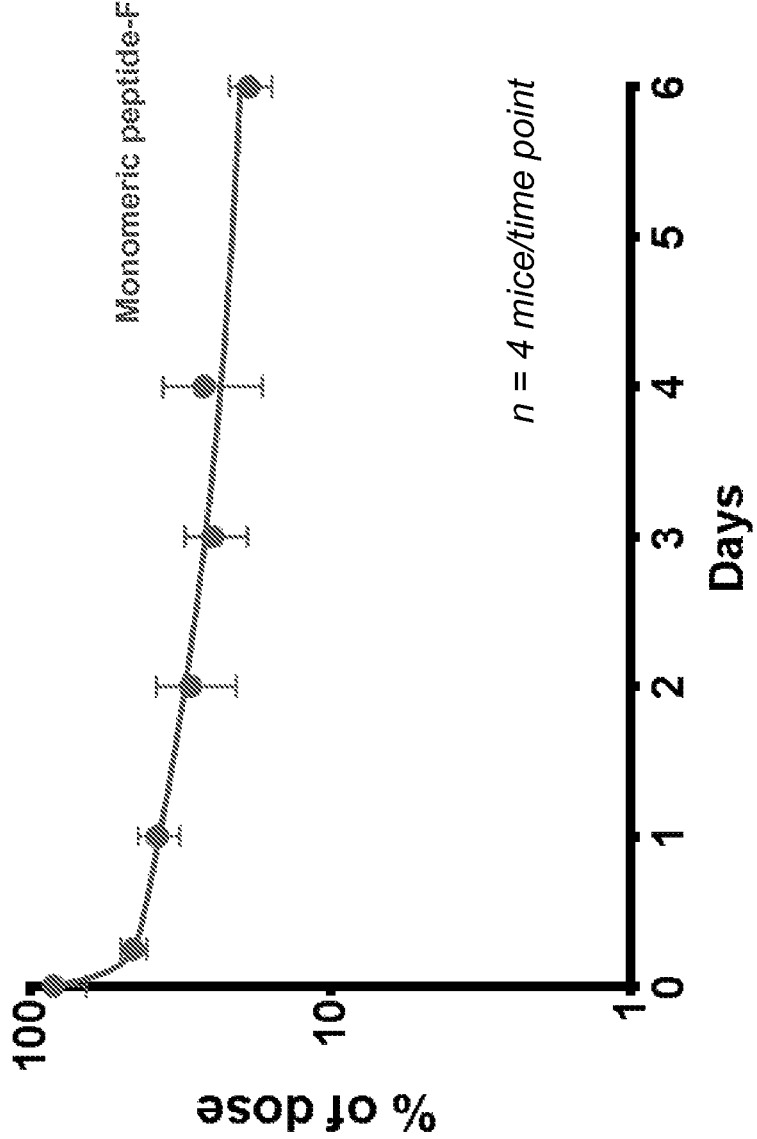

SEQUENCE LISTING

<160> NUMBER OF SEQ ID NOS: 52

<210> SEQ ID NO 1
<211> LENGTH: 6723
<212> TYPE: DNA
<213> ORGANISM: Artificial Sequence
<220> FEATURE:
<223> OTHER INFORMATION: pSYN-Fc-048

<400> SEQUENCE: 1

```
agcttgccgc caccatggag acagacacac tcctgctatg ggtactgctg ctctgggttc      60
caggttccac tggtggcagt cggattcgga cagtgagccc cggcagccgg agcgccagcg     120
gcaagagtac ctgcctggcc agctactgct ggctgttctg gaccggcatc gccggtggcg     180
gtggatccgg cggaggtggg tccggtggcg gcggatcagg tggggggtgga tcaggcggtg    240 gaggttccgg tggcggggga tcagacaaaa ctcacacatg cccaccgtgc ccagctccgg     300
aactcctggg cggaccgtca gtcttcctct tccccccaaa acccaaggac accctcatga     360
tctcccggac ccctgaggtc acatgcgtgg tggtggacgt gagccacgaa gaccctgagg     420
tcaagttcaa ctggtacgtg gacggcgtgg aggtgcataa tgccaagaca aagccgcggg     480
aggagcagta caacagcacg taccgtgtgg tcagcgtcct caccgtcctg caccaggact     540
```

```
ggctgaatgg caaggagtac aagtgcaagg tctccaacaa agccctccca gcccccatcg    600
agaaaaccat ctccaaagcc aaagggcagc cccgagaacc acaggtgtac accctgcccc    660
catcccggga tgagctgacc aagaaccagg tcagcctgac ctgcctggtc aaaggcttct    720
atcccagcga catcgccgtg gagtgggaga gcaatgggca gccggagaac aactacaaga    780
ccacgcctcc cgtgttggac tccgacggct ccttcttcct ctacagcaag ctcaccgtgg    840
acaagagcag gtggcagcag gggaacgtct tctcatgctc cgtgatgcat gaggctctgc    900
acaaccacta cacgcagaag agcctctccc tgtctccggg taaaggtggc ggcggatcag    960
gtggggtggg atcaggcggt ggaggttccg gtggcggggg atcagacaaa actcacacat   1020
gcccaccgtg cccagcacct gaactcctgg gaggaccgtc agtcttcctc ttccccccaa   1080
aacccaagga caccctcatg atctcccgga cccctgaggt cacatgcgtg gtggtggacg   1140
tgagccacga agaccctgag gtcaagttca actggtacgt ggacggcgtg gaggtgcata   1200
atgccaagac aaagccgcgg gaggagcagt acaacagcac gtaccgtgtg gtcagcgtcc   1260
tcaccgtcct gcaccaggac tggctgaatg gcaaggagta caagtgcaag gtctccaaca   1320
aagccctccc agccccatc gagaaaacca tctccaaagc caaagggcag ccccgagaac   1380
cacaggtgta caccctgccc ccatcccgcg atgagctgac caagaaccag gtcagcctga   1440
cctgcctggt caaaggcttc tatcccagcg acatcgccgt ggagtgggag agcaatgggc   1500
agccggagaa caactacaag accacgcctc ccgtgttgga ctccgacggc tccttcttcc   1560
tctacagcaa gctcaccgtg gacaagagca ggtggcagca ggggaacgtc ttctcatgct   1620
ccgtgatgca tgaggctctg cacaaccact acacgcagaa gagcctctcc ctgtctccgg   1680
gtaaatgaga attctgcaga tatccagcac agtggcggcc gctcgagtct agagggccct   1740
tcgaacaaaa actcatctca gaagaggatc tgaatatgca taccggtcat catcaccatc   1800
accattgagt ttaaacccgc tgatcagcct cgactgtgcc ttctagttgc cagccatctg   1860
ttgtttgccc ctcccccgtg ccttccttga ccctggaagg tgccactccc actgtccttt   1920
cctaataaaa tgaggaaatt gcatcgcatt gtctgagtag gtgtcattct attctggggg   1980
gtggggtggg gcaggacagc aagggggagg attgggaaga caatagcagg catgctgggg   2040
atgcggtggg ctctatggct tctgaggcgg aaagaaccag ctggggctct aggggggtatc  2100 cccacgcgcc ctgtagcggc gcattaagcg cggcgggtgt ggtggttacg cgcagcgtga   2160
ccgctacact tgccagcgcc ctagcgcccg ctcctttcgc tttcttccct tcctttctcg   2220
ccacgttcgc cggctttccc cgtcaagctc taaatcgggg gctcccttta gggttccgat   2280
ttagtgcttt acggcacctc gaccccaaaa aacttgatta gggtgatggt tcacgtagtg   2340
ggccatcgcc ctgatagacg gttttcgcc ctttgacgtt ggagtccacg ttctttaata    2400
gtggactctt gttccaaact ggaacaacac tcaaccctat ctcggtctat tcttttgatt   2460 tataaggat tttggggatt tcggcctatt ggttaaaaaa tgagctgatt taacaaaaat    2520
ttaacgcgaa ttaattctgt ggaatgtgtg tcagttaggg tgtggaaagt ccccaggctc   2580
cccaggcagg cagaagtatg caaagcatgc atctcaatta gtcagcaacc aggtgtggaa   2640
agtccccagg ctccccagca ggcagaagta tgcaaagcat gcatctcaat tagtcagcaa   2700
ccatagtccc gcccctaact ccgcccatcc cgcccctaac tccgcccagt tccgcccatt   2760
ctccgcccca tggctgacta atttttttta tttatgcaga ggccgaggcc gcctctgcct   2820
ctgagctatt ccagaagtag tgaggaggct ttttggagg cctaggcttt tgcaaaaagc    2880
```

```
tcccgggagc ttgtatatcc attttcggat ctgatcagca cgtgttgaca attaatcatc    2940
ggcatagtat atcggcatag tataatacga caaggtgagg aactaaacca tggccaagtt    3000
gaccagtgcc gttccggtgc tcaccgcgcg cgacgtcgcc ggagcggtcg agttctggac    3060
cgaccggctc gggttctccc gggacttcgt ggaggacgac ttcgccggtg tggtccggga    3120
cgacgtgacc ctgttcatca gcgcggtcca ggaccaggtg gtgccggaca cacccctggc    3180
ctgggtgtgg gtgcgcggcc tggacgagct gtacgccgag tggtcggagg tcgtgtccac    3240
gaacttccgg gacgcctccg gccggccat gaccgagatc ggcgagcagc cgtggggggcg    3300 ggagttcgcc ctgcgcgacc cggccggcaa ctgcgtgcac ttcgtggccg aggagcagga    3360
ctgacacgtg ctacgagatt tcgattccac cgccgccttc tatgaaaggt tgggcttcgg    3420
aatcgttttc cggacgccg gctggatgat cctccagcgc ggggatctca tgctggagtt    3480
cttcgcccac cccaacttgt ttattgcagc ttataatggt tacaaataaa gcaatagcat    3540
cacaaatttc acaaataaag cattttttc actgcattct agttgtggtt tgtccaaact    3600
catcaatgta tcttatcatg tctgtatacc gtcgacctct agctagagct tggcgtaatc    3660
atggtcatag ctgtttcctg tgtgaaattg ttatccgctc acaattccac acaacatacg    3720
agccggaagc ataaagtgta aagcctgggg tgcctaatga gtgagctaac tcacattaat    3780
tgcgttgcgc tcactgcccg ctttccagtc gggaaacctg tcgtgccagc tgcattaatg    3840
aatcggccaa cgcgcgggga gaggcggttt gcgtattggg cgctcttccg cttcctcgct    3900
cactgactcg ctgcgctcgg tcgttcggct gcggcgagcg gtatcagctc actcaaaggc    3960
ggtaatacgg ttatccacag aatcagggga taacgcagga agaacatgt gagcaaaagg    4020 ccagcaaaag gccaggaacc gtaaaaaggc cgcgttgctg gcgttttttcc ataggctccg    4080 ccccctgac gagcatcaca aaaatcgacg ctcaagtcag aggtggcgaa acccgacagg    4140
actataaaga taccaggcgt ttccccctgg aagctccctc gtgcgctctc ctgttccgac    4200
cctgccgctt accggatacc tgtccgcctt tctcccttcg ggaagcgtgg cgctttctca    4260
atgctcacgc tgtaggtatc tcagttcggt gtaggtcgtt cgctccaagc tgggctgtgt    4320
gcacgaaccc cccgttcagc ccgaccgctg cgccttatcc ggtaactatc gtcttgagtc    4380
caacccggta agacacgact tatcgccact ggcagcagcc actggtaaca ggattagcag    4440
agcgaggtat gtaggcggtg ctacagagtt cttgaagtgg tggcctaact acggctacac    4500
tagaaggaca gtatttggta tctgcgctct gctgaagcca gttaccttcg gaaaaagagt    4560
tggtagctct tgatccggca acaaaccac cgctggtagc ggtggttttt tgtttgcaa    4620 gcagcagatt acgcgcagaa aaaaggatc tcaagaagat cctttgatct tttctacggg    4680
gtctgacgct cagtggaacg aaaactcacg ttaagggatt ttggtcatga gattatcaaa    4740
aaggatcttc acctagatcc ttttaaatta aaaatgaagt tttaaatcaa tctaaagtat    4800
atatgagtaa acttggtctg acagttacca atgcttaatc agtgaggcac ctatctcagc    4860
gatctgtcta tttcgttcat ccatagttgc ctgactcccc gtcgtgtaga taactacgat    4920
acgggagggc ttaccatctg gccccagtgc tgcaatgata ccgcgagacc cacgctcacc    4980
ggctccagat ttatcagcaa taaaccagcc agccggaagg gccgagcgca gaagtggtcc    5040
tgcaacttta tccgcctcca tccagtctat taattgttgc cgggaagcta gagtaagtag    5100
ttcgccagtt aatagtttgc gcaacgttgt tgccattgct acaggcatcg tggtgtcacg    5160
ctcgtcgttt ggtatggctt cattcagctc cggttcccaa cgatcaaggc gagttacatg    5220
atcccccatg ttgtgcaaaa aagcggttag ctccttcggt cctccgatcg ttgtcagaag    5280
```

```
taagttggcc gcagtgttat cactcatggt tatggcagca ctgcataatt ctcttactgt    5340
catgccatcc gtaagatgct tttctgtgac tggtgagtac tcaaccaagt cattctgaga    5400
atagtgtatg cggcgaccga gttgctcttg cccggcgtca atacgggata ataccgcgcc    5460
acatagcaga actttaaaag tgctcatcat tggaaaacgt tcttcggggc gaaaactctc    5520
aaggatctta ccgctgttga tccagttcga tgtaaccc actcgtgcac ccaactgatc    5580
ttcagcatct tttactttca ccagcgtttc tgggtgagca aaaacaggaa ggcaaaatgc    5640
cgcaaaaaag ggaataaggg cgacacggaa atgttgaata ctcatactct ccttttttca    5700
atattattga agcatttatc agggttattg tctcatgagc ggatacatat ttgaatgtat    5760
ttagaaaaat aaacaaatag gggttccgcg cacatttccc cgaaaagtgc cacctgacgt    5820
cgacggatcg ggagatctcc cgatcccta tggtcgactc tcagtacaat ctgctctgat    5880
gccgcatagt taagccagta tctgctccct gcttgtgtgt tggaggtcgc tgagtagtgc    5940
gcgagcaaaa tttaagctac aacaaggcaa ggcttaccg acaattgcat gaagaatctg    6000
cttagggtta ggcgttttgc gctgcttcgc gatgtacggg ccagatatac gcgttgacat    6060
tgattattga ctagttatta atagtaatca attacgggt cattagttca tagcccatat    6120
atggagttcc gcgttacata acttacggta atggcccgc ctggctgacc gcccaacgac    6180
ccccgcccat tgacgtcaat aatgacgtat gttcccatag taacgccaat agggactttc    6240
cattgacgtc aatgggtgga ctatttacgg taaactgccc acttggcagt acatcaagtg    6300
tatcatatgc caagtacgcc ccctattgac gtcaatgacg gtaaatggcc cgcctggcat    6360
tatgcccagt acatgacctt atgggacttt cctacttggc agtacatcta cgtattagtc    6420
atcgctatta ccatggtgat gcggttttgg cagtacatca atgggcgtgg atagcggttt    6480
gactcacggg gatttccaag tctccacccc attgacgtca atgggagttt gttttggcac    6540
caaaatcaac gggactttcc aaaatgtcgt aacaactccg ccccattgac gcaaatgggc    6600
ggtaggcgtg tacggtggga ggtctatata agcagagctc tctggctaac tagagaaccc    6660
actgcttact ggcttatcga aattaatacg actcactata gggagaccca agctggctag    6720
tta                                                                  6723
```

<210> SEQ ID NO 2
<211> LENGTH: 558
<212> TYPE: PRT
<213> ORGANISM: Artificial Sequence
<220> FEATURE:
<223> OTHER INFORMATION: pSYN-Fc-048

<400> SEQUENCE: 2

Met Glu Thr Asp Thr Leu Leu Leu Trp Val Leu Leu Leu Trp Val Pro
1               5                   10                  15

Gly Ser Thr Gly Gly Ser Arg Ile Arg Thr Val Ser Pro Gly Ser Arg
            20                  25                  30

Ser Ala Ser Gly Lys Ser Thr Cys Leu Ala Ser Tyr Cys Trp Leu Phe
        35                  40                  45

Trp Thr Gly Ile Ala Gly Gly Gly Ser Gly Gly Gly Ser Gly
    50                  55                  60

Gly Gly Gly Ser Gly Gly Gly Ser Gly Gly Gly Ser Gly Gly
65                  70                  75                  80

Gly Gly Ser Asp Lys Thr His Thr Cys Pro Pro Cys Pro Ala Pro Glu
                85                  90                  95

-continued

Leu Leu Gly Gly Pro Ser Val Phe Leu Phe Pro Lys Pro Lys Asp
            100                 105                 110

Thr Leu Met Ile Ser Arg Thr Pro Glu Val Thr Cys Val Val Asp
        115                 120                 125

Val Ser His Glu Asp Pro Glu Val Lys Phe Asn Trp Tyr Val Asp Gly
130                 135                 140

Val Glu Val His Asn Ala Lys Thr Lys Pro Arg Glu Glu Gln Tyr Asn
145                 150                 155                 160

Ser Thr Tyr Arg Val Val Ser Val Leu Thr Val Leu His Gln Asp Trp
                165                 170                 175

Leu Asn Gly Lys Glu Tyr Lys Cys Lys Val Ser Asn Lys Ala Leu Pro
            180                 185                 190

Ala Pro Ile Glu Lys Thr Ile Ser Lys Ala Lys Gly Gln Pro Arg Glu
        195                 200                 205

Pro Gln Val Tyr Thr Leu Pro Pro Ser Arg Asp Glu Leu Thr Lys Asn
210                 215                 220

Gln Val Ser Leu Thr Cys Leu Val Lys Gly Phe Tyr Pro Ser Asp Ile
225                 230                 235                 240

Ala Val Glu Trp Glu Ser Asn Gly Gln Pro Glu Asn Asn Tyr Lys Thr
                245                 250                 255

Thr Pro Pro Val Leu Asp Ser Asp Gly Ser Phe Phe Leu Tyr Ser Lys
            260                 265                 270

Leu Thr Val Asp Lys Ser Arg Trp Gln Gln Gly Asn Val Phe Ser Cys
        275                 280                 285

Ser Val Met His Glu Ala Leu His Asn His Tyr Thr Gln Lys Ser Leu
290                 295                 300

Ser Leu Ser Pro Gly Lys Ser Gly Gly Gly Ser Gly Gly Gly Gly
305                 310                 315                 320

Ser Gly Gly Gly Gly Ser Gly Gly Gly Ser Asp Lys Thr His Thr
                325                 330                 335

Cys Pro Pro Cys Pro Ala Pro Glu Leu Leu Gly Gly Pro Ser Val Phe
            340                 345                 350

Leu Phe Pro Pro Lys Pro Lys Asp Thr Leu Met Ile Ser Arg Thr Pro
        355                 360                 365

Glu Val Thr Cys Val Val Val Asp Val Ser His Glu Asp Pro Glu Val
370                 375                 380

Lys Phe Asn Trp Tyr Val Asp Gly Val Glu Val His Asn Ala Lys Thr
385                 390                 395                 400

Lys Pro Arg Glu Glu Gln Tyr Asn Ser Thr Tyr Arg Val Val Ser Val
                405                 410                 415

Leu Thr Val Leu His Gln Asp Trp Leu Asn Gly Lys Glu Tyr Lys Cys
            420                 425                 430

Lys Val Ser Asn Lys Ala Leu Pro Ala Pro Ile Glu Lys Thr Ile Ser
        435                 440                 445

Lys Ala Lys Gly Gln Pro Arg Glu Pro Gln Val Tyr Thr Leu Pro Pro
450                 455                 460

Ser Arg Asp Glu Leu Thr Lys Asn Gln Val Ser Leu Thr Cys Leu Val
465                 470                 475                 480

Lys Gly Phe Tyr Pro Ser Asp Ile Ala Val Glu Trp Glu Ser Asn Gly
                485                 490                 495

Gln Pro Glu Asn Asn Tyr Lys Thr Thr Pro Pro Val Leu Asp Ser Asp
            500                 505                 510

Gly Ser Phe Phe Leu Tyr Ser Lys Leu Thr Val Asp Lys Ser Arg Trp

```
                515                 520                 525
Gln Gln Gly Asn Val Phe Ser Cys Ser Val Met His Glu Ala Leu His
            530                 535                 540

Asn His Tyr Thr Gln Lys Ser Leu Ser Leu Ser Pro Gly Lys
545                 550                 555

<210> SEQ ID NO 3
<211> LENGTH: 32
<212> TYPE: PRT
<213> ORGANISM: Artificial Sequence
<220> FEATURE:
<223> OTHER INFORMATION: Procoagulant Compound

<400> SEQUENCE: 3

Ser Arg Ile Arg Thr Val Ser Pro Gly Ser Arg Ser Ala Ser Gly Lys
1               5                   10                  15

Ser Thr Cys Leu Ala Ser Tyr Cys Trp Leu Phe Trp Thr Gly Ile Ala
            20                  25                  30

<210> SEQ ID NO 4
<211> LENGTH: 33
<212> TYPE: PRT
<213> ORGANISM: Artificial Sequence
<220> FEATURE:
<223> OTHER INFORMATION: Procoagulant Compound

<400> SEQUENCE: 4

Gly Ser Arg Ile Arg Thr Val Ser Pro Gly Ser Arg Ser Ala Ser Gly
1               5                   10                  15

Lys Ser Thr Cys Leu Ala Ser Tyr Cys Trp Leu Phe Trp Thr Gly Ile
            20                  25                  30

Ala

<210> SEQ ID NO 5
<211> LENGTH: 20
<212> TYPE: PRT
<213> ORGANISM: Artificial Sequence
<220> FEATURE:
<223> OTHER INFORMATION: Signal Peptide

<400> SEQUENCE: 5

Met Glu Thr Asp Thr Leu Leu Leu Trp Val Leu Leu Leu Trp Val Pro
1               5                   10                  15

Gly Ser Thr Gly
            20

<210> SEQ ID NO 6
<211> LENGTH: 5
<212> TYPE: PRT
<213> ORGANISM: Artificial Sequence
<220> FEATURE:
<223> OTHER INFORMATION: Blood Coagulation Factor Region

<400> SEQUENCE: 6

Met Phe Cys Ala Gly
1               5

<210> SEQ ID NO 7
<211> LENGTH: 7583
<212> TYPE: DNA
<213> ORGANISM: Artificial Sequence
<220> FEATURE:
<223> OTHER INFORMATION: pSYN-FIX-030
<220> FEATURE:
```

```
<221> NAME/KEY: misc_feature
<222> LOCATION: (690)..(777)
<223> OTHER INFORMATION: FIX exon 1 (signal peptide, 1st amino acid
      propeptide)
<220> FEATURE:
<221> NAME/KEY: misc_feature
<222> LOCATION: (778)..(1076)
<223> OTHER INFORMATION: FIX mini intron
<220> FEATURE:
<221> NAME/KEY: misc_feature
<222> LOCATION: (1077)..(1126)
<223> OTHER INFORMATION: FIX propeptide sequence
<220> FEATURE:
<221> NAME/KEY: misc_feature
<222> LOCATION: (1127)..(2371)
<223> OTHER INFORMATION: Mature FIX sequence
<220> FEATURE:
<221> NAME/KEY: misc_feature
<222> LOCATION: (2372)..(3052)
<223> OTHER INFORMATION: Fc

<400> SEQUENCE: 7
gcgcgcgttg acattgatta ttgactagtt attaatagta atcaattacg gggtcattag      60
ttcatagccc atatatggag ttccgcgtta cataacttac ggtaaatggc ccgcctggct     120
gaccgcccaa cgaccccgc ccattgacgt caataatgac gtatgttccc atagtaacgc      180
caatagggac tttccattga cgtcaatggg tggagtattt acggtaaact gcccacttgg     240
cagtacatca agtgtatcat atgccaagta cgccccctat tgacgtcaat gacggtaaat     300
ggcccgcctg gcattatgcc cagtacatga ccttatggga ctttcctact tggcagtaca     360
tctacgtatt agtcatcgct attaccatgg tgatgcggtt ttggcagtac atcaatgggc     420
gtggatagcg gtttgactca cggggatttc caagtctcca ccccattgac gtcaatggga     480
gtttgttttg gcaccaaaat caacgggact ttccaaaatg tcgtaacaac tccgccccat     540
tgacgcaaat gggcggtagg cgtgtacggt gggaggtcta tataagcaga gctctctggc     600
taactagaga acccactgct tactggctta tcgaaattaa tacgactcac tatagggaga     660
cccaagcttc gcgacgtacg gccgccacca tgcagcgcgt gaacatgatc atggcagaat     720
caccaggcct catcaccatc tgccttttag gatatctact cagtgctgaa tgtacaggtt     780
tgtttccttt tttaaaatac attgagtatg cttgccttt agatatagaa atatctgatg     840
ctgtcttctt cactaaattt tgattacatg atttgacagc aatattgaag agtctaacag     900
ccagcacgca ggttggtaag tactgtggga acatcacaga ttttggctcc atgccctaaa     960
gagaaattgg ctttcagatt atttggatta aaacaaaga ctttcttaag agatgtaaaa    1020
ttttcatgat gttttctttt tgctaaaac taaagaatta ttcttttaca tttcagtttt    1080
tcttgatcat gaaaacgcca acaaaattct gaatcggcca agagggtata attcaggtaa    1140
attggaagag tttgttcaag ggaatctaga gagaatgt atggaagaaa agtgtagttt    1200
tgaagaagca cgagaagttt ttgaaaacac tgaaagaaca actgaatttt ggaagcagta    1260
tgttgatgga gatcagtgtg agtccaatcc atgtttaaat ggcggcagtt gcaaggatga    1320
cattaattcc tatgaatgtt ggtgtcccct tggatttgaa ggaaagaact gtgaattaga    1380
tgtaacatgt aacattaaga atggcagatg cgagcagttt tgtaaaaata gtgctgataa    1440
caaggtggtt tgctcctgta ctgagggata tcgacttgca gaaaaccaga agtcctgtga    1500
accagcagtg ccatttccat gtggaagagt ttctgtttca caaacttcta agctcacccg    1560
tgctgagact gttttttcctg atgtggacta tgtaaattct actgaagctg aaaccatttt    1620
ggataacatc actcaaagca cccaatcatt taatgacttc actcgggttg ttggtggaga    1680
```

-continued

```
agatgccaaa ccaggtcaat tcccttggca ggttgttttg aatggtaaag ttgatgcatt    1740
ctgtggaggc tctatcgtta atgaaaaatg gattgtaact gctgcccact gtgttgaaac    1800
tggtgttaaa attacagttg tcgcaggtga acataatatt gaggagacag aacatacaga    1860
gcaaaagcga aatgtgattc gaattattcc tcaccacaac tacaatgcag ctattaataa    1920
gtacaaccat gacattgccc ttctggaact ggacgaaccc ttagtgctaa acagctacgt    1980
tacacctatt tgcattgctg acaaggaata cacgaacatc ttcctcaaat ttggatctgg    2040
ctatgtaagt ggctggggaa gagtcttcca caaagggaga tcagctttag ttcttcagta    2100
ccttagagtt ccacttgttg accgagccac atgtcttcga tctacaaagt tcaccatcta    2160
taacaacatg ttctgtgctg gcttccatga aggaggtaga gattcatgtc aaggagatag    2220
tgggggaccc catgttactg aagtggaagg gaccagtttc ttaactggaa ttattagctg    2280
gggtgaagag tgtgcaatga aaggcaaata tggaatatat accaaggtgt cccggtatgt    2340
caactggatt aaggaaaaaa caaagctcac tgacaaaact cacacatgcc caccgtgccc    2400
agctccggaa ctcctgggcg gaccgtcagt cttcctcttc cccccaaaac ccaaggacac    2460
cctcatgatc tcccggaccc ctgaggtcac atgcgtggtg gtggacgtga gccacgaaga    2520
ccctgaggtc aagttcaact ggtacgtgga cggcgtggag gtgcataatg ccaagacaaa    2580
gccgcgggag gagcagtaca acagcacgta ccgtgtggtc agcgtcctca ccgtcctgca    2640
ccaggactgg ctgaatggca aggagtacaa gtgcaaggtc tccaacaaag ccctcccagc    2700
ccccatcgag aaaaccatct ccaaagccaa agggcagccc cgagaaccac aggtgtacac    2760
cctgccccca tcccgggatg agctgaccaa gaaccaggtc agcctgacct gcctggtcaa    2820
aggcttctat cccagcgaca tcgccgtgga gtgggagagc aatgggcagc cggagaacaa    2880
ctacaagacc acgcctcccg tgttggactc cgacggctcc ttcttcctct acagcaagct    2940
caccgtggac aagagcaggt ggcagcaggg gaacgtcttc tcatgctccg tgatgcatga    3000
ggctctgcac aaccactaca cgcagaagag cctctccctg tctccgggta atgagaatt    3060
cagacatgat aagatacatt gatgagtttg gacaaaccac aactagaatg cagtgaaaaa    3120
aatgctttat ttgtgaaatt tgtgatgcta ttgctttatt tgtaaccatt ataagctgca    3180
ataaacaagt tggggtgggc gaagaactcc agcatgagat ccccgcgctg gaggatcatc    3240
cagccggcgt cccggaaaac gattccgaag cccaaccttt catagaaggc ggcggtggaa    3300
tcgaaatctc gtagcacgtg tcagtcctgc tcctcggcca cgaagtgcac gcagttgccg    3360
gccgggtcgc gcagggcgaa ctcccgcccc cacggctgct cgccgatctc ggtcatggcc    3420
ggcccggagg cgtcccggaa gttcgtggac acgacctccg accactcggc gtacagctcg    3480
tccaggccgc gcacccacac ccaggccagg gtgttgtccg gcaccacctg gtcctggacc    3540
gcgctgatga cagggtcacg tcgtcccgg accacaccgg cgaagtcgtc ctccacgaag    3600
tcccgggaga cccgagccg gtcggtccag aactcgaccg ctccggcgac gtcgcgcgcg    3660
gtgagcaccg gaacggcact ggtcaacttg gccatggttt agttcctcac cttgtcgtat    3720
tatactatgc cgatatacta tgccgatgat taattgtcaa cacgtgctga tcagatccga    3780
aaatggatat acaagctccc gggagctttt tgcaaaagcc taggcctcca aaaaagcctc    3840
ctcactactt ctggaatagc tcagaggcag aggcggcctc ggcctctgca taaataaaaa    3900
aaattagtca gccatgggc ggagaatggg cggaactggg cggagttagg gcgggatgg    3960
gcggagttag gggcgggact atggttgctg actaattgag atgcatgctt tgcatacttc    4020
tgcctgctgg ggagcctggg gactttccac acctggttgc tgactaattg agatgcatgc    4080
```

```
tttgcatact tctgcctgct ggggagcctg gggactttcc acaccctcgt cgagctagct    4140
tcgtgaggct ccggtgcccg tcagtgggca gagcgcacat cgcccacagt ccccgagaag    4200
ttggggggag gggtcggcaa ttgaaccggt gcctagagaa ggtggcgcgg ggtaaactgg    4260
gaaagtgatg tcgtgtactg gctccgcctt tttcccgagg gtgggggaga accgtatata    4320
agtgcagtag tcgccgtgaa cgttcttttt cgcaacgggt ttgccgccag aacacaggta    4380
agtgccgtgt gtggttcccg cgggcctggc ctctttacgg gttatggccc ttgcgtgcct    4440
tgaattactt ccacctggct ccagtacgtg attcttgatc ccgagctgga gccaggggcg    4500
ggccttgcgc tttaggagcc ccttcgcctc gtgcttgagt tgaggcctgg cctgggcgct    4560
ggggccgccg cgtgcgaatc tggtggcacc ttcgcgcctg tctcgctgct tcgataagt    4620 ctctagccat ttaaaatttt tgatgacctg ctgcgacgct tttttctgg caagatagtc    4680 ttgtaaatgc gggccaggat ctgcacactg gtatttcggt ttttgggcc gcgggcggcg    4740 acggggcccg tgcgtcccag cgcacatgtt cggcgaggcg gggcctgcga gcgcggccac    4800
cgagaatcgg acggggtag tctcaagctg gccggcctgc tctggtgcct ggcctcgcgc    4860
cgccgtgtat cgccccgccc tgggcggcaa ggctggcccg gtcggcacca gttgcgtgag    4920
cggaaagatg gccgcttccc ggccctgctc caggggctc aaaatggagg acgcggcgct    4980
cgggagagcg ggcgggtgag tcacccacac aaaggaaagg ggcctttccg tcctcagccg    5040
tcgcttcatg tgactccacg gagtaccggg cgccgtccag gcacctcgat tagttctgga    5100
gcttttggag tacgtcgtct ttaggttggg gggaggggtt ttatgcgatg gagtttcccc    5160
acactgagtg ggtggagact gaagttaggc cagcttggca cttgatgtaa ttctccttgg    5220
aatttgccct ttttgagttt ggatcttggt tcattctcaa gcctcagaca gtggttcaaa    5280
gtttttttct tccatttcag gtgtcgtgaa cacgtggtcg cggccgcgcc gccaccatgg    5340
agacagacac actcctgcta tgggtactgc tgctctgggt tccaggttcc actggtgaca    5400
aaactcacac atgcccaccg tgcccagcac ctgaactcct gggaggaccg tcagtcttcc    5460
tcttcccccc aaaacccaag gacaccctca tgatctcccg gacccctgag gtcacatgcg    5520
tggtggtgga cgtgagccac gaagaccctg aggtcaagtt caactggtac gtggacggcg    5580
tggaggtgca taatgccaag acaaagccgc gggaggagca gtacaacagc acgtaccgtg    5640
tggtcagcgt cctcaccgtc ctgcaccagg actggctgaa tggcaaggag tacaagtgca    5700
aggtctccaa caaagccctc ccagccccca tcgagaaaac catctccaaa gccaagggc    5760 agccccgaga accacaggtg tacaccctgc ccccatcccg cgatgagctg accaagaacc    5820
aggtcagcct gacctgcctg gtcaaaggct tctatcccag cgacatcgcc gtggagtggg    5880
agagcaatgg gcagccggag aacaactaca agaccacgcc tcccgtgttg gactccgacg    5940
gctccttctt cctctacagc aagctcaccg tggacaagag caggtggcag caggggaacg    6000
tcttctcatg ctccgtgatg catgaggctc tgcacaacca ctacacgcag aagagcctct    6060
ccctgtctcc gggtaaatga ctcgagagat ctggccggct gggcccgttt cgaaggtaag    6120
cctatcccta accctctcct cggtctcgat tctacgcgta ccggtcatca tcaccatcac    6180
cattgagttt aaacccgctg atcagcctcg actgtgcctt ctagttgcca gccatctgtt    6240
gtttgcccct cccccgtgcc ttccttgacc ctggaaggtg ccactcccac tgtcctttcc    6300
taataaaatg aggaaattgc atcgcattgt ctgagtaggt gtcattctat tctggggggt    6360
ggggtggggc aggacagcaa gggggaggat tgggaagaca atagcaggca tgctgggat    6420
```

```
gcggtgggct ctatggcttc tgaggcggaa agaaccagtg cggtaatac ggttatccac    6480
agaatcaggg gataacgcag gaaagaacat gtgagcaaaa ggccagcaaa aggccaggaa    6540
ccgtaaaaag gccgcgttgc tggcgttttt ccataggctc cgcccccctg acgagcatca    6600
caaaatcga cgctcaagtc agaggtggcg aaacccgaca ggactataaa gataccaggc    6660
gtttccccct agaagctccc tcgtgcgctc tcctgttccg accctgccgc ttaccggata    6720
cctgtccgcc tttctccctt cgggaagcgt ggcgctttct catagctcac gctgtaggta    6780
tctcagttcg gtgtaggtcg ttcgctccaa gctgggctgt gtgcacgaac cccccgttca    6840
gcccgaccgc tgcgccttat ccggtaacta tcgtcttgag tccaacccgg taagacacga    6900
cttatcgcca ctggcagcag ccactggtaa caggattagc agagcgaggt atgtaggcgg    6960
tgctacagag ttcttgaagt ggtggcctaa ctacggctac actagaagaa cagtatttgg    7020
tatctgcgct ctgctgaagc cagttacctt cggaaaaaga gttggtagct cttgatccgg    7080
caaacaaacc accgctggta gcggtggttt ttttgtttgc aagcagcaga ttacgcgcag    7140
aaaaaaagga tctcaagaag atcctttgat cttttctacg gggtctgacg ctcagtggaa    7200
cgaaaactca cgttaaggga ttttggtcat gacattaacc tataaaaata ggcgtatcac    7260
gaggcccttt cgtctcgcgc gtttcggtga tgacggtgaa aacctctgac acatgcagct    7320
cccggagacg gtcacagctt gtctgtaagc ggatgccggg agcagacaag cccgtcaggg    7380
cgcgtcagcg ggtgttggcg ggtgtcgggg ctggcttaac tatgcggcat cagagcagat    7440
tgtactgaga gtgcaccata tatgcggtgt gaaataccgc acagatgcgt aaggagaaaa    7500
taccgcatca ggcgccattc gccattcagg ctgcgcaact gttgggaagg gcgatcggtg    7560
cgggcctctt cgctattacg cca                                            7583
```

<210> SEQ ID NO 8
<211> LENGTH: 688
<212> TYPE: PRT
<213> ORGANISM: Artificial Sequence
<220> FEATURE:
<223> OTHER INFORMATION: FIX-Fc chain

<400> SEQUENCE: 8

```
Met Gln Arg Val Asn Met Ile Met Ala Glu Ser Pro Gly Leu Ile Thr
1               5                   10                  15

Ile Cys Leu Leu Gly Tyr Leu Leu Ser Ala Glu Cys Thr Val Phe Leu
            20                  25                  30

Asp His Glu Asn Ala Asn Lys Ile Leu Asn Arg Pro Lys Arg Tyr Asn
        35                  40                  45

Ser Gly Lys Leu Glu Glu Phe Val Gln Gly Asn Leu Glu Arg Glu Cys
    50                  55                  60

Met Glu Glu Lys Cys Ser Phe Glu Glu Ala Arg Glu Val Phe Glu Asn
65                  70                  75                  80

Thr Glu Arg Thr Thr Glu Phe Trp Lys Gln Tyr Val Asp Gly Asp Gln
                85                  90                  95

Cys Glu Ser Asn Pro Cys Leu Asn Gly Gly Ser Cys Lys Asp Asp Ile
            100                 105                 110

Asn Ser Tyr Glu Cys Trp Cys Pro Phe Gly Phe Glu Gly Lys Asn Cys
        115                 120                 125

Glu Leu Asp Val Thr Cys Asn Ile Lys Asn Gly Arg Cys Glu Gln Phe
    130                 135                 140

Cys Lys Asn Ser Ala Asp Asn Lys Val Val Cys Ser Cys Thr Glu Gly
145                 150                 155                 160
```

-continued

```
Tyr Arg Leu Ala Glu Asn Gln Lys Ser Cys Glu Pro Ala Val Pro Phe
            165                 170                 175

Pro Cys Gly Arg Val Ser Val Ser Gln Thr Ser Lys Leu Thr Arg Ala
            180                 185                 190

Glu Thr Val Phe Pro Asp Val Asp Tyr Val Asn Ser Thr Glu Ala Glu
            195                 200                 205

Thr Ile Leu Asp Asn Ile Thr Gln Ser Thr Gln Ser Phe Asn Asp Phe
    210                 215                 220

Thr Arg Val Val Gly Gly Glu Asp Ala Lys Pro Gly Gln Phe Pro Trp
225                 230                 235                 240

Gln Val Val Leu Asn Gly Lys Val Asp Ala Phe Cys Gly Gly Ser Ile
            245                 250                 255

Val Asn Glu Lys Trp Ile Val Thr Ala Ala His Cys Val Glu Thr Gly
            260                 265                 270

Val Lys Ile Thr Val Val Ala Gly Glu His Asn Ile Glu Glu Thr Glu
        275                 280                 285

His Thr Glu Gln Lys Arg Asn Val Ile Arg Ile Ile Pro His His Asn
    290                 295                 300

Tyr Asn Ala Ala Ile Asn Lys Tyr Asn His Asp Ile Ala Leu Leu Glu
305                 310                 315                 320

Leu Asp Glu Pro Leu Val Leu Asn Ser Tyr Val Thr Pro Ile Cys Ile
            325                 330                 335

Ala Asp Lys Glu Tyr Thr Asn Ile Phe Leu Lys Phe Gly Ser Gly Tyr
            340                 345                 350

Val Ser Gly Trp Gly Arg Val Phe His Lys Gly Arg Ser Ala Leu Val
        355                 360                 365

Leu Gln Tyr Leu Arg Val Pro Leu Val Asp Arg Ala Thr Cys Leu Arg
    370                 375                 380

Ser Thr Lys Phe Thr Ile Tyr Asn Asn Met Phe Cys Ala Gly Phe His
385                 390                 395                 400

Glu Gly Gly Arg Asp Ser Cys Gln Gly Asp Ser Gly Gly Pro His Val
            405                 410                 415

Thr Glu Val Glu Gly Thr Ser Phe Leu Thr Gly Ile Ile Ser Trp Gly
            420                 425                 430

Glu Glu Cys Ala Met Lys Gly Lys Tyr Gly Ile Tyr Thr Lys Val Ser
        435                 440                 445

Arg Tyr Val Asn Trp Ile Lys Glu Lys Thr Lys Leu Thr Asp Lys Thr
    450                 455                 460

His Thr Cys Pro Pro Cys Pro Ala Pro Glu Leu Leu Gly Gly Pro Ser
465                 470                 475                 480

Val Phe Leu Phe Pro Pro Lys Pro Lys Asp Thr Leu Met Ile Ser Arg
            485                 490                 495

Thr Pro Glu Val Thr Cys Val Val Val Asp Val Ser His Glu Asp Pro
            500                 505                 510

Glu Val Lys Phe Asn Trp Tyr Val Asp Gly Val Glu Val His Asn Ala
        515                 520                 525

Lys Thr Lys Pro Arg Glu Glu Gln Tyr Asn Ser Thr Tyr Arg Val Val
    530                 535                 540

Ser Val Leu Thr Val Leu His Gln Asp Trp Leu Asn Gly Lys Glu Tyr
545                 550                 555                 560

Lys Cys Lys Val Ser Asn Lys Ala Leu Pro Ala Pro Ile Glu Lys Thr
            565                 570                 575
```

Ile Ser Lys Ala Lys Gly Gln Pro Arg Glu Pro Gln Val Tyr Thr Leu
            580                 585                 590

Pro Pro Ser Arg Asp Glu Leu Thr Lys Asn Gln Val Ser Leu Thr Cys
        595                 600                 605

Leu Val Lys Gly Phe Tyr Pro Ser Asp Ile Ala Val Glu Trp Glu Ser
    610                 615                 620

Asn Gly Gln Pro Glu Asn Asn Tyr Lys Thr Thr Pro Pro Val Leu Asp
625                 630                 635                 640

Ser Asp Gly Ser Phe Phe Leu Tyr Ser Lys Leu Thr Val Asp Lys Ser
                645                 650                 655

Arg Trp Gln Gln Gly Asn Val Phe Ser Cys Ser Val Met His Glu Ala
            660                 665                 670

Leu His Asn His Tyr Thr Gln Lys Ser Leu Ser Leu Ser Pro Gly Lys
        675                 680                 685

<210> SEQ ID NO 9
<211> LENGTH: 741
<212> TYPE: DNA
<213> ORGANISM: Artificial Sequence
<220> FEATURE:
<223> OTHER INFORMATION: Fc chain

<400> SEQUENCE: 9
atggagacag acacactcct gctatgggta ctgctgctct gggttccagg ttccactggt      60
gacaaaactc acacatgccc accgtgccca gcacctgaac tcctgggagg accgtcagtc     120
ttcctcttcc ccccaaaacc caaggacacc ctcatgatct cccggacccc tgaggtcaca     180
tgcgtggtgg tggacgtgag ccacgaagac cctgaggtca agttcaactg gtacgtggac     240
ggcgtggagg tgcataatgc caagacaaag ccgcgggagg agcagtacaa cagcacgtac     300
cgtgtggtca gcgtcctcac cgtcctgcac caggactggc tgaatggcaa ggagtacaag     360
tgcaaggtct ccaacaaagc cctcccagcc cccatcgaga aaaccatctc caaagccaaa     420
gggcagcccc gagaaccaca ggtgtacacc ctgcccccat cccgcgatga gctgaccaag     480
aaccaggtca gcctgacctg cctggtcaaa ggcttctatc ccagcgacat cgccgtggag     540
tgggagagca atgggcagcc ggagaacaac tacaagacca cgcctcccgt gttggactcc     600
gacggctcct tcttcctcta cagcaagctc accgtggaca agagcaggtg gcagcagggg     660
aacgtcttct catgctccgt gatgcatgag gctctgcaca accactacac gcagaagagc     720
ctctccctgt ctccgggtaa a     741

<210> SEQ ID NO 10
<211> LENGTH: 247
<212> TYPE: PRT
<213> ORGANISM: Artificial Sequence
<220> FEATURE:
<223> OTHER INFORMATION: Fc chain

<400> SEQUENCE: 10

Met Glu Thr Asp Thr Leu Leu Leu Trp Val Leu Leu Leu Trp Val Pro
1               5                   10                  15

Gly Ser Thr Gly Asp Lys Thr His Thr Cys Pro Pro Cys Pro Ala Pro
            20                  25                  30

Glu Leu Leu Gly Gly Pro Ser Val Phe Leu Phe Pro Pro Lys Pro Lys
        35                  40                  45

Asp Thr Leu Met Ile Ser Arg Thr Pro Glu Val Thr Cys Val Val Val
    50                  55                  60

```
Asp Val Ser His Glu Asp Pro Glu Val Lys Phe Asn Trp Tyr Val Asp
 65                  70                  75                  80

Gly Val Glu Val His Asn Ala Lys Thr Lys Pro Arg Glu Glu Gln Tyr
                 85                  90                  95

Asn Ser Thr Tyr Arg Val Val Ser Val Leu Thr Val Leu His Gln Asp
            100                 105                 110

Trp Leu Asn Gly Lys Glu Tyr Lys Cys Lys Val Ser Asn Lys Ala Leu
        115                 120                 125

Pro Ala Pro Ile Glu Lys Thr Ile Ser Lys Ala Lys Gly Gln Pro Arg
    130                 135                 140

Glu Pro Gln Val Tyr Thr Leu Pro Pro Ser Arg Asp Glu Leu Thr Lys
145                 150                 155                 160

Asn Gln Val Ser Leu Thr Cys Leu Val Lys Gly Phe Tyr Pro Ser Asp
                165                 170                 175

Ile Ala Val Glu Trp Glu Ser Asn Gly Gln Pro Glu Asn Asn Tyr Lys
            180                 185                 190

Thr Thr Pro Pro Val Leu Asp Ser Asp Gly Ser Phe Phe Leu Tyr Ser
        195                 200                 205

Lys Leu Thr Val Asp Lys Ser Arg Trp Gln Gln Gly Asn Val Phe Ser
    210                 215                 220

Cys Ser Val Met His Glu Ala Leu His Asn His Tyr Thr Gln Lys Ser
225                 230                 235                 240

Leu Ser Leu Ser Pro Gly Lys
                245
```

<210> SEQ ID NO 11
<211> LENGTH: 5052
<212> TYPE: DNA
<213> ORGANISM: Artificial Sequence
<220> FEATURE:
<223> OTHER INFORMATION: B-Domain Deleted FVIIIFc

<400> SEQUENCE: 11

```
atgcaaatag agctctccac ctgcttcttt ctgtgccttt tgcgattctg ctttagtgcc      60
accagaagat actacctggg tgcagtggaa ctgtcatggg actatatgca aagtgatctc     120
ggtgagctgc ctgtggacgc aagatttcct cctagagtgc caaaatcttt tccattcaac     180
acctcagtcg tgtacaaaaa gactctgttt gtagaattca cggatcacct tttcaacatc     240
gctaagccaa ggccaccctg gatgggtctg ctaggtccta ccatccaggc tgaggtttat     300
gatacagtgg tcattacact taagaacatg gcttcccatc ctgtcagtct tcatgctgtt     360
ggtgtatcct actggaaagc ttctgaggga gctgaatatg atgatcagac cagtcaaagg     420
gagaaagaag atgataaagt cttccctggt ggaagccata catatgtctg gcaggtcctg     480
aaagagaatg gtccaatggc ctctgaccca ctgtgcctta cctactcata tctttctcat     540
gtggacctgg taaagactt gaattcaggc ctcattggag ccctactagt atgtagagaa     600
gggagtctgg ccaaggaaaa gacacagacc ttgcacaaat ttatactact ttttgctgta     660
tttgatgaag ggaaaagttg gcactcagaa acaagaact ccttgatgca ggatagggat     720
gctgcatctg ctcgggcctg gcctaaaatg cacacagtca atggttatgt aaacaggtct     780
ctgccaggtc tgattggatg ccacaggaaa tcagtctatt ggcatgtgat tggaatgggc     840
accactcctg aagtgcactc aatattcctc gaaggtcaca catttcttgt gaggaaccat     900
cgccaggcgt cctgaaat ctcgccaata actttcctta ctgctcaaac actcttgatg     960
gaccttggac agtttctact gttttgtcat atctcttccc accaacatga tggcatggaa    1020
```

```
gcttatgtca aagtagacag ctgtccagag gaaccccaac tacgaatgaa aaataatgaa   1080
gaagcggaag actatgatga tgatcttact gattctgaaa tggatgtggt caggtttgat   1140
gatgacaact ctccttcctt tatccaaatt cgctcagttg ccaagaagca tcctaaaact   1200
tgggtacatt acattgctgc tgaagaggag gactgggact atgctccctt agtcctcgcc   1260
cccgatgaca gaagttataa aagtcaatat ttgaacaatg gccctcagcg gattggtagg   1320
aagtacaaaa aagtccgatt tatggcatac acagatgaaa cctttaagac tcgtgaagct   1380
attcagcatg aatcaggaat cttgggacct ttactttatg ggaagttgg agacacactg    1440 ttgattatat ttaagaatca agcaagcaga ccatataaca tctaccctca cggaatcact   1500
gatgtccgtc ctttgtattc aaggagatta ccaaaaggtg taaaacattt gaaggatttt   1560
ccaattctgc caggagaaat attcaaatat aaatggacag tgactgtaga agatgggcca   1620
actaaatcag atcctcggtg cctgacccgc tattactcta gtttcgttaa tatggagaga   1680
gatctagctt caggactcat tggccctctc ctcatctgct acaaagaatc tgtagatcaa   1740
agaggaaacc agataatgtc agacaagagg aatgtcatcc tgttttctgt atttgatgag   1800
aaccgaagct ggtacctcac agagaatata caacgctttc tccccaatcc agctggagtg   1860
cagcttgagg atccagagtt ccaagcctcc aacatcatgc acagcatcaa tggctatgtt   1920
tttgatagtt tgcagttgtc agtttgtttg catgaggtgg catactggta cattctaagc   1980
attggagcac agactgactt cctttctgtc ttcttctctg gatataacct caaacacaaa   2040
atggtctatg aagacacact caccctattc ccattctcag gagaaactgt cttcatgtcg   2100
atggaaaacc caggtctatg gattctgggg tgccacaact cagactttcg gaacagaggc   2160
atgaccgcct tactgaaggt ttctagttgt gacaagaaca ctggtgatta ttacgaggac   2220
agttatgaag atatttcagc atacttgctg agtaaaaaca atgccattga accaagaagc   2280
ttctctcaaa acccaccagt cttgaaacgc catcaacggg aaataactcg tactactctt   2340
cagtcagatc aagaggaaat tgactatgat gataccatat cagttgaaat gaagaaggaa   2400
gattttgaca tttatgatga ggatgaaaat cagagcccc gcagctttca aaagaaaaca    2460
cgacactatt ttattgctgc agtggagagg ctctgggatt atgggatgag tagctcccca   2520
catgttctaa gaaacagggc tcagagtggc agtgtccctc agttcaagaa agttgttttc   2580
caggaattta ctgatggctc ctttactcag cccttatacc gtggagaact aaatgaacat   2640
ttgggactcc tggggccata tataagagca gaagttgaag ataatatcat ggtaactttc   2700
agaaatcagg cctctcgtcc ctattccttc tattctagcc ttatttctta tgaggaagat   2760
cagaggcaag gagcagaacc tagaaaaaac tttgtcaagc ctaatgaaac caaaacttac   2820
ttttggaaag tgcaacatca tatggcaccc actaaagatg agtttgactg caaagcctgg   2880
gcttatttct ctgatgttga cctggaaaaa gatgtgcact caggcctgat tggacccctt   2940
ctggtctgcc acactaacac actgaaccct gctcatggga gacaagtgac agtacaggaa   3000
tttgctctgt ttttcaccat cttttgatgag accaaaagct ggtacttcac tgaaaatatg   3060
gaaagaaact gcagggctcc ctgcaatatc cagatggaag atcccacttt taaagagaat   3120
tatcgcttcc atgcaatcaa tggctacata atggatacac tacctggctt agtaatggct   3180
caggatcaaa ggattcgatg gtatctgctc agcatgggca gcaatgaaaa catccattct   3240
attcatttca gtgacatgt gttcactgta cgaaaaaaag aggagtataa aatggcactg   3300
tacaatctct atccaggtgt ttttgagaca gtggaaatgt taccatccaa agctggaatt   3360
```

```
tggcgggtgg aatgccttat tggcgagcat ctacatgctg ggatgagcac acttttctg      3420 gtgtacagca ataagtgtca gactcccctg ggaatggctt ctggacacat tagagatttt      3480
cagattacag cttcaggaca atatggacag tgggcccaa agctggccag acttcattat       3540
tccggatcaa tcaatgcctg gagcaccaag gagcccttt cttggatcaa ggtggatctg       3600
ttggcaccaa tgattattca cggcatcaag acccagggtg cccgtcagaa gttctccagc     3660
ctctacatct ctcagtttat catcatgtat agtcttgatg gaagaagtg gcagacttat       3720 cgaggaaatt ccactggaac cttaatggtc ttctttggca atgtggattc atctgggata     3780
aaacacaata tttttaaccc tccaattatt gctcgataca tccgtttgca cccaactcat     3840
tatagcattc gcagcactct tcgcatggag ttgatgggct gtgatttaaa tagttgcagc     3900
atgccattgg gaatggagag taaagcaata tcagatgcac agattactgc ttcatcctac     3960
tttaccaata tgtttgccac ctggtctcct tcaaaagctc gacttcacct ccaagggagg     4020
agtaatgcct ggagacctca ggtgaataat ccaaaagagt ggctgcaagt ggacttccag     4080
aagacaatga aagtcacagg agtaactact cagggagtaa aatctctgct taccagcatg    4140
tatgtgaagg agttcctcat ctccagcagt caagatggcc atcagtggac tctctttttt     4200
cagaatggca agtaaaggt ttttcaggga aatcaagact ccttcacacc tgtggtgaac      4260
tctctagacc caccgttact gactcgctac cttcgaattc accccagag ttgggtgcac      4320 cagattgccc tgaggatgga ggttctgggc tgcgaggcac aggacctcta cgacaaaact     4380
cacacatgcc caccgtgccc agctccagaa ctcctgggcg gaccgtcagt cttcctcttc     4440 ccccaaaac ccaaggacac cctcatgatc tcccggaccc ctgaggtcac atgcgtggtg     4500
gtggacgtga gccacgaaga ccctgaggtc aagttcaact ggtacgtgga cggcgtggag    4560
gtgcataatg ccaagacaaa gccgcgggag gagcagtaca acagcacgta ccgtgtggtc    4620
agcgtcctca ccgtcctgca ccaggactgg ctgaatggca aggagtacaa gtgcaaggtc    4680
tccaacaaag ccctcccagc ccccatcgag aaaaccatct ccaaagccaa agggcagccc    4740
cgagaaccac aggtgtacac cctgcccca tcccgggatg agctgaccaa gaaccaggtc    4800
agcctgacct gcctggtcaa aggcttctat cccagcgaca tcgccgtgga gtgggagagc    4860
aatgggcagc cggagaacaa ctacaagacc acgcctcccg tgttggactc cgacggctcc    4920
ttcttcctct acagcaagct caccgtggac aagagcaggt ggcagcaggg gaacgtcttc    4980
tcatgctccg tgatgcatga ggctctgcac aaccactaca cgcagaagag cctctccctg    5040
tctccgggta aa                                                         5052
```

<210> SEQ ID NO 12
<211> LENGTH: 1684
<212> TYPE: PRT
<213> ORGANISM: Artificial Sequence
<220> FEATURE:
<223> OTHER INFORMATION: B-Domain Deleted FVIIIFc

<400> SEQUENCE: 12

```
Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60
```

-continued

```
Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
            85                  90                  95

Ala Glu Val Tyr Asp Thr Val Val Ile Thr Leu Lys Asn Met Ala Ser
        100                 105                 110

His Pro Val Ser Leu His Ala Val Gly Val Ser Tyr Trp Lys Ala Ser
    115                 120                 125

Glu Gly Ala Glu Tyr Asp Asp Gln Thr Ser Gln Arg Glu Lys Glu Asp
130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asp Asn Ser
    370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480
```

```
Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
    530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
        595                 600                 605

Asn Ile Gln Arg Phe Leu Pro Asn Pro Ala Gly Val Gln Leu Glu Asp
    610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
        675                 680                 685

Leu Phe Pro Phe Ser Gly Glu Thr Val Phe Met Ser Met Glu Asn Pro
    690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asn Pro Pro Val Leu
        755                 760                 765

Lys Arg His Gln Arg Glu Ile Thr Arg Thr Thr Leu Gln Ser Asp Gln
    770                 775                 780

Glu Glu Ile Asp Tyr Asp Asp Thr Ile Ser Val Glu Met Lys Lys Glu
785                 790                 795                 800

Asp Phe Asp Ile Tyr Asp Glu Asp Glu Asn Gln Ser Pro Arg Ser Phe
                805                 810                 815

Gln Lys Lys Thr Arg His Tyr Phe Ile Ala Ala Val Glu Arg Leu Trp
            820                 825                 830

Asp Tyr Gly Met Ser Ser Pro His Val Leu Arg Asn Arg Ala Gln
        835                 840                 845

Ser Gly Ser Val Pro Gln Phe Lys Lys Val Val Phe Gln Glu Phe Thr
    850                 855                 860

Asp Gly Ser Phe Thr Gln Pro Leu Tyr Arg Gly Glu Leu Asn Glu His
865                 870                 875                 880

Leu Gly Leu Leu Gly Pro Tyr Ile Arg Ala Glu Val Glu Asp Asn Ile
                885                 890                 895

Met Val Thr Phe Arg Asn Gln Ala Ser Arg Pro Tyr Ser Phe Tyr Ser
```

```
                  900              905              910
Ser Leu Ile Ser Tyr Glu Glu Asp Gln Arg Gln Gly Ala Glu Pro Arg
            915              920              925

Lys Asn Phe Val Lys Pro Asn Glu Thr Lys Thr Tyr Phe Trp Lys Val
        930              935              940

Gln His His Met Ala Pro Thr Lys Asp Glu Phe Asp Cys Lys Ala Trp
945              950              955              960

Ala Tyr Phe Ser Asp Val Asp Leu Glu Lys Asp Val His Ser Gly Leu
            965              970              975

Ile Gly Pro Leu Leu Val Cys His Thr Asn Thr Leu Asn Pro Ala His
            980              985              990

Gly Arg Gln Val Thr Val Gln Glu  Phe Ala Leu Phe Phe  Thr Ile Phe
            995             1000              1005

Asp Glu  Thr Lys Ser Trp Tyr  Phe Thr Glu Asn Met  Glu Arg Asn
        1010             1015             1020

Cys Arg  Ala Pro Cys Asn Ile  Gln Met Glu Asp Pro  Thr Phe Lys
        1025             1030             1035

Glu Asn  Tyr Arg Phe His Ala  Ile Asn Gly Tyr Ile  Met Asp Thr
        1040             1045             1050

Leu Pro  Gly Leu Val Met Ala  Gln Asp Gln Arg Ile  Arg Trp Tyr
        1055             1060             1065

Leu Leu  Ser Met Gly Ser Asn  Glu Asn Ile His Ser  Ile His Phe
        1070             1075             1080

Ser Gly  His Val Phe Thr Val  Arg Lys Lys Glu Glu  Tyr Lys Met
        1085             1090             1095

Ala Leu  Tyr Asn Leu Tyr Pro  Gly Val Phe Glu Thr  Val Glu Met
        1100             1105             1110

Leu Pro  Ser Lys Ala Gly Ile  Trp Arg Val Glu Cys  Leu Ile Gly
        1115             1120             1125

Glu His  Leu His Ala Gly Met  Ser Thr Leu Phe Leu  Val Tyr Ser
        1130             1135             1140

Asn Lys  Cys Gln Thr Pro Leu  Gly Met Ala Ser Gly  His Ile Arg
        1145             1150             1155

Asp Phe  Gln Ile Thr Ala Ser  Gly Gln Tyr Gly Gln  Trp Ala Pro
        1160             1165             1170

Lys Leu  Ala Arg Leu His Tyr  Ser Gly Ser Ile Asn  Ala Trp Ser
        1175             1180             1185

Thr Lys  Glu Pro Phe Ser Trp  Ile Lys Val Asp Leu  Leu Ala Pro
        1190             1195             1200

Met Ile  Ile His Gly Ile Lys  Thr Gln Gly Ala Arg  Gln Lys Phe
        1205             1210             1215

Ser Ser  Leu Tyr Ile Ser Gln  Phe Ile Ile Met Tyr  Ser Leu Asp
        1220             1225             1230

Gly Lys  Lys Trp Gln Thr Tyr  Arg Gly Asn Ser Thr  Gly Thr Leu
        1235             1240             1245

Met Val  Phe Phe Gly Asn Val  Asp Ser Ser Gly Ile  Lys His Asn
        1250             1255             1260

Ile Phe  Asn Pro Pro Ile Ile  Ala Arg Tyr Ile Arg  Leu His Pro
        1265             1270             1275

Thr His  Tyr Ser Ile Arg Ser  Thr Leu Arg Met Glu  Leu Met Gly
        1280             1285             1290

Cys Asp  Leu Asn Ser Cys Ser  Met Pro Leu Gly Met  Glu Ser Lys
        1295             1300             1305
```

```
Ala Ile Ser Asp Ala Gln Ile Thr Ala Ser Ser Tyr Phe Thr Asn
    1310            1315                1320

Met Phe Ala Thr Trp Ser Pro Ser Lys Ala Arg Leu His Leu Gln
    1325            1330                1335

Gly Arg Ser Asn Ala Trp Arg Pro Gln Val Asn Asn Pro Lys Glu
    1340            1345                1350

Trp Leu Gln Val Asp Phe Gln Lys Thr Met Lys Val Thr Gly Val
    1355            1360                1365

Thr Thr Gln Gly Val Lys Ser Leu Leu Thr Ser Met Tyr Val Lys
    1370            1375                1380

Glu Phe Leu Ile Ser Ser Ser Gln Asp Gly His Gln Trp Thr Leu
    1385            1390                1395

Phe Phe Gln Asn Gly Lys Val Lys Val Phe Gln Gly Asn Gln Asp
    1400            1405                1410

Ser Phe Thr Pro Val Val Asn Ser Leu Asp Pro Pro Leu Leu Thr
    1415            1420                1425

Arg Tyr Leu Arg Ile His Pro Gln Ser Trp Val His Gln Ile Ala
    1430            1435                1440

Leu Arg Met Glu Val Leu Gly Cys Glu Ala Gln Asp Leu Tyr Asp
    1445            1450                1455

Lys Thr His Thr Cys Pro Pro Cys Pro Ala Pro Glu Leu Leu Gly
    1460            1465                1470

Gly Pro Ser Val Phe Leu Phe Pro Pro Lys Pro Lys Asp Thr Leu
    1475            1480                1485

Met Ile Ser Arg Thr Pro Glu Val Thr Cys Val Val Val Asp Val
    1490            1495                1500

Ser His Glu Asp Pro Glu Val Lys Phe Asn Trp Tyr Val Asp Gly
    1505            1510                1515

Val Glu Val His Asn Ala Lys Thr Lys Pro Arg Glu Glu Gln Tyr
    1520            1525                1530

Asn Ser Thr Tyr Arg Val Val Ser Val Leu Thr Val Leu His Gln
    1535            1540                1545

Asp Trp Leu Asn Gly Lys Glu Tyr Lys Cys Lys Val Ser Asn Lys
    1550            1555                1560

Ala Leu Pro Ala Pro Ile Glu Lys Thr Ile Ser Lys Ala Lys Gly
    1565            1570                1575

Gln Pro Arg Glu Pro Gln Val Tyr Thr Leu Pro Pro Ser Arg Asp
    1580            1585                1590

Glu Leu Thr Lys Asn Gln Val Ser Leu Thr Cys Leu Val Lys Gly
    1595            1600                1605

Phe Tyr Pro Ser Asp Ile Ala Val Glu Trp Glu Ser Asn Gly Gln
    1610            1615                1620

Pro Glu Asn Asn Tyr Lys Thr Thr Pro Pro Val Leu Asp Ser Asp
    1625            1630                1635

Gly Ser Phe Phe Leu Tyr Ser Lys Leu Thr Val Asp Lys Ser Arg
    1640            1645                1650

Trp Gln Gln Gly Asn Val Phe Ser Cys Ser Val Met His Glu Ala
    1655            1660                1665

Leu His Asn His Tyr Thr Gln Lys Ser Leu Ser Leu Ser Pro Gly
    1670            1675                1680

Lys
```

```
<210> SEQ ID NO 13
<211> LENGTH: 7734
<212> TYPE: DNA
<213> ORGANISM: Artificial Sequence
<220> FEATURE:
<223> OTHER INFORMATION: FVIIIFc chain

<400> SEQUENCE: 13
atgcaaatag agctctccac ctgcttcttt ctgtgccttt tgcgattctg ctttagtgcc      60
accagaagat actacctggg tgcagtggaa ctgtcatggg actatatgca aagtgatctc     120
ggtgagctgc ctgtggacgc aagatttcct cctagagtgc aaaatctttt ccattcaac     180 acctcagtcg tgtacaaaaa gactctgttt gtagaattca cggatcacct tttcaacatc     240
gctaagccaa ggccaccctg gatgggtctg ctaggtccta ccatccaggc tgaggtttat     300
gatacagtgt cattacact taagaacatg gcttcccatc ctgtcagtct tcatgctgtt     360
ggtgtatcct actggaaagc ttctgaggga gctgaatatg atgatcagac cagtcaaagg     420
gagaaagaag atgataaagt cttccctggt ggaagccata catatgtctg gcaggtcctg     480
aaagagaatg gtccaatggc ctctgaccca ctgtgcctta cctactcata tctttctcat     540
gtggacctgg taaaagactt gaattcaggc ctcattggag ccctactagt atgtagagaa     600
gggagtctgg ccaaggaaaa gacacagacc ttgcacaaat ttatactact ttttgctgta     660
tttgatgaag ggaaaagttg gcactcagaa acaaagaact ccttgatgca ggatagggat     720
gctgcatctg ctcgggcctg gcctaaaatg cacacagtca atggttatgt aaacaggtct     780
ctgccaggtc tgattggatg ccacaggaaa tcagtctatt ggcatgtgat tggaatgggc     840
accactcctg aagtgcactc aatattcctc gaaggtcaca catttcttgt gaggaaccat     900
cgccaggcgt ccttggaaat ctcgccaata actttcctta ctgctcaaac actcttgatg     960
gaccttggac agtttctact gttttgtcat atctcttccc accaacatga tggcatggaa    1020
gcttatgtca agtagacag ctgtccagag aaccccaac tacgaatgaa aaataatgaa    1080
gaagcggaag actatgatga tgatcttact gattctgaaa tggatgtggt caggtttgat    1140
gatgacaact ctccttcctt tatccaaatt cgctcagttg ccaagaagca tcctaaaact    1200
tgggtacatt acattgctgc tgaagaggag gactgggact atgctccctt agtcctcgcc    1260
cccgatgaca aagttataa agtcaatat ttgaacaatg ccctcagcg gattggtagg    1320 aagtacaaaa aagtccgatt tatggcatac acagatgaaa cctttaagac tcgtgaagct    1380
attcagcatg aatcaggaat cttgggacct ttactttatg gggaagttgg agacacactg    1440
ttgattatat taagaatca agcaagcaga ccatataaca tctaccctca cggaatcact    1500
gatgtccgtc ctttgtattc aaggagatta ccaaaaggtg taaacatttt gaaggatttt    1560
ccaattctgc aggagaaat attcaaatat aaatggacag tgactgtaga agatgggcca    1620
actaaatcag atcctcggtg cctgaccgc tattactcta gtttcgttaa tatggagaga    1680
gatctagctt caggactcat ggccctctc ctcatctgct acaaagaatc tgtagatcaa    1740
agaggaaacc agataatgtc agacaagagg aatgtcatcc tgttttctgt atttgatgag    1800
aaccgaagct ggtacctcac agagaatata caacgctttc tccccaatcc agctggagtg    1860
cagcttgagg atccagagtt ccaagcctcc aacatcatgc acagcatcaa tggctatgtt    1920
tttgatagtt tgcagttgtc agtttgtttg catgaggtgg catactggta cattctaagc    1980
attggagcac agactgactt cctttctgtc ttcttctctg atataccctt caaacacaaa    2040
atggtctatg aagacacact caccctattc ccattctcag gagaaactgt cttcatgtcg    2100
```

```
atggaaaacc caggtctatg gattctgggg tgccacaact cagactttcg gaacagaggc    2160
atgaccgcct tactgaaggt ttctagttgt gacaagaaca ctggtgatta ttacgaggac    2220
agttatgaag atatttcagc atacttgctg agtaaaaaca atgccattga accaagaagc    2280
ttctcccaga attcaagaca ccctagcact aggcaaaagc aatttaatgc caccacaatt    2340
ccagaaaatg acatagagaa gactgaccct tggtttgcac acagaacacc tatgcctaaa    2400
atacaaaatg tctcctctag tgatttgttg atgctcttgc gacagagtcc tactccacat    2460
gggctatcct tatctgatct ccaagaagcc aaatatgaga cttttctga tgatccatca    2520 cctggagcaa tagacagtaa taacagcctg tctgaaatga cacacttcag gccacagctc    2580
catcacagtg gggacatggt atttacccct gagtcaggcc tccaattaag attaaatgag    2640
aaactgggga caactgcagc aacagagttg aagaaacttg atttcaaagt ttctagtaca    2700
tcaaataatc tgatttcaac aattccatca gacaatttgg cagcaggtac tgataataca    2760
agttccttag accccccaag tatgccagtt cattatgata gtcaattaga taccactcta    2820
tttggcaaaa agtcatctcc ccttactgag tctggtggac ctctgagctt gagtgaagaa    2880
aataatgatt caaagttgtt agaatcaggt ttaatgaata gccaagaaag ttcatgggga    2940
aaaaatgtat cgtcaacaga gagtggtagg ttatttaaag ggaaaagagc tcatggacct    3000
gctttgttga ctaaagataa tgccttattc aaagttagca tctctttgtt aaagacaaac    3060
aaaacttcca ataattcagc aactaataga agactcaca ttgatggccc atcattata    3120 attgagaata gtccatcagt ctggcaaaat atattagaaa gtgacactga gtttaaaaaa    3180
gtgacacctt tgattcatga cagaatgctt atggacaaaa atgctacagc tttgaggcta    3240
aatcatatgt caaataaaac tacttcatca aaaaacatgg aaatggtcca acagaaaaaa    3300 gagggccca ttccaccaga tgcacaaaat ccagatatgt cgttctttaa gatgctattc    3360
ttgccagaat cagcaaggtg gatacaaagg actcatggaa agaactctct gaactctggg    3420
caaggcccca gtccaaagca attagtatcc ttaggaccag aaaaatctgt ggaaggtcag    3480
aatttcttgt ctgagaaaaa caaagtggta gtaggaaagg gtgaatttac aaaggacgta    3540
ggactcaaag agatggtttt tccaagcagc agaaacctat ttcttactaa cttggataat    3600
ttacatgaaa ataatacaca caatcaagaa aaaaaattc aggaagaaat agaaaagaag    3660
gaaacattaa tccaagagaa tgtagttttg cctcagatac atacagtgac tggcactaag    3720
aatttcatga agaacctttt cttactgagc actaggcaaa atgtagaagg ttcatatgac    3780
ggggcatatg ctccagtact tcaagatttt aggtcattaa atgattcaac aaatagaaca    3840
aagaaacaca cagctcattt ctcaaaaaaa ggggaggaag aaaacttgga aggcttggga    3900
aatcaaacca gcaaattgt agagaaatat gcatgcacca caaggatatc tcctaataca    3960
agccagcaga attttgtcac gcaacgtagt aagagagctt tgaaacaatt cagactccca    4020
ctagaagaaa cagaacttga aaaaggata attgtggatg acacctcaac ccagtggtcc    4080
aaaaacatga acatttgac cccgagcacc ctcacacaga tagactacaa tgagaaggag    4140
aaaggggcca ttactcagtc tcccttatca gattgcctta cgaggagtca tagcatccct    4200
caagcaaata gatctccatt acccattgca aaggtatcat catttccatc tattagacct    4260
atatatctga ccagggtcct attccaagac aactcttctc atcttccagc agcatcttat    4320
agaaagaaag attctggggt ccaagaaagc agtcatttct acaaggagc caaaaaaaat    4380 aacctttctt tagccattct aaccttggag atgactggtg atcaaagaga ggttggctcc    4440
ctggggacaa gtgccacaaa ttcagtcaca tacaagaaag ttgagaacac tgttctcccg    4500
```

```
aaaccagact tgcccaaaac atctggcaaa gttgaattgc ttccaaaagt tcacatttat    4560
cagaaggacc tattccctac ggaaactagc aatgggtctc ctggccatct ggatctcgtg    4620
gaagggagcc ttcttcaggg aacagaggga gcgattaagt ggaatgaagc aaacagacct    4680
ggaaaagttc cctttctgag agtagcaaca gaaagctctg caaagactcc ctccaagcta    4740
ttggatcctc ttgcttggga taaccactat ggtactcaga taccaaaaga gagtggaaa    4800 tcccaagaga agtcaccaga aaaaacagct tttaagaaaa aggataccat tttgtccctg    4860
aacgcttgtg aaagcaatca tgcaatagca gcaataaatg agggacaaaa taagcccgaa    4920
atagaagtca cctgggcaaa gcaaggtagg actgaaaggc tgtgctctca aaacccacca    4980
gtcttgaaac gccatcaacg ggaaataact cgtactactc ttcagtcaga tcaagaggaa    5040
attgactatg atgataccat atcagttgaa atgaagaagg aagattttga catttatgat    5100
gaggatgaaa atcagagccc ccgcagcttt caaaagaaaa cacgacacta ttttattgct    5160
gcagtggaga ggctctggga ttatgggatg agtagctccc cacatgttct aagaaacagg    5220
gctcagagtg gcagtgtccc tcagttcaag aaagttgttt tccaggaatt tactgatggc    5280
tcctttactc agcccttata ccgtggagaa ctaaatgaac atttgggact cctggggcca    5340
tatataagag cagaagttga agataatatc atggtaactt tcagaaatca ggcctctcgt    5400
ccctattcct tctattctag ccttatttct tatgaggaag atcagaggca aggagcagaa    5460
cctagaaaaa actttgtcaa gcctaatgaa accaaaactt acttttggaa agtgcaacat    5520
catatggcac ccactaaaga tgagtttgac tgcaaagcct gggcttattt ctctgatgtt    5580
gacctggaaa aagatgtgca ctcaggcctg attggacccc ttctggtctg ccacactaac    5640
acactgaacc ctgctcatgg gagacaagtg acagtacagg aatttgctct gtttttcacc    5700
atctttgatg agaccaaaag ctggtacttc actgaaaata tggaaagaaa ctgcagggct    5760
ccctgcaata tccagatgga agatcccact tttaaagaga attatcgctt ccatgcaatc    5820
aatggctaca ataatggatac actacctggc ttagtaatgg ctcaggatca aaggattcga    5880
tggtatctgc tcagcatggg cagcaatgaa acatccattc tattcatttt cagtggacat    5940
gtgttcactg tacgaaaaaa agaggagtat aaaatggcac tgtacaatct ctatccaggt    6000 gttttttgaga cagtggaaat gttaccatcc aaagctggaa tttggcgggt ggaatgcctt    6060
attggcgagc atctacatgc tgggatgagc acacttttc tggtgtacag caataagtgt    6120
cagactcccc tgggaatggc ttctggacac attagagatt ttcagattac agcttcagga    6180
caatatggac agtgggcccc aaagctggcc agacttcatt attccggatc aatcaatgcc    6240
tggagcacca aggagccctt ttcttggatc aaggtggatc tgttggcacc aatgattatt    6300
cacggcatca gacccaggg tgcccgtcag aagttctcca gcctctacat ctctcagttt    6360
atcatcatgt atagtcttga tgggaagaag tggcagactt atcgaggaaa ttccactgga    6420
accttaatgg tcttctttgg caatgtggat tcatctggga taaacacaa tattttttaac    6480 cctccaatta ttgctcgata catccgtttg cacccaactc attatagcat tcgcagcact    6540
cttcgcatgg agttgatggg ctgtgattta aatagttgca gcatgccatt gggaatggag    6600
agtaaagcaa tatcagatgc acagattact gcttcatcct actttaccaa tatgtttgcc    6660
acctggtctc cttcaaaagc tcgacttcac ctccaaggga ggagtaatgc ctggagacct    6720
caggtgaata atccaaaaga gtggctgcaa gtggacttcc agaagacaat gaaagtcaca    6780
ggagtaacta ctcagggagt aaaatctctg cttaccagca tgtatgtgaa ggagttcctc    6840
```

-continued

```
atctccagca gtcaagatgg ccatcagtgg actctctttt ttcagaatgg caaagtaaag    6900
gtttttcagg gaaatcaaga ctccttcaca cctgtggtga actctctaga cccaccgtta    6960
ctgactcgct accttcgaat tcaccccag agttgggtgc accagattgc cctgaggatg    7020
gaggttctgg gctgcgaggc acaggacctc tacgacaaaa ctcacacatg cccaccgtgc    7080
ccagctccag aactcctggg cggaccgtca gtcttcctct tccccccaaa acccaaggac    7140
accctcatga tctcccggac ccctgaggtc acatgcgtgg tggtggacgt gagccacgaa    7200
gaccctgagg tcaagttcaa ctggtacgtg gacggcgtgg aggtgcataa tgccaagaca    7260
aagccgcggg aggagcagta caacagcacg taccgtgtgg tcagcgtcct caccgtcctg    7320
caccaggact ggctgaatgg caaggagtac aagtgcaagg tctccaacaa agccctccca    7380
gcccccatcg agaaaaccat ctccaaagcc aaagggcagc cccgagaacc acaggtgtac    7440
accctgcccc catcccggga tgagctgacc aagaaccagg tcagcctgac ctgcctggtc    7500
aaaggcttct atcccagcga catcgccgtg gagtgggaga gcaatgggca gccggagaac    7560
aactacaaga ccacgcctcc cgtgttggac tccgacggct ccttcttcct ctacagcaag    7620
ctcaccgtgg acaagagcag gtggcagcag gggaacgtct tctcatgctc cgtgatgcat    7680
gaggctctgc acaaccacta cacgcagaag agcctctccc tgtctccggg taaa           7734
```

<210> SEQ ID NO 14
<211> LENGTH: 2578
<212> TYPE: PRT
<213> ORGANISM: Artificial Sequence
<220> FEATURE:
<223> OTHER INFORMATION: FVIIIFc chain

<400> SEQUENCE: 14

```
Met Gln Ile Glu Leu Ser Thr Cys Phe Phe Leu Cys Leu Leu Arg Phe
  1               5                  10                  15

Cys Phe Ser Ala Thr Arg Arg Tyr Tyr Leu Gly Ala Val Glu Leu Ser
                 20                  25                  30

Trp Asp Tyr Met Gln Ser Asp Leu Gly Glu Leu Pro Val Asp Ala Arg
             35                  40                  45

Phe Pro Pro Arg Val Pro Lys Ser Phe Pro Phe Asn Thr Ser Val Val
         50                  55                  60

Tyr Lys Lys Thr Leu Phe Val Glu Phe Thr Asp His Leu Phe Asn Ile
 65                  70                  75                  80

Ala Lys Pro Arg Pro Pro Trp Met Gly Leu Leu Gly Pro Thr Ile Gln
                 85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
            115                 120                 125

Glu Gly Ala Glu Tyr Asp Asp Gln Thr Ser Gln Arg Glu Lys Glu Asp
        130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205
```

```
Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
                340                 345                 350

Gln Leu Arg Met Lys Asn Asn Glu Glu Ala Glu Asp Tyr Asp Asp Asp
            355                 360                 365

Leu Thr Asp Ser Glu Met Asp Val Val Arg Phe Asp Asp Asp Asn Ser
370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
            435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
            515                 520                 525

Lys Tyr Lys Trp Thr Val Thr Val Glu Asp Gly Pro Thr Lys Ser Asp
    530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
                595                 600                 605

Asn Ile Gln Arg Phe Leu Pro Asn Pro Ala Gly Val Gln Leu Glu Asp
    610                 615                 620

Pro Glu Phe Gln Ala Ser Asn Ile Met His Ser Ile Asn Gly Tyr Val
```

```
                625              630              635              640
    Phe Asp Ser Leu Gln Leu Ser Val Cys Leu His Glu Val Ala Tyr Trp
                    645              650              655
    Tyr Ile Leu Ser Ile Gly Ala Gln Thr Asp Phe Leu Ser Val Phe Phe
                    660              665              670
    Ser Gly Tyr Thr Phe Lys His Lys Met Val Tyr Glu Asp Thr Leu Thr
                    675              680              685
    Leu Phe Pro Phe Ser Gly Glu Thr Val Phe Met Ser Met Glu Asn Pro
                690              695              700
    Gly Leu Trp Ile Leu Gly Cys His Asn Ser Asp Phe Arg Asn Arg Gly
    705              710              715              720
    Met Thr Ala Leu Leu Lys Val Ser Ser Cys Asp Lys Asn Thr Gly Asp
                    725              730              735
    Tyr Tyr Glu Asp Ser Tyr Glu Asp Ile Ser Ala Tyr Leu Leu Ser Lys
                    740              745              750
    Asn Asn Ala Ile Glu Pro Arg Ser Phe Ser Gln Asn Ser Arg His Pro
                    755              760              765
    Ser Thr Arg Gln Lys Gln Phe Asn Ala Thr Thr Ile Pro Glu Asn Asp
                770              775              780
    Ile Glu Lys Thr Asp Pro Trp Phe Ala His Arg Thr Pro Met Pro Lys
    785              790              795              800
    Ile Gln Asn Val Ser Ser Ser Asp Leu Leu Met Leu Leu Arg Gln Ser
                    805              810              815
    Pro Thr Pro His Gly Leu Ser Leu Ser Asp Leu Gln Glu Ala Lys Tyr
                    820              825              830
    Glu Thr Phe Ser Asp Asp Pro Ser Pro Gly Ala Ile Asp Ser Asn Asn
                    835              840              845
    Ser Leu Ser Glu Met Thr His Phe Arg Pro Gln Leu His His Ser Gly
                    850              855              860
    Asp Met Val Phe Thr Pro Glu Ser Gly Leu Gln Leu Arg Leu Asn Glu
    865              870              875              880
    Lys Leu Gly Thr Thr Ala Ala Thr Glu Leu Lys Lys Leu Asp Phe Lys
                    885              890              895
    Val Ser Ser Thr Ser Asn Asn Leu Ile Ser Thr Ile Pro Ser Asp Asn
                    900              905              910
    Leu Ala Ala Gly Thr Asp Asn Thr Ser Ser Leu Gly Pro Pro Ser Met
                    915              920              925
    Pro Val His Tyr Asp Ser Gln Leu Asp Thr Thr Leu Phe Gly Lys Lys
                930              935              940
    Ser Ser Pro Leu Thr Glu Ser Gly Gly Pro Leu Ser Leu Ser Glu Glu
    945              950              955              960
    Asn Asn Asp Ser Lys Leu Leu Glu Ser Gly Leu Met Asn Ser Gln Glu
                    965              970              975
    Ser Ser Trp Gly Lys Asn Val Ser Ser Thr Glu Ser Gly Arg Leu Phe
                    980              985              990
    Lys Gly Lys Arg Ala His Gly Pro Ala Leu Leu Thr Lys Asp Asn Ala
                995              1000             1005
    Leu Phe Lys Val Ser Ile Ser Leu Leu Lys Thr Asn Lys Thr Ser
                1010             1015             1020
    Asn Asn Ser Ala Thr Asn Arg Lys Thr His Ile Asp Gly Pro Ser
                1025             1030             1035
    Leu Leu Ile Glu Asn Ser Pro Ser Val Trp Gln Asn Ile Leu Glu
                1040             1045             1050
```

```
Ser Asp Thr Glu Phe Lys Lys Val Thr Pro Leu Ile His Asp Arg
1055                1060                1065

Met Leu Met Asp Lys Asn Ala Thr Ala Leu Arg Leu Asn His Met
1070                1075                1080

Ser Asn Lys Thr Thr Ser Ser Lys Asn Met Glu Met Val Gln Gln
1085                1090                1095

Lys Lys Glu Gly Pro Ile Pro Pro Asp Ala Gln Asn Pro Asp Met
1100                1105                1110

Ser Phe Phe Lys Met Leu Phe Leu Pro Glu Ser Ala Arg Trp Ile
1115                1120                1125

Gln Arg Thr His Gly Lys Asn Ser Leu Asn Ser Gly Gln Gly Pro
1130                1135                1140

Ser Pro Lys Gln Leu Val Ser Leu Gly Pro Glu Lys Ser Val Glu
1145                1150                1155

Gly Gln Asn Phe Leu Ser Glu Lys Asn Lys Val Val Gly Lys
1160                1165                1170

Gly Glu Phe Thr Lys Asp Val Gly Leu Lys Glu Met Val Phe Pro
1175                1180                1185

Ser Ser Arg Asn Leu Phe Leu Thr Asn Leu Asp Asn Leu His Glu
1190                1195                1200

Asn Asn Thr His Asn Gln Glu Lys Lys Ile Gln Glu Glu Ile Glu
1205                1210                1215

Lys Lys Glu Thr Leu Ile Gln Glu Asn Val Val Leu Pro Gln Ile
1220                1225                1230

His Thr Val Thr Gly Thr Lys Asn Phe Met Lys Asn Leu Phe Leu
1235                1240                1245

Leu Ser Thr Arg Gln Asn Val Glu Gly Ser Tyr Asp Gly Ala Tyr
1250                1255                1260

Ala Pro Val Leu Gln Asp Phe Arg Ser Leu Asn Asp Ser Thr Asn
1265                1270                1275

Arg Thr Lys Lys His Thr Ala His Phe Ser Lys Lys Gly Glu Glu
1280                1285                1290

Glu Asn Leu Glu Gly Leu Gly Asn Gln Thr Lys Gln Ile Val Glu
1295                1300                1305

Lys Tyr Ala Cys Thr Thr Arg Ile Ser Pro Asn Thr Ser Gln Gln
1310                1315                1320

Asn Phe Val Thr Gln Arg Ser Lys Arg Ala Leu Lys Gln Phe Arg
1325                1330                1335

Leu Pro Leu Glu Glu Thr Glu Leu Glu Lys Arg Ile Ile Val Asp
1340                1345                1350

Asp Thr Ser Thr Gln Trp Ser Lys Asn Met Lys His Leu Thr Pro
1355                1360                1365

Ser Thr Leu Thr Gln Ile Asp Tyr Asn Glu Lys Glu Lys Gly Ala
1370                1375                1380

Ile Thr Gln Ser Pro Leu Ser Asp Cys Leu Thr Arg Ser His Ser
1385                1390                1395

Ile Pro Gln Ala Asn Arg Ser Pro Leu Pro Ile Ala Lys Val Ser
1400                1405                1410

Ser Phe Pro Ser Ile Arg Pro Ile Tyr Leu Thr Arg Val Leu Phe
1415                1420                1425

Gln Asp Asn Ser Ser His Leu Pro Ala Ala Ser Tyr Arg Lys Lys
1430                1435                1440
```

```
Asp Ser Gly Val Gln Glu Ser Ser His Phe Leu Gln Gly Ala Lys
    1445                1450                1455

Lys Asn Asn Leu Ser Leu Ala Ile Leu Thr Leu Glu Met Thr Gly
    1460                1465                1470

Asp Gln Arg Glu Val Gly Ser Leu Gly Thr Ser Ala Thr Asn Ser
    1475                1480                1485

Val Thr Tyr Lys Lys Val Glu Asn Thr Val Leu Pro Lys Pro Asp
    1490                1495                1500

Leu Pro Lys Thr Ser Gly Lys Val Glu Leu Leu Pro Lys Val His
    1505                1510                1515

Ile Tyr Gln Lys Asp Leu Phe Pro Thr Glu Thr Ser Asn Gly Ser
    1520                1525                1530

Pro Gly His Leu Asp Leu Val Glu Gly Ser Leu Leu Gln Gly Thr
    1535                1540                1545

Glu Gly Ala Ile Lys Trp Asn Glu Ala Asn Arg Pro Gly Lys Val
    1550                1555                1560

Pro Phe Leu Arg Val Ala Thr Glu Ser Ser Ala Lys Thr Pro Ser
    1565                1570                1575

Lys Leu Leu Asp Pro Leu Ala Trp Asp Asn His Tyr Gly Thr Gln
    1580                1585                1590

Ile Pro Lys Glu Glu Trp Lys Ser Gln Glu Lys Ser Pro Glu Lys
    1595                1600                1605

Thr Ala Phe Lys Lys Lys Asp Thr Ile Leu Ser Leu Asn Ala Cys
    1610                1615                1620

Glu Ser Asn His Ala Ile Ala Ala Ile Asn Glu Gly Gln Asn Lys
    1625                1630                1635

Pro Glu Ile Glu Val Thr Trp Ala Lys Gln Gly Arg Thr Glu Arg
    1640                1645                1650

Leu Cys Ser Gln Asn Pro Pro Val Leu Lys Arg His Gln Arg Glu
    1655                1660                1665

Ile Thr Arg Thr Thr Leu Gln Ser Asp Gln Glu Glu Ile Asp Tyr
    1670                1675                1680

Asp Asp Thr Ile Ser Val Glu Met Lys Lys Glu Asp Phe Asp Ile
    1685                1690                1695

Tyr Asp Glu Asp Glu Asn Gln Ser Pro Arg Ser Phe Gln Lys Lys
    1700                1705                1710

Thr Arg His Tyr Phe Ile Ala Ala Val Glu Arg Leu Trp Asp Tyr
    1715                1720                1725

Gly Met Ser Ser Ser Pro His Val Leu Arg Asn Arg Ala Gln Ser
    1730                1735                1740

Gly Ser Val Pro Gln Phe Lys Lys Val Val Phe Gln Glu Phe Thr
    1745                1750                1755

Asp Gly Ser Phe Thr Gln Pro Leu Tyr Arg Gly Glu Leu Asn Glu
    1760                1765                1770

His Leu Gly Leu Leu Gly Pro Tyr Ile Arg Ala Glu Val Glu Asp
    1775                1780                1785

Asn Ile Met Val Thr Phe Arg Asn Gln Ala Ser Arg Pro Tyr Ser
    1790                1795                1800

Phe Tyr Ser Ser Leu Ile Ser Tyr Glu Glu Asp Gln Arg Gln Gly
    1805                1810                1815

Ala Glu Pro Arg Lys Asn Phe Val Lys Pro Asn Glu Thr Lys Thr
    1820                1825                1830

Tyr Phe Trp Lys Val Gln His His Met Ala Pro Thr Lys Asp Glu
```

-continued

```
            1835                1840                1845
Phe Asp Cys Lys Ala Trp Ala Tyr Phe Ser Asp Val Asp Leu Glu
            1850                1855                1860
Lys Asp Val His Ser Gly Leu Ile Gly Pro Leu Leu Val Cys His
            1865                1870                1875
Thr Asn Thr Leu Asn Pro Ala His Gly Arg Gln Val Thr Val Gln
            1880                1885                1890
Glu Phe Ala Leu Phe Phe Thr Ile Phe Asp Glu Thr Lys Ser Trp
            1895                1900                1905
Tyr Phe Thr Glu Asn Met Glu Arg Asn Cys Arg Ala Pro Cys Asn
            1910                1915                1920
Ile Gln Met Glu Asp Pro Thr Phe Lys Glu Asn Tyr Arg Phe His
            1925                1930                1935
Ala Ile Asn Gly Tyr Ile Met Asp Thr Leu Pro Gly Leu Val Met
            1940                1945                1950
Ala Gln Asp Gln Arg Ile Arg Trp Tyr Leu Leu Ser Met Gly Ser
            1955                1960                1965
Asn Glu Asn Ile His Ser Ile His Phe Ser Gly His Val Phe Thr
            1970                1975                1980
Val Arg Lys Lys Glu Glu Tyr Lys Met Ala Leu Tyr Asn Leu Tyr
            1985                1990                1995
Pro Gly Val Phe Glu Thr Val Glu Met Leu Pro Ser Lys Ala Gly
            2000                2005                2010
Ile Trp Arg Val Glu Cys Leu Ile Gly Glu His Leu His Ala Gly
            2015                2020                2025
Met Ser Thr Leu Phe Leu Val Tyr Ser Asn Lys Cys Gln Thr Pro
            2030                2035                2040
Leu Gly Met Ala Ser Gly His Ile Arg Asp Phe Gln Ile Thr Ala
            2045                2050                2055
Ser Gly Gln Tyr Gly Gln Trp Ala Pro Lys Leu Ala Arg Leu His
            2060                2065                2070
Tyr Ser Gly Ser Ile Asn Ala Trp Ser Thr Lys Glu Pro Phe Ser
            2075                2080                2085
Trp Ile Lys Val Asp Leu Leu Ala Pro Met Ile Ile His Gly Ile
            2090                2095                2100
Lys Thr Gln Gly Ala Arg Gln Lys Phe Ser Ser Leu Tyr Ile Ser
            2105                2110                2115
Gln Phe Ile Ile Met Tyr Ser Leu Asp Gly Lys Lys Trp Gln Thr
            2120                2125                2130
Tyr Arg Gly Asn Ser Thr Gly Thr Leu Met Val Phe Phe Gly Asn
            2135                2140                2145
Val Asp Ser Ser Gly Ile Lys His Asn Ile Phe Asn Pro Pro Ile
            2150                2155                2160
Ile Ala Arg Tyr Ile Arg Leu His Pro Thr His Tyr Ser Ile Arg
            2165                2170                2175
Ser Thr Leu Arg Met Glu Leu Met Gly Cys Asp Leu Asn Ser Cys
            2180                2185                2190
Ser Met Pro Leu Gly Met Glu Ser Lys Ala Ile Ser Asp Ala Gln
            2195                2200                2205
Ile Thr Ala Ser Ser Tyr Phe Thr Asn Met Phe Ala Thr Trp Ser
            2210                2215                2220
Pro Ser Lys Ala Arg Leu His Leu Gln Gly Arg Ser Asn Ala Trp
            2225                2230                2235
```

Arg Pro Gln Val Asn Asn Pro Lys Glu Trp Leu Gln Val Asp Phe
    2240            2245                2250

Gln Lys Thr Met Lys Val Thr Gly Val Thr Gln Gly Val Lys
    2255            2260                2265

Ser Leu Leu Thr Ser Met Tyr Val Lys Glu Phe Leu Ile Ser Ser
    2270            2275                2280

Ser Gln Asp Gly His Gln Trp Thr Leu Phe Phe Gln Asn Gly Lys
    2285            2290                2295

Val Lys Val Phe Gln Gly Asn Gln Asp Ser Phe Thr Pro Val Val
    2300            2305                2310

Asn Ser Leu Asp Pro Pro Leu Leu Thr Arg Tyr Leu Arg Ile His
    2315            2320                2325

Pro Gln Ser Trp Val His Gln Ile Ala Leu Arg Met Glu Val Leu
    2330            2335                2340

Gly Cys Glu Ala Gln Asp Leu Tyr Asp Lys Thr His Thr Cys Pro
    2345            2350                2355

Pro Cys Pro Ala Pro Glu Leu Leu Gly Gly Pro Ser Val Phe Leu
    2360            2365                2370

Phe Pro Pro Lys Pro Lys Asp Thr Leu Met Ile Ser Arg Thr Pro
    2375            2380                2385

Glu Val Thr Cys Val Val Val Asp Val Ser His Glu Asp Pro Glu
    2390            2395                2400

Val Lys Phe Asn Trp Tyr Val Asp Gly Val Glu Val His Asn Ala
    2405            2410                2415

Lys Thr Lys Pro Arg Glu Glu Gln Tyr Asn Ser Thr Tyr Arg Val
    2420            2425                2430

Val Ser Val Leu Thr Val Leu His Gln Asp Trp Leu Asn Gly Lys
    2435            2440                2445

Glu Tyr Lys Cys Lys Val Ser Asn Lys Ala Leu Pro Ala Pro Ile
    2450            2455                2460

Glu Lys Thr Ile Ser Lys Ala Lys Gly Gln Pro Arg Glu Pro Gln
    2465            2470                2475

Val Tyr Thr Leu Pro Pro Ser Arg Asp Glu Leu Thr Lys Asn Gln
    2480            2485                2490

Val Ser Leu Thr Cys Leu Val Lys Gly Phe Tyr Pro Ser Asp Ile
    2495            2500                2505

Ala Val Glu Trp Glu Ser Asn Gly Gln Pro Glu Asn Asn Tyr Lys
    2510            2515                2520

Thr Thr Pro Pro Val Leu Asp Ser Asp Gly Ser Phe Phe Leu Tyr
    2525            2530                2535

Ser Lys Leu Thr Val Asp Lys Ser Arg Trp Gln Gln Gly Asn Val
    2540            2545                2550

Phe Ser Cys Ser Val Met His Glu Ala Leu His Asn His Tyr Thr
    2555            2560                2565

Gln Lys Ser Leu Ser Leu Ser Pro Gly Lys
    2570            2575

<210> SEQ ID NO 15
<211> LENGTH: 2082
<212> TYPE: DNA
<213> ORGANISM: Artificial Sequence
<220> FEATURE:
<223> OTHER INFORMATION: FVII-Fc chain

<400> SEQUENCE: 15

```
atggtctccc aggccctcag gctcctctgc cttctgcttg ggcttcaggg ctgcctggct      60
gcaggcgggg tcgctaaggc ctcaggagga gaaacacggg acatgccgtg gaagccgggg     120
cctcacagag tcttcgtaac ccaggaggaa gcccacggcg tcctgcaccg gcgccggcgc     180
gccaacgcgt tcctggagga gctgcggccg ggctccctgg agagggagtg caaggaggag     240
cagtgctcct tcgaggaggc ccgggagatc ttcaaggacg cggagaggac gaagctgttc     300
tggatttctt acagtgatgg ggaccagtgt gcctcaagtc catgccagaa tgggggctcc     360
tgcaaggacc agctccagtc ctatatctgc ttctgcctcc ctgccttcga gggccggaac     420
tgtgagacgc acaaggatga ccagctgatc tgtgtgaacg agaacggcgg ctgtgagcag     480
tactgcagtg accacacggg caccaagcgc tcctgtcggt gccacgaggg gtactctctg     540
ctggcagacg gggtgtcctg cacccacaca gttaatatc  catgtggaaa aatacctatt     600
ctagaaaaaa gaaatgccag caaacccca  ggccgaattg tggggggcaa ggtgtgcccc     660
aaaggggagt gtccatggca ggtcctgttg ttggtgaatg gagctcagtt gtgtgggggg     720
accctgatca acaccatctg ggtggtctcc gcggcccact gtttcgacaa aatcaagaac     780
tggaggaacc tgatcgcggt gctgggcgag cacgacctca gcgagcacga cggggatgag     840
cagagccggc gggtggcgca ggtcatcatc cccagcacgt acgtcccggg caccaccaac     900
cacgacatcg cgctgctccg cctgcaccag cccgtggtcc tcactgacca tgtggtgccc     960
ctctgcctgc ccgaacggac gttctctgag aggacgctgg ccttcgtgcg cttctcattg    1020
gtcagcggct ggggccagct gctggaccgt ggcgccacgg ccctggagct catggtcctc    1080
aacgtgcccc ggctgatgac ccaggactgc ctgcagcagt cacggaaggt gggagactcc    1140
ccaaatatca cggagtacat gttctgtgcc ggctactcgg atggcagcaa ggactcctgc    1200
aaggggaca gtggaggccc acatgccacc cactaccggg gcacgtggta cctgacgggc    1260
atcgtcagct ggggccaggg ctgcgcaacc gtgggccact tggggtgta caccagggtc    1320
tcccagtaca tcgagtggct gcaaaagctc atgcgctcag agccacgccc aggagtcctc    1380
ctgcgagccc catttcccta ggacaaaact cacacatgcc caccgtgccc agctccagaa    1440
ctcctgggcg gaccgtcagt cttcctcttc cccccaaaac ccaaggacac cctcatgatc    1500
tcccggaccc ctgaggtcac atgcgtggtg gtggacgtga gccacgaaga ccctgaggtc    1560
aagttcaact ggtacgtgga cggcgtggag gtgcataatg ccaagacaaa gccgcgggag    1620
gagcagtaca acagcacgta ccgtgtggtc agcgtcctca ccgtcctgca ccaggactgg    1680
ctgaatggca aggagtacaa gtgcaaggtc tccaacaaag ccctcccagc ccccatcgag    1740
aaaaccatct ccaaagccaa agggcagccc cgagaaccac aggtgtacac cctgccccca    1800
tcccgggatg agctgaccaa gaaccaggtc agcctgacct gcctggtcaa aggcttctat    1860
cccagcgaca tcgccgtgga gtgggagagc aatgggcagc cggagaacaa ctacaagacc    1920
acgcctcccg tgttggactc cgacggctcc ttcttcctct acagcaagct caccgtggac    1980
aagagcaggt ggcagcaggg gaacgtcttc tcatgctccg tgatgcatga ggctctgcac    2040
aaccactaca cgcagaagag cctctcccctg tctccgggta aa                      2082
```

<210> SEQ ID NO 16
<211> LENGTH: 693
<212> TYPE: PRT
<213> ORGANISM: Artificial Sequence
<220> FEATURE:
<223> OTHER INFORMATION: FVII-Fc chain

<400> SEQUENCE: 16

```
Met Val Ser Gln Ala Leu Arg Leu Leu Cys Leu Leu Leu Gly Leu Gln
1               5                   10                  15

Gly Cys Leu Ala Ala Gly Gly Val Ala Lys Ala Ser Gly Gly Glu Thr
            20                  25                  30

Arg Asp Met Pro Trp Lys Pro Gly Pro His Arg Val Phe Val Thr Gln
        35                  40                  45

Glu Glu Ala His Gly Val Leu His Arg Arg Arg Ala Asn Ala Phe
    50                  55                  60

Leu Glu Glu Leu Arg Pro Gly Ser Leu Glu Arg Glu Cys Lys Glu Glu
65                  70                  75                  80

Gln Cys Ser Phe Glu Glu Ala Arg Glu Ile Phe Lys Asp Ala Glu Arg
                85                  90                  95

Thr Lys Leu Phe Trp Ile Ser Tyr Ser Asp Gly Asp Gln Cys Ala Ser
            100                 105                 110

Ser Pro Cys Gln Asn Gly Gly Ser Cys Lys Asp Gln Leu Gln Ser Tyr
            115                 120                 125

Ile Cys Phe Cys Leu Pro Ala Phe Glu Gly Arg Asn Cys Glu Thr His
        130                 135                 140

Lys Asp Asp Gln Leu Ile Cys Val Asn Glu Asn Gly Gly Cys Glu Gln
145                 150                 155                 160

Tyr Cys Ser Asp His Thr Gly Thr Lys Arg Ser Cys Arg Cys His Glu
                165                 170                 175

Gly Tyr Ser Leu Leu Ala Asp Gly Val Ser Cys Thr Pro Thr Val Glu
            180                 185                 190

Tyr Pro Cys Gly Lys Ile Pro Ile Leu Glu Lys Arg Asn Ala Ser Lys
        195                 200                 205

Pro Gln Gly Arg Ile Val Gly Gly Lys Val Cys Pro Lys Gly Glu Cys
210                 215                 220

Pro Trp Gln Val Leu Leu Leu Val Asn Gly Ala Gln Leu Cys Gly Gly
225                 230                 235                 240

Thr Leu Ile Asn Thr Ile Trp Val Val Ser Ala Ala His Cys Phe Asp
                245                 250                 255

Lys Ile Lys Asn Trp Arg Asn Leu Ile Ala Val Leu Gly Glu His Asp
            260                 265                 270

Leu Ser Glu His Asp Gly Asp Glu Gln Ser Arg Arg Val Ala Gln Val
        275                 280                 285

Ile Ile Pro Ser Thr Tyr Val Pro Gly Thr Thr Asn His Asp Ile Ala
290                 295                 300

Leu Leu Arg Leu His Gln Pro Val Val Leu Thr Asp His Val Val Pro
305                 310                 315                 320

Leu Cys Leu Pro Glu Arg Thr Phe Ser Glu Arg Thr Leu Ala Phe Val
                325                 330                 335

Arg Phe Ser Leu Val Ser Gly Trp Gly Gln Leu Leu Asp Arg Gly Ala
            340                 345                 350

Thr Ala Leu Glu Leu Met Val Leu Asn Val Pro Arg Leu Met Thr Gln
        355                 360                 365

Asp Cys Leu Gln Gln Ser Arg Lys Val Gly Asp Ser Pro Asn Ile Thr
370                 375                 380

Glu Tyr Met Phe Cys Ala Gly Tyr Ser Asp Gly Ser Lys Asp Ser Cys
385                 390                 395                 400

Lys Gly Asp Ser Gly Gly Pro His Ala Thr His Tyr Arg Gly Thr Trp
                405                 410                 415
```

```
Tyr Leu Thr Gly Ile Val Ser Trp Gly Gln Gly Cys Ala Thr Val Gly
                420                 425                 430

His Phe Gly Val Tyr Thr Arg Val Ser Gln Tyr Ile Glu Trp Leu Gln
            435                 440                 445

Lys Leu Met Arg Ser Glu Pro Arg Pro Gly Val Leu Leu Arg Ala Pro
450                 455                 460

Phe Pro Asp Lys Thr His Thr Cys Pro Pro Cys Pro Ala Pro Glu Leu
465                 470                 475                 480

Leu Gly Gly Pro Ser Val Phe Leu Phe Pro Pro Lys Pro Lys Asp Thr
                485                 490                 495

Leu Met Ile Ser Arg Thr Pro Glu Val Thr Cys Val Val Val Asp Val
            500                 505                 510

Ser His Glu Asp Pro Glu Val Lys Phe Asn Trp Tyr Val Asp Gly Val
515                 520                 525

Glu Val His Asn Ala Lys Thr Lys Pro Arg Glu Glu Gln Tyr Asn Ser
                530                 535                 540

Thr Tyr Arg Val Val Ser Val Leu Thr Val Leu His Gln Asp Trp Leu
545                 550                 555                 560

Asn Gly Lys Glu Tyr Lys Cys Lys Val Ser Asn Lys Ala Leu Pro Ala
                565                 570                 575

Pro Ile Glu Lys Thr Ile Ser Lys Ala Lys Gly Gln Pro Arg Glu Pro
            580                 585                 590

Gln Val Tyr Thr Leu Pro Pro Ser Arg Asp Glu Leu Thr Lys Asn Gln
595                 600                 605

Val Ser Leu Thr Cys Leu Val Lys Gly Phe Tyr Pro Ser Asp Ile Ala
                610                 615                 620

Val Glu Trp Glu Ser Asn Gly Gln Pro Glu Asn Asn Tyr Lys Thr Thr
625                 630                 635                 640

Pro Pro Val Leu Asp Ser Asp Gly Ser Phe Phe Leu Tyr Ser Lys Leu
                645                 650                 655

Thr Val Asp Lys Ser Arg Trp Gln Gln Gly Asn Val Phe Ser Cys Ser
            660                 665                 670

Val Met His Glu Ala Leu His Asn His Tyr Thr Gln Lys Ser Leu Ser
625                 675                 680                 685

Leu Ser Pro Gly Lys
    690

<210> SEQ ID NO 17
<211> LENGTH: 591
<212> TYPE: PRT
<213> ORGANISM: Homo sapiens

<400> SEQUENCE: 17

Arg Gly Val Phe Arg Arg Asp Ala His Lys Ser Glu Val Ala His Arg
1               5                   10                  15

Phe Lys Asp Leu Gly Glu Glu Asn Phe Lys Ala Leu Val Leu Ile Ala
            20                  25                  30

Phe Ala Gln Tyr Leu Gln Gln Cys Pro Phe Glu Asp His Val Lys Leu
        35                  40                  45

Val Asn Glu Val Thr Glu Phe Ala Lys Thr Cys Val Ala Asp Glu Ser
    50                  55                  60

Ala Glu Asn Cys Asp Lys Ser Leu His Thr Leu Phe Gly Asp Lys Leu
65                  70                  75                  80

Cys Thr Val Ala Thr Leu Arg Glu Thr Tyr Gly Glu Met Ala Asp Cys
```

-continued

```
                    85                  90                  95
Cys Ala Lys Gln Glu Pro Glu Arg Asn Glu Cys Phe Leu Gln His Lys
                100                 105                 110
Asp Asp Asn Pro Asn Leu Pro Arg Leu Val Arg Pro Glu Val Asp Val
                115                 120                 125
Met Cys Thr Ala Phe His Asp Asn Glu Glu Thr Phe Leu Lys Lys Tyr
            130                 135                 140
Leu Tyr Glu Ile Ala Arg Arg His Pro Tyr Phe Tyr Ala Pro Glu Leu
145                 150                 155                 160
Leu Phe Phe Ala Lys Arg Tyr Lys Ala Ala Phe Thr Glu Cys Cys Gln
                165                 170                 175
Ala Ala Asp Lys Ala Ala Cys Leu Leu Pro Lys Leu Asp Glu Leu Arg
            180                 185                 190
Asp Glu Gly Lys Ala Ser Ser Ala Lys Gln Arg Leu Lys Cys Ala Ser
            195                 200                 205
Leu Gln Lys Phe Gly Glu Arg Ala Phe Lys Ala Trp Ala Val Ala Arg
            210                 215                 220
Leu Ser Gln Arg Phe Pro Lys Ala Glu Phe Ala Glu Val Ser Lys Leu
225                 230                 235                 240
Val Thr Asp Leu Thr Lys Val His Thr Glu Cys Cys His Gly Asp Leu
                245                 250                 255
Leu Glu Cys Ala Asp Asp Arg Ala Asp Leu Ala Lys Tyr Ile Cys Glu
            260                 265                 270
Asn Gln Asp Ser Ile Ser Ser Lys Leu Lys Glu Cys Cys Glu Lys Pro
            275                 280                 285
Leu Leu Glu Lys Ser His Cys Ile Ala Glu Val Glu Asn Asp Glu Met
        290                 295                 300
Pro Ala Asp Leu Pro Ser Leu Ala Ala Asp Phe Val Glu Ser Lys Asp
305                 310                 315                 320
Val Cys Lys Asn Tyr Ala Glu Ala Lys Asp Val Phe Leu Gly Met Phe
                325                 330                 335
Leu Tyr Glu Tyr Ala Arg Arg His Pro Asp Tyr Ser Val Val Leu Leu
            340                 345                 350
Leu Arg Leu Ala Lys Thr Tyr Glu Thr Thr Leu Glu Lys Cys Cys Ala
            355                 360                 365
Ala Ala Asp Pro His Glu Cys Tyr Ala Lys Val Phe Asp Glu Phe Lys
        370                 375                 380
Pro Leu Val Glu Glu Pro Gln Asn Leu Ile Lys Gln Asn Cys Glu Leu
385                 390                 395                 400
Phe Glu Gln Leu Gly Glu Tyr Lys Phe Gln Asn Ala Leu Leu Val Arg
                405                 410                 415
Tyr Thr Lys Lys Val Pro Gln Val Ser Thr Pro Thr Leu Val Glu Val
            420                 425                 430
Ser Arg Asn Leu Gly Lys Val Gly Ser Lys Cys Cys Lys His Pro Glu
            435                 440                 445
Ala Lys Arg Met Pro Cys Ala Glu Asp Tyr Leu Ser Val Val Leu Asn
        450                 455                 460
Gln Leu Cys Val Leu His Glu Lys Thr Pro Val Ser Asp Arg Val Thr
465                 470                 475                 480
Lys Cys Cys Thr Glu Ser Leu Val Asn Arg Arg Pro Cys Phe Ser Ala
                485                 490                 495
Leu Glu Val Asp Glu Thr Tyr Val Pro Lys Glu Phe Asn Ala Glu Thr
            500                 505                 510
```

```
Phe Thr Phe His Ala Asp Ile Cys Thr Leu Ser Glu Lys Glu Arg Gln
        515                 520                 525

Ile Lys Lys Gln Thr Ala Leu Val Glu Leu Val Lys His Lys Pro Lys
    530                 535                 540

Ala Thr Lys Glu Gln Leu Lys Ala Val Met Asp Asp Phe Ala Ala Phe
545                 550                 555                 560

Val Glu Lys Cys Cys Lys Ala Asp Asp Lys Glu Thr Cys Phe Ala Glu
            565                 570                 575

Glu Gly Lys Lys Leu Val Ala Ala Ser Gln Ala Ala Leu Gly Leu
            580                 585                 590

<210> SEQ ID NO 18
<211> LENGTH: 18
<212> TYPE: PRT
<213> ORGANISM: Artificial Sequence
<220> FEATURE:
<223> OTHER INFORMATION: Albumin binding peptide 1

<400> SEQUENCE: 18

Arg Leu Ile Glu Asp Ile Cys Leu Pro Arg Trp Gly Cys Leu Trp Glu
1               5                   10                  15

Asp Asp

<210> SEQ ID NO 19
<211> LENGTH: 20
<212> TYPE: PRT
<213> ORGANISM: Artificial Sequence
<220> FEATURE:
<223> OTHER INFORMATION: Albumin binding peptide 2

<400> SEQUENCE: 19

Gln Arg Leu Met Glu Asp Ile Cys Leu Pro Arg Trp Gly Cys Leu Trp
1               5                   10                  15

Glu Asp Asp Phe
            20

<210> SEQ ID NO 20
<211> LENGTH: 21
<212> TYPE: PRT
<213> ORGANISM: Artificial Sequence
<220> FEATURE:
<223> OTHER INFORMATION: Albumin binding peptide 3

<400> SEQUENCE: 20

Gln Gly Leu Ile Gly Asp Ile Cys Leu Pro Arg Trp Gly Cys Leu Trp
1               5                   10                  15

Gly Asp Ser Val Lys
            20

<210> SEQ ID NO 21
<211> LENGTH: 20
<212> TYPE: PRT
<213> ORGANISM: Artificial Sequence
<220> FEATURE:
<223> OTHER INFORMATION: Albumin binding peptide 4

<400> SEQUENCE: 21

Gly Glu Trp Trp Glu Asp Ile Cys Leu Pro Arg Trp Gly Cys Leu Trp
1               5                   10                  15

Glu Glu Glu Asp
            20
```

```
<210> SEQ ID NO 22
<211> LENGTH: 50
<212> TYPE: PRT
<213> ORGANISM: Artificial Sequence
<220> FEATURE:
<223> OTHER INFORMATION: Gly/Ser Linker
<220> FEATURE:
<221> NAME/KEY: MISC_FEATURE
<222> LOCATION: (6)..(50)
<223> OTHER INFORMATION: Amino acid residues 6-50 optionally may be
      absent
<220> FEATURE:
<221> NAME/KEY: MISC_FEATURE
<222> LOCATION: (11)..(50)
<223> OTHER INFORMATION: Amino acid residues 11-50 optionally may be
      absent
<220> FEATURE:
<221> NAME/KEY: MISC_FEATURE
<222> LOCATION: (16)..(50)
<223> OTHER INFORMATION: Amino acid residues 16-50 optionally may be
      absent
<220> FEATURE:
<221> NAME/KEY: MISC_FEATURE
<222> LOCATION: (21)..(50)
<223> OTHER INFORMATION: Amino acid residues 21-50 optionally may be
      absent
<220> FEATURE:
<221> NAME/KEY: MISC_FEATURE
<222> LOCATION: (26)..(50)
<223> OTHER INFORMATION: Amino acid residues 26-50 optionally may be
      absent
<220> FEATURE:
<221> NAME/KEY: MISC_FEATURE
<222> LOCATION: (31)..(50)
<223> OTHER INFORMATION: Amino acid residues 31-50 optionally may be
      absent
<220> FEATURE:
<221> NAME/KEY: MISC_FEATURE
<222> LOCATION: (36)..(50)
<223> OTHER INFORMATION: Amino acid residues 36-50 optionally may be
      absent
<220> FEATURE:
<221> NAME/KEY: MISC_FEATURE
<222> LOCATION: (41)..(50)
<223> OTHER INFORMATION: Amino acid residues 41-50 optionally may be
      absent
<220> FEATURE:
<221> NAME/KEY: MISC_FEATURE
<222> LOCATION: (46)..(50)
<223> OTHER INFORMATION: Amino acid residues 46-50 optionally may be
      absent

<400> SEQUENCE: 22

Gly Gly Gly Gly Ser Gly Gly Gly Ser Gly Gly Gly Ser Gly
1               5                   10                  15

Gly Gly Gly Ser Gly Gly Gly Ser Gly Gly Gly Ser Gly Gly
                20                  25                  30

Gly Gly Ser Gly Gly Gly Gly Ser Gly Gly Gly Ser Gly Gly Gly
            35                  40                  45

Gly Ser
    50

<210> SEQ ID NO 23
<211> LENGTH: 20
<212> TYPE: PRT
<213> ORGANISM: Artificial Sequence
<220> FEATURE:
<223> OTHER INFORMATION: Gly/Ser Linker

<400> SEQUENCE: 23

Gly Gly Gly Gly Ser Gly Gly Gly Gly Ser Gly Gly Gly Gly Ser Gly
1               5                   10                  15
```

```
Gly Gly Gly Ser
            20

<210> SEQ ID NO 24
<211> LENGTH: 30
<212> TYPE: PRT
<213> ORGANISM: Artificial Sequence
<220> FEATURE:
<223> OTHER INFORMATION: Gly/Ser linker

<400> SEQUENCE: 24

Gly Gly Gly Gly Ser Gly Gly Gly Ser Gly Gly Gly Gly Ser Gly
1               5                   10                  15

Gly Gly Gly Ser Gly Gly Gly Gly Ser Gly Gly Gly Ser
            20                  25                  30

<210> SEQ ID NO 25
<211> LENGTH: 200
<212> TYPE: PRT
<213> ORGANISM: Artificial Sequence
<220> FEATURE:
<223> OTHER INFORMATION: Gly/Ser linker

<400> SEQUENCE: 25

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser Gly Gly Gly Ser
            20                  25                  30

Gly Gly Gly Ser Gly Gly Gly Ser Gly Gly Gly Ser Gly Gly Gly Ser
        35                  40                  45

Gly Gly Gly Ser Gly Gly Gly Ser Gly Gly Gly Ser Gly Gly Gly Ser
    50                  55                  60

Gly Gly Gly Ser Gly Gly Gly Ser Gly Gly Gly Ser Gly Gly Gly Ser
65                  70                  75                  80

Gly Gly Gly Ser Gly Gly Gly Ser Gly Gly Gly Ser Gly Gly Gly Ser
                85                  90                  95

Gly Gly Gly Ser Gly Gly Gly Ser Gly Gly Gly Ser Gly Gly Gly Ser
            100                 105                 110

Gly Gly Gly Ser Gly Gly Gly Ser Gly Gly Gly Ser Gly Gly Gly Ser
        115                 120                 125

Gly Gly Gly Ser Gly Gly Gly Ser Gly Gly Gly Ser Gly Gly Gly Ser
    130                 135                 140

Gly Gly Gly Ser Gly Gly Gly Ser Gly Gly Gly Ser Gly Gly Gly Ser
145                 150                 155                 160

Gly Gly Gly Ser Gly Gly Gly Ser Gly Gly Gly Ser Gly Gly Gly Ser
                165                 170                 175

Gly Gly Gly Ser Gly Gly Gly Ser Gly Gly Gly Ser Gly Gly Gly Ser
            180                 185                 190

Gly Gly Gly Ser Gly Gly Gly Ser
        195                 200

<210> SEQ ID NO 26
<211> LENGTH: 250
<212> TYPE: PRT
<213> ORGANISM: Artificial Sequence
<220> FEATURE:
<223> OTHER INFORMATION: Gly/Ser linker

<400> SEQUENCE: 26
```

Gly Gly Gly Gly Ser Gly Gly Gly Gly Ser Gly Gly Gly Gly Ser Gly
1               5                   10                  15

Gly Gly Gly Ser Gly Gly Gly Ser Gly Gly Gly Ser Gly Gly
            20              25              30

Gly Gly Ser Gly Gly Gly Ser Gly Gly Gly Ser Gly Gly Gly
        35              40              45

Gly Ser Gly Gly Gly Ser Gly Gly Gly Ser Gly Gly Gly Gly
    50              55              60

Ser Gly Gly Gly Gly Ser Gly Gly Gly Gly Ser Gly Gly Ser
65                  70                  75                  80

Gly Gly Gly Gly Ser Gly Gly Gly Ser Gly Gly Gly Ser Gly
            85              90              95

Gly Gly Gly Ser Gly Gly Gly Ser Gly Gly Gly Ser Gly Gly
            100             105             110

Gly Gly Ser Gly Gly Gly Gly Ser Gly Gly Gly Ser Gly Gly
        115             120             125

Gly Ser Gly Gly Gly Ser Gly Gly Gly Ser Gly Gly Gly Gly
    130             135             140

Ser Gly Gly Gly Ser Gly Gly Gly Ser Gly Gly Gly Gly Ser
145             150             155             160

Gly Gly Gly Gly Ser Gly Gly Gly Ser Gly Gly Gly Ser Gly
            165             170             175

Gly Gly Gly Ser Gly Gly Gly Ser Gly Gly Gly Ser Gly Gly
            180             185             190

Gly Gly Ser Gly Gly Gly Ser Gly Gly Gly Ser Gly Gly Gly
        195             200             205

Gly Ser Gly Gly Gly Ser Gly Gly Gly Ser Gly Gly Gly Gly
    210             215             220

Ser Gly Gly Gly Gly Ser Gly Gly Gly Gly Ser Gly Gly Ser
225                 230                 235                 240

Gly Gly Gly Gly Ser Gly Gly Gly Gly Ser
            245                 250

<210> SEQ ID NO 27
<211> LENGTH: 32
<212> TYPE: PRT
<213> ORGANISM: Artificial Sequence
<220> FEATURE:
<223> OTHER INFORMATION: CTP peptide

<400> SEQUENCE: 27

Asp Pro Arg Phe Gln Asp Ser Ser Ser Lys Ala Pro Pro Pro Ser
1               5                   10                  15

Leu Pro Ser Pro Ser Arg Leu Pro Gly Pro Ser Asp Thr Pro Ile Leu
                20                  25                  30

<210> SEQ ID NO 28
<211> LENGTH: 28
<212> TYPE: PRT
<213> ORGANISM: Artificial Sequence
<220> FEATURE:
<223> OTHER INFORMATION: CTP peptide

<400> SEQUENCE: 28

Ser Ser Ser Ser Lys Ala Pro Pro Pro Ser Leu Pro Ser Pro Ser Arg
1               5                   10                  15

Leu Pro Gly Pro Ser Asp Thr Pro Ile Leu Pro Gln
                20                  25

<210> SEQ ID NO 29
<211> LENGTH: 11
<212> TYPE: PRT
<213> ORGANISM: Artificial Sequence
<220> FEATURE:
<223> OTHER INFORMATION: Albumin-binding peptide core sequence

<400> SEQUENCE: 29

```
Asp Ile Cys Leu Pro Arg Trp Gly Cys Leu Trp
1               5                   10
```

<210> SEQ ID NO 30
<211> LENGTH: 11
<212> TYPE: PRT
<213> ORGANISM: Artificial Sequence
<220> FEATURE:
<223> OTHER INFORMATION: FIXa interaction region

<400> SEQUENCE: 30

```
Tyr Asn Asn Met Phe Cys Ala Gly Phe His Glu
1               5                   10
```

<210> SEQ ID NO 31
<211> LENGTH: 26
<212> TYPE: PRT
<213> ORGANISM: Artificial Sequence
<220> FEATURE:
<223> OTHER INFORMATION: FIXa interaction region

<400> SEQUENCE: 31

```
Arg Ser Thr Lys Phe Thr Ile Tyr Asn Asn Met Phe Cys Ala Gly Phe
1               5                   10                  15

His Glu Gly Gly Arg Asp Ser Cys Gln Gly
            20                  25
```

<210> SEQ ID NO 32
<211> LENGTH: 6
<212> TYPE: PRT
<213> ORGANISM: Artificial Sequence
<220> FEATURE:
<223> OTHER INFORMATION: Albumin binding peptide
<220> FEATURE:
<221> NAME/KEY: MISC_FEATURE
<222> LOCATION: (2)..(2)
<223> OTHER INFORMATION: Xaa is Asp, Asn, Ser, Thr, or Trp
<220> FEATURE:
<221> NAME/KEY: MISC_FEATURE
<222> LOCATION: (3)..(3)
<223> OTHER INFORMATION: Xaa is Asn, Gln, His, Ile, Leu, or Lys
<220> FEATURE:
<221> NAME/KEY: MISC_FEATURE
<222> LOCATION: (4)..(4)
<223> OTHER INFORMATION: Xaa is Ala, Asp, Phe, Trp, or Tyr
<220> FEATURE:
<221> NAME/KEY: MISC_FEATURE
<222> LOCATION: (5)..(5)
<223> OTHER INFORMATION: Xaa is Asp, Gly, Leu, Phe, Ser, or Thr

<400> SEQUENCE: 32

```
Cys Xaa Xaa Xaa Xaa Cys
1               5
```

<210> SEQ ID NO 33
<211> LENGTH: 20
<212> TYPE: PRT
<213> ORGANISM: Artificial Sequence
<220> FEATURE:
<223> OTHER INFORMATION: PAS sequence

```
<400> SEQUENCE: 33

Ala Ser Pro Ala Ala Pro Ala Pro Ala Ser Pro Ala Ala Pro Ala Pro
1               5                   10                  15

Ser Ala Pro Ala
            20

<210> SEQ ID NO 34
<211> LENGTH: 20
<212> TYPE: PRT
<213> ORGANISM: Artificial Sequence
<220> FEATURE:
<223> OTHER INFORMATION: PAS sequence

<400> SEQUENCE: 34

Ala Ala Pro Ala Ser Pro Ala Pro Ala Ala Pro Ser Ala Pro Ala Pro
1               5                   10                  15

Ala Ala Pro Ser
            20

<210> SEQ ID NO 35
<211> LENGTH: 20
<212> TYPE: PRT
<213> ORGANISM: Artificial Sequence
<220> FEATURE:
<223> OTHER INFORMATION: PAS sequence

<400> SEQUENCE: 35

Ala Pro Ser Ser Pro Ser Pro Ser Ala Pro Ser Ser Pro Ser Pro Ala
1               5                   10                  15

Ser Pro Ser Ser
            20

<210> SEQ ID NO 36
<211> LENGTH: 19
<212> TYPE: PRT
<213> ORGANISM: Artificial Sequence
<220> FEATURE:
<223> OTHER INFORMATION: PAS sequence

<400> SEQUENCE: 36

Ala Pro Ser Ser Pro Ser Pro Ser Ala Pro Ser Ser Pro Ser Pro Ala
1               5                   10                  15

Ser Pro Ser

<210> SEQ ID NO 37
<211> LENGTH: 20
<212> TYPE: PRT
<213> ORGANISM: Artificial Sequence
<220> FEATURE:
<223> OTHER INFORMATION: PAS sequence

<400> SEQUENCE: 37

Ser Ser Pro Ser Ala Pro Ser Pro Ser Ser Pro Ala Ser Pro Ser Pro
1               5                   10                  15

Ser Ser Pro Ala
            20

<210> SEQ ID NO 38
<211> LENGTH: 24
<212> TYPE: PRT
<213> ORGANISM: Artificial Sequence
<220> FEATURE:
<223> OTHER INFORMATION: PAS sequence
```

<400> SEQUENCE: 38

Ala Ala Ser Pro Ala Ala Pro Ser Ala Pro Pro Ala Ala Ala Ser Pro
1               5                   10                  15

Ala Ala Pro Ser Ala Pro Pro Ala
            20

<210> SEQ ID NO 39
<211> LENGTH: 20
<212> TYPE: PRT
<213> ORGANISM: Artificial Sequence
<220> FEATURE:
<223> OTHER INFORMATION: PAS sequence

<400> SEQUENCE: 39

Ala Ser Ala Ala Ala Pro Ala Ala Ala Ser Ala Ala Ala Ser Ala Pro
1               5                   10                  15

Ser Ala Ala Ala
            20

<210> SEQ ID NO 40
<211> LENGTH: 200
<212> TYPE: PRT
<213> ORGANISM: Artificial Sequence
<220> FEATURE:
<223> OTHER INFORMATION: Gly linker

<400> SEQUENCE: 40

Gly Gly Gly Gly Gly Gly Gly Gly Gly Gly Gly Gly Gly Gly Gly Gly
1               5                   10                  15

Gly Gly Gly Gly Gly Gly Gly Gly Gly Gly Gly Gly Gly Gly Gly Gly
            20                  25                  30

Gly Gly Gly Gly Gly Gly Gly Gly Gly Gly Gly Gly Gly Gly Gly Gly
        35                  40                  45

Gly Gly Gly Gly Gly Gly Gly Gly Gly Gly Gly Gly Gly Gly Gly Gly
    50                  55                  60

Gly Gly Gly Gly Gly Gly Gly Gly Gly Gly Gly Gly Gly Gly Gly Gly
65                  70                  75                  80

Gly Gly Gly Gly Gly Gly Gly Gly Gly Gly Gly Gly Gly Gly Gly Gly
                85                  90                  95

Gly Gly Gly Gly Gly Gly Gly Gly Gly Gly Gly Gly Gly Gly Gly Gly
            100                 105                 110

Gly Gly Gly Gly Gly Gly Gly Gly Gly Gly Gly Gly Gly Gly Gly Gly
        115                 120                 125

Gly Gly Gly Gly Gly Gly Gly Gly Gly Gly Gly Gly Gly Gly Gly Gly
    130                 135                 140

Gly Gly Gly Gly Gly Gly Gly Gly Gly Gly Gly Gly Gly Gly Gly Gly
145                 150                 155                 160

Gly Gly Gly Gly Gly Gly Gly Gly Gly Gly Gly Gly Gly Gly Gly Gly
                165                 170                 175

Gly Gly Gly Gly Gly Gly Gly Gly Gly Gly Gly Gly Gly Gly Gly Gly
            180                 185                 190

Gly Gly Gly Gly Gly Gly Gly Gly
        195                 200

<210> SEQ ID NO 41
<211> LENGTH: 1000
<212> TYPE: PRT
<213> ORGANISM: Artificial Sequence

```
<220> FEATURE:
<223> OTHER INFORMATION: Gly/Ser linker

<400> SEQUENCE: 41

Gly Gly Gly Gly Ser Gly Gly Gly Gly Ser Gly Gly Gly Gly Ser Gly
1               5                   10                  15
Gly Gly Gly Ser Gly Gly Gly Gly Ser Gly Gly Gly Gly Ser Gly Gly
                20                  25                  30
Gly Gly Ser Gly Gly Gly Gly Ser Gly Gly Gly Gly Ser Gly Gly Gly
            35                  40                  45
Gly Ser Gly Gly Gly Ser Gly Gly Gly Ser Gly Gly Gly Gly
        50                  55                  60
Ser Gly Gly Gly Gly Ser Gly Gly Gly Gly Ser Gly Gly Gly Gly Ser
65                  70                  75                  80
Gly Gly Gly Gly Ser Gly Gly Gly Gly Ser Gly Gly Gly Gly Ser Gly
                85                  90                  95
Gly Gly Gly Ser Gly Gly Gly Gly Ser Gly Gly Gly Gly Ser Gly Gly
                100                 105                 110
Gly Gly Ser Gly Gly Gly Gly Ser Gly Gly Gly Gly Ser Gly Gly Gly
            115                 120                 125
Gly Ser Gly Gly Gly Gly Ser Gly Gly Gly Gly Ser Gly Gly Gly Gly
        130                 135                 140
Ser Gly Gly Gly Gly Ser Gly Gly Gly Gly Ser Gly Gly Gly Gly Ser
145                 150                 155                 160
Gly Gly Gly Gly Ser Gly Gly Gly Gly Ser Gly Gly Gly Gly Ser Gly
                165                 170                 175
Gly Gly Gly Ser Gly Gly Gly Gly Ser Gly Gly Gly Gly Ser Gly Gly
                180                 185                 190
Gly Gly Ser Gly Gly Gly Gly Ser Gly Gly Gly Gly Ser Gly Gly Gly
            195                 200                 205
Gly Ser Gly Gly Gly Gly Ser Gly Gly Gly Gly Ser Gly Gly Gly Gly
        210                 215                 220
Ser Gly Gly Gly Gly Ser Gly Gly Gly Gly Ser Gly Gly Gly Gly Ser
225                 230                 235                 240
Gly Gly Gly Gly Ser Gly Gly Gly Gly Ser Gly Gly Gly Gly Ser Gly
                245                 250                 255
Gly Gly Gly Ser Gly Gly Gly Gly Ser Gly Gly Gly Gly Ser Gly Gly
                260                 265                 270
Gly Gly Ser Gly Gly Gly Gly Ser Gly Gly Gly Gly Ser Gly Gly Gly
            275                 280                 285
Gly Ser Gly Gly Gly Gly Ser Gly Gly Gly Gly Ser Gly Gly Gly Gly
        290                 295                 300
Ser Gly Gly Gly Gly Ser Gly Gly Gly Gly Ser Gly Gly Gly Gly Ser
305                 310                 315                 320
Gly Gly Gly Gly Ser Gly Gly Gly Gly Ser Gly Gly Gly Gly Ser Gly
                325                 330                 335
Gly Gly Gly Ser Gly Gly Gly Gly Ser Gly Gly Gly Gly Ser Gly Gly
                340                 345                 350
Gly Gly Ser Gly Gly Gly Gly Ser Gly Gly Gly Gly Ser Gly Gly Gly
            355                 360                 365
Gly Ser Gly Gly Gly Gly Ser Gly Gly Gly Gly Ser Gly Gly Gly Gly
        370                 375                 380
Ser Gly Gly Gly Gly Ser Gly Gly Gly Gly Ser Gly Gly Gly Gly Ser
385                 390                 395                 400
```

-continued

Gly Gly Gly Gly Ser Gly Gly Gly Ser Gly Gly Gly Ser Gly
            405             410             415
Gly Gly Gly Ser Gly Gly Gly Ser Gly Gly Gly Ser Gly Gly
            420             425             430
Gly Gly Ser Gly Gly Gly Ser Gly Gly Gly Ser Gly Gly Gly
        435             440             445
Gly Ser Gly Gly Gly Ser Gly Gly Gly Ser Gly Gly Gly Gly
    450             455             460
Ser Gly Gly Gly Gly Ser Gly Gly Gly Ser Gly Gly Gly Ser
465             470             475             480
Gly Gly Gly Gly Ser Gly Gly Gly Ser Gly Gly Gly Ser Gly
            485             490             495
Gly Gly Gly Ser Gly Gly Gly Ser Gly Gly Gly Ser Gly Gly
            500             505             510
Gly Gly Ser Gly Gly Gly Ser Gly Gly Gly Ser Gly Gly Gly
        515             520             525
Gly Ser Gly Gly Gly Ser Gly Gly Gly Ser Gly Gly Gly Gly
    530             535             540
Ser Gly Gly Gly Gly Ser Gly Gly Gly Ser Gly Gly Gly Ser
545             550             555             560
Gly Gly Gly Gly Ser Gly Gly Gly Ser Gly Gly Gly Ser Gly
            565             570             575
Gly Gly Gly Ser Gly Gly Gly Ser Gly Gly Gly Ser Gly Gly
            580             585             590
Gly Gly Ser Gly Gly Gly Ser Gly Gly Gly Ser Gly Gly Gly
        595             600             605
Gly Ser Gly Gly Gly Ser Gly Gly Gly Ser Gly Gly Gly Gly
    610             615             620
Ser Gly Gly Gly Gly Ser Gly Gly Gly Ser Gly Gly Gly Ser
625             630             635             640
Gly Gly Gly Gly Ser Gly Gly Gly Ser Gly Gly Gly Ser Gly
            645             650             655
Gly Gly Gly Ser Gly Gly Gly Ser Gly Gly Gly Ser Gly Gly
            660             665             670
Gly Gly Ser Gly Gly Gly Ser Gly Gly Gly Ser Gly Gly Gly
        675             680             685
Gly Ser Gly Gly Gly Ser Gly Gly Gly Ser Gly Gly Gly Gly
    690             695             700
Ser Gly Gly Gly Gly Ser Gly Gly Gly Ser Gly Gly Gly Ser
705             710             715             720
Gly Gly Gly Gly Ser Gly Gly Gly Ser Gly Gly Gly Ser Gly
            725             730             735
Gly Gly Gly Ser Gly Gly Gly Ser Gly Gly Gly Ser Gly Gly
            740             745             750
Gly Gly Ser Gly Gly Gly Ser Gly Gly Gly Ser Gly Gly Gly
        755             760             765
Gly Ser Gly Gly Gly Ser Gly Gly Gly Ser Gly Gly Gly Gly
    770             775             780
Ser Gly Gly Gly Gly Ser Gly Gly Gly Ser Gly Gly Gly Ser
785             790             795             800
Gly Gly Gly Gly Ser Gly Gly Gly Ser Gly Gly Gly Ser Gly
            805             810             815

Gly Gly Gly Ser Gly Gly Gly Gly Ser Gly Gly Gly
            820                 825                 830

Gly Gly Ser Gly Gly Gly Ser Gly Gly Gly Ser Gly Gly Gly
        835                 840                 845

Gly Ser Gly Gly Gly Gly Ser Gly Gly Gly Ser Gly Gly Gly
    850                 855                 860

Ser Gly Gly Gly Gly Ser Gly Gly Gly Ser Gly Gly Gly Ser
865                 870                 875                 880

Gly Gly Gly Gly Ser Gly Gly Gly Ser Gly Gly Gly Ser Gly
            885                 890                 895

Gly Gly Ser Gly Gly Gly Ser Gly Gly Gly Ser Gly Gly Gly
        900                 905                 910

Gly Gly Ser Gly Gly Gly Ser Gly Gly Gly Ser Gly Gly Gly
    915                 920                 925

Gly Ser Gly Gly Gly Ser Gly Gly Gly Ser Gly Gly Gly Gly
    930                 935                 940

Ser Gly Gly Gly Ser Gly Gly Gly Ser Gly Gly Gly Gly Ser
945                 950                 955                 960

Gly Gly Gly Ser Gly Gly Gly Ser Gly Gly Gly Ser Gly
            965                 970                 975

Gly Gly Gly Ser Gly Gly Gly Ser Gly Gly Gly Ser Gly Gly
        980                 985                 990

Gly Gly Ser Gly Gly Gly Ser
    995                 1000

<210> SEQ ID NO 42
<211> LENGTH: 1001
<212> TYPE: PRT
<213> ORGANISM: Artificial Sequence
<220> FEATURE:
<223> OTHER INFORMATION: Gly/Ser linker

<400> SEQUENCE: 42

Ser Gly Gly Gly Gly Ser Gly Gly Gly Gly Ser Gly Gly Gly Gly Ser
1               5                   10                  15

Gly Gly Gly Gly Ser Gly Gly Gly Gly Ser Gly Gly Gly Gly Ser Gly
            20                  25                  30

Gly Gly Gly Ser Gly Gly Gly Gly Ser Gly Gly Gly Gly Ser Gly Gly
        35                  40                  45

Gly Gly Ser Gly Gly Gly Gly Ser Gly Gly Gly Gly Ser Gly Gly Gly
    50                  55                  60

Gly Ser Gly Gly Gly Gly Ser Gly Gly Gly Gly Ser Gly Gly Gly Gly
65                  70                  75                  80

Ser Gly Gly Gly Gly Ser Gly Gly Gly Gly Ser Gly Gly Gly Gly Ser
                85                  90                  95

Gly Gly Gly Gly Ser Gly Gly Gly Gly Ser Gly Gly Gly Gly Ser Gly
            100                 105                 110

Gly Gly Gly Ser Gly Gly Gly Gly Ser Gly Gly Gly Gly Ser Gly Gly
        115                 120                 125

Gly Gly Ser Gly Gly Gly Gly Ser Gly Gly Gly Gly Ser Gly Gly Gly
    130                 135                 140

Gly Ser Gly Gly Gly Gly Ser Gly Gly Gly Gly Ser Gly Gly Gly Gly
145                 150                 155                 160

Ser Gly Gly Gly Gly Ser Gly Gly Gly Gly Ser Gly Gly Gly Gly Ser
                165                 170                 175

```
Gly Gly Gly Gly Ser Gly Gly Gly Ser Gly Gly Gly Ser Gly
            180             185             190

Gly Gly Gly Ser Gly Gly Gly Ser Gly Gly Gly Ser Gly Gly
        195             200             205

Gly Gly Ser Gly Gly Gly Ser Gly Gly Gly Ser Gly Gly Gly
    210             215             220

Gly Ser Gly Gly Gly Ser Gly Gly Gly Ser Gly Gly Gly Gly
225             230             235             240

Ser Gly Gly Gly Ser Gly Gly Gly Ser Gly Gly Gly Gly Ser
            245             250             255

Gly Gly Gly Gly Ser Gly Gly Gly Ser Gly Gly Gly Ser Gly
            260             265             270

Gly Gly Ser Gly Gly Gly Ser Gly Gly Gly Ser Gly Gly Gly
        275             280             285

Gly Gly Ser Gly Gly Gly Ser Gly Gly Gly Ser Gly Gly Gly
    290             295             300

Gly Ser Gly Gly Gly Ser Gly Gly Gly Ser Gly Gly Gly Gly
305             310             315             320

Ser Gly Gly Gly Ser Gly Gly Gly Ser Gly Gly Gly Gly Ser
            325             330             335

Gly Gly Gly Gly Ser Gly Gly Gly Ser Gly Gly Gly Ser Gly
            340             345             350

Gly Gly Gly Ser Gly Gly Gly Ser Gly Gly Gly Ser Gly Gly
        355             360             365

Gly Gly Ser Gly Gly Gly Ser Gly Gly Gly Ser Gly Gly Gly
    370             375             380

Gly Ser Gly Gly Gly Ser Gly Gly Gly Ser Gly Gly Gly Gly
385             390             395             400

Ser Gly Gly Gly Gly Ser Gly Gly Gly Gly Ser Gly Gly Gly Ser
            405             410             415

Gly Gly Gly Gly Ser Gly Gly Gly Ser Gly Gly Gly Ser Gly
            420             425             430

Gly Gly Gly Ser Gly Gly Gly Ser Gly Gly Gly Ser Gly Gly
        435             440             445

Gly Gly Ser Gly Gly Gly Ser Gly Gly Gly Ser Gly Gly Gly
    450             455             460

Gly Ser Gly Gly Gly Ser Gly Gly Gly Ser Gly Gly Gly Gly
465             470             475             480

Ser Gly Gly Gly Ser Gly Gly Gly Ser Gly Gly Gly Gly Ser
            485             490             495

Gly Gly Gly Gly Ser Gly Gly Gly Gly Ser Gly Gly Gly Ser Gly
            500             505             510

Gly Gly Gly Ser Gly Gly Gly Ser Gly Gly Gly Ser Gly Gly
        515             520             525

Gly Gly Ser Gly Gly Gly Ser Gly Gly Gly Ser Gly Gly Gly
    530             535             540

Gly Ser Gly Gly Gly Ser Gly Gly Gly Ser Gly Gly Gly Gly
545             550             555             560

Ser Gly Gly Gly Gly Ser Gly Gly Gly Gly Ser Gly Gly Gly Ser
            565             570             575

Gly Gly Gly Gly Ser Gly Gly Gly Gly Ser Gly Gly Gly Ser Gly
            580             585             590

Gly Gly Gly Ser Gly Gly Gly Gly Ser Gly Gly Gly Gly Ser Gly Gly
```

-continued

Gly Gly Ser Gly Gly Gly Gly Ser Gly Gly Gly Gly Ser Gly Gly Gly
            595                 600                 605
Gly Ser Gly Gly Gly Gly Ser Gly Gly Gly Gly Ser Gly Gly Gly Gly
610                 615                 620
Gly Ser Gly Gly Gly Gly Ser Gly Gly Gly Gly Ser Gly Gly Gly Gly
625                 630                 635                 640
Ser Gly Gly Gly Gly Ser Gly Gly Gly Gly Ser Gly Gly Gly Gly Ser
                645                 650                 655
Gly Gly Gly Gly Ser Gly Gly Gly Gly Ser Gly Gly Gly Gly Ser Gly
            660                 665                 670
Gly Gly Gly Ser Gly Gly Gly Gly Ser Gly Gly Gly Gly Ser Gly Gly
            675                 680                 685
Gly Gly Ser Gly Gly Gly Gly Ser Gly Gly Gly Gly Ser Gly Gly Gly
            690                 695                 700
Gly Ser Gly Gly Gly Gly Ser Gly Gly Gly Gly Ser Gly Gly Gly Gly
705                 710                 715                 720
Ser Gly Gly Gly Gly Ser Gly Gly Gly Gly Ser Gly Gly Gly Gly Ser
                725                 730                 735
Gly Gly Gly Gly Ser Gly Gly Gly Gly Ser Gly Gly Gly Gly Ser Gly
            740                 745                 750
Gly Gly Gly Ser Gly Gly Gly Gly Ser Gly Gly Gly Gly Ser Gly Gly
            755                 760                 765
Gly Gly Ser Gly Gly Gly Gly Ser Gly Gly Gly Gly Ser Gly Gly Gly
            770                 775                 780
Gly Ser Gly Gly Gly Gly Ser Gly Gly Gly Gly Ser Gly Gly Gly Gly
785                 790                 795                 800
Ser Gly Gly Gly Gly Ser Gly Gly Gly Gly Ser Gly Gly Gly Gly Ser
                805                 810                 815
Gly Gly Gly Gly Ser Gly Gly Gly Gly Ser Gly Gly Gly Gly Ser Gly
            820                 825                 830
Gly Gly Gly Ser Gly Gly Gly Gly Ser Gly Gly Gly Gly Ser Gly Gly
            835                 840                 845
Gly Gly Ser Gly Gly Gly Gly Ser Gly Gly Gly Gly Ser Gly Gly Gly
            850                 855                 860
Gly Ser Gly Gly Gly Gly Ser Gly Gly Gly Gly Ser Gly Gly Gly Gly
865                 870                 875                 880
Ser Gly Gly Gly Gly Ser Gly Gly Gly Gly Ser Gly Gly Gly Gly Ser
                885                 890                 895
Gly Gly Gly Gly Ser Gly Gly Gly Gly Ser Gly Gly Gly Gly Ser Gly
            900                 905                 910
Gly Gly Gly Ser Gly Gly Gly Gly Ser Gly Gly Gly Gly Ser Gly Gly
            915                 920                 925
Gly Gly Ser Gly Gly Gly Gly Ser Gly Gly Gly Gly Ser Gly Gly Gly
            930                 935                 940
Gly Ser Gly Gly Gly Gly Ser Gly Gly Gly Gly Ser Gly Gly Gly Gly
945                 950                 955                 960
Ser Gly Gly Gly Gly Ser Gly Gly Gly Gly Ser Gly Gly Gly Gly Ser
                965                 970                 975
Gly Gly Gly Gly Ser Gly Gly Gly Gly Ser Gly Gly Gly Gly Ser Gly
            980                 985                 990
Gly Gly Gly Ser Gly Gly Gly Gly Ser
            995                 1000

<210> SEQ ID NO 43

```
<211> LENGTH: 9
<212> TYPE: PRT
<213> ORGANISM: Artificial Sequence
<220> FEATURE:
<223> OTHER INFORMATION: FXIa cleavage site

<400> SEQUENCE: 43

Thr Gln Ser Phe Asn Asp Phe Thr Arg
1               5

<210> SEQ ID NO 44
<211> LENGTH: 10
<212> TYPE: PRT
<213> ORGANISM: Artificial Sequence
<220> FEATURE:
<223> OTHER INFORMATION: FXIa cleavage site

<400> SEQUENCE: 44

Ser Val Ser Gln Thr Ser Lys Leu Thr Arg
1               5                   10

<210> SEQ ID NO 45
<211> LENGTH: 10
<212> TYPE: PRT
<213> ORGANISM: Artificial Sequence
<220> FEATURE:
<223> OTHER INFORMATION: Thrombin cleavage site

<400> SEQUENCE: 45

Asp Phe Leu Ala Glu Gly Gly Gly Val Arg
1               5                   10

<210> SEQ ID NO 46
<211> LENGTH: 11
<212> TYPE: PRT
<213> ORGANISM: Artificial Sequence
<220> FEATURE:
<223> OTHER INFORMATION: Thrombin cleavage site

<400> SEQUENCE: 46

Asp Phe Leu Ala Glu Glu Gly Gly Gly Val Arg
1               5                   10

<210> SEQ ID NO 47
<211> LENGTH: 7
<212> TYPE: PRT
<213> ORGANISM: Artificial Sequence
<220> FEATURE:
<223> OTHER INFORMATION: Thrombin cleavage site

<400> SEQUENCE: 47

Thr Thr Lys Ile Lys Pro Arg
1               5

<210> SEQ ID NO 48
<211> LENGTH: 5
<212> TYPE: PRT
<213> ORGANISM: Artificial Sequence
<220> FEATURE:
<223> OTHER INFORMATION: Thrombin cleavage site

<400> SEQUENCE: 48

Ala Leu Val Pro Arg
1               5

<210> SEQ ID NO 49
<211> LENGTH: 5
```

```
<212> TYPE: PRT
<213> ORGANISM: Artificial Sequence
<220> FEATURE:
<223> OTHER INFORMATION: Thrombin cleavage site

<400> SEQUENCE: 49

Ala Leu Arg Pro Arg
1               5

<210> SEQ ID NO 50
<211> LENGTH: 10
<212> TYPE: PRT
<213> ORGANISM: Artificial Sequence
<220> FEATURE:
<223> OTHER INFORMATION: Thrombin cleavage site

<400> SEQUENCE: 50

Ala Leu Arg Pro Arg Val Val Gly Gly Ala
1               5                   10

<210> SEQ ID NO 51
<211> LENGTH: 15
<212> TYPE: PRT
<213> ORGANISM: Artificial Sequence
<220> FEATURE:
<223> OTHER INFORMATION: Gly/Ser linker

<400> SEQUENCE: 51

Gly Gly Gly Gly Ser Gly Gly Gly Gly Ser Gly Gly Gly Gly Ser
1               5                   10                  15

<210> SEQ ID NO 52
<211> LENGTH: 150
<212> TYPE: PRT
<213> ORGANISM: Artificial Sequence
<220> FEATURE:
<223> OTHER INFORMATION: Gly/Ser linker

<400> SEQUENCE: 52

Gly Gly Ser Gly Gly Ser Gly Gly Ser Gly Gly Ser Gly Gly Ser Gly
1               5                   10                  15

Gly Ser Gly Gly Ser Gly Gly Ser Gly Gly Ser Gly Gly Ser Gly Gly
                20                  25                  30

Ser Gly Gly Ser Gly Gly Ser Gly Gly Ser Gly Gly Ser Gly Gly Ser
            35                  40                  45

Gly Gly Ser Gly Gly Ser Gly Gly Ser Gly Gly Ser Gly Gly Ser Gly
        50                  55                  60

Gly Ser Gly Gly Ser Gly Gly Ser Gly Gly Ser Gly Gly Ser Gly Gly
65                  70                  75                  80

Ser Gly Gly Ser Gly Gly Ser Gly Gly Ser Gly Gly Ser Gly Gly Ser
            85                  90                  95

Gly Gly Ser Gly Gly Ser Gly Gly Ser Gly Gly Ser Gly Gly Ser Gly
            100                 105                 110

Gly Ser Gly Gly Ser Gly Gly Ser Gly Gly Ser Gly Gly Ser Gly Gly
        115                 120                 125

Ser Gly Gly Ser Gly Gly Ser Gly Gly Ser Gly Gly Ser Gly Gly Ser
    130                 135                 140

Gly Gly Ser Gly Gly Ser
145                 150
```

PROCOAGULANT FUSION COMPOUND

REFERENCE TO A SEQUENCE LISTING SUBMITTED ELECTRONICALLY

The content of the electronically submitted sequence listing (Name: 2159_4380002_SequenceListing_ST25.txt; 133,000 bytes; and Date of Creation: May 2, 2016) was originally submitted in the International Application No. PCT/US2014/064541 and is incorporated herein by reference in its entirety.

BACKGROUND OF THE INVENTION

Field of the Invention

The present invention relates to procoagulant compounds useful for the treatment of coagulation disorders, such as hemophilia A and B.

Background of the Invention

The blood coagulation pathway, in part, involves the formation of an enzymatic complex of Factor VIIIa (FVIIIa) and Factor IXa (FIXa) (Xase complex) on the surface of platelets. FIXa is a serine protease with relatively weak catalytic activity without its cofactor FVIIIa. The Xase complex cleaves Factor X (FX) into Factor Xa (FXa), which in turn interacts with Factor Va (FVa) to cleave prothrombin and generate thrombin.

Hemophilia A is a bleeding disorder caused by mutations and/or deletions in the Factor VIII (FVIII) gene resulting in a deficiency of FVIII activity. In some cases, patients have reduced levels of FVIII due to the presence of FVIII inhibitors, such as anti-FVIII antibodies. Hemophilia B (also known as Christmas disease) is one of the most common inherited bleeding disorders in the world. It results in decreased in vivo and in vitro blood clotting activity and requires extensive medical monitoring throughout the life of the affected individual.

Hemophilia A can be treated by replacement therapy targeting restoration of FVIII activity to 1 to 5% of normal levels to prevent spontaneous bleeding. There are plasma-derived and recombinant FVIII products available to treat bleeding episodes on-demand or to prevent bleeding episodes from occurring by treating prophylactically.

Hemophilia B is caused by a deficiency in Factor IX that may result from either the decreased synthesis of the Factor IX protein or a defective molecule with reduced activity. The treatment of hemophilia B occurs by replacement of the missing clotting factor by exogenous factor concentrates highly enriched in Factor IX.

Reduced mortality, prevention of joint damage and improved quality of life have been important achievements due to the development of plasma-derived and recombinant clotting factors. However, there remains a great need for improved procoagulant therapies for the treatment (e.g., prophylactic treatment) of hemophilia and other blood coagulation disorders that are more tolerable, effective, and/or convenient than current therapies.

BRIEF SUMMARY OF THE INVENTION

The present invention provides a fusion compound comprising a procoagulant compound fused to an immunoglobulin constant region or a portion thereof, wherein the procoagulant compound comprises an amino acid sequence at least 95% identical to SRIRTVSPGSRSASGKSTCLASYCWLFWTGIA (SEQ ID NO: 3).

In some aspects, the invention includes a method of reducing or preventing aggregates which comprise a procoagulant compound comprising fusing the procoagulant compound to an immunoglobulin constant region or a portion thereof, wherein the procoagulant compound comprises an amino acid sequence at least 95% identical to SRIRTVSPGSRSASGKSTCLASYCWLFWTGIA (SEQ ID NO: 3).

In one embodiment, the procoagulant compound comprises SRIRTVSPGSRSASGKSTCLASYCWLFWTGIA (SEQ ID NO: 3).

In another embodiment, the fusion compound forms less aggregates compared to a compound consisting of the procoagulant compound. In other embodiments, the fusion compound forms at least about 10%, at least about 20%, at least about 30%, at least about 40%, at least about 50%, at least about 60%, at least about 70%, at least about 80%, at least about 90%, or at least about 100% less aggregates compared to a compound consisting of the procoagulant compound.

In some embodiments, the immunoglobulin constant region or a portion thereof in the fusion compound is an Fc fragment or an FcRn binding partner. In other embodiments, the procoagulant compound is linked to the immunoglobulin constant region or a portion thereof by a linker. In some embodiments, the procoagulant compound in the fusion compound comprises a free N-terminal.

In other embodiments, the linker comprises (GGGGS), (SEQ ID NO: 22), wherein n is 1, 2, 3, 4, 5, 6, 7, 8, 9, or 10, e.g., (GGGGS)$_6$ (SEQ ID NO: 24).

In still other embodiments, the fusion compound comprises the procoagulant compound, an immunoglobulin constant region or a portion thereof which is linked to the procoagulant compound, and an additional immunoglobulin constant region or a portion thereof, wherein the additional immunoglobulin constant region or a portion thereof is covalently linked to the immunoglobulin constant region or a portion thereof. In still other embodiments, the additional immunoglobulin constant region or a portion thereof is linked to the immunoglobulin constant region or a portion thereof by a second linker. In a particular embodiment, the second linker is (GGGGS), (SEQ ID NO: 22), wherein n is 1, 2, 3, 4, 5, 6, 7, 8, 9, or 10, e.g., (GGGGS)$_4$ (SEQ ID NO: 23).

In other embodiments, the fusion compound comprises amino acids 22 to 558 of SEQ ID NO: 2 or the amino acid sequence encoded by a nucleotide sequence of SEQ ID NO: 1.

The invention also includes a polynucleotide sequence encoding a fusion compound, a vector comprising the polynucleotide sequence, a pharmaceutical composition comprising the fusion compound, the vector, or the polynucleotide sequences, or the host cell comprising the polynucleotide sequence.

Also provided is a method of making a fusion compound comprising the procoagulant compound fused to an immunoglobulin constant region or a portion thereof, the method comprising culturing a host cell comprising a polynucleotide encoding the procoagulant compound which comprises an amino acid sequence at least 95% identical to SRIRTVSPGSRSASGKSTCLASYCWLFWTGIA (SEQ ID NO: 3) under suitable condition, wherein the fusion compound is expressed. In other embodiments, the invention includes a method of reducing, ameliorating, or preventing a bleeding episode in a subject in need thereof comprising administering the fusion compound, the polynucleotide sequence, the vector, or the host cell to the subject.

BRIEF DESCRIPTION OF THE FIGURES

FIG. 1A shows a schematic diagram of Fc-048 comprising a procoagulant compound (SYN4022) linked to a first Fc region by a linker (e.g., (GGGGS)$_6$) (SEQ ID NO: 24), in which the first Fc region is further linked to a second Fc region by a second linker (e.g., (GGGGS)$_4$) (SEQ ID NO: 23). FIG. 1B shows a schematic diagram of a linker capped analog of Fc-048, i.e., Fc-050, which comprises a procoagulant compound linked to a first Fc region by a first linker through its C-terminal and to a second Fc region by a second linker through its N-terminal.

FIG. 2 shows analytical SEC spectra of isolated monomeric, medium and large aggregate of Fc-048 after 5 g infection of each fusion compound.

FIG. 3A shows TGA profile of Fc-048 containing a mixture of monomer and aggregates. The top peak is for Fc-048 1 µM; the second peak is for Fc-048 0.333 µM; the third peak is for Fc-048 0.111 µM, the fourth peak is for Fc-048 0.037 µM; the fifth peak is for Fc-048 0.0123 µM; the sixth peak is for Fc-048 0.0041 µM; the seventh peak is for Fc-048 0.0014 µM; and the last peak is plasma alone. FIG. 3B shows TGA profile of Fc-050 containing a mixture of monomer and aggregates. The top peak is for Fc-050 0.14 µM; the second peak is for Fc-050 0.29 µM; the third peak is for plasma alone, the fourth peak is for Fc-050 0.57 µM; the fifth peak is for Fc-050 1.14 µM; the sixth peak is for Fc-050 4.57 µM; the seventh peak is for 2.29 µM.

FIG. 4 shows TGA profile of isolated monomeric and aggregate Fc-048.

FIG. 5 is a diagram showing the mouse plasma levels of Fc-048 (expressed as percentages of initial dose) over the course of 6 days following intravenous injection of 1.15 mg/kg in hemophilia A mice.

DETAILED DESCRIPTION OF THE INVENTION

The present invention provides a fusion compound comprising a procoagulant compound fused to an immunoglobulin constant region or a portion thereof and methods of making and using thereof.

I. Definitions

It must be noted that, as used in this specification and the appended claims, the singular forms "a", "an" and "the" include plural referents unless the context clearly dictates otherwise. The terms "a" (or "an"), as well as the terms "one or more," and "at least one" can be used interchangeably herein.

The term "about" is used herein to mean approximately, roughly, around, or in the regions of. When the term "about" is used in conjunction with a numerical range, it modifies that range by extending the boundaries above and below the numerical values set forth. In general, the term "about" is used herein to modify a numerical value above and below the stated value by a variance of 10 percent, up or down (higher or lower).

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

It is understood that wherever embodiments are described herein with the language "comprising," otherwise analogous embodiments described in terms of "consisting of" and/or "consisting essentially of" are also provided.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Système International de Unites (SI) accepted form. Numeric ranges are inclusive of the numbers defining the range. Unless otherwise indicated, amino acid sequences are written left to right in amino to carboxy orientation. The headings provided herein are not limitations of the various aspects or embodiments of the disclosure, which can be had by reference to the specification as a whole. Accordingly, the terms defined immediately below are more fully defined by reference to the specification in its entirety. Amino acids are referred to herein by either their commonly known three letter symbols or by the one-letter symbols recommended by the IUPAC-IUB Biochemical Nomenclature Commission. Nucleotides, likewise, are referred to by their commonly accepted single-letter codes.

The terms "polypeptide," "peptide" and "protein" are used interchangeably and refer to a polymeric compound comprised of covalently linked amino acid residues.

The terms "polynucleotide" and "nucleic acid" are used interchangeably and refer to a polymeric compound comprised of covalently linked nucleotide residues. Polynucleotides can be DNA, cDNA, RNA, single stranded, or double stranded, vectors, plasmids, phage, or viruses. Polynucleotides include the sequence in SEQ ID NO: 1, which encode the polypeptides of SEQ ID NO: 2. Polynucleotides also include fragments of the polynucleotides of SEQ ID NO: 1, e.g., those that encode fragments of the polypeptides of SEQ ID NO: 2, such as the procoagulant compound, Fc, signal sequence, and other fragments of the polypeptides of SEQ ID NO: 2.

"Administering," as used herein, means to proscribe or give a pharmaceutically acceptable fusion compound of the invention to a subject via a pharmaceutically acceptable route. Examples of routes of administration include, but are not limited to, intravenous, e.g., intravenous injection and intravenous infusion, e.g., via central venous access. Additional routes of administration include subcutaneous, intramuscular, oral, nasal, and pulmonary administration.

The term "treatment" or "treating" as used herein means amelioration or reduction of one or more symptoms of bleeding diseases or disorders including, but not limited to, hemophilia. In one embodiment, "treatment of" or "treating" a bleeding disease or disorder includes prevention of one or more symptoms of a bleeding disease or disorder. In other embodiments, "treatment" or "treating" means reduction of the frequency of one or more symptoms of bleeding diseases or disorders, e.g., spontaneous or uncontrollable bleeding episodes. "Treatment," however, need not be a cure.

"Subject," as used herein means a human or a non-human mammal. Non-human mammals include, e.g., mice, dogs, primates, monkeys, cats, horses, cows, pigs, and other domestic animals and small animals. In one embodiment, the "subject" is a human patient. Subject as used herein includes an individual who is known to have at least one incidence of uncontrolled bleeding episodes, who has been diagnosed with a disease or disorder associated with uncontrolled bleeding episodes, e.g., a bleeding disease or disorder, e.g., hemophilia, who is susceptible to uncontrolled bleeding episodes, e.g., hemophilia, or any combinations thereof. Subjects can also include an individual who is in danger of one or more uncontrollable bleeding episodes prior to a certain activity, e.g., a surgery, a sport activity, or any strenuous activities.

The term "bleeding episode" as used herein adopts a standardized definition of a bleeding episode. A bleeding episode started from the first sign of bleeding, and ended 72 hours after the last treatment for the bleeding, within which any symptoms of bleeding at the same location, or injections less than or equal to 72 hours apart, were considered the same bleeding episode. Any injection to treat the bleeding episode, taken more than 72 hours after the preceding one, was considered the first injection to treat a new bleeding episode at the same location. Any bleeding at a different location was considered a separate bleeding episode regardless of time from last injection. This definition has been proposed by the Subcommittee on Standards and Criteria, FVIII/FIX subcommittee of the International Society of Thrombosis and Hemostasis and has been used by the PedNet multicenter study in hemophilia.

As used herein, the term "pharmaceutically acceptable" means approved by a regulatory agency of US or EU or other government or listed in the U.S. Pharmacopeia or other generally recognized pharmacopeia for use in humans. Hence, the term "pharmaceutically acceptable" refers to those properties and/or substances that are acceptable to a patient (e.g., human patient) from a toxicological and/or safety point of view.

The term compound and molecule are used interchangeably. Other forms contemplated by the invention when the word "molecule" or "compound" is employed are salts, prodrugs, solvates, tautomers, stereoisomers and mixtures of stereoisomers. The compounds of this invention can be in the form of a pharmaceutically acceptable salt.

The term "amino acid" within the scope of the present invention means alpha-amino acid unless otherwise specified. The term "amino acid" includes naturally occurring, and non-naturally occurring (i.e., non-proteinogenic) amino acids. The one and three letter abbreviations for naturally occurring amino acids are used herein (see, e.g., Lehninger, Biochemistry, 2nd ed., Worth Publishers, New York, 1995: 71-92). The term "amino acid" also includes stereoisomers (for example D-amino acids) and modifications of naturally occurring amino acids (e.g., alpha-N-alkylated amino acids; modified phenylalanine or tyrosine derivatives, and the like).

Conventionally, L-amino acids are designated using upper case letters (e.g., the upper case letter "C" refers to L-cysteine), and D-amino acids are designated in lower case (e.g., the lower case letter "c" refers to D-cysteine). Where no indication of the isomer is given, both isomers are intended. For example, when the amino acid is referred to with its name, both L- and D-amino acids are included (e.g., the term "cysteine" includes both, L-cysteine and D-cysteine).

The term "modified amino acid" refers to amino acids, which are altered with respect to their original structure, e.g., by substitution. Examples of modified amino acids include, e.g., alpha-N-alkylated amino acids, tyrosine derivatives (e.g., those in which the hydroxyl group is converted to an ether or ester group, or those in which the phenyl ring is substituted, e.g., with a halogen atom), phenylalanine derivatives (e.g., those in which the phenyl ring is substituted, e.g., with a halogen atom), lysine derivatives (e.g., those in which the $NH_2$ group is converted to an amide group or sulfonamide group), and amino acids, in which a carboxylic acid group is derivatized, e.g., esterified, converted to an amide group, and the like. In one example, the modified amino acid is a tyrosine residue modified at the hydroxyl group and having the formula $Y—OR^b$, wherein $R^b$ is selected from straight or branched alkyl, e.g., $(C_1-C_{10})$alkyl, straight or branched heteroalkyl, e.g., $(C_1-C_{10})$heteroalkyl comprising from 1 to 5 heteroatoms selected from O, S and N, and a water-soluble polymer (e.g., a PEG moiety). In another example, the modified tyrosine is methoxy-tyrosine (Y—OMe).

Introduction of at least one non-natural amino acid, or modification of at least one amino acid can improve the stability or solubility of a peptide. It can further increase the resistance to protease degradation or alter the biological (e.g., in vitro biological) activity of the peptide.

Other modified and non-proteinogenic amino acids useful in the present invention are described, e.g., in Grant, Synthetic Peptides: A Users Guide. Oxford University Press, 1992, which is incorporated herein by reference in its entirety.

Non-proteinogenic amino acids may include but are not limited to norvaline (Nva), norleucine (Nle), 4-aminobutyric acid (gamma-Abu), 2-aminoisobutyric acid (Aib), 6-aminohexanoic acid (gamma-Ahx), ornithine (Orn), hydroxyproline (Hyp), sarcosine, citrulline, cysteic acid (Coh), cyclohexylalanine, methioninesulfoxide (Meo), methioninesulfone (Moo), homoserinemethylester (Hsm), propargylglycine (Eag), 5-fluorotryptophan (5Fw), 6-fluorotryptophan (6Fw), 3',4'-dimethoxyphenyl-alanine (Ear), 3',4'-difluorophenylalanine (Dff), 4'-fluorophenyl-alanine (Pff), 1-naphthyl-alanine (1-Nal), 1-naphthyl-alanine, 1-methyl-tryptophan (1Mw), penicillamine (Pen), homoserine (HSe). Further, such amino acids may include but are not limited to, alpha-amino isobutyric acid, t-butylglycine, t-butylalanine, phenylglycine (Phg), benzothienylalanine (Bta), L-homocysteine (L-Hcys), N-methyl-phenylalanine (NMF), 2-thienylalanine (Thi), 3,3-diphenylalanine (Ebw), homophenylalanine (Hfe), s-benzyl-L-cysteine (Ece) or cyclohexylalanine (Cha). These and other non-proteinogenic amino acids may exist as D- or L-isomers.

The term "inverso-variant" of a peptide as used in this application means an enantiomer or mirror-image of a peptide. An "inverso-variant" is a peptide having the same amino acid sequence as its corresponding native peptide, but includes the corresponding D-amino acid for each L-amino acid in the native peptide, and the corresponding L-amino acid for each D-amino acid present in the native peptide (i.e., the chirality for each amino acid is inverted).

The term "retro-variant" of a peptide, means a peptide having the same amino acid sequence but in which the amino acids are assembled in opposite direction (reverse order) to the native peptide.

The term "retro-inverso variant" as used in this application means a retro-peptide as described herein, which is also reversed in its amino acid sequence as in a retro-variant described herein. Thus, a "retro-inverso variant" of a peptide refers to a peptide is made up of amino acid residues which are assembled in the opposite direction and which have inverted chirality with respect to the native peptide to which it is retro-inverso modified.

A retro-inverso variant can maintain the topology of the side chains as in the native peptide sequence. For example, Guichard et al. (1994) *Proc. Natl. Acad. Sci. USA* 91:9765-9769 described that a retro-inverso peptide mimicked the structure and antigenic activity of the natural L-peptide IRGERA, but not of the D- and retro peptides. Such retro-inverso peptidomimetics may be made using methods known in the art, for example such as those described in Meziere et al. (1997) *J. Immunol.* 159, 3230-3237, incorporated herein by reference in its entirety. Partial retro-inverso peptide analogues are polypeptides in which only part of the sequence is reversed and replaced with enantiomeric amino acid residues. Processes for making such analogues are described, e.g., in European Patent EP0097994 to Pessi et al., which is incorporated by reference herein in its entirety.

Conventionally, where the amino acids are joined by peptide bonds, a peptide is represented such that the amino group at the N-terminus appears to the left and the carboxyl group at the C-terminus to the right. Peptides and peptide derivatives according to the present invention are represented in this manner.

A "peptide derivative" contains a modification of one or more amino acid residues or a linker group or other covalently linked group. Examples of amino acid derivatives include N-acyl derivatives of the amino terminal or of another free amino group, esters of the carboxyl terminal or of another free carboxyl or hydroxy group, amides of the carboxyl terminal or of another free carboxyl group produced by reaction with ammonia or with a suitable amine, glycosylated derivatives, hydroxylated derivatives, nucleotidylated derivatives, ADP-ribosylated derivatives, pegylated derivatives, phosphorylated derivatives, biotinylated derivatives, derivatives conjugated to an antibody or antibody fragment, albumin, transferrin, HES, and the like. Also included among the chemical derivatives are those obtained by modification of the peptide bond —CO—NH—, for example by reduction to —CH$_2$—NH— or alkylation to —CO—N(alkyl)-. Other derivatives include amide bond bioisosteres, ketomethylene and hydroxyethylene derivatives, as well as thioesters, thioamides and the like.

Other modifications include, e.g., acetylation, acylation, ADP-ribosylation, amidation, covalent attachment of flavin, covalent attachment of a heme moiety, covalent attachment of a nucleotide or nucleotide derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, halogenation (e.g., iodination), methylation, myristoylation, oxidation, pegylation (Mei et al., Blood 116:270-79 (2010), which is incorporated herein by reference in its entirety), proteolytic processing, phosphorylation, prenylation, racemization, selenoylation, sulfation, transfer-RNA mediated addition of amino acids to proteins such as arginylation, and ubiquitination.

In one example, derivatisation is C-terminal amidation. C-terminal amidation of a peptide removes the negative charge of the C-terminal carboxyl group. Peptide derivatives having a C-terminal amide can be represented with "NH$_2$" at the C-terminus, for example SRIRTVSPGSRSASGKST-CLASYCWLFWTGIA-NH$_2$. Another derivatisation is N-terminal acetylation. This removes the positive charge at the N-terminus. Blocking of the C- or N-terminus, such as by C-terminal amidation or N-terminal acetylation, may improve proteolytic stability due to reduced susceptibility to exoproteolytic digestion.

By "procoagulant activity" is meant the ability to promote thrombin generation and/or fibrin deposition in a suitable test system. Exemplary assays useful to measure the procoagulant activity of a fusion compound of the present invention are described herein and include, e.g., thrombin generation assays.

The term "antibody variant" or "modified antibody" includes an antibody which does not occur in nature and which has an amino acid sequence or amino acid side chain chemistry which differs from that of a naturally-derived antibody by at least one amino acid or amino acid modification as described herein. As used herein, the term "antibody variant" includes synthetic forms of antibodies which are altered such that they are not naturally occurring, e.g., antibodies that comprise at least two heavy chain portions but not two complete heavy chains (such as, domain deleted antibodies or minibodies); multispecific forms of antibodies (e.g., bispecific, trispecific, etc.) altered to bind to two or more different antigens or to different epitopes on a single antigen); heavy chain molecules joined to scFv molecules; single-chain antibodies; diabodies; triabodies; and antibodies with altered effector function and the like.

The term "procoagulant compound" or "procoagulant compound of the invention" as used herein including plural forms shall mean an amino acid sequence having at least 95% identical to SRIRTVSPGSRSASGKSTCLASY-CWLFWTGIA (SEQ ID NO: 3), or a variant or derivative of SEQ ID NO: 3.

As used herein the term "scFv molecule" includes binding molecules which consist of one light chain variable domain (VL) or portion thereof, and one heavy chain variable domain (VH) or portion thereof, wherein each variable domain (or portion thereof) is derived from the same or different antibodies. scFv molecules can comprise an scFv linker interposed between the VH domain and the VL domain. ScFv molecules are known in the art and are described, e.g., in U.S. Pat. No. 5,892,019, Ho et al. 1989. *Gene* 77:51; Bird et al. 1988 *Science* 242:423; Pantoliano et al. 1991. *Biochemistry* 30:10117; Milenic et al. 1991. *Cancer Research* 51:6363; Takkinen et al. 1991. *Protein Engineering* 4:837.

A "scFv linker" as used herein refers to a moiety interposed between the VL and VH domains of the scFv. scFv linkers can maintain the scFv molecule in an antigen binding conformation. In one embodiment, an scFv linker comprises or consists of an scFv linker peptide. In certain embodiments, an scFv linker peptide comprises or consists of a gly-ser polypeptide linker. In other embodiments, an scFv linker comprises a disulfide bond.

As used herein the term "disulfide bond" includes the covalent bond formed between two sulfur atoms. The amino acid cysteine comprises a thiol group that can form a disulfide bond or bridge with a second thiol group. In most naturally occurring IgG molecules, the CH1 and CL regions are linked by native disulfide bonds and the two heavy chains are linked by two native disulfide bonds at positions corresponding to 239 and 242 using the Kabat numbering system (position 226 or 229, EU numbering system).

The term "vector" or "expression vector" is used herein to mean vectors used in accordance with the present invention as a vehicle for introducing into and expressing a desired polynucleotide in a cell. As known to those skilled in the art, such vectors may easily be selected from plasmids, phages, viruses and retroviruses. In general, vectors compatible with the instant invention will comprise a selection marker, appropriate restriction sites to facilitate cloning of the desired gene and the ability to enter and/or replicate in eukaryotic or prokaryotic cells.

Numerous expression vector systems may be employed to produce the fusion compounds of the invention. For example, one class of vector utilizes DNA elements which are derived from animal viruses such as bovine papilloma virus, polyoma virus, adenovirus, vaccinia virus, baculovirus, retroviruses (RSV, MMTV or MOMLV) or SV40 virus. Additionally, cells which have integrated the DNA into their chromosomes may be selected by introducing one or more markers which allow selection of transfected host cells. The marker may provide for prototrophy to an auxotrophic host, biocide resistance (e.g., antibiotics) or resistance to heavy metals such as copper. The selectable marker gene can either be directly linked to the DNA sequences to be expressed, or introduced into the same cell by cotransformation. In one embodiment, an inducible expression system can be employed. Additional elements may also be needed for optimal synthesis of mRNA. These elements may include signal sequences, splice signals, as well as transcriptional promoters, enhancers, and termination signals. In one embodiment, a secretion signal, e.g., any one of several well characterized bacterial leader peptides (e.g., pelB, phoA, or ompA), can be fused in-frame to the N terminus of a polypeptide of the invention to obtain optimal secretion of the polypeptide. (Lei et al. (1988), *Nature,* 331:543; Better et al. (1988) *Science,* 240:1041; Mullinax et al., (1990). *PNAS,* 87:8095).

The term "host cell" refers to a cell that has been transformed with a vector constructed using recombinant DNA techniques and encoding at least one heterologous gene. In descriptions of processes for isolation of proteins from recombinant hosts, the terms "cell" and "cell culture" are used interchangeably to denote the source of protein unless it is clearly specified otherwise. In other words, recovery of protein from the "cells" may mean either from spun down whole cells, or from the cell culture containing both the medium and the suspended cells. The host cell line used for protein expression can be of mammalian origin; those skilled in the art are credited with ability to preferentially determine particular host cell lines which are best suited for the desired gene product to be expressed therein. Exemplary host cell lines include, but are not limited to, DG44 and DUXB11 (Chinese Hamster Ovary lines, DHFR minus), HELA (human cervical carcinoma), CVI (monkey kidney line), COS (a derivative of CVI with SV40 T antigen), R1610 (Chinese hamster fibroblast) BALBC/3T3 (mouse fibroblast). HAK (hamster kidney line), SP2/O (mouse myeloma), P3x63-Ag3.653 (mouse mycloma), BFA-1c1BPT (bovine endothelial cells), RAJI (human lymphocyte) and 293 (human kidney). In a specific embodiment, the host cell is HEK293 cells. Host cell lines are typically available from commercial services, the American Tissue Culture Collection or from published literature. The fusion compounds of the invention can also be expressed in non-mammalian cells such as bacteria or yeast or plant cells. In this regard it will be appreciated that various unicellular non-mammalian microorganisms such as bacteria can also be transformed; i.e., those capable of being grown in cultures or fermentation. Bacteria, which are susceptible to transformation, include members of the enterobacteriaceae, such as strains of *Escherichia coli* or *Salmonella*; Bacillaceae, such as *Bacillus subtilis; Pneumococcus; Streptococcus,* and *Haemophilus influenzae.* It will further be appreciated that, when expressed in bacteria, the polypeptides typically become part of inclusion bodies. The fusion compound must be isolated, purified and then assembled into functional molecules.

In addition to prokaryotes, eukaryotic microbes may also be used. *Saccharomyces cerevisiae,* or common baker's yeast, is the most commonly used among eukaryotic microorganisms although a number of other strains are commonly available including *Pichia pastoris*. For expression in *Saccharomyces,* the plasmid YRp7, for example, (Stinchcomb et al., (1979), *Nature,* 282:39; Kingsman et al., (1979), Gene, 7:141; Tschemper et al., (1980), Gene, 10:157) is commonly used. This plasmid already contains the TRP1 gene which provides a selection marker for a mutant strain of yeast lacking the ability to grow in tryptophan, for example ATCC No. 44076 or PEP4-1 (Jones, (1977), *Genetics,* 85:12). The presence of the trpl lesion as a characteristic of the yeast host cell genome then provides an effective environment for detecting transformation by growth in the absence of tryptophan.

As used herein, the term "cleavage site" refers to a site recognized by an enzyme. In one embodiment, such an enzyme is one that is activated during the clotting cascade, such that cleavage of such sites occurs at the site of clot formation. Exemplary such sites include those recognized by thrombin, Factor XIa or Factor Xa In constructs that include more than one processing or cleavage site, it will be understood that such sites may be the same or different.

"Blood coagulation factor" or "coagulation factor" as used herein means FVIIa, FVIII, or FIX.

"Culture," "to culture" and "culturing," as used herein, means to incubate cells under in vitro conditions that allow for cell growth or division or to maintain cells in a "Variant," as used herein, refers to a polynucleotide or polypeptide differing from the original polynucleotide or polypeptide, but retaining essential properties thereof, e.g., FVIII coagulant activity or Fc (FcRn binding) activity. Generally, variants are overall closely similar, and, in many regions, identical to the original polynucleotide or polypeptide. Variants include, e.g., polypeptide and polynucleotide fragments, deletions, insertions, and modified versions of original polypeptides.

Naturally occurring variants are called "allelic variants," and refer to one of several alternate forms of a gene occupying a given locus on a chromosome of an organism (Genes II, Lewin, B., ed., John Wiley & Sons, New York (1985)). These allelic variants can vary at either the polynucleotide and/or polypeptide level and are included in the present invention. Alternatively, non-naturally occurring variants may be produced by mutagenesis techniques or by direct synthesis.

Using known methods of protein engineering and recombinant DNA technology, variants may be generated to improve or alter the characteristics of the polypeptides. For instance, one or more amino acids can be deleted from the N-terminus or C-terminus of the secreted protein without substantial loss of biological function. The authors of Ron et al., *J. Biol. Chem.* 268: 2984-2988 (1993), incorporated herein by reference in its entirety, reported variant KGF proteins having heparin binding activity even after deleting 3, 8, or 27 amino-terminal amino acid residues. Similarly, Interferon gamma exhibited up to ten times higher activity after deleting 8-10 amino acid residues from the carboxy terminus of this protein. (Dobeli et al., *J. Biotechnology* 7:199-216 (1988), incorporated herein by reference in its entirety.)

Moreover, ample evidence demonstrates that variants often retain a biological activity similar to that of the naturally occurring protein. For example, Gayle and coworkers (*J. Biol. Chem* 268:22105-22111 (1993), incorporated herein by reference in its entirety) conducted extensive mutational analysis of human cytokine IL-1a. They used random mutagenesis to generate over 3,500 individual IL-1a mutants that averaged 2.5 amino acid changes per variant over the entire length of the molecule. Multiple mutations were examined at every possible amino acid position. The investigators found that "most of the molecule could be altered with little effect on either binding or biological activity." In fact, only 23 unique amino acid sequences, out of more than 3,500 nucleotide sequences examined, produced a protein that significantly differed in activity from wild-type.

As stated above, polypeptide variants include, e.g., modified polypeptides. Modifications include, e.g., acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation (Mei et al., *Blood* 116:270-79 (2010), which is incorporated herein by reference in its entirety), proteolytic processing, phosphorylation, prenylation, racemization, selenoylation, sulfation, transfer-RNA mediated addition of amino acids to proteins such as arginylation, and ubiquitination.

By a nucleic acid having a nucleotide sequence at least, for example, 95% "identical" to a reference nucleotide sequence, it is intended that the nucleotide sequence of the nucleic acid is identical to the reference sequence except that the nucleotide sequence may include up to five point mutations per each 100 nucleotides of the reference nucleotide sequence. In other words, to obtain a nucleic acid having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence.

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted, deleted, (indels) or substituted with another amino acid. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular nucleic acid molecule or polypeptide is at least 85%, 90%, 95%, 96%, 97%, 98% or 99% identical to a nucleotide sequence or polypeptide of the present invention can be determined conventionally using known computer programs. A preferred method for determining the best overall match between a query sequence (reference or original sequence) and a subject sequence, also referred to as a global sequence alignment, can be determined using the FASTDB computer program based on the algorithm of Brutlag et al. (*Comp. App. Biosci.* (1990) 6:237-245). In a sequence alignment the query and subject sequences are both DNA sequences. An RNA sequence can be compared by converting U's to T's. The result of said global sequence alignment is in percent identity. Preferred parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the length of the subject nucleotide sequence, whichever is shorter.

If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of the present invention. Only bases outside the 5' and 3' bases of the subject sequence, as displayed by the FASTDB alignment, which are not matched/aligned with the query sequence, are calculated for the purposes of manually adjusting the percent identity score.

For example, a 90 base subject sequence is aligned to a 100 base query sequence to determine percent identity. The deletions occur at the 5' end of the subject sequence and therefore, the FASTDB alignment does not show a matched/alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are made for the purposes of the present invention.

If the subject sequence is shorter than the query sequence due to N- or C-terminal deletions, not because of internal deletions, a manual correction must be made to the results. This is because the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/ aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence.

For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for. No other manual corrections are to be made for the purposes of the present invention.

II. Fusion Compounds

The present invention includes a fusion compound comprising a procoagulant compound and an immunoglobulin constant region or a portion thereof. In one embodiment, the procoagulant compound comprises an amino acid sequence at least 90% or 95% identical to SRIRTVSPGSRSASGK-STCLASYCWLFWTGIA (SEQ ID NO: 3) or a peptide derivative or variant thereof. In another embodiment, the procoagulant compound comprises SRIRTVSPGSRSAS-GKSTCLASYCWLFWTGIA (SEQ ID NO: 3). In other embodiments, the procoagulant compound useful for the fusion compound comprises a retro-, an inverso- or a retro-inverso variant of the amino acid sequence of SEQ ID NO: 3.

In one embodiment, the fusion compound comprises at least about 90% or 95% identical to amino acids 22 to 558 of SEQ ID NO: 2. In another embodiments, the fusion compound comprises SEQ ID NO: 2. In other embodiments, the fusion compound is encoded by a nucleotide sequence of SEQ ID NO: 1.

In other embodiments, the fusion compound forms less aggregates compared to a compound consisting of the procoagulant compound. For example, the fusion compound forms at least about 10%, at least about 20%, at least about 30%, at least about 40%, at least about 50%, at least about 60%, at least about 70%, at least about 80%, at least about 90%, or at least about 100% less aggregates compared to a compound consisting of the procoagulant compound.

In some embodiments, the procoagulant compound (P) is linked to an immunoglobulin constant region or a portion thereof (F) by a linker (L), e.g., P-L-F. Non-limiting examples of the linker are shown at the relevant section below. In some embodiments, the linker is a gly-ser polypeptide linker. For example, a procoagulant compound can be linked to an immunoglobulin constant region or a portion thereof by $(GGGGS)_n$ (SEQ ID NO: 22), wherein n is 1, 2, 3, 4, 5, 6, 7, 8, 9, or 10, e.g., $(GGGGS)_6$ (SEQ ID NO: 24).

In other embodiments, a fusion compound of the invention comprises a procoagulant compound (P) comprising an amino acid sequence at least 90% or 95% identical to SRIRTVSPGSRSASGKSTCLASYCWLFWTGIA (SEQ ID NO: 3), a first immunoglobulin constant region or a portion thereof (F1) linked to the procoagulant compound by a first optional linker (L1), and a second immunoglobulin constant region or a portion thereof (F2) linked to the first immunoglobulin constant region or a portion thereof by a second optional linker (L2). In some embodiments, the first immunoglobulin constant region or a portion thereof and the second immunoglobulin constant region or a portion thereof are covalently linked, e.g., disulfide bond. In one embodiment, the first immunoglobulin constant region or a portion thereof and the second immunoglobulin constant region or a portion thereof are identical. In another embodiment, the first immunoglobulin constant region or a portion thereof and the second immunoglobulin constant region or a portion thereof are different. In other embodiments, the first linker and the second linker are identical or different.

In certain aspects, the immunoglobulin constant region or a portion thereof fused to the compound is at least one Fc region. The term "Fc," "Fc fragment," or "Fc region" as used herein, means a functional neonatal Fc receptor (FcRn) binding partner comprising an Fc domain, variant, or fragment thereof which maintains the desirable properties of an Fc region in a chimeric protein, e.g., an increase in in vivo half-life. Myriad mutants, fragments, variants, and derivatives are described, e.g., in PCT Publication Nos. WO 2011/069164 A2, WO 2012/006623 A2, WO 2012/006635 A2, or WO 2012/006633 A2, all of which are incorporated herein by reference in their entireties. An Fc region is comprised of domains denoted CH (constant heavy) domains (CH1, CH2, etc.). Depending on the isotype, (i.e. IgG, IgM, IgA IgD, or IgE), the Fc region can be comprised of three or four CH domains. Some isotypes (e.g. IgG) Fc regions also contain a hinge region. See Janeway et al. 2001, *Immunobiology*, Garland Publishing, N.Y., N.Y.

An Fc region or a portion thereof for producing the fusion of the present invention can be obtained from a number of different sources. In some embodiments, an Fc region or a portion thereof is derived from a human immunoglobulin. It is understood, however, that the Fc region or a portion thereof can be derived from an immunoglobulin of another mammalian species, including for example, a rodent (e.g. a mouse, rat, rabbit, guinea pig) or non-human primate (e.g. chimpanzee, macaque) species. Moreover, the Fc region or a portion thereof can be derived from any immunoglobulin class, including IgM, IgG, IgD, IgA and IgE, and any immunoglobulin isotype, including IgG1, IgG2, IgG3 and IgG4. In one embodiment, the human isotype IgG is used.

Fusion compounds comprising an Fc region of an immunoglobulin bestow several desirable properties including increased stability, increased serum half-life (see Capon et al., 1989. *Nature* 337:525) as well as binding to Fc receptors such as the neonatal Fc receptor (FcRn) (U.S. Pat. Nos.

6,086,875, 6,485,726, 6,030,613; WO 03/077834; US2003-0235536A1), which are incorporated herein by reference in their entireties.

In certain embodiments, the procoagulant compound is linked to one or more truncated Fc regions that are nonetheless sufficient to confer Fc receptor (FcR) binding properties to the Fc region. For example, the portion of an Fc region that binds to FcRn (i.e., the FcRn binding portion) comprises from about amino acids 282-438 of IgG1, EU numbering (with the primary contact sites being amino acids 248, 250-257, 272, 285, 288, 290-291, 308-311, and 314 of the CH2 domain and amino acid residues 385-387, 428, and 433-436 of the CH3 domain. Thus, an Fc region in a fusion compound of the invention may comprise or consist of an FcRn binding partner. FcRn binding partners may be derived from heavy chains of any isotype, including IgG1, IgG2, IgG3 and IgG4. In one embodiment, an FcRn binding partner from an antibody of the human isotype IgG1 is used. In another embodiment, an FcRn binding partner from an antibody of the human isotype IgG4 is used.

In certain embodiments, an Fc region comprises at least one of: a hinge (e.g., upper, middle, and/or lower hinge region) domain (about amino acids 216-230 of an antibody Fc region according to EU numbering), a CH12 domain (about amino acids 231-340 of an antibody Fc region according to EU numbering), a CH3 domain (about amino acids 341-438 of an antibody Fc region according to EU numbering), a CH4 domain, or a variant, portion, or fragment thereof. In other embodiments, an Fc region comprises a complete Fc domain (i.e., a hinge domain, a CH2 domain, and a CH3 domain). In some embodiments, an Fc region comprises, consists essentially of, or consists of a hinge domain (or a portion thereof) fused to a CH3 domain (or a portion thereof), a hinge domain (or a portion thereof) fused to a CH2 domain (or a portion thereof), a CH2 domain (or a portion thereof) fused to a CH3 domain (or a portion thereof), a CH2 domain (or a portion thereof) fused to both a hinge domain (or a portion thereof) and a CH3 domain (or a portion thereof). In still other embodiments, an Fc region lacks at least a portion of a CH2 domain (e.g., all or part of a CH2 domain). In a particular embodiment, an Fc region comprises or consists of amino acids corresponding to EU numbers 221 to 447.

An Fc in a fusion compound of the invention can include, for example, a change (e.g., a substitution) at one or more of the amino acid positions disclosed in Int'l. PCT Publs. WO88/07089A1, WO96/14339A1, WO98/05787A1, WO98/23289A1, WO99/51642A1, WO99/58572A1, WO00/09560A2, WO00/32767A1, WO00/42072A2, WO02/44215A2, WO02/060919A2, WO03/074569A2, WO04/016750A2, WO04/029207A2, WO04/035752A2, WO04/063351A2, WO04/074455A2. WO04/099249A2, WO05/040217A2, WO04/044859, WO05/070963A1, WO05/077981A2, WO05/092925A2, WO05/123780A2, WO06/019447A1, WO06/047350A2, and WO06/085967A2; U.S. Pat. Publ. Nos. US 2007/0231329, US2007/0231329. US2007/0237765, US2007/0237766, US2007/0237767, US2007/0243188, US2007/0248603, US2007/0286859, US2008/0057056; or U.S. Pat. Nos. 5,648,260; 5,739,277; 5,834,250; 5,869,046; 6,096,871; 6,121.022; 6,194,551; 6,242,195; 6,277,375; 6,528,624; 6,538,124; 6,737,056; 6,821,505; 6,998,253; 7,083,784; 7,404,956, and 7,317,091, each of which is incorporated by reference herein in its entirety. In one embodiment, the specific change (e.g., the specific substitution of one or more amino acids disclosed in the art) may be made at one or more of the disclosed amino acid positions. In another embodiment, a different change at one or more of the disclosed amino acid positions (e.g., the different substitution of one or more amino acid position disclosed in the art) may be made.

An Fc region used in the invention may also comprise an art recognized amino acid substitution which alters its glycosylation. For example, the Fc has a mutation leading to reduced glycosylation (e.g., N- or O-linked glycosylation) or may comprise an altered glycoform of the wild-type Fc moiety (e.g., a low fucose or fucose-free glycan).

In some embodiments, the procoagulant compound comprises GSRIRTVSPGSRSASGKSTCLASYCWLFWTGIA (SEQ ID NO: 4). In certain embodiments, the fusion compound further comprises a signal peptide, e.g., MET-DTLLLWV LLLWVPGSTG (SEQ ID NO: 5).

Fusion Compounds Linked to a Heterologous Moiety

In certain embodiments, the fusion compound of the present disclosure is further linked to a heterologous moiety. For example, the procoagulant compound of the present disclosure and/or the immunoglobulin constant region or a portion thereof of the fusion compound can be covalently linked to a heterologous moiety, optionally via a linker.

In one embodiment, a heterologous moiety useful for the invention is a blood coagulation factor and/or platelet targeting moieties. In another embodiment, the blood coagulation factor is selected from FVIIa, FVIII, and FIX. In one example, the procoagulant compound is linked to an internal amino acid residue of the polypeptide (e.g., FVIIa, FVIII, or FIX).

In other embodiments, the heterologous moiety is useful to increase the bioavailability or the in vivo stability/half-life of the compound. Exemplary heterologous moieties include, e.g., known half-life extending moieties, e.g., water-soluble polymers, such as polyethylene glycol (PEG) and polypropylene glycol (PPG), PAS, HES, XTEN, and albumin. In one example, the heterologous moiety is a polymer, e.g., a water-soluble polymer, such as polyethylene glycol (PEG). In another example, the heterologous moiety is a half-life prolonging protein, such as albumin. In another example, the heterologous moiety is a XTEN moiety. In another example, the heterologous moiety is a HES moiety. In another example, the heterologous moiety is a PAS moiety. Other useful heterologous moieties are known in the art and others are further described herein.

Fusion Compounds Linked to FVIII

In various embodiments, the procoagulant compound of the present disclosure and/or the immunoglobulin constant region or a portion thereof (a first immunoglobulin constant region or a portion thereof and/or a second immunoglobulin constant region or a portion thereof) is covalently linked to FVIII or its variant or derivative.

In one example, the fusion compound of the present disclosure includes the procoagulant compound covalently linked to another immunoglobulin constant region or a portion thereof (e.g., Fc) and a FVII-heterologous moiety construct (e.g., FVII-Fc).

The term "FVIII" or "Factor VIII", as used herein, means functional FVIII protein in its normal role in coagulation, unless otherwise specified (i.e., refers to any FVIII moiety which exhibits biological activity that is associated with native FVIII). Thus, the term FVIII includes FVIII variant proteins that are functional. In some embodiments, FVII proteins are primate (e.g., chimpanzee), human, porcine, canine, and murine FVIII proteins. The full length polypeptide and polynucleotide sequences of FVIII are known, as are many functional fragments, mutants and modified versions. Exemplary FVIII sequences are disclosed, e.g., in WO2011/069164. FVIII polypeptides include, e.g., full-length FVIII, full-length FVIII minus Met at the N-terminus, mature FVIII (minus the signal sequence), mature FVIII with an additional Met at the N-terminus, and/or FVIII with a full or partial deletion of the B domain. In one example, the FVIII is a variant in which the B domain is deleted, either partially or fully. An exemplary sequence of FVIII can be found as NCBI Accession Number NP000123 or UniProtKB/Swiss-Prot entry P00451.

A number of functional FVIII molecules, including B-domain deletions, are disclosed in the following patents: U.S. Pat. Nos. 6,316,226 and 6,346,513, both assigned to Baxter; U.S. Pat. No. 7,041,635 assigned to In2Gen; U.S. Pat. Nos. 5,789,203, 6,060,447, 5,595,886, and 6,228,620 assigned to Chiron; U.S. Pat. Nos. 5,972,885 and 6,048,720 assigned to Biovitrum, U.S. Pat. Nos. 5,543,502 and 5,610,278 assigned to Novo Nordisk; U.S. Pat. No. 5,171,844 assigned to Immuno Ag; U.S. Pat. No. 5,112,950 assigned to Transgene S.A.; U.S. Pat. No. 4,868,112 assigned to Genetics Institute, each of which is incorporated herein by reference in its entirety.

As used herein, "plasma-derived FVIII" includes all forms of the protein found in blood obtained from a mammal having the property of activating the coagulation pathway.

"B domain" of FVIII, as used herein, is the same as the B domain known in the art that is defined by internal amino acid sequence identity and sites of proteolytic cleavage by thrombin, e.g., residues Ser741-Arg1648 of full length human FVIII. The other human FVIII domains are defined by the following amino acid residues: A1, residues Ala1-Arg372; A2, residues Ser373-Arg740; A3, residues Ser1690-Ile2032; C1, residues Arg2033-Asn2172; C2, residues Ser2173-Tyr2332. The A3-C1-C2 sequence includes residues Ser1690-Tyr2332. The remaining sequence, residues Glu1649-Arg1689, is usually referred to as the FVIII light chain activation peptide. The locations of the boundaries for all of the domains, including the B domains, for porcine, mouse and canine FVIII are also known in the art. Preferably, the B domain of FVIII is deleted ("B domain deleted FVIII" or "BDD FVII"). An example of a BDD FVIII is REFACTO® (recombinant BDD FVIII).

A "B domain deleted FVIII" may have the full or partial deletions disclosed in U.S. Pat. Nos. 6,316,226, 6,346,513, 7,041,635, 5,789,203, 6,060,447, 5,595,886, 6,228,620, 5,972,885, 6,048,720, 5,543,502, 5,610,278, 5,171,844, 5,112,950, 4,868,112, and 6,458,563, each of which is incorporated herein by reference in its entirety. In some embodiments, a BDD FVIII sequence of the present invention comprises any one of the deletions disclosed at col. 4, line 4 to col. 5, line 28 and examples 1-5 of U.S. Pat. No. 6,316,226 (also in U.S. Pat. No. 6,346,513). In some embodiments, a BDD FVIII of the present invention has a deletion disclosed at col. 2, lines 26-51 and examples 5-8 of U.S. Pat. No. 5,789,203 (also U.S. Pat. Nos. 6,060,447, 5,595,886, and 6,228,620). In some embodiments, a BDD FVIII has a deletion described in col. 1, lines 25 to col. 2, line 40 of U.S. Pat. No. 5,972,885; col. 6, lines 1-22 and example 1 of U.S. Pat. No. 6,048,720; col. 2, lines 17-46 of U.S. Pat. No. 5,543,502; col. 4, line 22 to col. 5, line 36 of U.S. Pat. No. 5,171,844; col. 2, lines 55-68, FIG. 2, and example 1 of U.S. Pat. No. 5,112,950; col. 2, line 2 to col. 19, line 21 and table 2 of U.S. Pat. No. 4,868,112; col. 2, line 1 to col. 3, line 19, col. 3, line 40 to col. 4, line 67, col. 7, line 43 to col. 8, line 26, and col. 11, line 5 to col. 13, line 39 of U.S. Pat. No. 7,041,635; or col. 4, lines 25-53, of U.S. Pat. No. 6,458,563. In some embodiments, a BDD FVIII has a deletion of most of the B domain, but still contains amino-terminal sequences of the B domain that are essential for in vivo proteolytic processing of the primary translation product into two polypeptide chain, as disclosed in WO 91/09122, which is incorporated herein by reference in its entirety. In some embodiments, a BDD FVIII is constructed with a deletion of amino acids 747-1638, i.e., virtually a complete deletion of the B domain. Hoeben R. C., et al. *J. Biol. Chem.* 265 (13): 7318-7323 (1990), incorporated herein by reference in its entirety. A BDD FVIII may also contain a deletion of amino acids 771-1666 or amino acids 868-1562 of FVIII. Meulien P., et al. *Protein Eng.* 2(4): 301-6 (1988), incorporated herein by reference in its entirety. Additional B domain deletions that are part of the invention include, e.g.: deletion of amino acids 982 through 1562 or 760 through 1639 (Toole et al., Proc. Natl. Acad. Sci. U.S.A. (1986) 83, 5939-5942)), 797 through 1562 (Eaton, et al. Biochemistry (1986) 25:8343-8347)), 741 through 1646 (Kaufman (PCT published application No. WO 87/04187)), 747-1560 (Sarver, et al., DNA (1987) 6:553-564)), 741 through 1648 (Pasek (PCT application No. 88/00831)), 816 through 1598 or 741 through 1689 (Lagner (Behring Inst. Mitt. (1988) No 82:16-25, EP 295597)), each of which is incorporated herein by reference in its entirety. Each of the foregoing deletions may be made in any FVIII sequence.

In one example, the FVIII polypeptide is a single-chain FVIII. In some embodiments, the FVIII has an increased half-life (t1/2) due to linkage to a heterologous moiety that is a half-life extending moiety.

Functional FVIII variants are known, as is discussed herein. In addition, hundreds of nonfunctional mutations in FVIII have been identified in hemophilia patients, and it has been determined that the effect of these mutations on FVIII function is due more to where they lie within the 3-dimensional structure of FVIII than on the nature of the substitution (Cutler et al., *Hum. Mutat.* 19:274-8 (2002)), incorporated herein by reference in its entirety. In addition, comparisons between FVIII from humans and other species have identified conserved residues that are likely to be required for function (Cameron et al., *Thromb. Haemost.* 79:317-22 (1998); U.S. Pat. No. 6,251,632), incorporated herein by reference in its entirety.

The human FVIII gene was isolated and expressed in mammalian cells (Toole, J. J., et al., *Nature* 312:342-347 (1984); Gitschier, J., et al., *Nature* 312:326-330 (1984); Wood, W. I., et al., *Nature* 312:330-337 (1984); Vehar, G. A., et al., *Nature* 312:337-342 (1984); WO 87/04187; WO 88/08035; WO 88/03558; U.S. Pat. No. 4,757,006), each of which is incorporated herein by reference in its entirety, and the amino acid sequence was deduced from cDNA. Capon et al., U.S. Pat. No. 4,965,199, incorporated herein by reference in its entirety, disclose a recombinant DNA method for producing FVIII in mammalian host cells and purification of human FVIII. Human FVIII expression in CHO (Chinese hamster ovary) cells and BHKC (baby hamster kidney cells) has been reported. Human FVIII has been modified to delete part or all of the B domain (U.S. Pat. Nos. 4,994,371 and 4,868,112, each of which is incorporated herein by reference in its entirety), and replacement of the human FVIII B domain with the human factor V B domain has been performed (U.S. Pat. No. 5,004,803, incorporated herein by reference in its entirety). The cDNA sequence encoding human FVIII and predicted amino acid sequence are shown in SEQ ID NOs:1 and 2, respectively, of US Application Publ. No. 2005/0100990, incorporated herein by reference in its entirety.

U.S. Pat. No. 5,859,204, Lollar, J. S., incorporated herein by reference in its entirety, reports functional mutants of FVIII having reduced antigenicity and reduced immunoreactivity. U.S. Pat. No. 6,376,463, Lollar, J. S., incorporated herein by reference in its entirety, also reports mutants of FVIII having reduced immunoreactivity. US Application Publ. No. 2005/0100990, Saenko et al., incorporated herein by reference in its entirety, reports functional mutations in the A2 domain of FVIII.

The porcine FVIII sequence is published, (Toole, J. J., et al., *Proc. Natl. Acad. Sci. USA* 83:5939-5942 (1986)), incorporated herein by reference in its entirety, and the complete porcine cDNA sequence obtained from PCR amplification of FVIII sequences from a pig spleen cDNA library has been reported (Healey, J. F., et al., *Blood* 88:4209-4214 (1996), incorporated herein by reference in its entirety). Hybrid human/porcine FVIII having substitutions of all domains, all subunits, and specific amino acid sequences were disclosed in U.S. Pat. No. 5,364,771 by Lollar and Runge, and in WO 93/20093, incorporated herein by reference in its entirety. More recently, the nucleotide and corresponding amino acid sequences of the A1 and A2 domains of porcine FVIII and a chimeric FVIII with porcine A1 and/or A2 domains substituted for the corresponding human domains were reported in WO 94/11503, incorporated herein by reference in its entirety. U.S. Pat. No. 5,859,204, Lollar, J. S., also discloses the porcine cDNA and deduced amino acid sequences. U.S. Pat. No. 6,458,563, incorporated herein by reference in its entirety assigned to Emory discloses a B-domain deleted porcine FVIII.

In one example, a fusion compound comprises the procoagulant compound linked to a first Fc and FVIII linked to a second Fc. Exemplary FVIII and FVIII-Fc polypeptides useful for the invention include, e.g., SEQ ID NOs: 12 and 14 or a portion thereof.

The FVIII may be at least 85%, 90%, 95%, 96%, 97%, 98%, 99%, or 100% identical to a portion of the FVIII amino acid sequence of SEQ ID NOs: 12 or 14 without a signal sequence (e.g., amino acids 20 to 1457 of SEQ ID NO: 12; amino acids 20 to 2351 of SEQ ID NO: 14).

The FVIII may be at least 85%, 90%, 95%, 96%, 97%, 98%, 99%, or 100% identical to a portion of the FVIII amino acid sequence of SEQ ID NOs: 12 or 14 with a signal sequence (e.g., amino acids 1 to 1457 of SEQ ID NO: 12; amino acids 1 to 2351 of SEQ ID NO: 14).

The polynucleotide variants may contain alterations in the coding regions, non-coding regions, or both. Especially preferred are polynucleotide variants containing alterations which produce silent substitutions, additions, or deletions, but do not alter the properties or activities of the encoded polypeptide. Nucleotide variants produced by silent substitutions due to the degeneracy of the genetic code are preferred. Moreover, variants in which 5-10, 1-5, or 1-2 amino acids are substituted, deleted, or added in any combination are also preferred. Polynucleotide variants can be produced for a variety of reasons, e.g., to optimize codon expression for a particular host (change codons in the human mRNA to those preferred by a bacterial host such as *E. coli*).

In one example, the FVIII of the present disclosure is a polypeptide having FVIII-like activity, but does not have the amino acid sequence of FVIII. For example, the polypeptide having FVIII-like activity increases the catalytic activity of FIXa. In one example, the polypeptide having FVIII-like activity is an antibody (e.g., FIX/FIXa activating antibodies and antibody derivatives). Exemplary polypeptides having FVIII-like activity are disclosed in U.S. Pat. No. 7,033,590, which is incorporated herein by reference in its entirety.

Methods for the preparation of recombinant FVIII or FVIII-Fc constructs are disclosed, e.g., in WO2011/069164, which is incorporated herein by reference in its entirety.

Fusion Compounds Linked to FVII

In various embodiments, the procoagulant compound of the present disclosure and/or the immunoglobulin constant region or a portion thereof (a first immunoglobulin constant region or a portion thereof and/or a second immunoglobulin constant region or a portion thereof) is covalently linked to FVIIa or a variant or derivative thereof.

In one example, the fusion compound of the present disclosure includes the procoagulant compound covalently linked to an immunoglobulin constant region or a portion thereof (e.g., Fc) and a FVIIa-heterologous moiety construct (e.g., FVIIa-Fc).

The term "Factor VII" or "FVII", includes "Factor VIIa", or "FVIIa", and herein, means functional FVII protein or functional FVIIa protein in its normal role in coagulation, unless otherwise specified (i.e., refers to any FVII moiety which exhibits biological activity that is associated with native FVII). Thus, the term FVII includes variant proteins that are functional. FVII proteins can be primate (e.g., chimpanzee), human, porcine, canine, and murine FVII proteins. The full length polypeptide and polynucleotide sequences of FVII are known, as are many functional fragments, mutants and modified versions. Exemplary chimeric and hybrid FVII sequences are disclosed, e.g., in US 2009/0291890 A1, US2009/0041744 A1, and US 2008/0318276 A1. Factor VII polypeptides include, e.g., full-length FVII, full-length FVII minus Met at the N-terminus, mature FVII (minus the signal sequence), and mature FVII with an additional Met at the N-terminus. An exemplary sequence of FVII can be found as NCBI Accession Number NP000122.

As used herein, "plasma-derived FVII" includes all forms of the protein found in blood obtained from a mammal having the property of activating the coagulation pathway.

Examples of human FVII amino acid and DNA sequences are shown as subsequences in SEQ ID NO: 16 and SEQ ID NO: 15. FVII polypeptides include, e.g., full-length FVII, full-length FVII minus Met at the N-terminus, mature FVII (minus the signal sequence), and/or mature FVII with an additional Met at the N-terminus.

The term "activated Factor VII" or "FVIIa" refers to the enzymatically active two-chain form of circulating FVII generated as well as variants thereof in case coagulation activity (e.g., thrombin generation) is needed. The two-chain Factor VIIa is a polypeptide produced from FVII by hydrolysis of the Arg152-Ile153 peptide bond of FVII. FVIIa also comprises 406 amino acid residues, 10 of which are γ-carboxylated glutamic acid residues, N-glycosylated asparagines residues (no 145 and no 322), and O-glycosylated serine residues in position 52 and 60. The variant forms of FVIIa encompasses i.a. molecules wherein one or more amino acid residues have been substituted, added or deleted, molecules with different number of GLA residues, molecules with a modified or incomplete glycosylation pattern. The terms "FVII" and "activated FVII" include naturally occurring FVII and activated FVII but also encompass function conservative variants and modified forms thereof.

The term "Factor VIIa" or "FVIIa" includes activatable FVII.

Exemplary FVII sequences are disclosed herein. For example, the FVII may be at least 90% or 95% identical to a FVII amino acid sequence without a signal sequence (e.g., amino acids 61 to 466 of SEQ ID NO: 16). The FVII may be identical to a Factor VII amino acid sequence without a signal sequence (e.g., amino acids 61 to 466 of SEQ ID NO:16).

Exemplary FVII-Fc amino acid and DNA sequences are represented by SEQ ID NO:16 and 15. The FVII-Fc may comprise a sequence at least 90% or 95% identical to the FVII and Fc amino acid sequence without a signal sequence (e.g., amino acids 61 to 693 of SEQ ID NO:16) or at least 90% or 95% identical to the FVII and Fc amino acid sequence with a signal sequence (e.g., amino acids 1 to 693 of SEQ ID NO: 16).

The FVII-Fc may comprise a sequence identical to the FVII and Fc amino acid sequence without a signal sequence (e.g., amino acids 61 to 693 of SEQ ID NO:16) or identical to the FVII and Fc amino acid sequence with a signal sequence (e.g., amino acids 1 to 693 of SEQ ID NO:16).

FVII polynucleotides include, e.g., those of SEQ ID NO:15 and fragments thereof, e.g., those that encode the FVII fragment.

The term "Factor VIIa derivative" or "FVIIa derivative" as used herein, is intended to designate a FVIIa polypeptide exhibiting substantially the same or improved biological activity relative to wild-type Factor VIIa, in which one or more of the amino acids of the parent peptide have been genetically and/or chemically and/or enzymatically modified, e.g. by alkylation, glycosylation, deglycosylation, PEGylation, acylation, ester formation or amide formation or the like.

The term "improved biological activity" refers to FVIIa polypeptides with i) substantially the same or increased proteolytic activity compared to recombinant wild type human Factor VIIa or ii) to FVIIa polypeptides with substantially the same or increased TF binding activity compared to recombinant wild type human Factor VIIa or iii) to FVIIa polypeptides with substantially the same or increased half life in blood plasma compared to recombinant wild type human Factor VIIa.

Using known methods of protein engineering and recombinant DNA technology, variants may be generated to improve or alter the characteristics of the polypeptides. For instance, one or more amino acids can be deleted from the N-terminus or C-terminus of the secreted protein without substantial loss of biological function. The authors of Ron et al., *J. Biol. Chem.* 268: 2984-2988 (1993), incorporated herein by reference in its entirety, reported variant KGF proteins having heparin binding activity even after deleting 3, 8, or 27 amino-terminal amino acid residues. Similarly, Interferon gamma exhibited up to ten times higher activity after deleting 8-10 amino acid residues from the carboxy terminus of this protein. (Dobeli et al., *J. Biotechnology* 7:199-216 (1988), incorporated herein by reference in its entirety.)

As stated above, polypeptide variants include, e.g., modified polypeptides. Modifications include, e.g., acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation (Mei et al., Blood 116:270-79 (2010), which is incorporated herein by reference in its entirety), proteolytic processing, phosphorylation, prenylation, racemization, selenoylation, sulfation, transfer-RNA mediated addition of amino acids to proteins such as arginylation, and ubiquitination. In some embodiments, FVII is modified, e.g., pegylated, at any convenient location. In some embodiments, FVII is pegylated at a surface exposed amino acid of Factor VII, preferably a surface exposed.

Fusion Compounds Linked to FIX

In various embodiments, the procoagulant compound of the present disclosure and/or the immunoglobulin constant region or a portion thereof (a first immunoglobulin constant region or a portion thereof and/or a second immunoglobulin constant region or a portion thereof) is covalently linked to FIX or a variant or derivative thereof.

In one example, the fusion compound of the present disclosure includes the procoagulant compound covalently linked to an immunoglobulin constant region or a portion thereof (e.g., Fc) and a FIX-heterologous moiety construct (e.g., FIX-Fc).

"Factor IX" or "FIX," as used herein, means functional Factor IX polypeptide in its normal role in coagulation, unless otherwise specified. Thus, the term Factor IX includes FIX variant polypeptides that are functional and the polynucleotides that encode such functional variant polypeptides. Factor IX polypeptides can be the human, bovine, porcine, canine, feline, and murine Factor IX polypeptides. The full length polypeptide and polynucleotide sequences of Factor IX are known, as are many functional variants, e.g., fragments, mutants and modified versions. Factor IX polypeptides include full-length Factor IX, full-length Factor IX minus Met at the N-terminus, mature Factor IX (minus the signal sequence), and mature Factor IX with an additional Met at the N-terminus.

The FIX may be at least 85%, 90%, 95%, 96%, 97%, 98% or 99% identical to a FIX amino acid sequence without a signal sequence (e.g., amino acids 47 to 461 of SEQ ID NO:8). The FIX may be identical to a FIX amino acid sequence without a signal sequence (e.g., amino acids 47 to 461 of SEQ ID NO:8).

The FIX may be at least 85%, 90%, 95%, 96%, 97%, 98% or 99% identical to a FIX amino acid sequence with a signal sequence (e.g., amino acids 1 to 461 of SEQ ID NO:8). The FIX may be identical to a FIX amino acid sequence with a signal sequence (e.g., amino acids 1 to 461 of SEQ ID NO:8).

In one example, FIX is linked to Fc. Exemplary FIX-Fc amino acid and DNA sequences include SEQ ID NOs:7 and 8, with or without its signal sequence.

The FIX-Fc polypeptide may comprise a sequence at least 85%, 90%, 95%, 96%, 97%, 98% or 99% identical to the FIX and Fc amino acid sequences without a signal sequence (amino acids 47 to 688 of SEQ ID NO:8) or at least 85%, 90%, 95%, 96%, 97%, 98% or 99% identical to the Factor IX and Fc amino acid sequence with a signal sequence (amino acids 1 to 688 of SEQ ID NO:8).

The FIX-Fc polypeptide may comprise a sequence identical to the Factor IX and Fc amino acid sequence without a signal sequence (amino acids 47 to 688 of SEQ ID NO:8) or identical to the Factor IX and Fc amino acid sequence with a signal sequence (amino acids 1 to 688 of SEQ ID NO:8).

A great many functional FIX variants are known. International publication number WO 02/040544 A3, which is herein incorporated by reference in its entirety, discloses mutants that exhibit increased resistance to inhibition by heparin at page 4, lines 9-30 and page 15, lines 6-31. International publication number WO 03/020764 A2, which is herein incorporated by reference in its entirety, discloses Factor IX mutants with reduced T cell immunogenicity in Tables 2 and 3 (on pages 14-24), and at page 12, lines 1-27. International publication number WO 2007/149406 A2, which is herein incorporated by reference in its entirety, discloses functional mutant Factor IX molecules that exhibit increased protein stability, increased in vivo and in vitro half life, and increased resistance to proteases at page 4, line 1 to page 19, line 11. WO 2007/149406 A2 also discloses chimeric and other variant Factor IX molecules at page 19, line 12 to page 20, line 9. International publication number WO 08/118507 A2, which is herein incorporated by reference in its entirety, discloses Factor IX mutants that exhibit increased clotting activity at page 5, line 14 to page 6, line 5. International publication number WO 09/051717 A2, which is herein incorporated by reference in its entirety, discloses Factor IX mutants having an increased number of N-linked and/or O-linked glycosylation sites, which results in an increased half life and/or recovery at page 9, line 11 to page 20, line 2. International publication number WO 09/137254 A2, which is herein incorporated by reference in its entirety, also discloses Factor IX mutants with increased numbers of glycosylation sites at page 2, paragraph [006] to page 5, paragraph [011] and page 16, paragraph [044] to page 24, paragraph [057]. International publication number WO 09/130198 A2, which is herein incorporated by reference in its entirety, discloses functional mutant Factor IX molecules that have an increased number of glycosylation sites, which result in an increased half life, at page 4, line 26 to page 12, line 6. International publication number WO 09/140015 A2, which is herein incorporated by reference in its entirety, discloses functional Factor IX mutants that an increased number of Cys residues, which may be used for polymer (e.g., PEG) conjugation, at page 11, paragraph [0043] to page 13, paragraph [0053].

In addition, hundreds of non-functional mutations in Factor IX have been identified in hemophilia patients, many of which are disclosed in Table 1, at pages 11-14 of International publication number WO 09/137254 A2, which is herein incorporated by reference in its entirety. Such non-functional mutations are not included in the invention, but provide additional guidance for which mutations are more or less likely to result in a functional Factor IX polypeptide.

Variant FIX polynucleotides may comprise, or alternatively consist of, a nucleotide sequence which is at least 85%, 90%, 95%, 96%, 97%, 98% or 99% identical to, for example, the nucleotide coding sequence in SEQ ID NO: 7 (the Factor IX portion, the Fc portion, individually or together) or the complementary strand thereto, the nucleotide coding sequence of known mutant and recombinant Factor IX or Fc such as those disclosed in the publications and patents cited herein or the complementary strand thereto, a nucleotide sequence encoding the polypeptide of SEQ ID NO: 8 (the Factor IX portion, the Fc portion, individually or together), and/or polynucleotide fragments of any of these nucleic acid molecules (e.g., those fragments described herein). Polynucleotides which hybridize to these nucleic acid molecules under stringent hybridization conditions or lower stringency conditions are also included as variants, as are polypeptides encoded by these polynucleotides as long as they are functional.

Variant FIX polypeptides may comprise, or alternatively consist of, an amino acid sequence which is at least 85%, 90%, 95%, 96%, 97%, 98%, 99% identical to, for example, the polypeptide sequence shown in SEQ ID NO: 8 (the Factor IX portion, the Fc portion, individually or together), and/or polypeptide fragments of any of these polypeptides (e.g., those fragments described herein).

Fusion Compounds Linked to Platelet-Targeting Moiety (PTM)

In various embodiments, the procoagulant compound of the present disclosure is covalently linked to a PTM (e.g., PDG-13) or a PTM-heterologous moiety construct. In various embodiments the procoagulant compound of the present disclosure is covalently linked to a platelet targeting moiety.

Linking the fusion compound of the present disclosure to a platelet targeting moiety can be useful for targeting the fusion to the surface of platelets (e.g., in vivo). In one example, the fusion compound comprising the procoagulant compound is targeted to platelets in order to enhance its efficacy by localizing the procoagulant compound to the site of coagulation using a "targeting moiety" which binds to a molecule expressed on platelets. In addition to increasing the local concentration through the PTM, the concomitant interaction of the procoagulant compound with FIXa may stabilize FIX association with the Xase complex on platelet surfaces, similar to the mechanism of action of FVIIIa. The targeted molecules cannot be expressed on cells or tissues other than platelets, i.e., the targeting moieties specifically bind to platelets. Linking the procoagulant compound or an immunoglobulin constant region or a portion thereof to the targeting moiety may enhance its biological activity. This strategy may reduce the procoagulant compound dose necessary to obtain a desired pharmaceutical effect, and thus can reduce potential side effects that the compound may have. Accordingly, in one example, the fusion compound of the present disclosure bind (e.g., specifically) to platelets.

In one example, the targeting moiety binds to receptors/conformations found on resting platelets. By doing so, sites for coagulation could be primed for enhanced efficacy. Targeting such molecule may also extend half life of the compound and/or prevent clearance. Exemplary platelet targeting moieties according to this embodiment include GpIb (e.g., GpIbalpha) of the GpIbN/IX complex, GpVI, and nonactive forms of GPIIb/IIIa.

In another example, the platelet targeting moiety binds to receptors/conformations only found on activated platelets in order to localize the procoagulant compound to a site of active coagulation. Exemplary such molecules include the active form of GpIIb/IIIa as well as CD62P.

In another embodiment, the platelet targeting moiety selectively binds to a target selected from the group consisting of: P selectin, GMP-33, LAMP-1, LAMP-2, CD40L, and LOX-1.

The platelet targeting moiety can be, e.g., MB9, SCE5, scFv, AP3, or peptides (e.g., "RGD" peptides) targeting GPIIb/IIIa, a fatty acid or small molecule capable of inserting into plasma membranes, OS1, OS2, and PS4 targeting GP1b. In one embodiment, the platelet targeting moiety is OS1, OS2 and PS4 targeting GP1b.

In another embodiment, the platelet targeting moiety is a moiety that binds to GPIIb/IIa (e.g., PDG-13).

In one example, the fusion compound of the present disclosure includes a platelet targeting moiety-heterologous moiety construct (e.g., PTM-Fc) and the procoagulant compound covalently linked to an immunoglobulin constant region or a portion thereof (e.g., Fc).

In one embodiment, the platelet targeting moiety comprises at least one of an antigen binding site (e.g., an antigen binding site of an antibody, antibody variant, or antibody fragment), a polypeptide, a receptor binding portion of ligand, or a ligand binding portion of a receptor which specifically binds to platelets, e.g., resting or activated platelets. Exemplary targeting moieties include scFv molecules or peptides which bind to molecules to be targeted. In one embodiment, the targeting moiety binds to resting platelets. In one embodiment, the targeting moiety selectively binds to activated platelets.

In one embodiment, the targeting moiety selectively binds to a target selected from the group consisting of: GPIba, GPVI, and the nonactive form of GPIIb/IIIa. In another embodiment, the targeting moiety selectively binds to a target selected from the group consisting of: GPIIb/IIIa, P selectin, GMP-33, LAMP-1, LAMP-2, CD40L, and LOX-1. Examples of platelet targeting moieties are described below.

Antigen Binding Sites

In certain embodiments, the platelet targeting moiety is an antigen binding portion (e.g., binding site) of an antibody. In one embodiment, the antigen binding portion targets the composition to platelets In other embodiments, a binding site of a polypeptide of the invention may comprise an antigen binding fragment. The term "antigen-binding portion" refers to a polypeptide fragment of an immunoglobulin, antibody, or antibody variant which binds antigen or competes with intact antibody (i.e., with the intact antibody from which they were derived) for antigen binding (i.e., specific binding). For example, said antigen binding fragments can be derived from any of the antibodies or antibody variants described supra. Antigen binding portions can be produced by recombinant or biochemical methods that are well known in the art. Exemplary antigen-binding fragments include Fv, Fab, Fab', and (Fab')$_2$ as well as scFv molecules.

In other embodiments, the targeting moiety is a binding site from a single chain binding molecule (e.g., a single chain variable region or scFv). Techniques described for the production of single chain antibodies (U.S. Pat. No. 4,694,778; Bird, Science 242:423-442 (1988); Huston et al., *Proc. Natl. Acad. Sci. USA* 85:5879-5883 (1988); and Ward et al., *Nature* 334:544-554 (1989)) can be adapted to produce single chain binding molecules. Single chain antibodies are formed by linking the heavy and light chain fragments of the Fv region via an amino acid bridge, resulting in a single chain antibody. Techniques for the assembly of functional Fv fragments in *E. coli* may also be used (Skerra et al., *Science* 242:1038-1041 (1988)).

In certain embodiments, the platelet targeting moiety includes one or more binding sites or regions comprising or consisting of a single chain variable region sequence (scFv). Single chain variable region sequences comprise a single polypeptide having one or more antigen binding sites, e.g., a $V_L$ domain linked by a flexible linker to a $V_H$ domain. The VL and/or VH domains may be derived from any of the antibodies or antibody variants described supra. ScFv molecules can be constructed in a $V_H$-linker-$V_L$ orientation or $V_L$-linker-$V_H$ orientation. The flexible linker that links the $V_L$ and $V_H$ domains that make up the antigen binding site preferably comprises from about 10 to about 50 amino acid residues. In one embodiment, the polypeptide linker is a gly-ser polypeptide linker. An exemplary gly/ser polypeptide linker is of the formula (Gly4Ser)n (SEQ ID NO: 24), wherein n is a positive integer (e.g., 1, 2, 3, 4, 5, or 6). Other polypeptide linkers are known in the art. Antibodies having single chain variable region sequences (e.g. single chain Fv antibodies) and methods of making said single chain antibodies are well-known in the art (see e.g., Ho et al. 1989. *Gene* 77:51; Bird et al. 1988 *Science* 242:423; Pantoliano et al. 1991. *Biochemistry* 30:10117; Milenic et al. 1991. *Cancer Research* 51:6363; Takkinen et al. 1991. *Protein Engineering* 4:837).

In certain embodiments, a scFv molecule is a stabilized scFv molecule. In one embodiment, the stabilized scFv molecule may comprise a scFv linker interposed between a $V_H$ domain and a $V_L$ domain, wherein the $V_H$ and $V_L$ domains are linked by a disulfide bond between an amino acid in the $V_H$ and an amino acid in the $V_1$ domain. In other embodiments, the stabilized scFv molecule may comprise a scFv linker having an optimized length or composition. In yet other embodiments, the stabilized scFv molecule may comprise a $V_H$ or $V_L$ domain having at least one stabilizing amino acid substitution(s). In yet another embodiment, a stabilized scFv molecule may have at least two of the above listed stabilizing features.

Stabilized scFv molecules have improved protein stability or impart improved protein stability to the polypeptide to which it is operably linked. Preferred scFv linkers of the invention improve the thermal stability of a polypeptide of the invention by at least about 2° C. or 3° C. as compared to a conventional polypeptide Comparisons can be made, for example, between the scFv molecules of the invention. In certain embodiments, the stabilized scFv molecule comprises a (Gly$_4$Ser)$_4$ (SEQ ID NO: 23) scFv linker and a disulfide bond which links $V_H$ amino acid 44 and $V_L$ amino acid 100. Other exemplary stabilized scFv molecules which may be employed in the polypeptides of the invention are described in U.S. patent application Ser. No. 11/725,970, filed on Mar. 19, 2007, incorporated herein by reference in its entirety.

In one example, the platelet targeting moiety includes a variable region or portion thereof (e.g. a VL and/or VH domain) derived from an antibody using art recognized protocols. For example, the variable domain may be derived from antibody produced in a non-human mammal, e.g., murine, guinea pig, primate, rabbit or rat, by immunizing the mammal with the antigen or a fragment thereof. See Harlow & Lane, supra, incorporated by reference for all purposes. The immunoglobulin may be generated by multiple subcutaneous or intraperitoneal injections of the relevant antigen (e.g., purified tumor associated antigens or cells or cellular extracts comprising such antigens) and an adjuvant. This immunization typically elicits an immune response that comprises production of antigen-reactive antibodies from activated splenocytes or lymphocytes.

Optionally, antibodies may be screened for binding to platelets of a specific activation state or to a specific region or desired fragment of the antigen without binding to other nonoverlapping fragments of the antigen. The latter screening can be accomplished by determining binding of an antibody to a collection of deletion mutants of the antigen and determining which deletion mutants bind to the antibody. Binding can be assessed, for example, by Western blot or ELISA. The smallest fragment to show specific binding to the antibody defines the epitope of the antibody. Alternatively, epitope specificity can be determined by a competition assay is which a test and reference antibody compete for binding to the antigen. If the test and reference antibodies compete, then they bind to the same epitope or epitopes sufficiently proximal such that binding of one antibody interferes with binding of the other.

In other embodiments, the binding site is derived from a fully human antibody. Human or substantially human antibodies may be generated in transgenic animals (e.g., mice) that are incapable of endogenous immunoglobulin production (see e.g., U.S. Pat. Nos. 6,075,181, 5,939,598, 5,591,669 and 5,589,369, each of which is incorporated herein by reference). Another means of generating human antibodies using SCID mice is disclosed in U.S. Pat. No. 5,811,524 which is incorporated herein by reference. It will be appreciated that the genetic material associated with these human antibodies may also be isolated and manipulated as described herein.

Yet another highly efficient means for generating recombinant antibodies is disclosed by Newman, *Biotechnology*, 10: 1455-1460 (1992). Specifically, this technique results in the generation of primatized antibodies that contain monkey variable domains and human constant sequences. This reference is incorporated by reference in its entirety herein. Moreover, this technique is also described in commonly assigned U.S. Pat. Nos. 5,658,570, 5,693,780 and 5,756,096 each of which is incorporated herein by reference.

In another embodiment, a variable region domain of an altered antibody of the invention consists of a $V_H$ domain, e.g., derived from camelids, which is stable in the absence of a $V_L$ chain (Hamers-Castennan et al. (1993). *Nature*, 363:446; Desmyter et al. (1996). *Nat. Struct. Biol.* 3: 803; Decanniere et al. (1999). *Structure*, 7:361; Davies et al. (1996). *Protein Eng.*, 9:531; Kortt et al. (1995). *J. Protein Chem.*, 14:167).

Further, the platelet targeting moiety may comprise a variable domain or CDR derived from a fully murine, fully human, chimeric, humanized, non-human primate or primatized antibody. Non-human antibodies, or fragments or domains thereof, can be altered to reduce their immunogenicity using art recognized techniques.

In one embodiment, the variable domains are altered by at least partial replacement of one or more CDRs. In another embodiment, variable domains can optionally be altered, e.g., by partial framework region replacement and sequence changing. In making a humanized variable region the CDRs may be derived from an antibody of the same class or even subclass as the antibody from which the framework regions are derived, however, it is envisaged that the CDRs will be derived from an antibody of different class and from an antibody from a different species. It may not be necessary to replace all of the CDRs with the complete CDRs from the donor variable region to transfer the antigen binding capacity of one variable domain to another. Rather, it may only be necessary to transfer those residues that are necessary to maintain the activity of the binding domain. Given the explanations set forth in U.S. Pat. Nos. 5,585,089, 5,693,761 and 5,693,762, it will be well within the competence of those skilled in the art, either by carrying out routine experimentation or by trial and error testing to obtain a functional antigen binding site with reduced immunogenicity.

In other aspects, the polypeptides of the invention may comprise antigen binding sites, or portions thereof, derived from modified forms of antibodies. Exemplary such forms include, e.g., minibodies, diabodies, triabodies, nanobodies, camelids, Dabs, tetravalent antibodies, intradiabodies (e.g., Jendreyko et al. 2003. *J. Biol. Chem.* 278:47813), fusion compounds (e.g., antibody cytokine fusion compounds, proteins fused to at least a portion of an Fc receptor), and bispecific antibodies. Other modified antibodies are described, for example in U.S. Pat. No. 4,745,055; EP 256,654; Faulkner et al., *Nature* 298:286 (1982); EP 120, 694; EP 125,023; Morrison, *J. Immun.* 123:793 (1979); Kohler et al., *Proc. Natl. Acad. Sci. USA* 77:2197 (1980); Raso et al., *Cancer Res.* 41:2073 (1981); Morrison et al., *Ann. Rev. Immunol.* 2:239 (1984); Morrison, *Science* 229: 1202 (1985); Morrison et al., *Proc. Natl. Acad. Sci. USA* 81:6851 (1984); EP 255,694; EP 266,663; and WO 88/03559. Reassorted immunoglobulin chains also are known. See, for example, U.S. Pat. No. 4,444,878; WO 88/03565; and EP 68,763 and references cited therein.

In another embodiment, the platelet targeting moiety includes an antigen binding site or region which is a diabody or an antigen binding site derived therefrom. Diabodies are dimeric, tetravalent molecules each having a polypeptide similar to scFv molecules, but usually having a short (e.g., less than 10 and preferably 1-5) amino acid residue linker connecting both variable domains, such that the $V_L$ and $V_H$ domains on the same polypeptide chain cannot interact. Instead, the $V_L$ and $V_H$ domain of one polypeptide chain interact with the $V_H$ and $V_L$ domain (respectively) on a second polypeptide chain (see, for example, WO 02/02781). In one embodiment, an immature polypeptide of the invention comprises a diabody which is operably linked to the N-terminus and/or C-terminus of at least one geneticallyfused Fc region (i.e., scFc region).

Exemplary single-domain antibodies employed in the binding molecules of the invention include, for example, the Camelid heavy chain variable domain (about 118 to 136 amino acid residues) as described in Hamers-Casterman, et al., *Nature* 363:446-448 (1993), and Dumoulin, et al., *Protein Science* 11:500-515 (2002). Other exemplary single domain antibodies include single VH or VL domains, also known as DABS® (Domantis Ltd., Cambridge, UK). Yet other single domain antibodies include shark antibodies (e.g., shark Ig-NARs). Shark Ig-NARs comprise a homodimer of one variable domain (V-NAR) and five C-like constant domains (C-NAR), wherein diversity is concentrated in an elongated CDR3 region varying from 5 to 23 residues in length. In camelid species (e.g., llamas), the heavy chain variable region, referred to as VHH, forms the entire antigen-binding domain. Methods for making single domain binding molecules are described in U.S. Pat. Nos. 6,005,079 and 6,765,087, both of which are incorporated herein by reference. Exemplary single domain antibodies comprising VHH domains include NANOBODIES® (Ablynx Nev., Ghent, Belgium).

Exemplary antibodies from which binding sites can be derived for use in the binding molecules of the invention are known in the art. Antibodies known to bind to platelets can be used to derive binding sites, for example, the MB9 antibody described in US 2007/0218067 or the variable region or an scFv molecule comprising the variable region can be used as a targeting moiety in a construct of the invention.

Non-Immunoglobulin Platelet Binding Molecules

In certain other embodiments, the targeting moiety comprise one or more binding sites derived from a non-immunoglobulin binding molecule. As used herein, the term "non-immunoglobulin binding molecules" are binding molecules whose binding sites comprise a portion (e.g., a scaffold or framework) which is derived from a polypeptide other than an immunoglobulin, but which may be engineered (e.g., mutagenized) to confer a desired binding specificity.

Other examples of binding molecules comprising binding sites not derived from antibody molecules include receptor binding sites and ligand binding sites which bind to platelets.

Non-immunoglobulin binding molecules may be identified by selection or isolation of a target-binding variant from a library of binding molecules having artificially diversified binding sites. Diversified libraries can be generated using completely random approaches (e.g., error-prone PCR, exon shuffling, or directed evolution) or aided by art-recognized design strategies. For example, amino acid positions that are usually involved when the binding site interacts with its cognate target molecule can be randomized by insertion of degenerate codons, trinucleotides, random peptides, or entire loops at corresponding positions within the nucleic acid which encodes the binding site (see e.g., U.S. Pub. No. 20040132028). The location of the amino acid positions can be identified by investigation of the crystal structure of the binding site in complex with the target molecule. Candidate positions for randomization include loops, flat surfaces, helices, and binding cavities of the binding site. In certain embodiments, amino acids within the binding site that are likely candidates for diversification can be identified using techniques known in the art. Following randomization, the diversified library may then be subjected to a selection or screening procedure to obtain binding molecules with the desired binding characteristics, e.g., specific binding platelets using methods known in the art. Selection can be achieved by art-recognized methods such as phage display, yeast display, or ribosome display. In one embodiment, molecules known in the art to bind to platelets may be employed in the constructs of the invention. For example, peptides which bind to GPIba as described in the art (e.g., PS4, 0S1, or 0S2) may be used (Benard et al. 2008. *Biochemistry* 47:4674-4682).

In one example, the targeting moieties is linked to an Fc moiety.

In still other embodiments, the fusion compound further comprises a scFc linker (X), which links the first immunoglobulin constant region or a portion thereof to the second immunoglobulin constant region or a portion thereof. The term "scFv linker" as used herein means a processable linker comprising at least one intracellular processing site and a linker. In one embodiment, an intracellular processing site is interposed between the procoagulant compound and the linker, wherein the linker links the compound with the first immunoglobulin constant region or a portion thereof. In another embodiment, an intracellular processing site is interposed between the linker and the first immunoglobulin constant region or a portion thereof, wherein the linker links the compound with the first immunoglobulin constant region or a portion thereof. In other embodiments, an intracellular processing site is interposed between the first immunoglobulin constant region or a portion thereof and the linker, wherein the linker links the first immunoglobulin constant region or a portion thereof and the second immunoglobulin constant region or a portion thereof. In still other embodiments, an intracellular processing site is interposed between the linker and the second immunoglobulin constant region or a portion thereof, wherein the linker links the first immunoglobulin constant region or a portion thereof and the second immunoglobulin constant region or a portion thereof. In yet other embodiments, the fusion compound can have more than one intracellular processing site, two, three, or four. The intracellular processing site inserted therein can be processed (cleaved) by an intracellular processing enzyme upon expression in a host cell, thereby allowing formation of a zymogen-like heterodimer. Examples of the intracellular processing enzymes include furin, a yeast Kex2, PCSK1 (also known as PC1/Pc3), PCSK2 (also known as PC2), PCSK3 (also known as furin or PACE), PCSK4 (also known as PC4), PCSK5 (also known as PC5 or PC6), PCSK6 (also known as PACE4), or PCSK7 (also known as PC7/LPC, PC8, or SPC7). Other processing sites are known in the art.

Half-Life Extender Heterologous Moieties

In certain aspects, the procoagulant compound can be fused to a heterologous moiety, forming a fusion protein. In one embodiment, a heterologous moiety is a half-like extender, i.e., a heterologous moiety which increases the in vivo half-life of the procoagulant compound with respect to the in vivo half-life of the corresponding fusion compound lacking such heterologous moiety. The in vivo half-life can be determined by any method known to those of skill in the art, e.g., activity assays (chromogenic assay or one stage clotting aPTT assay), ELISA, etc.

In some embodiments, the presence of one or more half-life extenders results in the half-life of the procoagulant compound to be increased compared to the half life of the corresponding procoagulant compound lacking such one or more half-life extenders. The half-life of the procoagulant compound comprising a half-life extender is at least about 1.5 times, at least about 2 times, at least about 2.5 times, at least about 3 times, at least about 4 times, at least about 5 times, at least about 6 times, at least about 7 times, at least about 8 times, at least about 9 times, at least about 10 times, at least about 11 times, or at least about 12 times longer than the in vivo half-life of the corresponding procoagulant compound lacking such half-life extender.

In one embodiment, the half-life of the procoagulant compound linked to a half-life extender is about 1.5-fold to about 20-fold, about 1.5 fold to about 15 fold, or about 1.5 fold to about 10 fold longer than the in vivo half-life of the corresponding procoagulant compound not linked to such half-life extender. In another embodiment, the half-life of the procoagulant compound linked to a half-life extender is extended about 2-fold to about 10-fold, about 2-fold to about 9-fold, about 2-fold to about 8-fold, about 2-fold to about 7-fold, about 2-fold to about 6-fold, about 2-fold to about 5-fold, about 2-fold to about 4-fold, about 2-fold to about 3-fold, about 2.5-fold to about 10-fold, about 2.5-fold to about 9-fold, about 2.5-fold to about 8-fold, about 2.5-fold to about 7-fold, about 2.5-fold to about 6-fold, about 2.5-fold to about 5-fold, about 2.5-fold to about 4-fold, about 2.5-fold to about 3-fold, about 3-fold to about 10-fold, about 3-fold to about 9-fold, about 3-fold to about 8-fold, about 3-fold to about 7-fold, about 3-fold to about 6-fold, about 3-fold to about 5-fold, about 3-fold to about 4-fold, about 4-fold to about 6 fold, about 5-fold to about 7-fold, or about 6-fold to about 8 fold as compared to the in vivo half-life of the corresponding procoagulant compound not linked to such half-life extender.

In other embodiments, the half-life of the procoagulant compound linked to a half-life extender is at least about 10 hours, at least about 17 hours, at least about 18 hours, at least about 19 hours, at least about 20 hours, at least about 21 hours, at least about 22 hours, at least about 23 hours, at least about 24 hours, at least about 25 hours, at least about 26 hours, at least about 27 hours, at least about 28 hours, at least about 29 hours, at least about 30 hours, at least about 31 hours, at least about 32 hours, at least about 33 hours, at least about 34 hours, at least about 35 hours, at least about 36 hours, at least about 48 hours, at least about 60 hours, at least about 72 hours, at least about 84 hours, at least about 96 hours, or at least about 108 hours.

In still other embodiments, the half-life of the procoagulant compound linked to a half-life extender is about 15 hours to about two weeks, about 16 hours to about one week, about 17 hours to about one week, about 18 hours to about one week, about 19 hours to about one week, about 20 hours to about one week, about 21 hours to about one week, about 22 hours to about one week, about 23 hours to about one week, about 24 hours to about one week, about 36 hours to about one week, about 48 hours to about one week, about 60 hours to about one week, about 24 hours to about six days, about 24 hours to about five days, about 24 hours to about four days, about 24 hours to about three days, or about 24 hours to about two days.

In some embodiments, the average half-life per subject of the procoagulant compound linked to a half-life extender is about 15 hours, about 16 hours, about 17 hours, about 18 hours, about 19 hours, about 20 hours, about 21 hours, about 22 hours, about 23 hours, about 24 hours (1 day), about 25 hours, about 26 hours, about 27 hours, about 28 hours, about 29 hours, about 30 hours, about 31 hours, about 32 hours, about 33 hours, about 34 hours, about 35 hours, about 36 hours, about 40 hours, about 44 hours, about 48 hours (2 days), about 54 hours, about 60 hours, about 72 hours (3 days), about 84 hours, about 96 hours (4 days), about 108 hours, about 120 hours (5 days), about six days, about seven days (one week), about eight days, about nine days, about 10 days, about 11 days, about 12 days, about 13 days, or about 14 days.

(a) Low Complexity Polypeptides

In certain aspects, the procoagulant compound comprising an amino acid sequence at least 95% identical to SEQ ID NO: 3 is linked to a heterologous moiety comprising a polypeptide with low compositional and/or structural complexity (e.g., a disordered polypeptide with no secondary or tertiary structure in solution under physiologic conditions).

(b) CTP

In certain aspects, the procoagulant compound comprising an amino acid sequence at least 95% identical to SEQ ID NO: 3 is linked to a heterologous moiety comprising a 13 subunit of C-terminal peptide (CTP) of the human chorionic gonadotropin or fragment, variant, or derivative thereof. One or more CTP peptides inserted into a recombinant protein is known to increase the in vivo half-life of that protein. See, e.g., U.S. Pat. No. 5,712,122, incorporated by reference herein in its entirety. Exemplary CTP peptides include DPRFQDSSSSKAPPPSLPSPSRLPGPSDTPIL (SEQ ID NO: 27) or SSSSKAPPPSLPSPSRLPGPSDT-PILPQ (SEQ ID NO: 28). See, e.g., U.S. Patent Application Publication No. US 2009/0087411 A1, incorporated herein by reference in its entirety.

(c) Albumin or Fragment, or Variant Thereof

In certain embodiments, the procoagulant compound comprising an amino acid sequence at least 95% identical to SEQ ID NO: 3 is linked to a heterologous moiety comprising albumin or a functional fragment thereof. Human serum albumin (HSA, or HA), a protein of 609 amino acids in its full-length form, is responsible for a significant proportion of the osmotic pressure of serum and also functions as a carrier of endogenous and exogenous ligands. The term "albumin" as used herein includes full-length albumin or a functional fragment, variant, derivative, or analog thereof. Examples of albumin or the fragments or variants thereof are disclosed in US Pat. Publ. Nos. 2008/0194481A1, 2008/0004206 A1, 2008/0161243 A1, 2008/0261877 A1, or 2008/0153751 A1 or PCT Appl. Publ. Nos. 2008/033413 A2, 2009/058322 A1, or 2007/021494 A2, which are incorporated herein by reference in their entireties.

In one embodiment, the heterologous moiety is albumin, a fragment, or a variant thereof which is further linked to a heterologous moiety selected from the group consisting of an immunoglobulin constant region or portion thereof (e.g., an Fc region), a PAS sequence, HES, and PEG.

(d) Albumin Binding Moiety

In certain embodiments, the procoagulant compound comprising an amino acid sequence at least 95% identical to SEQ ID NO: 3 is linked to a heterologous moiety, which is an albumin binding moiety, which comprises an albumin binding peptide, a bacterial albumin binding domain, an albumin-binding antibody fragment, or any combinations thereof.

For example, the albumin binding protein can be a bacterial albumin binding protein, an antibody or an antibody fragment including domain antibodies (see U.S. Pat. No. 6,696,245). An albumin binding protein, for example, can be a bacterial albumin binding domain, such as the one of streptococcal protein G (Konig, T. and Skerra, A. (1998) *J. Immunol. Methods* 218, 73-83). Other examples of albumin binding peptides that can be used as conjugation partner are, for instance, those having a Cys-$Xaa_1$-$Xaa_2$-$Xaa_3$-$Xaa_4$-Cys (SEQ ID NO: 32) consensus sequence, wherein $Xaa_1$ is Asp, Asn, Ser, Thr, or Trp; $Xaa_2$ is Asn, Gln, His, Ile, Leu, or Lys; $Xaa_3$ is Ala, Asp, Phe, Trp, or Tyr; and $Xaa_4$ is Asp, Gly, Leu, Phe, Ser, or Thr as described in US patent application 2003/0069395 or Dennis et al. (Dennis et al. (2002) *J. Biol. Chem.* 277, 35035-35043).

Domain 3 from streptococcal protein G, as disclosed by Kraulis et al., *FEBS Lett.* 378:190-194 (1996) and Linhult et al., *Protein Sci.* 11:206-213 (2002) is an example of a bacterial albumin-binding domain. Examples of albumin-binding peptides include a series of peptides having the core sequence DICLPRWGCLW (SEQ ID NO:29). See, e.g., Dennis et al., J. Biol. Chem. 2002, 277: 35035-35043 (2002). Examples of albumin-binding antibody fragments are disclosed in Muller and Kontermann, Curr. Opin. Mol. Ther. 9:319-326 (2007); Roovers et al., Cancer Immunol. Immunother. 56:303-317 (2007), and Holt et al., Prot. Eng. Design Sci., 21:283-288 (2008), which are incorporated herein by reference in their entireties. An example of such albumin binding moiety is 2-(3-maleimidopropanamido)-6-(4-(4-iodophenyl)butanamido) hexanoate ("Albu" tag) as disclosed by Trussel et al., Bioconjugate Chem. 20:2286-2292 (2009).

(e) PAS Sequence

In other embodiments, the procoagulant compound comprising an amino acid sequence at least 95% identical to SEQ ID NO: 3 is linked to a heterologous moiety, which comprises a PAS sequence. A PAS sequence, as used herein, means an amino acid sequence comprising mainly alanine and serine residues or comprising mainly alanine, serine, and proline residues, the amino acid sequence forming random coil conformation under physiological conditions. Accordingly, the PAS sequence is a building block, an amino acid polymer, or a sequence cassette comprising, consisting essentially of, or consisting of alanine, serine, and proline which can be used as a part of the heterologous moiety in the procoagulant compound. Yet, the skilled person is aware that an amino acid polymer also may form random coil conformation when residues other than alanine, serine, and proline are added as a minor constituent in the PAS sequence. The term "minor constituent" as used herein means that amino acids other than alanine, serine, and proline may be added in the PAS sequence to a certain degree, e.g., up to about 12%, i.e., about 12 of 100 amino acids of the PAS sequence, up to about 10%, i.e. about 10 of 100 amino acids of the PAS sequence, up to about 9%, i.e., about 9 of 100 amino acids, up to about 8%, i.e., about 8 of 100 amino acids, about 6%, i.e., about 6 of 100 amino acids, about 5%, i.e., about 5 of 100 amino acids, about 4%. i.e., about 4 of 100 amino acids, about 3%, i.e., about 3 of 100 amino acids, about 2%, i.e., about 2 of 100 amino acids, about 1%, i.e., about 1 of 100 of the amino acids. The amino acids different from alanine, serine and proline may be selected from the group consisting of Arg, Asn, Asp, Cys, Gln, Glu, Gly, His, Ile, Leu, Lys, Met, Phe, Thr, Trp, Tyr, and Val.

Under physiological conditions, the PAS sequence stretch forms a random coil conformation and thereby can mediate an increased in vivo and/or in vitro stability to procoagulant compound. Since the random coil domain does not adopt a stable structure or function by itself, the biological activity mediated by the Pep1 and/or Pep2 polypeptides in the procoagulant compound is essentially preserved. In other embodiments, the PAS sequences that form random coil domain are biologically inert, especially with respect to proteolysis in blood plasma, immunogenicity, isoelectric point/electrostatic behaviour, binding to cell surface receptors or internalisation, but are still biodegradable, which provides clear advantages over synthetic polymers such as PEG.

Non-limiting examples of the PAS sequences forming random coil conformation comprise an amino acid sequence selected from the group consisting of ASPAAPAPASPAA-PAPSAPA (SEQ ID NO: 33), AAPASPAPAAPSAPAPAAPS (SEQ ID NO: 34), APSSPSPSAPSSPSPASPSS (SEQ ID NO: 35), APSSPSPSAPSSPSPASPS (SEQ ID NO: 36), SSPSAPSPSSPASPSPSSPA (SEQ ID NO: 37), AAS-PAAPSAPPAAASPAAPSAPPA (SEQ ID NO: 38), and ASAAAPAAASAAASAPSAAA (SEQ ID NO: 39), or any combinations thereof. Additional examples of PAS sequences are known from, e.g., US Pat. Publ. No. 2010/0292130 A1 and PCT Appl. Publ. No. WO 2008/155134 A1.

(f) HAP Sequence

In certain embodiments, the procoagulant compound comprising an amino acid sequence at least 95% identical to SEQ ID NO: 3 is linked to a heterologous moiety, which is a glycine-rich homo-amino-acid polymer (HAP). The HAP sequence can comprise a repetitive sequence of glycine, which has at least 50 amino acids, at least 100 amino acids, 120 amino acids, 140 amino acids, 160 amino acids, 180 amino acids, 200 amino acids, 250 amino acids, 300 amino acids, 350 amino acids, 400 amino acids, 450 amino acids, or 500 amino acids in length. In one embodiment, the HAP sequence is capable of extending half-life of a moiety fused to or linked to the HAP sequence. Non-limiting examples of the HAP sequence includes, but are not limited to $(Gly)_n$ (SEQ ID NO: 40), $(Gly_4Ser)_n$ (SEQ ID NO: 41) or $S(Gly_4Ser)_n$ (SEQ ID NO: 42), wherein n is 1, 2, 3, 4, 5, 6, 7, 8, 9, 10, 11, 12, 13, 14, 15, 16, 17, 18, 19, or 20. In one embodiment, n is 20, 21, 22, 23, 24, 25, 26, 26, 28, 29, 30, 31, 32, 33, 34, 35, 36, 37, 38, 39, or 40. In another embodiment, n is 50, 60, 70, 80, 90, 100, 110, 120, 130, 140, 150, 160, 170, 180, 190, or 200.

(g) Transferrin or Fragment Thereof

In certain embodiments, the procoagulant compound comprising an amino acid sequence at least 95% identical to SEQ ID NO: 3 is linked to a heterologous moiety, which is transferrin or a fragment thereof. Any transferrin may be used to make the conjugates of the invention. As an example, wild-type human Tf (Tf) is a 679 amino acid protein, of approximately 75 KDa (not accounting for glycosylation), with two main domains, N (about 330 amino acids) and C (about 340 amino acids), which appear to originate from a gene duplication. See GenBank accession numbers NM001063, XM002793, M12530, XM039845, XM 039847 and S95936 (www.ncbi.nlm.nih.gov/), all of which are herein incorporated by reference in their entirety. Transferrin comprises two domains, N domain and C domain. N domain comprises two subdomains, N1 domain and N2 domain, and C domain comprises two subdomains, C1 domain and C2 domain.

In one embodiment, the transferrin heterologous moiety includes a transferrin splice variant. In one example, a transferrin splice variant can be a splice variant of human transferrin, e.g., Genbank Accession AAA61140. In another embodiment, the transferrin portion of the chimeric protein includes one or more domains of the transferrin sequence, e.g., N domain, C domain, N1 domain, N2 domain, C1 domain, C2 domain or any combinations thereof.

(h) Polymer, e.g., Polyethylene Glycol (PEG)

In other embodiments, the procoagulant compound comprising an amino acid sequence at least 95% identical to SEQ ID NO: 3 is linked to a heterologous moiety, which is a soluble polymer known in the art, including, but not limited to, polyethylene glycol, ethylene glycol/propylene glycol copolymers, carboxymethylcellulose, dextran, or polyvinyl alcohol. Also provided by the invention are procoagulant compounds of the invention comprising heterologous moieties which may provide additional advantages such as increased solubility, stability and circulating time of the polypeptide, or decreased immunogenicity (see U.S. Pat. No. 4,179,337). Such heterologous moieties for modification can be selected from the group consisting of water soluble polymers including, but not limited to, polyethylene glycol, ethylene glycol/propylene glycol copolymers, carboxymethylcellulose, dextran, and polyvinyl alcohol, poly (alkylene oxide), poly(vinyl pyrrolidone), polyoxazoline, or poly(acryloylmorpholine).

The polymer can be of any molecular weight, and can be branched or unbranched. For polyethylene glycol, in one embodiment, the molecular weight is between about 1 kDa and about 100 kDa for ease in handling and manufacturing. Other sizes may be used, depending on the desired profile (e.g., the duration of sustained release desired, the effects, if any on biological activity, the ease in handling, the degree or lack of antigenicity and other known effects of the polyethylene glycol to a protein or analog). For example, the polyethylene glycol may have an average molecular weight of about 200, 500, 1000, 1500, 2000, 2500, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 25,000, 30,000, 35,000, 40,000, 45,000, 50,000, 55,000, 60,000, 65,000, 70,000, 75,000, 80.000, 85,000, 90,000, 95,000, or 100,000 kDa.

In some embodiments, the polyethylene glycol may have a branched structure. Branched polyethylene glycols are described, for example, in U.S. Pat. No. 5,643,575; Morpurgo et al., Appl. Biochem. Biotechnol. 56:59-72 (1996); Vorobjev et al., *Nucleosides Nucleotides* 18:2745-2750 (1999); and Caliceti et al., *Bioconjug. Chem.* 10:638-646 (1999), each of which is incorporated herein by reference in its entirety.

The number of polyethylene glycol moieties attached to each fusion compound of the invention (i.e., the degree of substitution) may also vary. For example, the PEGylated fusion compound may be linked, on average, to 1, 2, 3, 4, 5, 6, 7, 8, 9, 10, 12, 15, 17, 20, or more polyethylene glycol molecules. Similarly, the average degree of substitution within ranges such as 1-3, 2-4, 3-5, 4-6, 5-7, 6-8, 7-9, 8-10, 9-11, 10-12, 11-13, 12-14, 13-15, 14-16, 15-17, 16-18, 17-19, or 18-20 polyethylene glycol moieties per protein molecule. Methods for determining the degree of substitution are discussed, for example, in Delgado et al., *Crit. Rev. Thera. Drug Carrier Sys.* 9:249-304 (1992).

In one example, the heterologous moiety is a water-soluble polymer, e.g., a straight or branched polyethylene glycol (PEG) moieties, straight or branched polypropylene glycol (PPG) moiety, a hydroxyethyl starch (HES) moiety, or a half-life extension polypeptide (e.g., XTEN; see, e.g., Schellenberger V. et al., *Nat Biotechnol.* 2009 December; 27(12):1186-90, US20100189682, PCT/US07/05952, U.S.

Ser. No. 12/228,859, U.S. Ser. No. 12/646,566, PCT/US08/09787, U.S. Ser. No. 12/699,761, and PCT/US2010/23106, each of which is incorporated herein by reference in its entirety). The polymer can be attached to the N-terminus, the C-terminus of the peptide sequence or an internal amino acid of the compound or the polypeptide. In one example, the polymer is attached to the N-terminal amino acid, e.g. via an amide bond. In another example, the polymer is attached to the C-terminal amino acid via an amide bond. In yet another example, the polymer is attached to the peptide sequence through derivatization of an amino acid side chain located at an internal position of the amino acid sequence. For example, the polymer is attached to the peptide sequence via derivatization of a tyrosine side chain, a lysine side chain or a aspartic acid or glutamic acid side chain.

Suitable methods of PEGylation are disclosed, e.g., in U.S. Pat. No. 5,122,614 to Zalipsky et al., and U.S. Pat. No. 5,539,063 to Hakimi et al., all of which PEGylation methods are incorporated herein by reference. Various molecular weights of PEG may be used, suitably from 1000 Da to 80,000 Da (or from 5000 Da to 60,000 DA). In one example, the PEG is monodisperse, meaning that there is little variation in molecular weight between PEG molecules. PEGylation may improve the solubility and plasma half-life of a peptide.

(i) XTEN Moieties

In certain aspects, the procoagulant compound comprising an amino acid sequence at least 95% identical to SEQ ID NO: 3 ion is covalently linked to at least one heterologous moiety that is or comprises an XTEN polypeptide or fragment, variant, or derivative thereof. As used here "XTEN polypeptide" refers to extended length polypeptides with non-naturally occurring, substantially non-repetitive sequences that are composed mainly of small hydrophilic amino acids, with the sequence having a low degree or no secondary or tertiary structure under physiologic conditions. As a heterologous moiety, XTENs can serve as a half-life extension moiety. In addition, XTEN can provide desirable properties including but are not limited to enhanced pharmacokinetic parameters and solubility characteristics.

The incorporation of a heterologous moiety comprising an XTEN sequence into a conjugate of the invention can confer one or more of the following advantageous properties to the resulting conjugate: conformational flexibility, enhanced aqueous solubility, high degree of protease resistance, low immunogenicity, low binding to mammalian receptors, or increased hydrodynamic (or Stokes) radii.

In certain aspects, an XTEN moiety can increase pharmacokinetic properties such as longer in vivo half-life or increased area under the curve (AUC), so that a fusion compound of the invention stays in vivo and has procoagulant activity for an increased period of time compared to a fusion compound with the same but without the XTEN heterologous moiety.

Examples of XTEN moieties that can be used as heterologous moieties in procoagulant conjugates of the invention are disclosed, e.g., in U.S. Patent Publication Nos. 2010/0239554 A1, 2010/0323956 A1, 2011/0046060 A1, 2011/0046061 A1, 2011/0077199 A1, or 2011/0172146 A1, or International Patent Publication Nos. WO 2010091122 A1, WO 2010144502 A2, WO 2010144508 A1, WO 2011028228 A1, WO 2011028229 A1, or WO 2011028344 A2, each of which is incorporated by reference herein in its entirety.

(j) Hydroxyethyl Starch (HES)

In certain embodiments, the procoagulant compound comprising an amino acid sequence at least 95% identical to SEQ ID NO: 3 is linked to a heterologous moiety, which is hydroxyethyl starch (HES) or a derivative thereof. Hydroxyethyl starch (HES) is a derivative of naturally occurring amylopectin and is degraded by alpha-amylase in the body. HES is a substituted derivative of the carbohydrate polymer amylopectin, which is present in corn starch at a concentration of up to 95% by weight. HES exhibits advantageous biological properties and is used as a blood volume replacement agent and in hemodilution therapy in the clinics (Sommermeyer et al., *Krankenhauspharmazie*, 8(8), 271-278 (1987); and Weidler et al., *Arzneim.-Forschung/Drug Res.*, 41, 494-498 (1991)).

Amylopectin contains glucose moieties, wherein in the main chain alpha-1,4-glycosidic bonds are present and at the branching sites alpha-1,6-glycosidic bonds are found. The physical-chemical properties of this molecule are mainly determined by the type of glycosidic bonds. Due to the nicked alpha-1,4-glycosidic bond, helical structures with about six glucose-monomers per turn are produced. The physico-chemical as well as the biochemical properties of the polymer can be modified via substitution. The introduction of a hydroxyethyl group can be achieved via alkaline hydroxyethylation. By adapting the reaction conditions it is possible to exploit the different reactivity of the respective hydroxy group in the unsubstituted glucose monomer with respect to a hydroxyethylation. Owing to this fact, the skilled person is able to influence the substitution pattern to a limited extent.

HES is mainly characterized by the molecular weight distribution and the degree of substitution. The degree of substitution, denoted as DS, relates to the molar substitution, is known to the skilled people. See Sommermeyer et al., *Krankenhauspharmazie*, 8(8), 271-278 (1987), as cited above, in particular p. 273.

In one embodiment, hydroxyethyl starch has a mean molecular weight (weight mean) of from 1 to 300 kD, from 2 to 200 kD, from 3 to 100 kD, or from 4 to 70 kD, hydroxyethyl starch can further exhibit a molar degree of substitution of from 0.1 to 3, preferably 0.1 to 2, more preferred, 0.1 to 0.9, preferably 0.1 to 0.8, and a ratio between C2:C6 substitution in the range of from 2 to 20 with respect to the hydroxyethyl groups. A non-limiting example of HES having a mean molecular weight of about 130 kD is a HES with a degree of substitution of 0.2 to 0.8 such as 0.2, 0.3, 0.4, 0.5, 0.6, 0.7, or 0.8, preferably of 0.4 to 0.7 such as 0.4, 0.5, 0.6, or 0.7. In a specific embodiment, HES with a mean molecular weight of about 130 kD is VOLUVEN® from Fresenius. VOLUVEN® is an artificial colloid, employed, e.g., for volume replacement used in the therapeutic indication for therapy and prophylaxis of hypovolemia. The characteristics of VOLUVEN® are a mean molecular weight of 130,000+/−20,000 D, a molar substitution of 0.4 and a C2:C6 ratio of about 9:1. In other embodiments, ranges of the mean molecular weight of hydroxyethyl starch are, e.g., 4 to 70 kD or 10 to 70 kD or 12 to 70 kD or 18 to 70 kD or 50 to 70 kD or 4 to 50 kD or 10 to 50 kD or 12 to 50 kD or 18 to 50 kD or 4 to 18 kD or 10 to 18 kD or 12 to 18 kD or 4 to 12 kD or 10 to 12 kD or 4 to 10 kD. In still other embodiments, the mean molecular weight of hydroxyethyl starch employed is in the range of from more than 4 kD and below 70 kD, such as about 10 kD, or in the range of from 9 to 10 kD or from 10 to 11 kD or from 9 to 11 kD, or about 12 kD, or in the range of from 11 to 12 kD) or from 12 to 13 kD or from 11 to 13 kD, or about 18 kD, or in the range of from 17 to 18 kD or from 18 to 19 kD or from 17 to 19 kD, or about 30 kD, or in the range of from 29 to 30, or from 30 to 31 kD, or about 50 kD, or in the range of from 49 to 50 kD or from 50 to 51 kD or from 49 to 51 kD.

In certain embodiments, the heterologous moiety can be a mixture of hydroxyethyl starches having different mean molecular weights and/or different degrees of substitution and/or different ratios of C2:C6 substitution. Therefore, mixtures of hydroxyethyl starches may be employed having different mean molecular weights and different degrees of substitution and different ratios of C2:C6 substitution, or having different mean molecular weights and different degrees of substitution and the same or about the same ratio of C2:C6 substitution, or having different mean molecular weights and the same or about the same degree of substitution and different ratios of C2:C6 substitution, or having the same or about the same mean molecular weight and different degrees of substitution and different ratios of C2:C6 substitution, or having different mean molecular weights and the same or about the same degree of substitution and the same or about the same ratio of C2:C6 substitution, or having the same or about the same mean molecular weights and different degrees of substitution and the same or about the same ratio of C2:C6 substitution, or having the same or about the same mean molecular weight and the same or about the same degree of substitution and different ratios of C2:C6 substitution, or having about the same mean molecular weight and about the same degree of substitution and about the same ratio of C2:C6 substitution.

(k) Polysialic Acids (PSA)

In certain embodiments, the procoagulant compound comprising an amino acid sequence at least 95% identical to SEQ ID NO: 3 is linked to a heterologous moiety, which is a polysialic acids (PSAs) or a derivative thereof. Polysialic acids (PSAs) are naturally occurring unbranched polymers of sialic acid produced by certain bacterial strains and in mammals in certain cells Roth J., et al. (1993) in *Polysialic Acid: From Microbes to Man*, eds Roth J., Rutishauser U., Troy F. A. (Birkhtiuser Verlag, Basel, Switzerland), pp 335-348. They can be produced in various degrees of polymerisation from n=about 80 or more sialic acid residues down to n=2 by limited acid hydrolysis or by digestion with neuraminidases, or by fractionation of the natural, bacterially derived forms of the polymer. The composition of different polysialic acids also varies such that there are homopolymeric forms i.e. the alpha-2,8-linked polysialic acid comprising the capsular polysaccharide of *E. coli* strain K1 and the group-B meningococci, which is also found on the embryonic form of the neuronal cell adhesion molecule (N-CAM). Heteropolymeric forms also exist-such as the alternating alpha-2,8 alpha-2,9 polysialic acid of *E. coli* strain K92 and group C polysaccharides of *N. meningitidis*. Sialic acid may also be found in alternating copolymers with monomers other than sialic acid such as group W135 or group Y of *N. meningitidis*. Polysialic acids have important biological functions including the evasion of the immune and complement systems by pathogenic bacteria and the regulation of glial adhesiveness of immature neurons during foetal development (wherein the polymer has an anti-adhesive function) Cho and Troy, *P.N.A.S., USA*, 91 (1994) 11427-11431, although there are no known receptors for polysialic acids in mammals. The alpha-2,8-linked polysialic acid of *E. coli* strain K1 is also known as 'colominic acid' and is used (in various lengths) to exemplify the present invention. Various methods of attaching or conjugating polysialic acids to a polypeptide have been described (for example, see U.S. Pat. No. 5,846,951; WO-A-0187922, and US 2007/0191597 A1, which are incorporated herein by reference in their entireties.

(l) Clearance Receptors

In some embodiments the procoagulant compound comprising an amino acid sequence at least 95% identical to SEQ ID NO: 3 is linked to a heterologous moiety comprising a clearance receptor, fragment, variant, or derivative thereof. For example, soluble forms of clearance receptors, such as the low density lipoprotein-related protein receptor LRP1, or fragments thereof, can block binding of a polypeptide (e.g., FVIII or FIX) to clearance receptors and thereby extend its in vivo half-life.

LRP1 is a 600 kDa integral membrane protein that is implicated in the receptor-mediate clearance of a variety of proteins. See, e.g., Lenting et al., *Haemophilia* 16:6-16 (2010). LRP1 also mediates clearance of Factor IX (see, e.g., Strickland & Medved. *J. Thromb. Haemostat*. 4:1484-1486 (2006).

Other suitable clearance receptors are, e.g., LDLR (low-density lipoprotein receptor), VLDLR (very low-density lipoprotein receptor), and megalin (LRP-2), or fragments thereof. See, e.g., Bovenschen et al., *Blood* 106:906-912 (2005); *Bovenschen, Blood* 116:5439-5440 (2010); Martinelli et al., *Blood* 116:5688-5697 (2010).

Linker (L)

The linker is used to covalently link the procoagulant compound to the immunoglobulin constant region or a portion thereof or a heterologous moiety (e.g., a platelet targeting moiety, or a blood coagulation factor selected from FVIIa, FVIII, and FIX). The linker can also be used to covalently link the first immunoglobulin constant region or a portion thereof and the second immunoglobulin constant region or a portion thereof. Fusion compounds can contain more than one linker.

In some embodiments, the linker is a hydrophilic linker, e.g., a peptide linker, a gly-ser polypeptide linker such as those comprised of Gly and Ser or Gly and Val. An exemplary gly/ser polypeptide linker comprises the amino acid sequence (Gly$_4$ Ser)n (e.g., (GGGGS)$_n$ where n=1-50) (SEQ ID NO: 26). In one embodiment, n=1. In one embodiment, n=2. In another embodiment, n3, i.e., (Gly$_4$Ser)$_3$ (SEQ ID NO: 51). In another embodiment, n=4, i.e., (Gly$_4$ Ser)$_4$ (SEQ ID NO: 23). In another embodiment, n=5. In yet another embodiment, n=6. In another embodiment, n=7. In yet another embodiment, n=8. In another embodiment, n=9. In yet another embodiment, n=10. Another exemplary gly/ser polypeptide linker comprises the amino acid sequence Ser (Gly$_4$Ser)n (SEQ ID NO: 42). In one embodiment, n=1. In one embodiment, n=2. In a preferred embodiment, n=3. In another embodiment, n=4. In another embodiment, n=5. In yet another embodiment, n=6.

In other embodiments, the linker is a water-soluble polymer, such as polyethylene glycol (PEG) or polypropylene glycol (PPG). In one example, the linker is a PEG moiety. In other embodiments, the linker is a hydroxyethyl starch (HES) moiety.

The compound can be coupled with the heterologous moiety or the polypeptide chemically or using recombinant techniques, e.g., by recombinant expression of a fusion compound.

Chemical linkage can be achieved by linking together chemical moieties present on the compound and on the heterologous moiety or the polypeptide, e.g., using moieties such as amino, carboxyl, sulfydryl, hydroxyl groups, and carbohydrate groups. A variety of homo- and hetero-bifunctional linker molecules can be used that have groups that are activated, or can be activated to link these moieties. Some useful reactive groups on linker molecules include maleimides, N-hydroxy-succinimide esters and hydrazides. Many different spacers of different chemical composition and length can be used for separating these reactive groups including, for example, polyethylene glycol (PEG), aliphatic groups, alkylene groups, cycloalkylene groups, fused or linked aryl groups, peptides and/or peptidyl mimetics, e.g., peptides having from one to 20 amino acids or amino acid analogs.

In one embodiment, the linker is a non-cleavable linker. In one example according to this embodiment, the linker is a "gly-ser polypeptide linker", e.g., includes the amino acid sequence (GGS)$_n$ (SEQ ID NO: 52), (GGGS)$_n$ (SEQ ID NO: 25), or (GGGGS)$_n$ (SEQ ID NO: 26) where n is 1-50 (e.g., n is 6).

In another example, the linker is cleavable (e.g., cleavable in vivo). In one example, the compound is linked to the immunoglobulin constant region or a portion thereof or a heterologous moiety in such a way that the compound is released from the heterologous moiety or the immunoglobulin constant region or a portion thereof in vivo (e.g., near the site of biological activity of the compound in the body). In one example, the cleavage of such linker liberates the compound from a potential activity-compromising steric hindrance that may be caused by the heterologous moiety (e.g., PEG moiety).

In some embodiments, the linker is a peptide linker that is proteolytically cleavable. In other embodiments, the linker is cleavable by an enzyme from the coagulation cascade.

In one embodiment, the linker is cleavable by an enzyme from the coagulation cascade. In one example the linker includes a thrombin cleavable site (thrombin cleavable substrate moiety) or a FXIa cleavable site (FXIa cleavable substrate moiety). Exemplary FXIa cleavage sites include: TQSFNDFTR (SEQ ID NO: 43) and SVSQTSKLTR (SEQ ID NO: 44). Exemplary thrombin cleavage sites include: DFLAEGGGVR (SEQ ID NO: 45), DFLAEEGGGVR (SEQ ID NO: 46), TTKIKPR (SEQ ID NO: 47), ALVPR (SEQ ID NO: 48), ALRPR (SEQ ID NO: 49) and ALRPRVVGGA (SEQ ID NO: 50). In one embodiment, the thrombin cleavable site includes (D-Phe)-Pro-Arg. In one embodiment, the thrombin cleavable site includes (D-Phe)-Pip-Arg, wherein Pip is pipecolic acid.

In another example, the linker includes a thrombin-cleavable chimeric protein, such as those disclosed in U.S. Pat. No. 7,589,178 to Le Bonniec, which is herein incorporated by reference in its entirety.

Biological Activity

In various embodiments, the fusion compound of the present disclosure have procoagulant activity. It will be appreciated that different assays are available to measure procoagulant activity. In one example, the fusion compound has procoagulant activity when it shows activity in at least one of: a FXa generation assay, a thrombin generation assay (TGA), and a rotational thromboelastometry (ROTEM) assay.

A fusion compound of the present disclosure may promote coagulation in plasma depleted of FV, FVII, FVIII, FIX, FX, FXI, or vWF. In one example, the fusion compound of the present disclosure promotes thrombin generation and/or fibrin deposition in plasma in which FVIII is depleted or absent. This type of activity is referred to as coagulation FVIII activity. Where the plasma is from an individual lacking FVIII or having reduced levels of FVIII, the activity is typically referred to as FVIII equivalent activity. Where the plasma contains inhibitors against FVIII, the activity is typically referred to as FVIII inhibitor bypassing equivalent activity. Other procoagulant activities include FV activity, FVII activity, FX activity and FXI activity.

Individual fusion compound can vary in their relative efficacy between different types of assay. Therefore, even if a fusion compound appears to have a low efficacy in a particular assay, it may nevertheless possess a suitably high level of procoagulant activity in another assay.

Other suitable assays useful to determine procoagulant activity include those disclosed, e.g., in Patent Application Publication U.S. 2010/0022445 to Scheiflinger and Dockal, which is incorporated herein by reference in its entirety.

Methods of Making the Fusion Compounds

The invention also includes a method of reducing or preventing aggregates comprising a procoagulant compound comprising fusing a procoagulant compound to an immunoglobulin constant region or a portion thereof, wherein the procoagulant compound comprises an amino acid sequence at least 95% identical to SRIRTVSPGSRSASGKSTCLASYCWLFWTGIA (SEQ ID NO: 3). In one embodiment, the procoagulant compound comprises SRIRTVSPGSRSASGKSTCLASYCWLFWTGIA (SEQ ID NO: 3). In another embodiment, the fusion compound forms less aggregates compared to a compound consisting of the procoagulant compound. In other embodiments, the fusion compound forms at least about 10%, at least about 20%, at least about 30%, at least about 40%, at least about 50%, at least about 60%, at least about 70%, at least about 80%, at least about 90%, or at least about 100% less aggregates compared to a compound consisting of the procoagulant compound.

In still other embodiments, the immunoglobulin constant region or a portion thereof in the fusion protein is an Fc fragment or an FcRn binding partner. In certain embodiments, the procoagulant compound is linked to the immunoglobulin constant region or a portion thereof by a linker. In some embodiments, the linker comprises (GGGGS)$_n$ (SEQ ID NO:22), wherein n is 1, 2, 3, 4, 5, 6, 7, 8, 9, or 10, e.g., (GGGGS)$_6$ (SEQ ID NO: 24).

In other embodiments, the fusion compound further comprises an additional immunoglobulin constant region or a portion thereof, wherein the additional immunoglobulin constant region or a portion thereof is covalently linked to the immunoglobulin constant region or a portion thereof. In yet other embodiments, the additional immunoglobulin constant region or a portion thereof is linked to the immunoglobulin constant region or a portion thereof by a second linker. For example, the second linker can be (GGGGS), (SEQ ID NO: 22), wherein n is 1, 2, 3, 4, 5, 6, 7, 8, 9, or 10, e.g., (GGGGS)$_4$ (SEQ ID NO: 23). In other embodiments, the fusion compound further comprises a signal peptide, e.g., METDTLLLWVLLLWVPGSTG (SEQ ID NO: 5).

In other embodiments, the fusion compound comprises an amino acid sequence of SEQ ID NO: 2. In yet other embodiments, the fusion compound is encoded by a nucleotide sequence of SEQ ID NO: 1.

The fusion compound of the present disclosure can be produced by chemical synthesis, recombinant DNA technology, biochemical or enzymatic fragmentation of larger molecules, combinations of the foregoing or by any other method.

In one example, the method comprises forming the amino acid sequence of the compound, or a retro-, inverso- or retro-inverso variant thereof using solid-phase peptide synthesis. The methods of making the fusion compounds are known to those of skill in the art.

For example, the fusion compound of the present disclosure can be synthesized using solid-phase peptide synthesis as described in "*Fmoc Solid Phase Peptide Synthesis—A Practical Approach*", edited by W. C. Chan, P. D. White, Oxford University Press, New York 2000 and references therein. Temporary N-amino group protection is afforded, e.g., by a 9-fluorenylmethyloxycarbonyl (Fmoc) group. Repetitive cleavage of this highly base-labile protecting group is effected, e.g., using 20% piperidine in N,N-dimethylformamide. Side-chain functionalities may be protected as their butyl ethers (in the case of serine, threonine and tyrosine), butyl esters (in the case of glutamic acid and aspartic acid), butyloxycarbonyl derivative (in the case of lysine and histidine), trityl derivative (in the case of cysteine, asparagine and glutamine) and 4-methoxy-2,3,6-trimethylbenzenesulphonyl derivative (in the case of arginine). The solid-phase support can be based on a polydimethylacrylamide polymer constituted from the three monomers dirnethylacrylamide (backbone-monomer), bisacryloylethylene diamine (cross linker) and acryloylsarcosine methyl ester (functionalising agent), or can be based on polyethylene glycol (PEG), such as Rink Amide resin (e.g., NovaPEG Rink Amide). The peptide-to-resin cleavable linked agent can be the acid-labile 4-hydroxymethyl-phenoxyacetic acid derivative, or in case of C-terminal amides, the Rink-amide linker. All amino acid derivatives can be added as their preformed symmetrical anhydride derivatives with the exception of asparagine and glutamine, which are added using a reversed N,N-dicyclohexyl-carbodiimide/1-hydroxybenzotriazole mediated coupling procedure. Alternatively, other peptide coupling reagents, such as O-benzotriazole-N,N,N',N'-tetramethyl-uronium-hexafluorophosphate (HBTU) or 2-(6-chloro-1-H-benzotriazole-1-yl)-1,1,3,3-tetramethylaminium haxafluorophosphate (HCTU) can be used (e.g., in situ). Coupling and deprotection reactions can be monitored using ninhydin, trinitrobenzene sulphonic acid or isotin test procedures. Upon completion of synthesis, peptides are cleaved from the resin support with concomitant removal of side-chain protecting groups, e.g., by treatment with 95% trifluoroacetic acid containing about 5-50% scavenger. Scavengers commonly used are TIPS (triisopropylsilane), ethanedithiol, phenol, anisole water, and mixtures thereof. The exact choice depends on the constituent amino acids of the peptide being synthesised. For methionine containing peptides one can use, e.g., a mixture of TIPS (e.g., 2-5%) and ethanedithiol (e.g., 2-5%).

Trifluoroacetic acid can subsequently be removed by evaporation in vacuo, with subsequent trituration with diethyl ether affording the crude peptide. Any scavengers present can be removed by a simple extraction procedure which on lyophilisation of the aqueous phase affords the crude peptide free of scavengers.

Reagents for peptide synthesis are generally available, e.g., from Calbiochem-Novabiochem (UK), or EMD4Biosciences (U.S.).

Purification of the peptides may be effected by any one, or a combination of, techniques such as size exclusion chromatography, ion-exchange chromatography, affinity chromatography, differential solubility, and reverse-phase high performance liquid chromatography. Analysis of peptides may be carried out using thin layer chromatography, reverse-phase high performance liquid chromatography, mass spectroscopy (e.g., LC-MS), amino-acid analysis after acid hydrolysis and by fast atom bombardment (FAB) mass spectrometry.

SPOT-synthesis, which allows the positional addressable, chemical synthesis of peptides on continuous cellulose membranes may be also used (see, e.g., R. Frank, *Tetrahedron* (1992) 48, 9217).

The fusion compound of the present disclosure may also be produced by recombinant protein expression or in vitro translation systems (see, e.g., Sambrook et al., "*Molecular cloning: A laboratory manual*", 2001, 3rd edition, Cold Spring Harbor Laboratory Press, Cold Spring Harbor, N.Y.). Recombinant methods are generally preferred when the peptide is particularly large, e.g., larger than 50 amino acids, or larger than 100 amino acids. For example, the fusion compound of the present disclosure can be made recombinantly, see, e.g., procedures for FVIII-Fc expression and purification described in WO2011/069164, which is incorporated herein by reference in its entirety.

For example, the suitable expression vector or vectors are transfected or co-transfected into a suitable target cell, which will express the polypeptides. Transfection techniques known in the art include, but are not limited to, calcium phosphate precipitation (Wigler et al. (1978) *Cell* 14:725), electroporation (Neumann et al. (1982) *EMBO J* 1:841), and liposome-based reagents. A variety of host-expression vector systems may be utilized to express the proteins described herein including both prokaryotic and eukaryotic cells. These include, but are not limited to, microorganisms such as bacteria (e.g., *E. coli*) transformed with recombinant bacteriophage DNA or plasmid DNA expression vectors containing an appropriate coding sequence; yeast or filamentous fungi transformed with recombinant yeast or fungi expression vectors containing an appropriate coding sequence; insect cell systems infected with recombinant virus expression vectors (e.g., baculovirus) containing an appropriate coding sequence; plant cell systems infected with recombinant virus expression vectors (e.g., cauliflower mosaic virus or tobacco mosaic virus) or transformed with recombinant plasmid expression vectors (e.g., Ti plasmid) containing an appropriate coding sequence; or animal cell systems, including mammalian cells (e.g., HEK 293, CHO, Cos, HeLa, HKB11, and BHK cells).

In one embodiment, the host cell is a eukaryotic cell. As used herein, a eukaryotic cell refers to any animal or plant cell having a definitive nucleus. Eukaryotic cells of animals include cells of vertebrates, e.g., mammals, and cells of invertebrates, e.g., insects. Eukaryotic cells of plants specifically can include, without limitation, yeast cells. A eukaryotic cell is distinct from a prokaryotic cell, e.g., bacteria.

In certain embodiments, the eukaryotic cell is a mammalian cell. A mammalian cell is any cell derived from a mammal. Mammalian cells specifically include, but are not limited to, mammalian cell lines. In one embodiment, the mammalian cell is a human cell. In another embodiment, the mammalian cell is a HEK 293 cell, which is a human embryonic kidney cell line. HEK 293 cells are available as CRL-1533 from American Type Culture Collection, Manassas, Va., and as 293-H cells, Catalog No. 11631-017 or 293-F cells, Catalog No. 11625-019 from Invitrogen (Carlsbad, Calif.). In some embodiments, the mammalian cell is a PER.C6® cell, which is a human cell line derived from retina. PER.C6® cells are available from Crucell (Leiden, The Netherlands). In other embodiments, the mammalian cell is a Chinese hamster ovary (CHO) cell. CHO cells are available from American Type Culture Collection, Manassas, Va. (e.g., CHO-K1; CCL-61). In still other embodiments, the mammalian cell is a baby hamster kidney (BHK) cell. BHK cells are available from American Type Culture Collection, Manassas, Va. (e.g., CRL-1632). In some embodiments, the mammalian cell is a HKB11 cell, which is a hybrid cell line of a HEK293 cell and a human B cell line. Mei et al., *Mol. Biotechnol.* 34(2): 165-78 (2006).

In another example, the fusion compounds of the present disclosure can be made semi-recombinantly (see, e.g., U.S. Pat. No. 7,381,408 to Mezo, A. R. and Peters, R. P.; Dawson, P. E., Kent, S. B. *Ann. Rev. Biochem.* (2000) 69: 923-9600; Mei, B. et. al., *Blood* (2010) 116:270-279; and U.S. Patent Application Publication US2006/0115876 to Pan, C. et. al., each of which is incorporated herein in its entirety). In one example, the polypeptide or the polypeptide construct containing a suitable amino acid moiety is made recombinantly. The procoagulant compound is then attached to an immunoglobulin constant region or a portion thereof via chemical ligation as described herein.

Pharmaceutical Formulations

The invention also provides a pharmaceutical composition (also referred to as pharmaceutical formulation) containing at least one fusion compound of the present disclosure according to any of the above embodiments and a pharmaceutically acceptable carrier.

The term "pharmaceutically acceptable carrier" means all pharmaceutically acceptable ingredients known to those of skill in the art, which are typically considered non-active ingredients. The term "pharmaceutically acceptable carrier" includes, e.g., solvents, solid or liquid diluents, additives, vehicles, adjuvants, excipients, glidants, binders, granulating agents, dispersing agents, suspending agents, wetting agents, lubricating agents, disintegrants, solubilizers, stabilizers, preservatives, emulsifiers, fillers, preservatives (e.g., anti-oxidants), flavoring agents, sweetening agents, thickening agents, buffering agents, coloring agents and the like, as well as any mixtures thereof. Exemplary carriers (i.e., excipients) are described in, e.g., Handbook of Pharmaceutical Manufacturing Formulations, Volumes 1-6, Niazi, Sarfaraz K., Taylor & Francis Group 2005, which is incorporated herein by reference in its entirety. Pharmaceutical compositions may additionally comprise, for example, one or more of water, buffers (e.g., neutral buffered saline or phosphate buffered saline), ethanol, mineral oil, vegetable oil, dimethylsulfoxide, carbohydrates (e.g., glucose, mannose, sucrose or dextrans), mannitol, proteins, adjuvants, polypeptides or amino acids such as glycine, antioxidants, chelating agents such as EDTA or glutathione and/or preservatives.

Pharmaceutical compositions may be formulated for any appropriate manner of administration, including, for example, topical (e.g., transdermal or ocular), oral, buccal, nasal, vaginal, rectal or parenteral administration. In some embodiments, the fusion compound of the present disclosure is administered parenterally, e.g., intraveneously or subcutaneously.

The term parenteral as used herein includes subcutaneous, intradermal, intravascular (e.g., intravenous), intramuscular, spinal, intracranial, intrathecal, intraocular, periocular, intraorbital, intrasynovial and intraperitoneal injection, as well as any similar injection or infusion technique. It is preferred that subcutaneous, intraperitoneal, buccal, intravenous and other parenteral formulations are sterile and endotoxin free.

Fusion compounds of the present disclosure may be administered parenterally in a sterile medium. The fusion compound, depending on the vehicle and concentration used, can either be suspended or dissolved in the vehicle. In one embodiment, adjuvants such as local anesthetics, preservatives and buffering agents can be dissolved in the vehicle.

In one example, the fusion compounds of the present disclosure are administered to the subject using a non-intravenous route, e.g., by subcutaneous, nasal, buccal, oral or pulmonary delivery.

Forms suitable for oral use include, for example, tablets, troches, lozenges, aqueous or oily suspensions, dispersible powders or granules, emulsion, hard or soft capsules, or syrups or elixirs. Compositions provided herein may be formulated as a lyophilizate.

Compositions intended for oral use may be prepared according to any method known for the manufacture of pharmaceutical compositions. Such compositions may contain one or more agents chosen from the group consisting of sweetening agents, flavoring agents, coloring agents and preservative agents in order to provide pharmaceutically elegant and palatable preparations. Tablets can contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques. In some cases such coatings may be prepared by known techniques to delay disintegration and absorption in the gastrointestinal tract and thereby provide a sustained action over a longer period (i.e., tablets can be enterically coated). For example, a time delay material such as glyceryl monosterate or glyceryl distearate may be employed.

Formulations for oral use may also be presented as hard gelatin capsules, wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil. In another example, the active ingredient is formulated in capsules containing optionally coated microtablets or micropellets. Formulations for oral use may also be presented as lozenges. The composition can be also for example a suspension, emulsion, sustained release formulation, cream, gel or powder. The composition can be formulated as a suppository, with traditional binders and carriers such as triglycerides.

Oily suspensions may be formulated by suspending the active ingredients in a vegetable oil, for example *arachis* oil, olive oil, sesame oil or coconut oil, or in a mineral oil such as liquid paraffin. The oily suspensions may contain a thickening agent, for example beeswax, hard paraffin or cetyl alcohol. Sweetening agents and flavoring agents may be added to provide palatable oral preparations. These compositions may be preserved by the addition of an antioxidant such as ascorbic acid.

In one example, the pharmaceutical formulation is a liquid formulation, e.g., a buffered, isotonic, aqueous solution. In one example, the pharmaceutical composition has a pH that is physiologic, or close to physiologic. In another example, the aqueous formulation has a physiologic or close to physiologic osmolarity and salinity. It can contain sodium chloride and/or sodium acetate.

In another example, the pharmaceutical formulation further contains a blood coagulation factor selected from FVIII and FIX. In another example, the pharmaceutical formulation further includes FVIII. In another example, the pharmaceutical formulation further includes FIX. In another example, the pharmaceutical formulation includes desmopressin (DDVAP).

Methods

The invention further provides a method (e.g., an in vitro or an in vivo method) of increasing/enhancing the catalytic activity (kcat) of a blood coagulation factor (i.e., activating the blood coagulation factor). An exemplary method includes contacting the blood coagulation factor (e.g., FIXa or FVIIa) with a fusion compound of the present disclosure according to any of the above embodiments. In one example, the blood coagulation factor useful in this method includes the amino acid sequence: MFCAG (SEQ ID NO: 6) (e.g., FIXa, FXa, FVIIa and thrombin). In one example, the blood coagulation factor being activated is FXa. In another example, the blood coagulation factor being activated is thrombin.

The invention further provides a method of increasing/enhancing the catalytic activity (kcat) of FIXa (e.g., in vitro or in vivo), the method includes contacting the FIXa with a compound of the present disclosure according to any of the above embodiments.

The invention further provides a method of increasing/enhancing the catalytic activity (kcat) of FVIIa (e.g., in vitro or in vivo), the method includes contacting the FVIIa with a compound of the present disclosure according to any of the above embodiments.

In one example according to the above method, the compound interacts with the blood coagulation factor (e.g., binds to the blood coagulation factor) at a region corresponding to amino acid sequence: MFCAG (SEQ ID NO: 6).

In a further example, the blood coagulation factor being activated is FIXa (e.g., human or canine FIXa). In one example according to this embodiment, the compound of the present disclosure interacts with the FIXa at a region corresponding to amino acid sequence: YNNMFCAGFHE (SEQ ID NO: 30). In yet another example, the compound of the present disclosure interacts with the FIXa at a region corresponding to amino acid sequence: RSTKFTIYNNMFCAGFHEGGRDSCQG (SEQ ID NO: 31).

In another example according to any of the above embodiments, the method is an in vitro method involving measuring conversion of FX to FXa. Such method is also generally referred to as a "FXa generation assay".

In one embodiment the fusion compound is used in an in vitro assay system useful for the identification of other candidate compounds with procoagulant activity (e.g., a competition assay). In one example, the fusion compound of the present disclosure is used as a reference compound in such assay system. In another example, the fusion compound is used in a binding competition experiment as a probe. In one example, the fusion compound of the present disclosure is used as a probe to measure binding of a candidate compound to a polypeptide (e.g., FIXa, FVIIa, or peptide including the amino acid sequences of SEQ ID NO: 8, 10, 12, 14, 16, 18-21, and 32). For this purpose, the fusion compound of the present disclosure can be linked to a detection molecule, such as an antibody (e.g., ELISA assay), biotin, a fluorescent molecule, a phage particle (e.g., phage display competition assay), and the like.

Pharmaceutical Methods

The present invention further provides methods for treating bleeding diathesis in a mammalian subject (e.g., a human patient) using the fusion compound or the present disclosure.

In some embodiments, the present disclosure provides a method for treating a coagulation disorder in a mammalian subject (e.g., a human patient) having a deficiency in at least one blood coagulation factor selected from von Willebrand Factor (vWF), FV, FVII, FVIII, FIX, FX, FXI, and activated forms thereof (e.g., for both the prophylaxis and for the treatment of acute bleeds), the method comprising: administering to the subject in need thereof a therapeutically effective amount of a fusion compound of the present disclosure or a pharmaceutical composition comprising a fusion compound of the present disclosure.

In some embodiments, the present disclosure provides a method for treating bleeding diathesis in a mammalian subject (e.g., a human patient), comprising: administering to the subject in need thereof a therapeutically effective amount of a fusion compound of the present disclosure or a pharmaceutical composition comprising a fusion compound of the present disclosure.

In some embodiments of pharmaceutical method 1, the fusion compound containing the compound is administered to the subject orally. In other embodiments, the fusion compound or the pharmaceutical composition containing the fusion compound is administered to the subject parenterally, e.g., intravenously or subcutaneously.

In one example according to any of the above embodiments of pharmaceutical methods 1 and 2, the bleeding diathesis is caused by or associated with a blood coagulation disorder. A blood coagulation disorder can also be referred to as a coagulopathy. In a particular example, the blood coagulation disorder, which can be treated with a fusion compound of the current disclosure, is hemophilia or von Willebrand disease (vWD). In a particular example, the blood coagulation disorder, which can be treated is hemophilia. In another example, the hemophilia is hemophilia A. In yet another example, the hemophilia is hemophilia B.

In another example, the type of bleeding associated with the bleeding diathesis is selected from hemarthrosis, muscle bleed, oral bleed, hemorrhage, hemorrhage into muscles, oral hemorrhage, trauma, trauma capitis, gastrointestinal bleeding, intracranial hemorrhage, intra-abdominal hemorrhage, intrathoracic hemorrhage, bone fracture, central nervous system bleeding, bleeding in the retropharyngeal space, bleeding in the retroperitoneal space, and bleeding in the illiopsoas sheath.

In another example, the subject suffering from bleeding diathesis is in need of treatment for surgery, including, e.g., surgical prophylaxis or peri-operative management. In one example, the surgery is selected from minor surgery and major surgery. Exemplary surgical procedures include tooth extraction, tonsillectomy, inguinal herniotomy, synovectomy, craniotomy, osteosynthesis, trauma surgery, intracranial surgery, intra-abdominal surgery, intrathoracic surgery, joint replacement surgery (e.g., total knee replacement, hip replacement, and the like), heart surgery, and caesarean section.

In some embodiments, the coagulation disorder is caused by a deficiency in at least one blood coagulation factor (e.g., FVIII). The current disclosure provides methods of treating a mammalian subject (e.g., a human subject) having a deficiency in at least one blood coagulation factor selected from von Willebrand Factor (vWF), FV, FVII, FVIII, FIX, FX, FXI, and activated forms thereof (e.g., for both the prophylaxis and for the treatment of acute bleeds).

In some embodiments, the current disclosure provides a method of treating a mammalian subject (e.g., a human subject) having a deficiency in FVIII, the method includes administering to the subject a therapeutically effective amount of a fusion compound of the current disclosure or a pharmaceutical composition containing a fusion compound of the current disclosure.

Patients with a FVIII deficiency (i.e., hemophilia A) can develop inhibitor antibodies to FVIII. The biological activity of certain compounds or conjugates of the present disclosure is essentially not influenced by the presence of FVIII inhibitors, such as antibodies against FVIII. Hence, in one example according to any of the above embodiments of pharmaceutical methods 1-6, the mammalian subject (e.g., a human patient) suffering from a FVIII deficiency is a FVIII inhibitor patient (e.g., produces antibodies against FVIII). The magnitude of the antibody response to FVIII can be quantified using a functional inhibitor assay, such as that described in Kasper C K et al. (1975) Proceedings: A more uniform measurement of factor VIII inhibitors. *Thromb. Diath. Haemorrh.* 34(2):612. FXI inhibitors could be quantified by an aPTT assay as described by Kasper C K et al., Inhibitors of FV, FVII and FX could be quantified by a PT based assay following the procedure of Kasper C K et al.

Inhibitor development (to FIX) is also known in FIX deficiency (i.e., hemophilia B). The biological activity (e.g., FXa generation assay activity) of certain compounds of the present disclosure is essentially not influenced by the presence of FIX inhibitors, such as antibodies against FIX. Since FV, FVII, FXI and FX deficiencies are very rare congenital disorders little is known about inhibitor development, although it is feasible that patients having such disorders might develop inhibitors. Treatment of inhibitor patients is contemplated by the current invention. Such inhibitor patients may have either a high titer response of greater than 5 BU or a low titer response of between 0.5 and 5 BU. Typically, the inhibitors are directed against FVIII and the patients have hemophilia A.

In another example, the mammalian subject (e.g., human patient) is concomitantly treated with FIX. Because the fusion compound of the invention are capable of activating FIXa, they could be used to pre-activate the FIXa polypeptide before administration of the FIXa to the subject.

In yet another example, the mammalian subject (e.g., human subject) is concomitantly treated with desmopressin (DDVAP).

The methods of the invention may be practiced on a subject in need of prophylactic treatment or on-demand treatment.

In various embodiments, the fusion compound of the present disclosure can be used as a replacement therapy (e.g., replacing FVIII treatment) in subjects in need of treatment for hemophilia A. In other embodiments, the fusion compound of the present disclosure can be used in conjunction with other therapies (e.g., FVIII or FIX therapy) in subjects in need of treatment for hemophilia A or B. In other embodiments, the compounds of the present disclosure are useful as a bypass therapy in subjects in need of treatment for hemophilia A (e.g., hemophilia A patients with inhibitors).

Administration of Fusion Compound

The calculation of the required dosage for the fusion compound of the present disclosure is based upon the empirical finding that, on average, 1 IU of FVIII per kg body weight raises the plasma FVIII activity by approximately 2 IU/dL. The required dosage is determined using the following formula:

Required units=body weight (kg)×desired FVIII rise (IU/dL or % of normal)×0.5 (IU/kg per IU/dL).

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

Dosage levels of the order of from about 0.005 mg to about 80 mg per kilogram of body weight per day are useful in the treatment of the diseases and conditions described herein (e.g., about 0.35 mg to about 5.6 g per human patient per day, based on an average adult person weight of 70 kg). The amount of active ingredient that may be combined with the carrier materials to produce a single dosage form will vary depending upon the host treated and the particular mode of administration. Dosage unit forms will generally contain between from about 1 mg to about 500 mg of an active ingredient. The daily dose can be administered in one to four doses per day. In the case of skin conditions, it may, for example, be applied as a topical preparation of compounds of this present disclosure on the affected area one to four times a day.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

Having now described the present invention in detail, the same will be more clearly understood by reference to the following examples, which are included herewith for purposes of illustration only and are not intended to be limiting of the invention. All patents and publications referred to herein are expressly incorporated by reference.

EXAMPLES

Throughout the examples, the following materials and methods were used unless otherwise stated.

Materials and Methods

In general, the practice of the present invention employs, unless otherwise indicated, conventional techniques of chemistry, biophysics, molecular biology, recombinant DNA technology, immunology (especially, e.g., antibody technology), and standard techniques in electrophoresis. See, e.g., Sambrook, Fritsch and Maniatis, Molecular Cloning: Cold Spring Harbor Laboratory Press (1989); Antibody Engineering Protocols (Methods in Molecular Biology), 510, Paul, S., Humana Pr (1996); Antibody Engineering: A Practical Approach (Practical Approach Series, 169), McCafferty, Ed., Irl Pr (1996); Antibodies: A Laboratory Manual, Harlow et al., CS.H.L. Press, Pub. (1999); and Current Protocols in Molecular Biology, eds. Ausubel et al., John Wiley & Sons (1992).

Example 1

Expression of pSYN-Fc-048

Cloning of pSYN-Fc-048 was performed using Rapid DNA Ligation Kit from Roche Diagnostics (cat #11635379001) following manufacturer's guidelines. Briefly, 10-50 ng of vector or fragment DNA was added to a final volume of 10 μL ligation mixture containing 1× Rapid DNA Ligation buffer and 1 μL Rapid DNA Ligase. The reaction was allowed to proceed for 5-30 min at room temperature and placed on ice. 2 μL of the ligation reaction was transformed in 25 μL Mach 1 *E. coli* competent cells from Invitrogen (cat # C869601) and plated on an appropriate antibiotic for selection.

The 1.7 kb DNA fragment comprising the region from HindIII to EcoRI of pSYN-Fc-048 was synthesized and subcloned into the HindIII/EcoRI sites of pcDNA4MycHisA vector (Invitrogen) to generate pSYN-Fc-048.

For expression of Fc-048, HEK-293-F cells were grown in suspension in Freestyle media (Invitrogen) to 2 µg/liter (growth media) as suspension cells at 37° C./10% $CO_2$. Cells were subcultured every three to four days by seeding at cell density of $5 \times 10^5$ cells/mL.

Twenty-four hours prior to transfection, cells were seeded at a density of $7 \times 10^5$ cells/mL in growth media. On the day of transfection, a transfection solution was made with a volume equal to 5% of the total volume of the cell culture to be transfected. In the transfection solution, DNA was added (final concentration 20 mg/L) to a freshly made solution of PEI (60 mg/L) in growth media. The solution was swirled for 30 seconds and incubated for five minutes at room temperature before adding it directly to the cell culture. Four hours later a volume equal to the cell culture volume of OptiCHO (Invitrogen) supplemented 200 mM L-glutamine was added to the cells. The cell culture was allowed to grow as shown above and daily media samples were taken to assess protein expression. On the day of harvest, the cells were spun down and the media filtered in preparation for protein purification or protein analysis by FcRn pulldown.

```
DNA sequence of pSYN-Fc-048 (SEQ ID NO: 1):
   1 AGCTTGCCGC CACCATGGAG ACAGACACAC TCCTGCTATG GGTACTGCTG CTCTGGGTTC CAGGTTCCAC

71 TGGTGGCAGT CGGATTCGGA CAGTGAGCCC CGGCAGCCGG AGCGCCAGCG GCAAGAGTAC CTGCCTGGCC

141 AGCTACTGCT GGCTGTTCTG GACCGGCATC GCCGGTGGCG GTGGATCCGG CGGAGGTGGG TCCGGTGGCG

211 GCGGATCAGG TGGGGGTGGA TCAGGCGGTG GAGGTTCCGG TGGCGGGGGA TCAGACAAAA CTCACACATG

281 CCCACCGTGC CCAGCTCCGG AACTCCTGGG CGGACCGTCA GTCTTCCTCT TCCCCCCAAA ACCCAAGGAC

351 ACCCTCATGA TCTCCCGGAC CCCTGAGGTC ACATGCGTGG TGGTGGACGT GAGCCACGAA GACCCTGAGG

421 TCAAGTTCAA CTGGTACGTG GACGGCGTGG AGGTGCATAA TGCCAAGACA AAGCCGCGGG AGGAGCAGTA

491 CAACAGCACG TACCGTGTGG TCAGCGTCCT CACCGTCCTG CACCAGGACT GGCTGAATGG CAAGGAGTAC

561 AAGTGCAAGG TCTCCAACAA AGCCCTCCCA GCCCCCATCG AGAAAACCAT CTCCAAAGCC AAGGGCAGC

631 CCCGAGAACC ACAGGTGTAC ACCCTGCCCC CATCCCGGGA TGAGCTGACC AAGAACCAGG TCAGCCTGAC

701 CTGCCTGGTC AAAGGCTTCT ATCCCAGCGA CATCGCCGTG GAGTGGGAGA GCAATGGGCA GCCGGAGAAC

771 AACTACAAGA CCACGCCTCC CGTGTTGGAC TCCGACGGCT CCTTCTTCCT CTACAGCAAG CTCACCGTGG

841 ACAAGAGCAG GTGGCAGCAG GGGAACGTCT TCTCATGCTC CGTGATGCAT GAGGCTCTGC ACAACCACTA

911 CACGCAGAAG AGCCTCTCCC TGTCTCCGGG TAAAGGTGGC GGCGGATCAG GTGGGGGTGG ATCAGGCGGT

981 GGAGGTTCCG GTGGCGGGGG ATCAGACAAA ACTCACACAT GCCCACCGTG CCCAGCACCT GAACTCCTGG

1051 GAGGACCGTC AGTCTTCCTC TTCCCCCCAA AACCCAAGGA CACCCTCATG ATCTCCCGGA CCCCTGAGGT

1121 CACATGCGTG GTGGTGGACG TGAGCCACGA AGACCCTGAG GTCAAGTTCA ACTGGTACGT GGACGGCGTG

1191 GAGGTGCATA ATGCCAAGAC AAAGCCGCGG GAGGAGCAGT ACAACAGCAC GTACCGTGTG GTCAGCGTCC

1261 TCACCGTCCT GCACCAGGAC TGGCTGAATG GCAAGGAGTA CAAGTGCAAG GTCTCCAACA AAGCCCTCCC

1331 AGCCCCCATC GAGAAAACCA TCTCCAAAGC CAAAGGGCAG CCCCGAGAAC CACAGGTGTA CACCCTGCCC

1401 CCATCCCGCG ATGAGCTGAC CAAGAACCAG GTCAGCCTGA CCTGCCTGGT CAAAGGCTTC TATCCCAGCG

1471 ACATCGCCGT GGAGTGGGAG AGCAATGGGC AGCCGGAGAA CAACTACAAG ACCACGCCTC CCGTGTTGGA

1541 CTCCGACGGC TCCTTCTTCC TCTACAGCAA GCTCACCGTG GACAAGAGCA GGTGGCAGCA GGGGAACGTC

1611 TTCTCATGCT CCGTGATGCA TGAGGCTCTG CACAACCACT ACACGCAGAA GAGCCTCTCC CTGTCTCCGG

1681 GTAAATGAGA ATTCTGCAGA TATCCAGCAC AGTGGCGGCC GCTCGAGTCT AGAGGGCCCT TCGAACAAAA

1751 ACTCATCTCA GAAGAGGATC TGAATATGCA TACCGGTCAT CATCACCATC ACCATTGAGT TTAAACCCGC

1821 TGATCAGCCT CGACTGTGCC TTCTAGTTGC CAGCCATCTG TTGTTTGCCC CTCCCCCGTG CCTTCCTTGA

1891 CCCTGGAAGG TGCCACTCCC ACTGTCCTTT CCTAATAAAA TGAGGAAATT GCATCGCATT GTCTGAGTAG

1961 GTGTCATTCT ATTCTGGGGG GTGGGGTGGG GCAGGACAGC AAGGGGGAGG ATTGGGAAGA CAATAGCAGG

2031 CATGCTGGGG ATGCGGTGGG CTCTATGGCT TCTGAGGCGG AAAGAACCAG CTGGGGCTCT AGGGGGTATC

2101 CCCACGCGCC CTGTAGCGGC GCATTAAGCG CGGCGGGTGT GGTGGTTACG CGCAGCGTGA CCGCTACACT
```

```
2171 TGCCAGCGCC CTAGCGCCCG CTCCTTTCGC TTTCTTCCCT TCCTTTCTCG CCACGTTCGC CGGCTTTCCC

2241 CGTCAAGCTC TAAATCGGGG GCTCCCTTTA GGGTTCCGAT TTAGTGCTTT ACGGCACCTC GACCCCAAAA

2311 AACTTGATTA GGGTGATGGT TCACGTAGTG GGCCATCGCC CTGATAGACG GTTTTTCGCC CTTTGACGTT

2381 GGAGTCCACG TTCTTTAATA GTGGACTCTT GTTCCAAACT GGAACAACAC TCAACCCTAT CTCGGTCTAT

2451 TCTTTTGATT TATAAGGGAT TTTGGGGATT TCGGCCTATT GGTTAAAAAA TGAGCTGATT TAACAAAAAT

2521 TTAACGCGAA TTAATTCTGT GGAATGTGTG TCAGTTAGGG TGTGAAAGT CCCCAGGCTC CCCAGGCAGG

2591 CAGAAGTATG CAAAGCATGC ATCTCAATTA GTCAGCAACC AGGTGTGGAA AGTCCCCAGG CTCCCCAGCA

2661 GGCAGAAGTA TGCAAAGCAT GCATCTCAAT TAGTCAGCAA CCATAGTCCC GCCCCTAACT CCGCCCATCC

2731 CGCCCCTAAC TCCGCCCAGT TCCGCCCATT CTCCGCCCCA TGGCTGACTA ATTTTTTTTA TTTATGCAGA

2801 GGCCGAGGCC GCCTCTGCCT CTGAGCTATT CCAGAAGTAG TGAGGAGGCT TTTTTGGAGG CCTAGGCTTT

2871 TGCAAAAAGC TCCCGGGAGC TTGTATATCC ATTTTCGGAT CTGATCAGCA CGTGTTGACA ATTAATCATC

2941 GGCATAGTAT ATCGGCATAG TATAATACGA CAAGGTGAGG AACTAAACCA TGGCCAAGTT GACCAGTGCC

3011 GTTCCGGTGC TCACCGCGCG CGACGTCGCC GGAGCGGTCG AGTTCTGGAC CGACCGGCTC GGGTTCTCCC

3081 GGGACTTCGT GGAGGACGAC TTCGCCGGTG TGGTCCGGGA CGACGTGACC CTGTTCATCA GCGCGGTCCA

3151 GGACCAGGTG GTGCCGGACA ACACCCTGGC CTGGGTGTGG GTGCGCGGCC TGGACGAGCT GTACGCCGAG

3221 TGGTCGGAGG TCGTGTCCAC GAACTTCCGG GACGCCTCCG GCCGGCCAT GACCGAGATC GGCGAGCAGC

3291 CGTGGGGGCG GGAGTTCGCC CTGCGCGACC CGGCCGGCAA CTGCGTGCAC TTCGTGGCCG AGGAGCAGGA

3361 CTGACACGTG CTACGAGATT TCGATTCCAC CGCCGCCTTC TATGAAAGGT TGGGCTTCGG AATCGTTTTC

3431 CGGGACGCCG GCTGGATGAT CCTCCAGCGC GGGGATCTCA TGCTGGAGTT CTTCGCCCAC CCCAACTTGT

3501 TTATTGCAGC TTATAATGGT TACAAATAAA GCAATAGCAT CACAAATTTC ACAAATAAAG CATTTTTTTC

3571 ACTGCATTCT AGTTGTGGTT TGTCCAAACT CATCAATGTA TCTTATCATG TCTGTATACC GTCGACCTCT

3641 AGCTAGAGCT TGGCGTAATC ATGGTCATAG CTGTTTCCTG TGTGAAATTG TTATCCGCTC ACAATTCCAC

3711 ACAACATACG AGCCGGAAGC ATAAAGTGTA AAGCCTGGGG TGCCTAATGA GTGAGCTAAC TCACATTAAT

3781 TGCGTTGCGC TCACTGCCCG CTTTCCAGTC GGGAAACCTG TCGTGCCAGC TGCATTAATG AATCGGCCAA

3851 CGCGCGGGGA GAGGCGGTTT GCGTATTGGG CGCTCTTCCG CTTCCTCGCT CACTGACTCG CTGCGCTCGG

3921 TCGTTCGGCT GCGGCGAGCG GTATCAGCTC ACTCAAAGGC GGTAATACGG TTATCCACAG AATCAGGGGA

3991 TAACGCAGGA AAGAACATGT GAGCAAAAGG CCAGCAAAAG GCCAGGAACC GTAAAAAGGC CGCGTTGCTG

4061 GCGTTTTTCC ATAGGCTCCG CCCCCCTGAC GAGCATCACA AAAATCGACG CTCAAGTCAG AGGTGGCGAA

4131 ACCCGACAGG ACTATAAAGA TACCAGGCGT TTCCCCCTGG AAGCTCCCTC GTGCGCTCTC CTGTTCCGAC

4201 CCTGCCGCTT ACCGGATACC TGTCCGCCTT TCTCCCTTCG GGAAGCGTGG CGCTTTCTCA ATGCTCACGC

4271 TGTAGGTATC TCAGTTCGGT GTAGGTCGTT CGCTCCAAGC TGGGCTGTGT GCACGAACCC CCCGTTCAGC

4341 CCGACCGCTG CGCCTTATCC GGTAACTATC GTCTTGAGTC CAACCCGGTA AGACACGACT TATCGCCACT

4411 GGCAGCAGCC ACTGGTAACA GGATTAGCAG AGCGAGGTAT GTAGGCGGTG CTACAGAGTT CTTGAAGTGG

4481 TGGCCTAACT ACGGCTACAC TAGAAGGACA GTATTTGGTA TCTGCGCTCT GCTGAAGCCA GTTACCTTCG

4551 GAAAAAGAGT TGGTAGCTCT TGATCCGGCA AACAAACCAC CGCTGGTAGC GGTGGTTTTT TTGTTTGCAA

4621 GCAGCAGATT ACGCGCAGAA AAAAGGATC TCAAGAAGAT CCTTTGATCT TTTCTACGGG GTCTGACGCT

4691 CAGTGGAACG AAAACTCACG TTAAGGGATT TTGGTCATGA GATTATCAAA AAGGATCTTC ACCTAGATCC

4761 TTTTAAATTA AAAATGAAGT TTTAAATCAA TCTAAAGTAT ATATGAGTAA ACTTGGTCTG ACAGTTACCA

4831 ATGCTTAATC AGTGAGGCAC CTATCTCAGC GATCTGTCTA TTTCGTTCAT CCATAGTTGC CTGACTCCCC

4901 GTCGTGTAGA TAACTACGAT ACGGGAGGGC TTACCATCTG GCCCCAGTGC TGCAATGATA CCGCGAGACC

4971 CACGCTCACC GGCTCCAGAT TTATCAGCAA TAAACCAGCC AGCCGGAAGG GCCGAGCGCA GAAGTGGTCC
```

-continued

```
5041 TGCAACTTTA TCCGCCTCCA TCCAGTCTAT TAATTGTTGC CGGGAAGCTA GAGTAAGTAG TTCGCCAGTT
5111 AATAGTTTGC GCAACGTTGT TGCCATTGCT ACAGGCATCG TGGTGTCACG CTCGTCGTTT GGTATGGCTT
5181 CATTCAGCTC CGGTTCCCAA CGATCAAGGC GAGTTACATG ATCCCCCATG TTGTGCAAAA AAGCGGTTAG
5251 CTCCTTCGGT CCTCCGATCG TTGTCAGAAG TAAGTTGGCC GCAGTGTTAT CACTCATGGT TATGGCAGCA
5321 CTGCATAATT CTCTTACTGT CATGCCATCC GTAAGATGCT TTTCTGTGAC TGGTGAGTAC TCAACCAAGT
5391 CATTCTGAGA ATAGTGTATG CGGCGACCGA GTTGCTCTTG CCCGGCGTCA ATACGGGATA ATACCGCGCC
5461 ACATAGCAGA ACTTTAAAAG TGCTCATCAT TGGAAAACGT TCTTCGGGGC GAAAACTCTC AAGGATCTTA
5531 CCGCTGTTGA GATCCAGTTC GATGTAACCC ACTCGTGCAC CCAACTGATC TTCAGCATCT TTTACTTTCA
5601 CCAGCGTTTC TGGGTGAGCA AAAACAGGAA GGCAAAATGC CGCAAAAAAG GGAATAAGGG CGACACGGAA
5671 ATGTTGAATA CTCATACTCT TCCTTTTTCA ATATTATTGA AGCATTTATC AGGGTTATTG TCTCATGAGC
5741 GGATACATAT TTGAATGTAT TTAGAAAAAT AAACAAATAG GGGTTCCGCG CACATTTCCC CGAAAAGTGC
5811 CACCTGACGT CGACGGATCG GGAGATCTCC CGATCCCCTA TGGTCGACTC TCAGTACAAT CTGCTCTGAT
5881 GCCGCATAGT TAAGCCAGTA TCTGCTCCCT GCTTGTGTGT TGGAGGTCGC TGAGTAGTGC GCGAGCAAAA
5951 TTTAAGCTAC AACAAGGCAA GGCTTGACCG ACAATTGCAT GAAGAATCTG CTTAGGGTTA GGCGTTTTGC
6021 GCTGCTTCGC GATGTACGGG CCAGATATAC GCGTTGACAT TGATTATTGA CTAGTTATTA ATAGTAATCA
6091 ATTACGGGGT CATTAGTTCA TAGCCCATAT ATGGAGTTCC GCGTTACATA ACTTACGGTA ATGGCCCGC
6161 CTGGCTGACC GCCCAACGAC CCCCGCCCAT TGACGTCAAT AATGACGTAT GTTCCCATAG TAACGCCAAT
6231 AGGGACTTTC CATTGACGTC AATGGGTGGA CTATTTACGG TAAACTGCCC ACTTGGCAGT ACATCAAGTG
6301 TATCATATGC CAAGTACGCC CCCTATTGAC GTCAATGACG GTAAATGGCC CGCCTGGCAT TATGCCCAGT
6371 ACATGACCTT ATGGGACTTT CCTACTTGGC AGTACATCTA CGTATTAGTC ATCGCTATTA CCATGGTGAT
6441 GCGGTTTTGG CAGTACATCA ATGGGCGTGG ATAGCGGTTT GACTCACGGG GATTTCCAAG TCTCCACCCC
6511 ATTGACGTCA ATGGGAGTTT GTTTTGGCAC CAAAATCAAC GGGACTTTCC AAAATGTCGT AACAACTCCG
6581 CCCCATTGAC GCAAATGGGC GGTAGGCGTG TACGGTGGGA GGTCTATATA AGCAGAGCTC TCTGGCTAAC
6651 TAGAGAACCC ACTGCTTACT GGCTTATCGA AATTAATACG ACTCACTATA GGGAGACCCA AGCTGGCTAG
6721 TTA
```

Amino acid sequence (SEQ ID NO: 2):
Signal sequence is underlined, linker regions are in wave underline.

```
  1 METDTLLLWV LLLWVPGSTG GSRIRTVSPG SRSASGKSTC LASYCWLFWT GIAGGGGSGG
 61 GGSGGGGSGG GGSGGGGSGG GGSDKTHTCP PCPAPELLGG PSVFLFPPKP KDTLMISRTP
121 EVTCVVVDVS HEDPEVKFNW YVDGVEVHNA KTKPREEQYN STYRVVSVLT VLHQDWLNGK
181 EYKCKVSNKA LPAPIEKTIS KAKGQPREPQ VYTLPPSRDE LTKNQVSLTC LVKGFYPSDI
241 AVEWESNGQP ENNYKTTPPV LDSDGSFFLY SKLTVDKSRW QQGNVFSCSV MHEALHNHYT
301 QKSLSLSPGK SGGGGSGGGG SGGGGSGGGG SDKTHTCPPC PAPELLGGPS VFLFPPKPKD
361 TLMISRTPEV TCVVVDVSHE DPEVKFNWYV DGVEVHNAKT KPREEQYNST YRVVSVLTVL
421 HQDWLNGKEY KCKVSNKALP APIEKTISKA KGQPREPQVY TLPPSRDELT KNQVSLTCLV
481 KGFYPSDIAV EWESNGQPEN NYKTTPPVLD SDGSFFLYSK LTVDKSRWQQ GNVFSCSVMH
541 EALHNHYTQK SLSLSPGK
```

Example 2

Purification and Analysis of pSYN-Fc-048

FcRn Affinity Purification 6 mL of FcRn resin was packed into a column and equilibrated with equilibration buffer (50 mM MES, 100 mM NaCl pH 6.2). The pH of about 1500 mL media containing Fc-048 was adjusted to 6.2 by adding 0.5M MES pH 5.5 prior to loading the compound onto the column. The column was washed with two column volumes of equilibration buffer followed by twenty column volumes of wash buffer (50 mM MES pH 6.2). Fc-048 was eluted from the column using a step elution of 100% elution buffer (10 mM Tris, 250 mM NaCl pH 8.0). Fractions were analyzed by gel electrophoresis, analytical size-exclusion chromatography and UV-Vis spectrophotometry.

Size Exclusionary Chromatography (SEC) to Separate Monomer

Monomeric Fc-048 was separated from aggregates by size-exclusion chromatography using a silica-based TSKgel G3000SWx1 column with 5 μm particles and 250 Å pores from Tosoh Bioscience. The running buffer was composed of a phosphate buffered saline solution containing 250 mM sodium chloride and the absorbance was measured. Fractions were collected and concentrated through 30K 15 mL Amicon filters at 3000 rpm centrifugation. The monomer remained monomeric during the concentration step. Analytical SEC spectra of isolated monomeric, medium, and large aggregate Fc-048 can be seen in FIG. 2.

Thrombin Generation Assay (TGA)

A thrombogram was generated for the compounds of the present disclosure in order to assess the thrombin potential in a physiological plasma environment. The TGA assay was carried out using a Calibrated Automated Thrombogram (CAT) test in severe hemophilia A patient plasma from HRF (Raleigh, N.C., US). Briefly, dilutions of test compounds or controls such as FVIII were prepared in PBS (—Ca, —Mg) or directly in the FVIII-deficient patient plasma. In a 96-well round bottom plate, 20 μl of activator solution (PPP Low reagent [final 1 pM rTF, 4 μM phospholipids], Thrombinoscope bv) was added to each sample well and 20 μl of Thrombin calibrator (Thrombinoscope bv) was added to calibrator well. Subsequently, 80 μl of blank plasma was added to the calibrator well and 80 μl of plasma containing compounds of the present disclosure, controls such as FVIII or blank was added to sample wells. All samples were prepared in duplicates and the plate was incubated at 37° C. for 10 minutes. After the incubation, 20 μl of Fluca solution ($Ca^{2+}$, fluorogenic substrate, Diagnostica Stago) was added to each well and fluorescence was measured in a microtiter plate fluorometer (Fluroskan Ascent, Thermo Scientific, Thrombinoscope software) for 1 hr. A TGA profile of Fc-048 containing a mixture of monomer and aggregates can be seen in FIG. 3A. A TGA profile of isolated monomeric and aggregate Fc-048 can be seen in FIG. 4.

In Fc-048, the procoagulant peptide has a free N-terminus. Fc-050 is a linker capped analog of Fc-048 (see FIG. 1B), which has the N-terminal of the procoagulant peptide linked to a second Fc region. A TGA profile of Fc-050 can be seen in FIG. 3B.

Additional bleeding and thrombogenicity models can be used such as described in Tranholm, M, et al, *Blood* 2003, 102, 3615-3620; Tranholm, M, et al, *Thrombosis Research* 2003, 109, 217-223; Lauritzen, B, et al, *Journal of Thrombosis and Hemostasis* 2009, 7, 651-657.

Example 3

Pharmacokinetic Assessment of Monomeric Fc-048

Hemophilia A mice were treated with monomeric procoagulant fusion construct, Fc-048, intravenously at a dose of 1.15 mg/kg. The hemophilia A mice used for this study are FVIII deficient mice (B6; 129S-F8tm1Kaz/J, HemA). See also Bi L. et al., *Nat Genet.* 10(1):119-121 (1995). Blood samples were taken from the animal via retro-orbital bleeding at the following timepoint post-dose: 5 minutes, 6 hours, 24 hours, 48 hours, 72 hours, 96 hours, and 144 hours. Plasma concentrations of procoagulant fusion construct Fc-048 were determined using anti-human Fc-Fc ELISA. A diagram showing the plasma levels of Fc-048 (expressed as percentages of initial dose) over the course of 6 days can be seen in FIG. 5. Each data point is based on analysis of blood samples from 4 mice.

Pharmacokinetic parameters were calculated according to standard methods used in the art. The results are shown below:

| | |
|---|---|
| Cmax/dose: | 0.0215 kg/mL; |
| Recovery: | 84%; |
| Alpha-$t_{1/2}$: | 2.1 h; |
| Beta-$t_{1/2}$: | 131.5 h; |
| AUC/dose: | 1.95 h*kg/mL; |
| Cl; | 0.512 mL/h/kg; |
| $V_{ss}$: | 95.4 mL/kg. |

In summary, the Fc fusion construct improved the pharmacokinetic properties in hemophilia A mice. Monomeric Fc-048 was found to have prolonged half-life in hemophilia A mice compared to the parent peptide.

Having now fully described this invention, it will be understood by those of ordinary skill in the art that the same can be performed within a wide and equivalent range of conditions, formulations and other parameters without affecting the scope of the invention or any embodiment thereof.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

All patents and publications cited herein are incorporated by reference herein in their entirety.

The present application claims the benefit of U.S. Provisional Application No. 61/901,973, filed Nov. 8, 2013 and U.S. Provisional Application No. 61/981,446, filed Apr. 18, 2014, which are incorporated herein by reference in their entireties.

TABLE 1

Polynucleotide Sequences: FIX-Fc

A. FIX-Fc Chain DNA Sequence (SEQ ID NO: 7, which encodes SEQ ID NO: 8)

pSYN-FIX-030 Nucleotide sequence (nt 1 to 7583):
FIX exon 1 (signal peptide, 1st amino acid propeptide): nt 690-777
FIX mini intron: nt 778-1076
FIX propeptide sequence: nt 1077-1126
Mature FIX sequence: nt 1127-2371
Fc: nt 2372-3052 gcgcgcgttgacattgattattgactagttattaatagtaatcaattacggggtcattagttcatagcccatatatgg agttccgcgttacataacttacggtaaatggcccgcctggctgaccgcccaacgaccccgcccattgacgtcaataa tgacgtatgttcccatagtaacgccaatagggactttccattgacgtcaatgggtggagtatttacggtaaactgccc acttggcagtacatcaagtgtatcatatgccaagtacgccccctattgacgtcaatgacggtaaatggcccgcctggc attatgcccagtacatgaccttatgggactttcctacttggcagtacatctacgtattagtcatcgctattaccatgg tgatgcggttttggcagtacatcaatgggcgtggatagcggtttgactcacggggatttccaagtctccaccccattg acgtcaatgggagtttgttttggcaccaaaatcaacgggactttccaaaatgtcgtaacaactccgccccattgacgc aaatgggcggtaggcgtgtacggtgggaggtctatataagcagagctctctggctaactagagaacccactgcttact ggcttatcgaaattaatacgactcactataggggagacccaagcttcgcgacgtacggcgccaccatgcagcgcgtga acatgatcatggcagaatcaccaggcctcatcaccatctgccttttaggatatctactcagtgctgaatgtacaggtt tgtttcctttttttaaaatacattgagtatgcttgccttttagatatagaaatatctgatgctgtcttcttcactaaat tttgattacatgatttgacagcaatattgaagagtctaacagccagcacgcaggttggtaagtactgtgggaacatca cagattttggctccatgccctaaagagaaattggctttcagattatttggattaaaaacaaagactttcttaagagat gtaaaattttcatgatgttttcttttttgctaaaactaaagaattattcttttacatttcagttttttcttgatcatga aaacgccaacaaaattctgaatcggccaaagaggtataattcaggtaaattggaagagtttgttcaagggaatctaga gagagaatgtatggaagaaaagtgtagttttgaagaagcacgagaagttttgaaaacactgaaagaacaactgaatt ttggaagcagtatgttgatgaagatcagtgtgagtccaatccatgttaaatggcggcagttgcaaggatgacattaa ttcctatgaatgttggtgtcccctttggatttgaaggaaagaactgtgaattagatgtaacatgtaacattaagaatgg cagatgcgagcagttttgtaaaaatagtgctgataacaaggtggtttgctcctgtactgagggatatcgacttgcaga aaaccagaagtcctgtgaaccagcagtgccatttccatgtggaagagtttctgtttcacaaacttctaagctcacccg tgctgagactgttttcctgatgtggactatgtaaattctactgaagctgaaaccattttggataacatcactcaaag cacccaatcatttaatgacttcactcgggttgttggtggagaagatgccaaaccaggtcaattcccttggcaggttgt tttgaatggtaaagttgatgcattctgtggaggctctatcgttaatgaaaaatggattgtaactgctgcccactgtgt tgaaactggtgttaaaattacagttgtcgcaggtgaacataatattgaggagacagaacatacgagcaaaagcgaaa tgtgattcgaattattcctcaccacaactacaatgcagctattaataagtacaaccatgacattgcccttctggaact ggacgaacccttagtgctaaacagctacgttacacctattgcattgctgacaaggaatacacgaacatcttcctcaa atttggatctggctatgtaagtggctggggaagagtcttccacaaagggagatcagctttagttcttcagtaccttag agttccacttgttgaccgagccacatgtcttcgatctacaaagttccaccatctataacaacatgttctgtgctggctt ccatgaaggaggtagagattcatgtcaaggagatagtgggggaccccatgttactgaagtggaagggaccagtttctt aactggaattattagctggggtgaagagtgtgcaatgaaaggcaaatatggaatatataccaaggtgtcccggtatgt caactggattaaggaaaaaacaaagctcactgacaaaactcacacatgcccaccgtgcccagctccggaactcctggg cggaccgtcagtcttcctcttccccccaaaacccaaggacaccctcatgatctcccggacccctgaggtcacatgcgt ggtggtggacgtgagccacgaagaccctgaggtcaagttcaactggtacgtggacggcgtggaggtgcataatgccaa gacaaagccgcgggaggaacagtacaacagcacgtaccgtgtggtcagcgtcctcaccgtcctgcaccaggactggct gaatggcaaggagtacaagtgcaaggtctccaacaaagcccctcccagccccatcgagaaaaccatctccaaagccaa TABLE 1-continued Polynucleotide Sequences: FIX-Fc agggcagccccgagaaccacaggtgtacaccctgcccccatcccgggatgagctgaccaagaaccaggtcagcctgac
ctgcctggtcaaaggcttctatcccagcgacatcgccgtggagtgggagagcaatgggcagccggagaacaactacaa
gaccacgcctcccgtgttggactccgacggctccttcttcctctacagcaagctcaccgtggacaagagcaggtggca
gcaggggaacgtcttctcatgctccgtgatgcatgaggctctgcacaaccactacacgcagaagagcctctccctgtc
tccgggtaaatgagaattcagacatgataagatacattgatgagtttggacaaaccacaactagaatgcagtgaaaaa
aatgctttatttgtgaaatttgtgatgctattgctttatttgtaaccattataagctgcaataaacaagttggggtag
gcgaagaactccagcatgagatccccgcgctggaggatcatccagccggcgtcccggaaaacgattccgaagcccaac
ctttcatagaaggcggcggtggaatcgaaatctcgtagcacgtgtcagtcctgctcctcggccacgaagtgcacgcag
ttgccggccgggtcgcgcagggcgaactcccgcccccacggctgctcgccgatctcggtcatggccggcccggaggcg
tcccggaagttcgtggacacgacctccgaccactcggcgtacagctcgtccaggccgcgcacccacacccaggccagg
gtgttgtccggcaccacctggtcctggaccgcgctgatgaacagggtcacgtcgtcccgaccacaccggcgaagtcg
tcctccacgaagtcccgggagaacccgagccggtcggtccagaactcgaccgctccggcgacgtcgcgcgcggtgagc
accggaacggcactggtcaacttggccatggtttagttcctcaccttgtcgtattatactatgccgatatactatgcc
gatgattaattgtcaacacgtgctgatcagatccgaaaatggatatacaagctcccaggagcttttgcaaaagccta
ggcctccaaaaaagcctcctcactacttctggaatagctcagaggcagaggcggcctcggcctctgcataaataaaaa
aaattagtcagccatggggcggagaatgggcggaactgggcggagttaggggcgggatgggcggagttaggggcggga
ctatggttgctgactaattgagatgcatgctttgcatacttctgcctgctggggagcctggggactttccacacctgg
ttgctgactaattgagatgcatgctttgcatacttctgcctgctggggagcctggggactttccacacctcgtcgag
ctagcttcgtgaggctccggtgcccgtcagtgggcagagcgcacatcgcccacagtccccgagaagttgggggaggg
gtcggcaattgaaccggtgcctagagaaggtggcgcggggtaaactgggaaagtgatgtcgtgtactggctccgcctt
tttcccgagggtggggagaaccgtatataagtgcagtagtcgccgtgaacgttcttttttcgcaacgggtttgccgcc
agaacacaggtaagtgccgtgtgtggttcccgcgggcctggcctctttacgggttatggcccttgcgtgccttgaatt
acttccacctggctccagtacgtgattcttgatcccgagctggagccaggggcgggccttgcgctttaggagcccctt
cgcctcgtgcttgagttgaggcctggcctgggcgctggggccgccgcgtgcgaatctggtggcaccttcgcgcctgtc
tcgctgctttcgataagtctctagccatttaaaattttttgatgacctactgcgacgctttttttctggcaagatagtc
ttgtaaatgcgggccaggatctgcacactggtatttcggttttttggggccgcgggcggcgacggggcccgtgcgtccc
agcgcacatgttcggcgaggcggggcctgcgagcgcggccaccgagaatcggacgggggtagtctcaagctggccggc
ctgctctggtgcctggcctcgcgccgcgtgtatcgccccgccctgggcggcaaggctggccggtcggcaccagttg
cgtgagcggaaagatggccgcttcccggccctgctccaggggctcaaaatggaggacgcggcgctcgggagagcggg
cgggtgagtcacccacacaaaggaaaggggcctttccgtcctcagccgtcgcttcatgtgactccacggagtaccggg
cgccgtccaggcacctcgattagttctggagcttttggagtacgtcgtctttaggttggggggagggggtttatgcga
tggagtttccccacactgagtgggtggagactgaagttaggccagcttggcacttgatgtaattctccttggaatttg
ccctttttgagtttggatcttggttcattctcaagcctcagacagtggttcaaagttttttttcttccatttcaggtgt
cgtgaacacgtggtcgcggccgcgccgccaccatggagacagacacactcctgctatgggtactgctgctctgggttc
caggttccactggtgacaaaactcacacatgcccaccgtgcccagcacctgaactcctgggaggaccgtcagtcttcc
tcttccccccaaaacccaaggacaccctcatgatctcccggacccctgaggtcacatgcgtggtggtggacgtgagcc
acgaagaccctgaggtcaagttcaactggtacgtggacggcgtggaggtgcataatgccaagacaaagccgcgggagg
agcagtacaacagcacgtaccgtgtggtcagcgtcctcaccgtcctgcaccaggactggctgaatggcaaggagtaca
agtgcaaggtctccaacaaagccctcccagcccccatcgagaaaaccatctccaaagccaaagggcagccccgagaac TABLE 1-continued

| Polynucleotide Sequences: FIX-Fc |
|---| cacaggtgtacaccctgccccatcccgcgatgagctgaccaagaaccaggtcagcctgacctgcctggtcaaaggct tctatcccagcgacatcgccgtggagtgggagagcaatgggcagccggagaacaactacaagaccacgcctcccgtgt tggactccgacggctccttcttcctctacagcaagctcaccgtggacaagagcaggtggcagcaggggaacgtcttct catgctccgtgatgcatgaggctctgcacaaccactacacgcagaagagcctctccctgtctccgggtaaatgactcg agagatctggccggctgggcccgtttcgaaggtaagcctatccctaaccctctcctcggtctcgattctacgcgtacc ggtcatcatcaccatcaccattgagtttaaacccgctgatcagcctcgactgtgccttctagttgccagccatctgtt gtttgcccctcccccgtgccttccttgaccctggaaggtgccactcccactgtcctttcctaataaaatgaggaaatt gcatcgcattgtctgagtaggtgtcattctattctggggggtggggtggggcaggacagcaaggggaggattgggaa gacaatagcaggcatgctgggatgcggtgggctctatggcttctgaggcggaaagaaccagtggcggtaatacggtt atccacagaatcaggggataacgcaggaaagaacatgtgagcaaaaggccagcaaaaggccaggaaccgtaaaaggc cgcgttgctggcgtttttccataggctccgcccccctgacgagcatcacaaaaatcgacgctcaagtcagaggtggcg aaacccgacaggactataaagataccaggcgtttccccctagaagctccctcgtgcgctctcctgttccgaccctgcc gcttaccggatacctgtccgcctttctcccttcgggaagcgtggcgctttctcatagctcacgctgtaggtatctcag ttcggtgtaggtcgttcgctccaagctgggctgtgtgcacgaaccccccgttcagcccgaccgctgcgccttatccgg taactatcgtcttgagtccaacccggtaagacacgacttatcgccactggcagcagccactggtaacaggattagcag agcgaggtatgtaggcggtgctacagagttcttgaagtggtggcctaactacggctacactagaagaacagtatttgg tatctgcgctctgctgaagccagttaccttcggaaaaagagttggtagctcttgatccggcaaacaaaccaccgctgg tagcggtggtttttttgtttgcaagcagcagattacgcgcagaaaaaaaggatctcaagaagatcctttgatcttttc tacggggtctgacgctcagtggaacgaaaactcacgttaagggattttggtcatgacattaacctataaaaataggcg tatcacgaggccctttcgtctcgcgcgtttcggtgatgacggtgaaaacctctgacacatgcagctcccggagacggt cacagcttgtctgtaagcggatgccgggagcagacaagcccgtcaaggcgcgtcagcgggtgttggcgggtgtcgggg ctggcttaactatgcggcatcagagcagattgtactgagagtgcaccatatgcggtgtgaaataccgcacagatgc gtaaggagaaaataccgcatcaggcgccattcgccattcaggctgcgcaactgttgggaagggcgatcggtgcgggcc tcttcgctattacgcca B. Fc DNA sequence (mouse Igκ signal peptide underlined)
(SEQ ID NO: 9, which encodes SEQ ID NO: 10)

<u>ATGGA GACAGACACA</u>

<u>CTCCTGCTAT GGGTACTGCT GCTCTGGGTT CCAGGTTCCA CTGGTGACAA</u> AACTCACACA

TGCCCACCGT GCCCAGCACC TGAACTCCTG GGAGGACCGT CAGTCTTCCT CTTCCCCCCA

AAACCCAAGG ACACCCTCAT GATCTCCCGG ACCCCTGAGG TCACATGCGT GGTGGTGGAC

GTGAGCCACG AAGACCCTGA GGTCAAGTTC AACTGGTACG TGGACGGCGT GGAGGTGCAT

AATGCCAAGA CAAAGCCGCG GGAGGAGCAG TACAACAGCA CGTACCGTGT GGTCAGCGTC

CTCACCGTCC TGCACCAGGA CTGGCTGAAT GGCAAGGAGT ACAAGTGCAA GGTCTCCAAC

AAAGCCCTCC CAGCCCCCAT CGAGAAAACC ATCTCCAAAG CCAAAGGGCA GCCCCGAGAA

CCACAGGTGT ACACCCTGCC CCCATCCCGC GATGAGCTGA CCAAGAACCA GGTCAGCCTG

ACCTGCCTGG TCAAAGGCTT CTATCCCAGC GACATCGCCG TGGAGTGGGA GAGCAATGGG

CAGCCGGAGA ACAACTACAA GACCACGCCT CCCGTGTTGG ACTCCGACGG CTCCTTCTTC

TABLE 1-continued

Polynucleotide Sequences: FIX-Fc

CTCTACAGCA AGCTCACCGT GGACAAGAGC AGGTGGCAGC AGGGGAACGT CTTCTCATGC

TCCGTGATGC ATGAGGCTCT GCACAACCAC TACACGCAGA AGAGCCTCTC CCTGTCTCCG

GGTAAA

TABLE 2

Polypeptide Sequences: FIX-Fc

A. FIX-Fc chain (SEQ ID NO: 8): (28 amino acid signal sequence underlined, 18 amino acid propeptide double underlined, Fc portion in italics.) The C-terminal lysine is not present in either subunit; this processing is often observed in recombinant proteins produced in mammalian cell culture, as well as with plasma derived proteins.

FIXFC-SC SUBUNIT:
FIX Signal Peptide: -46 MQRVNMIMAE SPGLITICLL GYLLSAEC

FIX Propeptide: -18 TVFLDHENAN KILNRPKR

1 YNSGKLEEFV QGNLERECME EKCSFEEARE VFENTERTTE FWKQYVDGDQ

51 CESNPCLNGG SCKDDINSYE CWCPFGFEGK NCELDVTCNI KNGRCEQFCK

101 NSADNKVVCS CTEGYRLAEN QKSCEPAVPF PCGRVSVSQT SKLTRAETVF

151 PDVDYVNSTE AETILDNITQ STQSFNDFTR VVGGEDAKPG QFPWQVVLNG

201 KVDAFCGGSI VNEKWIVTAA HCVETGVKIT VVAGEHNIEE TEHTEQKRNV

251 IRIIPHHNYN AAINKYNHDI ALLELDEPLV LNSYVTPICI ADKEYTNIFL

301 KFGSGYVSGW GRVFHKGRSA LVLQYLRVPL VDRATCLRST KFTIYNNMFC

351 AGFHEGGRDS CQGDSGGPHV TEVEGTSFLT GIISWGEECA MKGKYGIYTK

401 VSRYVNWIKE KTKLT*DKTHT CPPCPAPELL GGPSVFLFPP KPKDTLMISR*

451 *TPEVTCVVVD VSHEDPEVKF NWYVDGVEVH NAKTKPREEQ YNSTYRVVSV*

501 *LTVLHQDWLN GKEYKCKVSN KALPAPIEKT ISKAKGQPRE PQVYTLPPSR*

551 *DELTKNQVSL TCLVKGFYPS DIAVEWESNG QPENNYKTTP PVLDSDGSFF*

601 *LYSKLTVDKS RWQQGNVFSC SVMHEALHNH YTQKSLSLSP GK*

MQRVNMIMAESPGLITICLLGYLLSAECTVFLDHENANKILNRP

KRYNSGKLEEFVQGNLERECMEEKCSFEEAREVFENTERTTEFWKQYVDGDQCESNPC

LNGGSCKDDINSYECWCPFGFEGKNCELDVTCNIKNGRCEQFCKNSADNKVVCSCTEG

YRLAENQKSCEPAVPFPCGRVSVSQTSKLTRAETVFPDVDYVNSTEAETILDNITQST

QSFNDFTRVVGGEDAKPGQFPWQVVLNGKVDAFCGGSIVNEKWIVTAAHCVETGVKIT

VVAGEHNIEETEHTEQKRNVIRIIPHHNYNAAINKYNHDIALLELDEPLVLNSYVTPI

CIADKEYTNIFLKFGSGYVSGWGRVFHKGRSALVLQYLRVPLVDRATCLRSTKFTIYN

NMFCAGFHEGGRDSCQGDSGGPHVTEVEGTSFLTGIISWGEECAMKGKYGIYTKVSRY

VNWIKEKTKLT

TABLE 2-continued

Polypeptide Sequences: FIX-Fc

B. Fc chain (SEQ ID NO: 10) 20 amino acid heterologous mouse Igκ light chain signal peptide (underlined):

METDTLLLWV LLLWVPGSTG

Mature Fc sequence (corresponding to human IgG1 amino acids 221 to 447, EU numbering)
```
  1 DKTHTCPPCP APELLGGPSV FLFPPKPKDT LMISRTPEVT CVVVDVSHED

51 PEVKFNWYVD GVEVHNAKTK PREEQYNSTY RVVSVLTVLH QDWLNGKEYK

101 CKVSNKALPA PIEKTISKAK GQPREPQVYT LPPSRDELTK NQVSLTCLVK

151 GFYPSDIAVE WESNGQPENN YKTTPPVLDS DGSFFLYSKL TVDKSRWQQG

201 NVFSCSVMHE ALHNHYTQKS LSLSPGK
```

TABLE 3

Polynucleotide Sequence: FVIII-Fc

A. B-Domain Deleted FVIIIFc
(i) B-Domain Deleted FVIIIFc Chain DNA Sequence (FVIII signal peptide underlined, Fc region in bold) (SEQ ID NO: 11, which encodes SEQ ID NO: 12)
```
 661                                          A TGCAAATAGA GCTCTCCACC TGCTTCTTTC

721 TGTGCCTTTT GCGATTCTGC TTTAGTGCCA CCAGAAGATA CTACCTGGGT GCAGTGGAAC

781 TGTCATGGGA CTATATGCAA AGTGATCTCG GTGAGCTGCC TGTGGACGCA AGATTTCCTC

841 CTAGAGTGCC AAAATCTTTT CCATTCAACA CCTCAGTCGT GTACAAAAAG ACTCTGTTTG

901 TAGAATTCAC GGATCACCTT TTCAACATCG CTAAGCCAAG GCCACCCTGG ATGGGTCTGC

961 TAGGTCCTAC CATCCAGGCT GAGGTTTATG ATACAGTGGT CATTACACTT AAGAACATGG

1021 CTTCCCATCC TGTCAGTCTT CATGCTGTTG GTGTATCCTA CTGGAAAGCT TCTGAGGGAG

1081 CTGAATATGA TGATCAGACC AGTCAAAGGG AGAAAGAAGA TGATAAAGTC TTCCCTGGTG

1141 GAAGCCATAC ATATGTCTGG CAGGTCCTGA AGAGAATGG TCCAATGGCC TCTGACCCAC

1201 TGTGCCTTAC CTACTCATAT CTTTCTCATG TGGACCTGGT AAAAGACTTG AATTCAGGCC

1261 TCATTGGAGC CCTACTAGTA TGTAGAGAAG GGAGTCTGGC CAAGGAAAAG ACACAGACCT

1321 TGCACAAATT TATACTACTT TTTGCTGTAT TTGATGAAGG GAAAAGTTGG CACTCAGAAA

1381 CAAAGAACTC CTTGATGCAG GATAGGGATG CTGCATCTGC TCGGGCCTGG CCTAAAATGC

1441 ACACAGTCAA TGGTTATGTA AACAGGTCTC TGCCAGGTCT GATTGGATGC ACAGGAAAT

1501 CAGTCTATTG GCATGTGATT GGAATGGGCA CCACTCCTGA AGTGCACTCA ATATTCCTCG

1561 AAGGTCACAC ATTTCTTGTG AGGAACCATC GCCAGGCGTC CTTGGAAATC TCGCCAATAA

1621 CTTTCCTTAC TGCTCAAACA CTCTTGATGG ACCTTGGACA GTTTCTACTG TTTTGTCATA

1681 TCTCTTCCCA CCAACATGAT GGCATGGAAG CTTATGTCAA AGTAGACAGC TGTCCAGAGG

1741 AACCCCAACT ACGAATGAAA AATAATGAAG AAGCGGAAGA CTATGATGAT GATCTTACTG

1801 ATTCTGAAAT GGATGTGGTC AGGTTTGATG ATGACAACTC TCCTTCCTTT ATCCAAATTC

1861 GCTCAGTTGC CAAGAAGCAT CCTAAAACTT GGGTACATTA CATTGCTGCT GAAGAGGAGG

1921 ACTGGGACTA TGCTCCCTTA GTCCTCGCCC CCGATGACAG AAGTTATAAA AGTCAATATT

1981 TGAACAATGG CCCTCAGCGG ATTGGTAGGA AGTACAAAAA AGTCCGATTT ATGGCATACA

2041 CAGATGAAAC CTTTAAGACT CGTGAAGCTA TTCAGCATGA ATCAGGAATC TTGGGACCTT

2101 TACTTTATGG GGAAGTTGGA GACACACTGT TGATTATATT TAAGAATCAA GCAAGCAGAC
```

TABLE 3-continued

| Polynucleotide Sequence: FVIII-Fc |
|---|

```
2161 CATATAACAT CTACCCTCAC GGAATCACTG ATGTCCGTCC TTTGTATTCA AGGAGATTAC
2221 CAAAAGGTGT AAAACATTTG AAGGATTTTC CAATTCTGCC AGGAGAAATA TTCAAATATA
2281 AATGGACAGT GACTGTAGAA GATGGGCCAA CTAAATCAGA TCCTCGGTGC CTGACCCGCT
2341 ATTACTCTAG TTTCGTTAAT ATGGAGAGAG ATCTAGCTTC AGGACTCATT GGCCCTCTCC
2401 TCATCTGCTA CAAAGAATCT GTAGATCAAA GAGGAAACCA GATAATGTCA GACAAGAGGA
2461 ATGTCATCCT GTTTTCTGTA TTTGATGAGA ACCGAAGCTG GTACCTCACA GAGAATATAC
2521 AACGCTTTCT CCCCAATCCA GCTGGAGTGC AGCTTGAGGA TCCAGAGTTC CAAGCCTCCA
2581 ACATCATGCA CAGCATCAAT GGCTATGTTT TTGATAGTTT GCAGTTGTCA GTTTGTTTGC
2641 ATGAGGTGGC ATACTGGTAC ATTCTAAGCA TTGGAGCACA GACTGACTTC CTTTCTGTCT
2701 TCTTCTCTGG ATATACCTTC AAACACAAAA TGGTCTATGA AGACACACTC ACCCTATTCC
2761 CATTCTCAGG AGAAACTGTC TTCATGTCGA TGGAAAACCC AGGTCTATGG ATTCTGGGGT
2821 GCCACAACTC AGACTTTCGG AACAGAGGCA TGACCGCCTT ACTGAAGGTT TCTAGTTGTG
2881 ACAAGAACAC TGGTGATTAT TACGAGGACA GTTATGAAGA TATTGCTGCA TACTTGCTGA
2941 GTAAAAACAA TGCCATTGAA CCAAGAAGCT TCTCTCAAAA CCCACCAGTC TTGAAACGCC
3001 ATCAACGGGA ATAACTCGT ACTACTCTTC AGTCAGATCA AGAGGAAATT GACTATGATG
3061 ATACCATATC AGTTGAAATG AAGAAGGAAG ATTTTGACAT TTATGATGAG GATGAAAATC
3121 AGAGCCCCCG CAGCTTTCAA AAGAAAACAC GACACTATTT TATTGCTGCA GTGGAGAGGC
3181 TCTGGGATTA TGGGATGAGT AGCTCCCCAC ATGTTCTAAG AAACAGGGCT CAGAGTGGCA
3241 GTGTCCCTCA GTTCAAGAAA GTTGTTTTCC AGGAATTTAC TGATGGCTCC TTTACTCAGC
3301 CCTTATACCG TGGAGAACTA AATGAACATT TGGGACTCCT GGGGCCATAT ATAAGAGCAG
3361 AAGTTGAAGA TAATATCATG GTAACTTTCA GAAATCAGGC CTCTCGTCCC TATTCCTTCT
3421 ATTCTAGCCT TATTTCTTAT GAGGAAGATC AGAGGCAAGG AGCAGAACCT AGAAAAAACT
3481 TTGTCAAGCC TAATGAAACC AAAACTTACT TTTGGAAAGT GCAACATCAT ATGGCACCCA
3541 CTAAAGATGA GTTTGACTGC AAAGCCTGGG CTTATTTCTC TGATGTTGAC CTGGAAAAAG
3601 ATGTGCACTC AGGCCTGATT GGACCCCTTC TGGTCTGCCA CACTAACACA CTGAACCCTG
3661 CTCATGGGAG ACAAGTGACA GTACAGGAAT TTGCTCTGTT TTTCACCATC TTTGATGAGA
3721 CCAAAAGCTG GTACTTCACT GAAAATATGG AAAGAAACTG CAGGGCTCCC TGCAATATCC
3781 AGATGGAAGA TCCCACTTTT AAAGAGAATT ATCGCTTCCA TGCAATCAAT GGCTACATAA
3841 TGGATACACT ACCTGGCTTA GTAATGGCTC AGGATCAAAG GATTCGATGG TATCTGCTCA
3901 GCATGGGCAG CAATGAAAAC ATCCATTCTA TTCATTTCAG TGGACATGTG TTCACTGTAC
3961 GAAAAAAAGA GGAGTATAAA ATGGCACTGT ACAATCTCTA TCCAGGTGTT TTTGAGACAG
4021 TGGAAATGTT ACCATCCAAA GCTGGAATTT GGCGGGTGGA ATGCCTTATT GGCGAGCATC
4081 TACATGCTGG GATGAGCACA CTTTTTCTGG TGTACAGCAA TAAGTGTCAG ACTCCCCTGG
4141 GAATGGCTTC TGGACACATT AGAGATTTTC AGATTACAGC TTCAGGACAA TATGGACAGT
4201 GGGCCCCAAA GCTGGCCAGA CTTCATTATT CCGGATCAAT CAATGCCTGG AGCACCAAGG
4261 AGCCCTTTTC TTGGATCAAG GTGGATCTGT TGGCACCAAT GATTATTCAC GGCATCAAGA
4321 CCCAGGGTGC CCGTCAGAAG TTCTCCAGCC TCTACATCTC TCAGTTTATC ATCATGTATA
4381 GTCTTGATGG GAAGAAGTGG CAGACTTATC GAGGAAATTC CACTGGAACC TTAATGGTCT
4441 TCTTTGGCAA TGTGGATTCA TCTGGGATAA AACACAATAT TTTTAACCCT CCAATTATTG
```

TABLE 3-continued

| Polynucleotide Sequence: FVIII-Fc |
|---|

```
4501 CTCGATACAT CCGTTTGCAC CCAACTCATT ATAGCATTCG CAGCACTCTT CGCATGGAGT
4561 TGATGGGCTG TGATTTAAAT AGTTGCAGCA TGCCATTGGG AATGGAGAGT AAAGCAATAT
4621 CAGATGCACA GATTACTGCT TCATCCTACT TTACCAATAT GTTTGCCACC TGGTCTCCTT
4681 CAAAAGCTCG ACTTCACCTC CAAGGGAGGA GTAATGCCTG AGACCTCAG GTGAATAATC
4741 CAAAAGAGTG GCTGCAAGTG GACTTCCAGA AGACAATGAA AGTCACAGGA GTAACTACTC
4801 AGGGAGTAAA ATCTCTGCTT ACCAGCATGT ATGTGAAGGA GTTCCTCATC TCCAGCAGTC
4861 AAGATGGCCA TCAGTGGACT CTCTTTTTTC AGAGTGCCAA AGTAAAGGTT TTTCAGGGAA
4921 ATCAAGACTC CTTCACACCT GTGGTGAACT CTCTAGACCC ACCGTTACTG ACTCGCTACC
4981 TTCGAATTCA CCCCCAGAGT TGGGTGCACC AGATTGCCCT GAGGATGGAG GTTCTGGGCT
5041 GCGAGGCACA GGACCTCTAC GACAAAACTC ACACATGCCC ACCGTGCCCA GCTCCAGAAC
5101 TCCTGGGCGG ACCGTCAGTC TTCCTCTTCC CCCCAAAACC CAAGGACACC CTCATGATCT
5161 CCCGGACCCC TGAGGTCACA TGCGTGGTGG TGGACGTGAG CCACGAAGAC CCTGAGGTCA
5221 AGTTCAACTG GTACGTGGAC GGCGTGGAGG TGCATAATGC CAAGACAAAG CCGCGGGAGG
5281 AGCAGTACAA CAGCACGTAC CGTGTGGTCA GCGTCCTCAC CGTCCTGCAC CAGGACTGGC
5341 TGAATGGCAA GGAGTACAAG TGCAAGGTCT CCAACAAAGC CCTCCCAGCC CCCATCGAGA
5401 AAACCATCTC CAAAGCCAAA GGGCAGCCCC GAGAACCACA GGTGTACACC CTGCCCCCAT
5461 CCCGGGATGA GCTGACCAAG AACCAGGTCA GCCTGACCTG CCTGGTCAAA GGCTTCTATC
5521 CCAGCGACAT CGCCGTGGAG TGGGAGAGCA ATGGGCAGCC GGAGAACAAC TACAAGACCA
5581 CGCCTCCCGT GTTGGACTCC GACGGCTCCT TCTTCCTCTA CAGCAAGCTC ACCGTGGACA
5641 AGAGCAGGTG GCAGCAGGGG AACGTCTTCT CATGCTCCGT GATGCATGAG GCTCTGCACA
5701 ACCACTACAC GCAGAAGAGC CTCTCCCTGT CTCCGGGTAA A
```

B. Full-length FVIIIFc
(i): Full-length FVIIIFc DNA Sequence (FVIII signal peptide underlined.
Fc region in bold) (SEQ ID NO: 13, which encodes SEQ ID NO: 14)

```
 661                                         ATG CAAATAGAGC TCTCCACCTG
 721 CTTCTTTCTG TGCCTTTTGC GATTCTGCTT TAGTGCCACC AGAAGATACT ACCTGGGTGC
 781 AGTGGAACTG TCATGGGACT ATATGCAAAG TGATCTCGGT GAGCTGCCTG TGGACGCAAG
 841 ATTTCCTCCT AGAGTGCCAA ATCTTTTCC ATTCAACACC TCAGTCGTGT ACAAAAAGAC
 901 TCTGTTTGTA GAATTCACGG ATCACCTTTT CAACATCGCT AAGCCAAGGC CACCCTGGAT
 961 GGGTCTGCTA GGTCCTACCA TCCAGGCTGA GGTTTATGAT ACAGTGGTCA TTACACTTAA
1021 GAACATGGCT TCCCATCCTG TCAGTCTTCA TGCTGTTGGT GTATCCTACT GGAAAGCTTC
1081 TGAGGGAGCT GAATATGATG ATCAGACCAG TCAAAGGGAG AAAGAAGATG ATAAAGTCTT
1141 CCCTGGTGGA AGCCATACAT ATGTCTGGCA GGTCCTGAAA GAGAATGGTC CAATGGCCTC
1201 TGACCCACTG TGCCTTACCT ACTCATATCT TTCTCATGTG GACCTGGTAA AAGACTTGAA
1261 TTCAGGCCTC ATTGGAGCCC TACTAGTATG TAGAGAAGGG AGTCTGGCCA AGGAAAAGAC
1321 ACAGACCTTG CACAAATTTA TACTACTTTT TGCTGTATTT GATGAAGGGA AAGTTGGCA
1381 CTCAGAAACA AAGAACTCCT TGATGCAGGA TAGGGATGCT GCATCTGCTC GGGCCTGGCC
1441 TAAAATGCAC ACAGTCAATG GTTATGTAAA CAGGTCTCTG CCAGGTCTGA TTGGATGCCA
1501 CAGGAAATCA GTCTATTGGC ATGTGATTGG AATGGGCACC ACTCCTGAAG TGCACTCAAT
1561 ATTCCTCGAA GGTCACACAT TCTTGTGAG GAACCATCGC CAGGCGTCCT TGGAAATCTC
```

TABLE 3-continued

| Polynucleotide Sequence: FVIII-Fc |
|---|

```
1621 GCCAATAACT TCCTTACTG CTCAAACACT CTTGATGGAC CTTGGACAGT TTCTACTGTT

1681 TTGTCATATC TCTTCCCACC AACATGATGG CATGGAAGCT TATGTCAAAG TAGACAGCTG

1741 TCCAGAGGAA CCCCAACTAC GAATGAAAAA TAATGAAGAA GCGGAAGACT ATGATGATGA

1801 TCTTACTGAT TCTGAAATGG ATGTGGTCAG GTTTGATGAT GACAACTCTC CTTCCTTTAT

1861 CCAAATTCGC TCAGTTGCCA AGAAGCATCC TAAAACTTGG GTACATTACA TTGCTGCTGA

1921 AGAGGAGGAC TGGGACTATG CTCCCTTAGT CCTCGCCCCC GATGACAGAA GTTATAAAAG

1981 TCAATATTTG AACAATGGCC CTCAGCGGAT TGGTAGGAAG TACAAAAAAG TCCGATTTAT

2041 GGCATACACA GATGAAACCT TTAAGACTCG TGAAGCTATT CAGCATGAAT CAGGAATCTT

2101 GGGACCTTTA CTTTATGGGG AAGTTGGAGA CACACTGTTG ATTATATTTA AGAATCAAGC

2161 AAGCAGACCA TATAACATCT ACCCTCACGG AATCACTGAT GTCCGTCCTT TGTATTCAAG

2221 GAGATTACCA AAAGGTGTAA ACATTTGAA GGATTTTCCA ATTCTGCCAG AGAAATATT

2281 CAAATATAAA TGGACAGTGA CTGTAGAAGA TGGGCCAACT AAATCAGATC CTCGGTGCCT

2341 GACCCGCTAT TACTCTAGTT TCGTTAATAT GGAGAGAGAT CTAGCTTCAG GACTCATTGG

2401 CCCTCTCCTC ATCTGCTACA AGAATCTGT AGATCAAAGA GGAAACCAGA TAATGTCAGA

2461 CAAGAGGAAT GTCATCCTGT TTTCTGTATT TGATGAGAAC CGAAGCTGGT ACCTCACAGA

2521 GAATATACAA CGCTTTCTCC CCAATCCAGC TGGAGTGCAG CTTGAGGATC CAGAGTTCCA

2581 AGCCTCCAAC ATCATGCACA GCATCAATGG CTATGTTTTT GATAGTTTGC AGTTGTCAGT

2641 TTGTTTGCAT GAGGTGGCAT ACTGGTACAT TCTAAGCATT GGAGCACAGA CTGACTTCCT

2701 TTCTGTCTTC TTCTCTGGAT ATACCTTCAA ACACAAAATG GTCTATGAAG ACACACTCAC

2761 CCTATTCCCA TTCTCAGGAG AAACTGTCTT CATGTCGATG GAAAACCCAG GTCTATGGAT

2821 TCTGGGGTGC CACAACTCAG ACTTTCGGAA CAGAGGCATG ACCGCCTTAC TGAAGGTTTC

2881 TAGTTGTGAC AAGAACACTG GTGATTATTA CGAGGACAGT TATGAAGATA TTTCAGCATA

2941 CTTGCTGAGT AAAAACAATG CCATTGAACC AAGAAGCTTC TCCCAGAATT CAAGACACCC

3001 TAGCACTAGG CAAAAGCAAT TTAATGCCAC CACAATTCCA GAAAATGACA TAGAGAAGAC

3061 TGACCCTTGG TTTGCACACA GAACACCTAT GCCTAAAATA CAAAATGTCT CCTCTAGTGA

3121 TTTGTTGATG CTCTTGCGAC AGAGTCCTAC TCCACATGGG CTATCCTTAT CTGATCTCCA

3181 AGAAGCCAAA TATGAGACTT TTTCTGATGA TCCATCACCT GGAGCAATAG ACAGTAATAA

3241 CAGCCTGTCT GAAATGACAC ACTTCAGGCC ACAGCTCCAT CACAGTGGGG ACATGGTATT

3301 TACCCCTGAG TCAGGCCTCC AATTAAGATT AAATGAGAAA CTGGGGACAA CTGCAGCAAC

3361 AGAGTTGAAG AAACTTGATT TCAAAGTTTC TAGTACATCA AATAATCTGA TTTCAACAAT

3421 TCCATCAGAC AATTTGGCAG CAGGTACTGA TAATACAAGT TCCTTAGGAC CCCCAAGTAT

3481 GCCAGTTCAT TATGATAGTC AATTAGATAC CACTCTATTT GGCAAAAAGT CATCTCCCCT

3541 TACTGAGTCT GGTGGACCTC TGAGCTTGAG TGAAGAAAAT AATGATTCAA AGTTGTTAGA

3601 ATCAGGTTTA ATGAATAGCC AAGAAAGTTC ATGGGGAAAA AATGTATCGT CAACAGAGAG

3661 TGGTAGGTTA TTTAAAGGGA AAAGAGCTCA TGGACCTGCT TTGTTGACTA AAGATAATGC

3721 CTTATTCAAA GTTAGCATCT CTTTGTTAAA GACAAACAAA ACTTCCAATA ATTCAGCAAC

3781 TAATAGAAAG ACTCACATTG ATGGCCCATC ATTATTAATT GAGAATAGTC CATCAGTCTG

3841 GCAAAATATA TTAGAAAGTG ACACTGAGTT TAAAAAAGTG ACACCTTTGA TTCATGACAG

3901 AATGCTTATG GACAAAAATG CTACAGCTTT GAGGCTAAAT CATATGTCAA ATAAAACTAC
```

TABLE 3-continued

| Polynucleotide Sequence: FVIII-Fc |
|---|

```
3961 TTCATCAAAA AACATGGAAA TGGTCCAACA GAAAAAGAG GGCCCCATTC CACCAGATGC

4021 ACAAAATCCA GATATGTCGT TCTTTAAGAT GCTATTCTTG CCAGAATCAG CAAGGTGGAT

4081 ACAAAGGACT CATGGAAAGA ACTCTCTGAA CTCTGGGCAA GGCCCCAGTC CAAAGCAATT

4141 AGTATCCTTA GGACCAGAAA AATCTGTGGA AGGTCAGAAT TCTTGTCTG AGAAAAACAA

4201 AGTGGTAGTA GGAAAGGGTG AATTTACAAA GGACGTAGGA CTCAAAGAGA TGGTTTTTCC

4261 AAGCAGCAGA AACCTATTTC TTACTAACTT GGATAATTTA CATGAAAATA ATACACACAA

4321 TCAAGAAAAA AAAATTCAGG AAGAAATAGA AAAGAAGGAA ACATTAATCC AAGAGAATGT

4381 AGTTTTGCCT CAGATACATA CAGTGACTGG CACTAAGAAT TTCATGAAGA ACCTTTTCTT

4441 ACTGAGCACT AGGCAAAATG TAGAAGGTTC ATATGACGGG GCATATGCTC AGTACTTCA

4501 AGATTTTAGG TCATTAAATG ATTCAACAAA TAGAACAAAG AAACACACAG CTCATTTCTC

4561 AAAAAAGGG GAGGAAGAAA ACTTGGAAGG CTTGGGAAAT CAAACCAAGC AAATTGTAGA

4621 GAAATATGCA TGCACCACAA GGATATCTCC TAATACAAGC CAGCAGAATT TTGTCACGCA

4681 ACGTAGTAAG AGAGCTTTGA ACAATTCAG ACTCCCACTA GAAGAAACAG AACTTGAAAA

4741 AAGGATAATT GTGGATGACA CCTCAACCCA GTGGTCCAAA ACATGAAAC ATTTGACCCC

4801 GAGCACCCTC ACACAGATAG ACTACAATGA AAGGAGAAA GGGGCCATTA CTCAGTCTCC

4861 CTTATCAGAT TGCCTTACGA GGAGTCATAG CATCCCTCAA GCAAATAGAT CTCCATTACC

4921 CATTGCAAAG GTATCATCAT TTCCATCTAT TAGACCTATA TATCTGACCA GGGTCCTATT

4981 CCAAGACAAC TCTTCTCATC TTCCAGCAGC ATCTTATAGA AAGAAAGATT CTGGGGTCCA

5041 AGAAAGCAGT CATTTCTTAC AAGGAGCCAA AAAAATAAC CTTTCTTTAG CCATTCTAAC

5101 CTTGGAGATG ACTGGTGATC AAAGAGAGGT TGGCTCCCTG GGGACAAGTG CCACAAATTC

5161 AGTCACATAC AAGAAAGTTG AGAACACTGT TCTCCCGAAA CCAGACTTGC CCAAAACATC

5221 TGGCAAAGTT GAATTGCTTC CAAAAGTTCA CATTTATCAG AAGGACCTAT TCCCTACGGA

5281 AACTAGCAAT GGGTCTCCTG GCCATCTGGA TCTCGTGGAA GGGAGCCTTC TTCAGGGAAC

5341 AGAGGGAGCG ATTAAGTGGA ATGAAGCAAA CAGACCTGGA AAAGTTCCCT TTCTGAGAGT

5401 AGCAACAGAA AGCTCTGCAA AGACTCCCTC CAAGCTATTG GATCCTCTTG CTTGGGATAA

5461 CCACTATGGT ACTCAGATAC CAAAAGAAGA GTGGAAATCC AAGAGAAGT CACCAGAAAA

5521 AACAGCTTTT AAGAAAAAGG ATACCATTTT GTCCCTGAAC GCTTGTGAAA GCAATCATGC

5581 AATAGCAGCA ATAAATGAGG GACAAAATAA GCCCGAAATA GAAGTCACCT GGGCAAAGCA

5641 AGGTAGGACT GAAAGGCTGT GCTCTCAAAA CCCACCAGTC TTGAAACGCC ATCAACGGGA

5701 AATAACTCGT ACTACTCTTC AGTCAGATCA AGAGGAAATT GACTATGATG ATACCATATC

5761 AGTTGAAATG AAGAAGGAAG ATTTTGACAT TTATGATGAG GATGAAAATC AGAGCCCCCG

5821 CAGCTTTCAA AAGAAAACAC GACACTATTT TATTGCTGCA GTGGAGAGGC TCTGGGATTA

5881 TGGGATGAGT AGCTCCCCAC ATGTTCTAAG AAACAGGGCT CAGAGTGGCA GTGTCCCTCA

5941 GTTCAAGAAA GTTGTTTTCC AGGAATTTAC TGATGGCTCC TTTACTCAGC CCTTATACCG

6001 TGGAGAACTA AATGAACATT TGGGACTCCT GGGGCCATAT ATAAGAGCAG AAGTTGAAGA

6061 TAATATCATG GTAACTTTCA GAAATCAGGC CTCTCGTCCC TATTCCTTCT ATTCTAGCCT

6121 TATTTCTTAT GAGGAAGATC AGAGGCAAGG AGCAGAACCT AGAAAAAACT TGTCAAGCC

6181 TAATGAAACC AAAACTTACT TTTGGAAAGT GCAACATCAT ATGGCACCCA CTAAAGATGA

6241 GTTTGACTGC AAAGCCTGGG CTTATTTCTC TGATGTTGAC CTGGAAAAAG ATGTGCACTC
```

TABLE 3-continued

Polynucleotide Sequence: FVIII-Fc

```
8301 AGGCCTGATT GGACCCCTTC TGGTCTGCCA CACTAACACA CTGAACCCTG CTCATGGGAG
6361 ACAAGTGACA GTACAGGAAT TGCTCTGTT TTTCACCATC TTTGATGAGA CCAAAAGCTG
6421 GTACTTCACT GAAATATGG AAGAAACTG CAGGGCTCCC TGCAATATCC AGATGGAAGA
8481 TCCCACTTTT AAAGAGAATT ATCGCTTCCA TGCAATCAAT GGCTACATAA TGGATACACT
6541 ACCTGGCTTA GTAATGGCTC AGGATCAAAG GATTCGATGG TATCTGCTCA GCATGGGCAG
6601 CAATGAAAAC ATCCATTCTA TTCATTTCAG TGGACATGTG TTCACTGTAC GAAAAAAGA
6861 GGAGTATAAA ATGGCACTGT ACAATCTCTA TCCAGGTGTT TTTGAGACAG TGGAAATGTT
6721 ACCATCCAAA GCTGGAATTT GGCGGGTGGA ATGCCTTATT GGCGAGCATC TACATGCTGG
6781 GATGAGCACA CTTTTTCTGG TGTACAGCAA TAAGTGTCAG ACTCCCCTGG GAATGGCTTC
6841 TGGACACATT AGAGATTTTC AGATTACAGC TTCAGGACAA TATGGACAGT GGGCCCCAAA
6901 GCTGGCCAGA CTTCATTATT CCGGATCAAT CAATGCCTGG AGCACCAAGG AGCCCTTTTC
6961 TTGGATCAAG GTGGATCTGT TGGCACCAAT GATTATTCAC GGCATCAAGA CCCAGGGTGC
7021 CCGTCAGAAG TTCTCCAGCC TCTACATCTC TCAGTTTATC ATCATGTATA GTCTTGATGG
7081 GAAGAAGTGG CAGACTTATC GAGGAAATTC CACTGGAACC TTAATGGTCT TCTTTGGCAA
7141 TGTGGATTCA TCTGGGATAA AACACAATAT TTTTAACCCT CCAATTATTG CTCGATACAT
7201 CCGTTTGCAC CCAACTCATT ATAGCATTCG CAGCACTCTT CGCATGGAGT TGATGGGCTG
7261 TGATTTAAAT AGTTGCAGCA TGCCATTGGG AATGGAGAGT AAAGCAATAT CAGATGCACA
7321 GATTACTGCT TCATCCTACT TTACCAATAT GTTTGCCACC TGGTCTCCTT CAAAAGCTCG
7381 ACTTCACCTC CAAGGGAGGA GTAATGCCTG GAGACCTCAG GTGAATAATC CAAAAGAGTG
7441 GCTGCAAGTG GACTTCCAGA AGACAATGAA AGTCACAGGA GTAACTACTC AGGGAGTAAA
7501 ATCTCTGCTT ACCAGCATGT ATGTGAAGGA GTTCCTCATC TCCAGCAGTC AAGATGGCCA
7561 TCAGTGGACT CTCTTTTTTC AGAATGGCAA AGTAAAGGTT TTTCAGGGAA ATCAAGACTC
7621 CTTCACACCT GTGGTGAACT CTCTAGACCC ACCGTTACTG ACTCGCTACC TTCGAATTCA
7681 CCCCCAGAGT TGGGTGCACC AGATTGCCCT GAGGATGGAG GTTCTGGGCT GCGAGGCACA
7741 GGACCTCTAC **GACAAAACTC ACACATGCCC ACCGTGCCCA GCTCCAGAAC TCCTGGGCGG
7801 ACCGTCAGTC TTCCTCTTCC CCCCAAAACC CAAGGACACC CTCATGATCT CCCGGACCCC
7861 TGAGGTCACA TGCGTGGTGG TGGACGTGAG CCACGAAGAC CCTGAGGTCA AGTTCAACTG
7921 GTACGTGGAC GGCGTGGAGG TGCATAATGC CAAGACAAAG CCGCGGGAGG AGCAGTACAA
7981 CAGCACGTAC CGTGTGGTCA GCGTCCTCAC CGTCCTGCAC CAGGACTGGC TGAATGGCAA
8041 GGAGTACAAG TGCAAGGTCT CCAACAAAGC CCTCCCAGCC CCCATCGAGA AAACCATCTC
8101 CAAAGCCAAA GGGCAGCCCC GAGAACCACA GGTGTACACC CTGCCCCCAT CCCGGGATGA
8161 GCTGACCAAG AACCAGGTCA GCCTGACCTG CCTGGTCAAA GGCTTCTATC CAGCGACAT
8221 CGCCGTGGAG TGGGAGAGCA ATGGGCAGCC GGAGAACAAC TACAAGACCA CGCCTCCCGT
8281 GTTGGACTCC GACGGCTCCT TCTTCCTCTA CAGCAAGCTC ACCGTGGACA AGAGCAGGTG
8341 GCAGCAGGGG AACGTCTTCT CATGCTCCGT GATGCATGAG GCTCTGCACA ACCACTACAC
8401 GCAGAAGAGC CTCTCCCTGT CTCCGGGTAA A**
```

TABLE 4

Polypeptide Sequence: FVIII-Fc

A. B-Domain Deleted FVIII-Fc (BDD FVIIIFc):
Construct = HC-LC-Fc fusion. An Fc expression cassette is cotransfected withBDDFVIII-Fc to
generate the BDD FVIIIFc monomer. For the BDD FVIIIFc chain,the Fc sequence is shown in bold;
HC sequence is shown in double underline; remaining B domain sequence is shown in italics.
Signal peptides are underlined.
i) B domain deleted FVIII-Fc chain (19 amino acid signal sequence underlined) (SEQ ID NO: 12)

FVIII SIGNAL PEPTIDE: MQIELSTCFFLCLLRFCFS

FVIII MATURE POLYPEPTIDE SEQUENCE:
ATRRYYLGAVELSWDYMQSDLGELPVDARFPPRVPKSFPFNTSVVYKKILFVEFTDHLFNIAKPRPPWMGLLGPTIQAEVYDTVVITLKNMASHPVS

LHAVGVSYWKASEGAEYDDQTSQREKEDDKVFPGGSHTYVWQVLKENGPMASDPLCLTYSYLSHVDLVKDLNSGLIGALLVCREGSLAKEKTQTLH

KFILLFAVFDEGKSWHSETKNSLMQDRDAASARAWPKMHTVNGYVNRSLPGLIGCHRKSVYWHVIGMGTTPEVHSIFLEGHTFLVRNHRQASLEIS

PITFLTAQTLLMDLGQPLLFCHISSHQHDGMEAYVKVDSCPEEPQLRMKNNEEAEDYDDDLTDSEMDVVREDDDNSPSFIQIRSVAKKHPKTWVH

YIAAEEEDWDYAPLVLAPDDRSYKSQYLNNGPQRIGRKYKKVRFMAYTDETFKTREAIQHESGILGPLLYGEVGDTLLIIFKNQASRPYNIYPHGITDVR

PLYSRRLPKGVKHLKDFPILPGEIFKYKWTVTVEDGPTKSDPRCLTRYYSSFVNMERDLASGLIGPLLICYKESVDQRGNQIMSDKRNVILFSVFDENRS

WYLTENIQRFLPNPAGVQLEDPEFQASNIMHSINGYVFDSLQLSVCLHEVAYWYILSIGAQTDFLSVFFSGYTFKHKMVYEDTLTLFPFSGETVFMSM

ENPGLWILGCHNSDFRNRGMTALLKVSSCDKNTGDVYEDSYEDISAYLLSKNNAIEPR*SFSQNPPVLKRHQR*EITRTTLQSDQEEIDYDDTISVEMKK

EDFDIYDEDENQSPRSFQKKTRHYFIAAVERLWDYGMSSSPHVLRNRAQSGSVPQFKKVVFQEFTDGSFTQPLYRGELNEHLGLLGPYIRAEVEDNI

MVTFRNQASRPYSFYSSLISYEEDQRQGAEPRKNFVKPNETKTYFWKVQHHMAPTKDEFDCKAWAYFSDVDLEKDVHSGLIGPLLVCHTNTLNPA

HGRQVTVQEFALFFTIFDETKSWYFTENMERNCRAPCNIQMEDPTFKENYRFHAINGYIMDTLPGLVMAQDQRIRWYLLSMGSNENIHSIHFSGH

VFTVRKKEEYKMALYNLYPGVFETVEMLPSKAGIWRVECLIGEHLHAGMSTLFLVYSNKCQTPLGMASGHIRDFQITASGQYGQWAPKLARLHYSG

SINAWSTKEPFSWIKVDLLAPMIIHGIKTQGARQKFSSLYISQFIIMYSLDGKKWQTYRGNSTGTLMVFFGNVDSSGIKHNIFNPPIIARYIRLHPTHYSI

RSTLRMELMGCDLNSCSMPLGMESKAISDAQITASSYFTNMFATWSPSKARLHLQGRSNAWRPQVNNPKEWLQVDFQKTMKVTGVTTQGVKSL

LTSMYVKEFLISSSQDGHQWTLFFQNGKVKVFQGNQDSFTPVVNSLDPPLLTRYLRIHPQSWVHQIALRMEVLGCEAQDLYDKTHTCPPCPAPELL

GGPSVFLFPPKPKDTLMISRTPEVTCVVVDVSHEDPEVKFNWYVDGVEVHNAKTKPREEQYNSTYRVVSVLTVLHQDWLNGKEYKCKVSNKAL

PAPIEKTISKAKGQPREPQVYTLPPSRDELTKNQVSLTCLVKGFYPSDIAVEWESNGQPENNYKTTPPVLDSDGSFFLYSKLTVDKSRWQQGNVF

SCSVMHEALHNHYTQKSLSLSPGK

B. Full-length FVIIIFc.
Construct = HC-B-LC-Fc fusion. An Fc expression cassette is cotransfected with full-length
FVIII-Fc to generate the full-length FVIIIFc monomer. For the FVIIIFc chain, the Fc sequence is
shown in bold; HC sequence is shown in double underline; B domain sequence is shown in italics.
Signal peptides are underlined.
i) Full-length FVIIIFc chain (FVIII signal peptide underlined (SEQ ID NO: 14)

FVIII SIGNAL PEPTIDE: MQIELSTCFFLCLLRFCFS

FVIII MATURE SEQUENCE:
ATRRYYLGAVELSWDYMQSDLGELPVDARFPPRVPKSFPFNTSVVYKKTLFVEFTDHLFNIAKPRPPWMGLLGPTIQAEVYDTVVI

TLKNMASHPVSLHAVGVSYWKASEGAEYDDQTSQREKEDDKVFPGGSHTYVWQVLKENGPMASDPLCLTYSYLSHVDLVKDLNSGL

IGALLVCREGSLAKEKTQTLHKFILLFAVFDEGKSWHSETKNSLMQDRDAASARAWPKMHTVNGYVNRSLPGLIGCHRKSVYWHVI

GMGTTPEVHSIFLEGHTFLVRNHRQASLEISPITFLTAQTLLMDLGQFLLFCHISSHQHDGMEAYVKVDSCPEEPQLRMKNNEEAE

DYDDDLTDSEMDVVRFDDDNSPSFIQIRSVAKKHPKTWVHYIAAEEEDWDYAPLVLAPDDRSYKSQYLNNGPQRIQRKYKKVRFMA

YTDETFKTREAIQHESGILGPLLYGEVGDTLLIIFKNQASRPYNIYPHGITDVRPLYSRRLPKGVKHLKDFPILPGEIFKYKWTVT

VEDGPTKSDPRCLTRYYSSFVNMERDLASGLIGPLLICYKESVDQRGNQIMSDKRNVILFSVFDENRSWYLTENIQRFLPNPAGVQ

LEDPEFQASNIMHSINGYVFDSLQLSVCLHEVAYWYILSIGAQTDFLSVFPSGYTFKHKMVYEDTLTLFPFSGETVFMSMENPGLW

ILGCHNSDFRNRGMTALLKVSSCDKNTGDYYEDSYERISAYLLSKNNAIEPR*SFSQNSRHPSTRQKQFNATTIPENDIEKTDPWFA*

*HRTPMPKIQNVSSSDLLMLLROSPTPHGLSLSDLQEAKYETFSDDPSPGAIDSNNSLSEMTHFRPQLHHSGDMVFTPESGLQLRLN*

*EKLGTTAATELKKLDFKVSSTSNNLISTIPSDNLAAGTDNTSSLGPPSMPVHYDSQLDTTLFGKKSSPLETSGGPLSLSEENNDSK*

TABLE 4-continued

| Polypeptide Sequence: FVIII-Fc |
|---|
| *LLESGLMNSQESSWGKNVSSTESGRLFKGKRAHGPALLTKDNALFKVSISLLKTNKTSNNSATNRKTHIDGPSLLIENSPSVWQNI* |
| *LESDTEFKKVTPLIHDRMLMDKNATALRLNHMSNKTTSSKNMEMVQQKKEGPIPPDAQNPDMSFFKMLFLPESARWIQRTHGKNSL* |
| *NSGQGPSPKQLVSLGPEKSVEGQNFLSEKNKVVVGKGEFTKDVGLKEMVFPSSRNLFLTNLDNLHENNTHNQEKKIQEEIEKKITL* |
| *IQENVVLPQIHTVTGTKNFMKNLFLLSTRQNVEGSYDGAYAPVLQDFRSLNDSTNRTKKHTAHFSKKGEEENLEGLGNQTKQIVEK* |
| *YACTTRISPNTSQQNFVTQRSKRALKQFRLPLEETELEKRIIVDDTSTQWSKNMKHLTPSTLTQIDYNEKEKGAITQSPLSDCLTR* |
| *SHSIPQANRSPLPIAKVSSFPSIRPIYLTRVLFQDNSSHLPAASYRKKDSGVQESSHFLQGAKKNNLSLAILTLEMTGDQREVGSL* |
| *GTSATNSVTYKKVENTVLPKPDLPKTSGKVELLPKVHIYQKDLFPTETSNGSPGHLVLVEGSLLQGTEGAIKWNEANRPGKVPFLR* |
| *VATESSAKTPSKLLDPLAWDNHYGTQIPKEEWKSQEKSPEKTAFKKKDTILSLNACESNHAIAAINEGQNKPEIEVTWAKQGRTER* |
| *LCSQNPPVLKRHQREITRTTLQSGQEEIDYDDTISVEMKKEDFDIYDEDENQSPRSFQKKTRHYFIAAVERLWDYGMSSSPHVLRN* |
| *RAQSGSVPQFKKVVFQEFTDGSPTQPLYRGELNEHLGLLGPYIRAEVEDNIMVTFRNQASRPYSFYSSLISYEEDQRQGAEPRKNF* |
| *VKPNETKTYFWKVQHHMAPTKDEFDCKAWAYFSDVDLEKDVHSGLIGPLLVCHTNTLNPAHGRQVTVQEPALFFTIFDETKSWYFT* |
| *ENMERNCRAPCNIQMEDPTFKENYRFHAINGYIMDTLPGLVMAQDQRIRWYLLSMGSNENIHSIHFSGHVFTVRKKEEYKMALYNL* |
| *YPGVFETVEMLPSKAGIWRVECLIGEHLHAGMSTLFLVYSNKCQTPLGMASGHIRDFQITASGQYGQWAPKLARLHYSGSINAWST* |
| *KEPFSWIKVDLLAPMIIHGIKTQGARQKFSSLYISQFIIMYSLDGKKWQTYRGNSTGTLMVFFGNVDSSGIKHNIFNPPIIARYIR* |
| *LHPTHYSIRSTLRMELMGCDLNSCSMPLGMESKIASDAQITASSYFTNMFATWSPSKARLHLQGRSNAWRPQVNNPKEWLQVDFQK* |
| *TMKVTGVTTQGVKSLLTSMYVKEFLISSSQDGHQWTLFFQNGKVKVFQGNQDSFTPVVNSLDPPLLTRYLRIHPQSWVHQIALRME* |
| *VLGCEAWDLY***DKTHTCPPCPAPELLGGPSVFLFPPKPKDTLMISRTPEVTCVVVDVSHEDPEVKFNWYVDGVEVHNAKTKPREEQY* |
| *NSTYRVVSVLTVLHQDWLNGHEYKCKVSNKALPAPIEKTISKAKGQPREPQVYTLPPSRDELTKNQVSLTCLVKGFYPSDIAVEWE* |
| *SNGQPENNYKTTPPVLDSDGSFFLYSKLTVDKSRWQQGNVFSCSVMHEALHNHYTQKSLSLSPGK* |

TABLE 5

| Polynucleotide Sequences: FVII-Fc<br>FVII-Fc Chain DNA Sequence (SEQ ID NO: 15, which encodes<br>SEQ ID NO: 16) |
|---|
| <223> Full Length FVII-Fc DNA Sequence |
| <220> |
| <221> sig_peptide |
| <222> (1) . . . (180) |
| <223> FVII signal |
| <220> |
| <221> misc_feature |
| <222> (1402) . . . (2082) |
| <223> Fc region |

```
atggtctccc aggccctcag gtcctctgc cttctgcttg gcttcagggg ctgcctggct    60
gcaggcgggg tcgctaaggc ctcaggagga gaaacacggg acatgccgtg gaagccgggg   120
cctcacagag tcttcgtaac ccaggaggaa gcccacggcg tcctgcaccg cgccggcgc   180
gccaacgcgt tcctgaagga gctgcggccg ggctccctgg agagggagtg caaggaggag   240
cagtgctcct tcgaggaggc ccgggagatc ttcaaggacg cggagaggac gaagctgttc   300
tggatttctt acagtgatgg ggaccagtgt gcctcaagtc catgccagaa tggggggctcc   360
tgcaaggacc agctccagtc ctatatctgc ttctgcctcc ctgccttcga gggccggaac   420
```

TABLE 5-continued

Polynucleotide Sequences: FVII-Fc
FVII-Fc Chain DNA Sequence (SEQ ID NO: 15, which encodes
SEQ ID NO: 16)

```
tgtgagacgc acaaggatga ccagctgatc tgtgtgaacg agaacggcgg ctgtgagcag   480
tactgcagtg accacacggg caccaagcgc tcctgtcggt gccacgaggg gtactctctg   540
ctggcagacg gggtgtcctg cacacccaca gttgaatatc catgtggaaa aatacctatt   600
ctagaaaaaa gaaatgccag caaaccccaa ggccgaattg tgggggcaa ggtgtgcccc    660
aaagggagt gtccatggca ggtcctgttg ttggtgaatg gagctcagtt gtgtgggggg    720
accctgatca acaccatctg gtggtctcc gcggcccact gtttcgacaa atcaagaac     780
tggaggaacc tgatcgcggt gctgggcgag cacgacctca gcgagcacga cggggatgag   840
cagagccggc gggtggcgca ggtcatcatc ccagcacgt acgtcccggg caccaccaac    900
cacgacatcg cgctgctccg cctgcaccag cccgtggtcc tcactgacca tgtggtgccc   960
ctctgcctgc ccgaacggac gttctctgag gaggacgctgg ccttcgtgcg cttctcattg  1020
gtcagcggct ggggccagct gctggaccgt ggcgccacgg ccctggagct catggtcctc   1080
aacgtgcccc ggctgatgac ccaggactgc ctgcagcagt cacggaaggt gggagactcc   1140
ccaaatatca cggagtacat gttctgtgcc ggctactcgg atggcagcaa ggactcctgc   1200
aaggggggaca gtgaggcccc acatgccacc cactaccggg gcacgtggta cctgacgggc   1260
atcgtcagct ggggccaggg ctgcgcaacc gtgggccact tggggtgta caccagggtc    1320
tcccagtaca tcgagtggct gcaaaagctc atgcgctcag agccacgccc aggagtcctc   1380
ctgcgagccc catttcccta ggacaaaact cacacatgcc caccgtgccc agctccagaa   1440
ctcctgggcg accgtcagt cttcctcttc ccccaaaac ccaaggacac cctcatgatc     1500
tcccggaccc ctgaggtcac atgcgtggtg gtggacgtga gccacgaaga ccctgaggtc   1560
aagttcaact ggtacgtgga cggcgtggag gtgcataatg ccaagacaaa gccgcgggag   1620
gagcagtaca acagcacgta ccgtgtggtc agcgtcctca ccgtcctgca ccaggactgg   1680
ctgaatggca aggagtacaa gtgcaaggtc tccaacaaag ccctcccagc ccccatcgag   1740
aaaaccatct ccaaagccaa agggcagccc cgagaaccac aggtgtacac cctgccccca   1800
tcccgggatg agctgaccaa gaaccaggtc agcctgacct gcctggtcaa aggcttctat   1860
cccagcgaca tcgccgtgga gtgggagagc aatgggcagc cggagaacaa ctacaagacc   1920
acgcctcccg tgttggactc cgacggctcc ttcttcctct acagcaagct caccgtggac   1980
aagagcaggt ggcagcaggg gaacgtcttc tcatgctccg tgatgcatga ggctctgcac   2040
aaccactaca cgcagaagag cctctccctg tctccgggta aa                      2082
```

TABLE 6

Polypeptide Sequences: FVII-Fc
FVII-Fc Chain Polypeptide Sequence (SEQ ID NO: 16)

<211> 693

<212> PRT

<213> Artificial Sequence

<220>

<223> Full Length FVII-Fc polypeptide

<220>

<221> SIGNAL

<222> (1)...(60)

<220>

<221> MISC_FEATURE

<222> (467)...(693)

TABLE 6-continued

Polypeptide Sequences: FVII-Fc
FVII-Fc Chain Polypeptide Sequence (SEQ ID NO: 16)

<223> Fc Sequence

MVSQALRLLCLLLGLQGCLAAGGVAKASGGETRDMPWKPGPHRVFVTQEE

AHGVLHRRRRANAFLEELRPGSLERECKEEQCSFEEAREIFKDAERTKLF

WISYSDGDQCASSPCQNGGSCKDQLQSYICFCLPAFEGRNCETHKDDQLI

CVNENGGCEQYCSDHTGTKRSCRCHEGYSLLADGVSCTPTVEYPCGKIPI

LEKRNASKPQGRIVGGKVCPKGECPWQVLLLVNGAQLCGGTLINTIWVVS

AAHCFDKIKNWRNLIAVLGEHDLSEHDGDEQSRRVAQVIIPSTYVPGTTN

HDIALLRLHQPVVLTDHVVPLCLPERTFSERTLAFVRFSLVSGWGQLLDR

GATALELMVLNVPRLMTQDCLQQSRKVGDSPNITEYMFCAGYSDGSKDSC

KGDSGGPHATHYRGTWYLTGIVSWGQGCATVGHFGVYTRVSQYIEWLQKL

MRSEPRPGVLLRAPFPDKTHTCPPCPAPELLGGPSVFLFPPKPKDTLMIS

RTPEVTCVVVDVSHEDPEVKFNWYVDGVEVHNAKTKPREEQYNSTYRVVS

VLTVLHQDWLNGKEYKCKVSNKALPAPIEKTISKAKSGQREPQVYTLPPS

REDLTKNQVSLTCLVKGFYPSDIAVEWESNGQPENNYKTTPPVLDSDGSF

FLYSKLTVDKSRWQQGNVFSCSVMHEALHNHYTQKSLSLSPGK

TABLE 7

Additional Sequences

SEQ ID NO: 17
>Mature human albumin protein sequence
(derived from NCBI Ref. Sequence NP_000468):

RGVFRRDAHKSEVAHRFKDLGEENFKALVLIAFAQYLQQCPFEDHVKLVN

EVTEFAKTCVADESAENCDKSLHTLFGDKLCTVATLRETYGEMADCCAKQ

EPERNECFLQHKDDNPNLPRLVRPEVDVMCTAFHDNEETFLKKYLYEIAR

RHPYFYAPELLFFAKRYKAAFTECCQAADKAACLLPKLDELRDEGKASSA

KQRLKCASLQKFGERAFKAWAVARLSQRFPKAEFAEVSKLVTDLTKVHTE

CCHGDLLECADDRADLAKYICENQDSISSKLKECCEKPLLEKSHCIAEVE

NDEMPADLPSLAADFVESKDVCKNYAEAKDVFLGMFLYEYARRHPDYSVV

LLLRLAKTYETTLEKCCAAADPHECYAKVFDEFKPLVEEPQNLIKQNCEL

FEQLGEYKFQNALLVRYTKKVPQVSTPTLVEVSRNLGKVGSKCCKHPEAK

RMPCAEDYLSVVLNQLCVLHEKTPVSDRVTKCCTESLVNRRPCFSALEVD

ETYVPKEFNAETFTFHADICTLSEKERQIKKQTALVELVKHKPKATKEQL

KAVMDDFAAFVEKCCKADDKETCFAEEGKKLVAASQAALGL

SEQ ID NO: 18
>Albumin binding peptide 1

RLIEDICLPRWGCLWEDD

SEQ ID NO: 19
>Albumin binding peptide 2

QRLMEDICLPRWGCLWEDDF

SEQ ID NO: 20
>Albumin binding peptide 3

QGLIGDICLPRWGCLWGDSVK

SEQ ID NO: 21
>Albumin binding peptide 4

GEWWEDICLPRWGCLWEEED

---

What is claimed is:

1. A polynucleotide encoding a fusion compound of the structure P-L1-F1-L2-F2, the fusion compound comprising a procoagulant compound (P), a first immunoglobulin constant region or portion thereof (F1), and a second immunoglobulin constant region or portion thereof (F2), wherein P is linked through its C-terminal to the N-terminal of F1 with a first linker (L1) comprising an amino acid sequence as set forth in SEQ ID NO: 22, wherein F1 is linked through its C-terminal to the N-terminal of F2 with a second linker (L2) comprising an amino acid sequence as set forth in SEQ ID NO: 22, and wherein P comprises the amino acid sequence GSRIRT-VSPGSRSASGKSTCLASYCWLFWTGIA (SEQ ID NO: 4).

2. The polynucleotide of claim 1, which comprises pSYN-Fc-048 (SEQ ID NO: 1).

3. The polynucleotide of claim 1, wherein the first immunoglobulin constant region or portion thereof is an Fc fragment or an FcRn binding ligand.

4. The polynucleotide of claim 1, wherein the fusion compound comprises amino acids 22 to 558 of SEQ ID NO: 2.

5. The polynucleotide of claim 1, wherein the fusion compound further comprises a heterologous moiety.

6. The polynucleotide of claim 5, wherein the heterologous moiety comprises a polypeptide comprising FVIII, FIX, FVIIa, or a platelet targeting moiety.

7. The polynucleotide of claim 6, comprising the pSYN-FIX-030 nucleotide sequence of SEQ ID NO:7.

8. The polynucleotide of claim 6, comprising the B-domain deleted FVIIIFc chain DNA sequence of SEQ ID NO:11 or SEQ ID NO:12.

9. The polynucleotide of claim 5, wherein the heterologous moiety is selected from polyethylene glycol (PEG), albumin, an XTEN moiety, a HES moiety, or a PAS moiety.

10. The polynucleotide of claim 5, wherein the heterologous moiety is linked to the procoagulant compound (P1) via a third linker (L3).

11. The polynucleotide of claim 5, wherein the heterologous moiety is linked to the first immunoglobulin constant region (F1) or second immunoglobulin constant region (F2) via a third linker (L3).

12. The polynucleotide of claim 1, wherein first linker (L1) and second linker (L2) are different.

13. The polynucleotide of claim 1, wherein first immunoglobulin constant region or portion thereof (F1) and second immunoglobulin constant region or portion thereof (F2) are the same.

14. The polynucleotide of claim 1, wherein first immunoglobulin constant region or portion thereof (F1) and second immunoglobulin constant region or portion thereof (F2) form an Fc region comprising amino acids corresponding to EU numbers 221-447 of human IgG1.

15. The polynucleotide of claim 1, wherein the fusion compound further comprises the signal peptide, MET-DTLLLWVLLLWVPGSTG (SEQ ID NO: 5).

16. A method of making a fusion compound, the method comprising culturing a host cell in a culture medium under suitable conditions sufficient to produce the fusion compound, and isolating the fusion compound from the culture medium, thereby producing the fusion compound, wherein the host cell comprises a vector comprising a polynucleotide encoding a fusion compound of the structure P-L1-F1-L2-F2, the fusion compound comprising a procoagulant compound (P), a first immunoglobulin constant region or portion thereof (F1), and a second immunoglobulin constant region or portion thereof (F2), wherein P is linked through its C-terminal to the N-terminal of F1 with a first linker (L1) comprising an amino acid sequence as set forth in SEQ ID NO: 22, wherein F1 is linked through its C-terminal to the N-terminal of F2 with a second linker (L2) comprising an amino acid sequence as set forth in SEQ ID NO: 22, and wherein P comprises the amino acid sequence GSRIRT-VSPGSRSASGKSTCLASYCWLFWTGIA (SEQ ID NO: 4).

* * * * *